(12) United States Patent
Bachovchin

(10) Patent No.: US 7,691,967 B2
(45) Date of Patent: Apr. 6, 2010

(54) SMART PRO-DRUGS OF SERINE PROTEASE INHIBITORS

(75) Inventor: William W. Bachovchin, Melrose, MA (US)

(73) Assignee: Trustees of Tufts College, Medford, MA (US)

( * ) Notice: Subject to any disclaimer, the term of this patent is extended or adjusted under 35 U.S.C. 154(b) by 898 days.

(21) Appl. No.: 10/512,213

(22) PCT Filed: Apr. 30, 2003

(86) PCT No.: PCT/US03/13561

§ 371 (c)(1),
(2), (4) Date: Aug. 29, 2005

(87) PCT Pub. No.: WO03/092605

PCT Pub. Date: Nov. 13, 2003

(65) Prior Publication Data

US 2006/0089312 A1 Apr. 27, 2006

Related U.S. Application Data

(60) Provisional application No. 60/376,636, filed on Apr. 30, 2002.

(51) Int. Cl.
*A61K 38/06* (2006.01)
*A61K 38/00* (2006.01)
*A61K 51/00* (2006.01)

(52) U.S. Cl. .............................. 530/330; 514/18; 514/2; 424/1.69

(58) Field of Classification Search .................... 514/18
See application file for complete search history.

(56) References Cited

U.S. PATENT DOCUMENTS

| 4,499,082 | A | 2/1985 | Shenvi et al. |
|---|---|---|---|
| 4,935,493 | A | 6/1990 | Bachovchin et al. |
| 5,462,928 | A | 10/1995 | Bachovchin et al. |
| 5,580,979 | A | 12/1996 | Bachovchin |
| 5,776,902 | A | 7/1998 | Bachovchin |
| 6,180,402 | B1 | 1/2001 | Granville et al. |
| 6,258,597 | B1 | 7/2001 | Bachovchin et al. |
| 6,277,818 | B1 | 8/2001 | Mazar et al. |
| 6,300,314 | B1 | 10/2001 | Wallner et al. |
| 6,355,614 | B1 | 3/2002 | Wallner |
| 6,703,238 | B2 | 3/2004 | Bachovchin et al. |
| 6,770,628 | B2 | 8/2004 | Wallner et al. |
| 6,803,357 | B1 | 10/2004 | Bachovchin et al. |
| 6,825,169 | B1 | 11/2004 | Bachovchin et al. |
| 6,890,898 | B2 | 5/2005 | Bachovchin |
| 6,890,904 | B1 * | 5/2005 | Wallner et al. ................. 514/14 |
| 6,949,514 | B2 * | 9/2005 | Wallner et al. ................. 514/14 |
| 6,979,697 | B1 | 12/2005 | Wallner |
| 7,259,138 | B2 * | 8/2007 | Wallner et al. ................. 514/2 |
| 7,282,484 | B2 * | 10/2007 | Wallner et al. ................. 514/19 |
| 2003/0153509 | A1 | 8/2003 | Bachovchin et al. |
| 2003/0158114 | A1 | 8/2003 | Wallner et al. |
| 2004/0077601 | A1 | 4/2004 | Adams et al. |
| 2004/0152192 | A1 | 8/2004 | Bachovchin et al. |
| 2004/0176307 | A1 | 9/2004 | Bachovchin et al. |
| 2004/0229820 | A1 | 11/2004 | Bachovchin et al. |
| 2005/0037976 | A1 | 2/2005 | Wallner et al. |
| 2005/0049177 | A1 | 3/2005 | Bachovchin et al. |
| 2005/0070459 | A1 * | 3/2005 | Bachovchin et al. ........... 514/2 |
| 2005/0070482 | A1 | 3/2005 | Bachovchin |
| 2005/0084490 | A1 | 4/2005 | Adams et al. |
| 2005/0203027 | A1 | 9/2005 | Bachovchin et al. |
| 2005/0272703 | A1 | 12/2005 | Wallner et al. |
| 2006/0052310 | A1 | 3/2006 | Wallner |
| 2006/0063719 | A1 | 3/2006 | Jesson et al. |
| 2006/0287245 | A1 * | 12/2006 | Wallner et al. ................. 514/15 |

FOREIGN PATENT DOCUMENTS

| EP | 0 195 212 | 9/1986 |
|---|---|---|
| WO | WO 89/03223 | 4/1989 |

OTHER PUBLICATIONS

Bachovchin, et al., "Inhibition of IgA1 Proteinases from *Neisseria gonorrhoeae* and *Hemophilus influenzae* by Peptide Prolyl Boronic Acids,"*J. Biol. Chem.*, 265(7):3738-3743 (1990).
Gao, et al., "Direct Selection for Catalysis from Combinatorial Antibody Libraries Using a Boronic Acid Probe: Primary Amide Bond Hydrolysis," *J. Am. Chem. Soc.*, 120(10):2211-2217 (1998).
Tsilikounas et al., "B NMR Spectroscopy of Peptide Boronic Acid Inhibitor Complexes of α-Lytic Protease. Direct Evidence for Tetrahedral Boron in both Boron-Histidine and Boron-Serine Adduct Complexes," *Biochemistry*, 32:12651-12655 (1993).

* cited by examiner

*Primary Examiner*—Maury Audet
(74) *Attorney, Agent, or Firm*—Dana M. Gordon; Foley Hoag LLP

(57) ABSTRACT

The present invention relates to prodrugs of protease inhibitors, such as inhibitors of proteosome, DPOP IV, FAPα and the like. These "pro-inhibitors" are activated, i.e., cleaved by an "activated protease" to release an active inhibitor moiety in proximity to a "target protease". The identity of activating protease and target protease can be the same (such pro-inhibitors being referred to as "Target-Activated Smart Protease Inhibitors" or "TASPI") or different (e.g., "Target-Directed Smart Protease Inhibitors" or "TDSPI"). After activation of the pro-inhibitor, the active inhibitor moiety can self-inactive by, e.g., intramolecular-cyclization or cis-trans isomerization.

15 Claims, 106 Drawing Sheets

CD26/DP IV
Xaa - Pro - Xaa
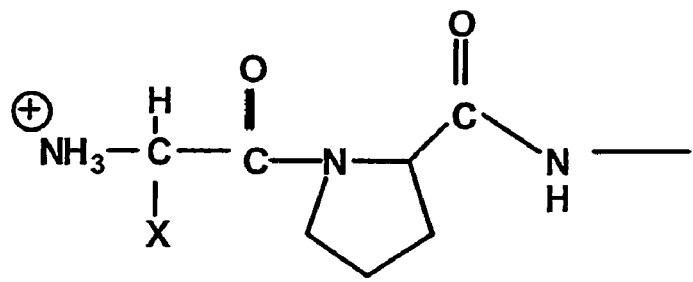
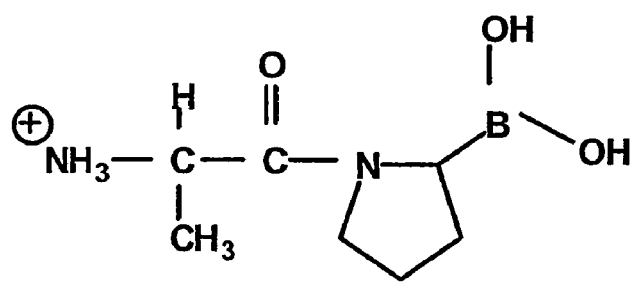
*Ala-boroPro*     $Ki < 1.6 \times 10^{11} M$
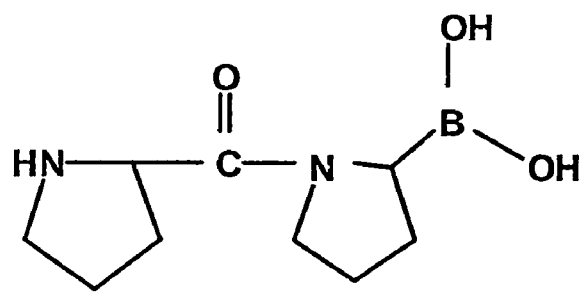
*Pro-boroPro*     $Ki = 1.6 \times 10^{11} M$
Figure 1: Structures of Ala-boroPro and Pro-boroPro in aligment with a CD26/DP IV cleavable peptide substrate.

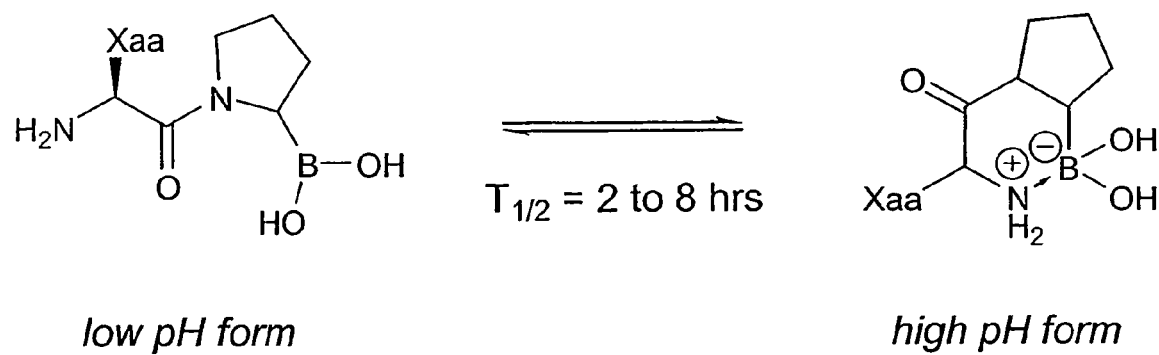
Figure 2. pH dependent conformational equilibrium of Xaa-boroPro's. Open chain form is favored at low pH values, cyclic structure is favored at high pH values.

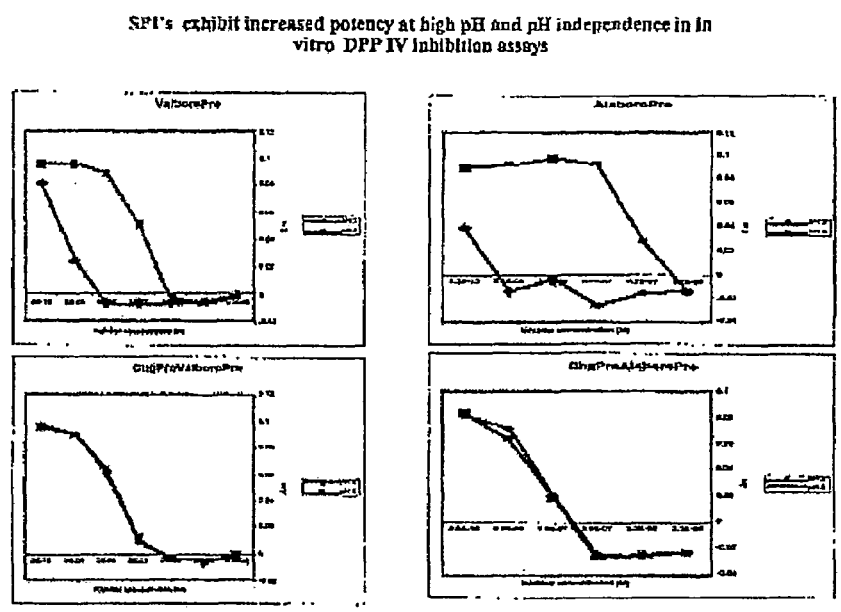
Figure 3. pH dependence of DPP IV inhibition by Val-boroPro (top left) and Ala-boroPro (top right) compared to the pH independence of the corresponding smart drugs. Inhibitors were incubated overnight in pH 2 or pH 8 solutions and then added directly to an enzyme assay solution at pH 8.0.

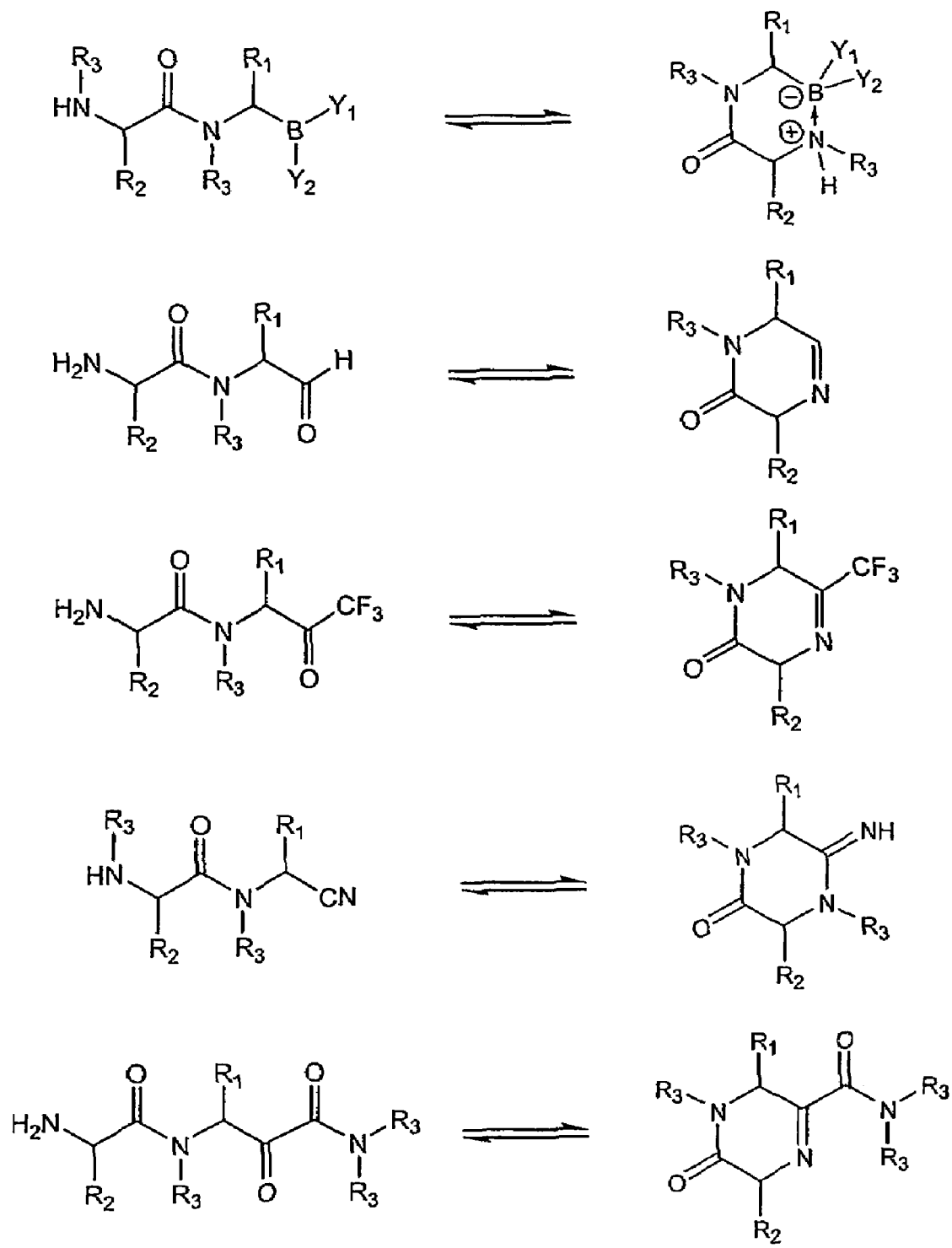
Figure 4. Examples of pH-dependent conformational equilibrium for different electron deficient functional groups.

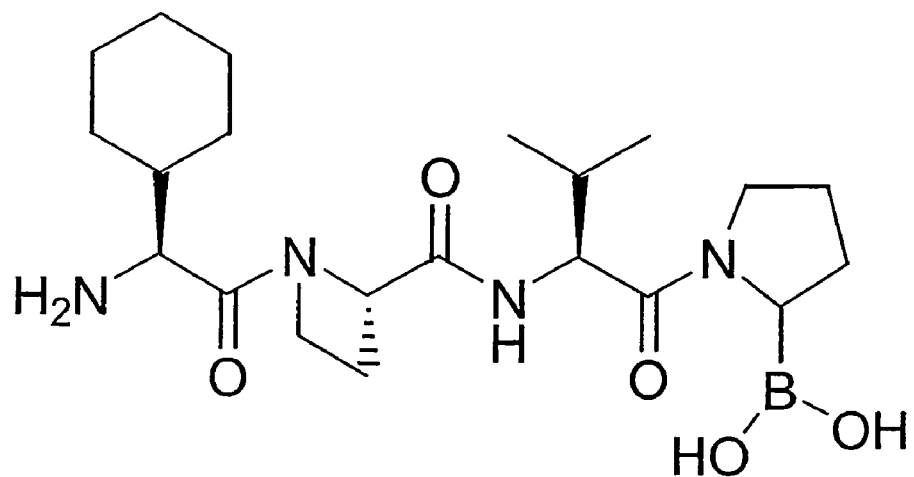
Figure 5. Cyclohexylglycine-Proline (or Proline analog)-Valine-boroProline

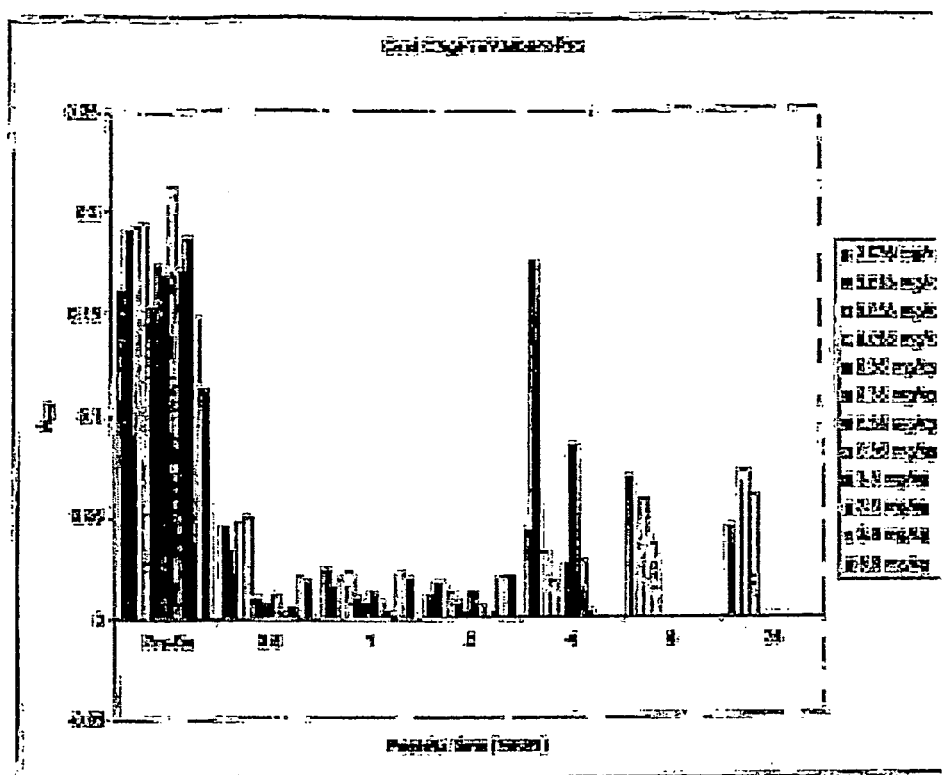
Figure 6. Serum DPP IV activity in rats as a function of time following three different doses of CHG-Pro-Val-boroPro given orally. Results demonstrate that CHG-Pro-Val-boro-Pro is orally active.

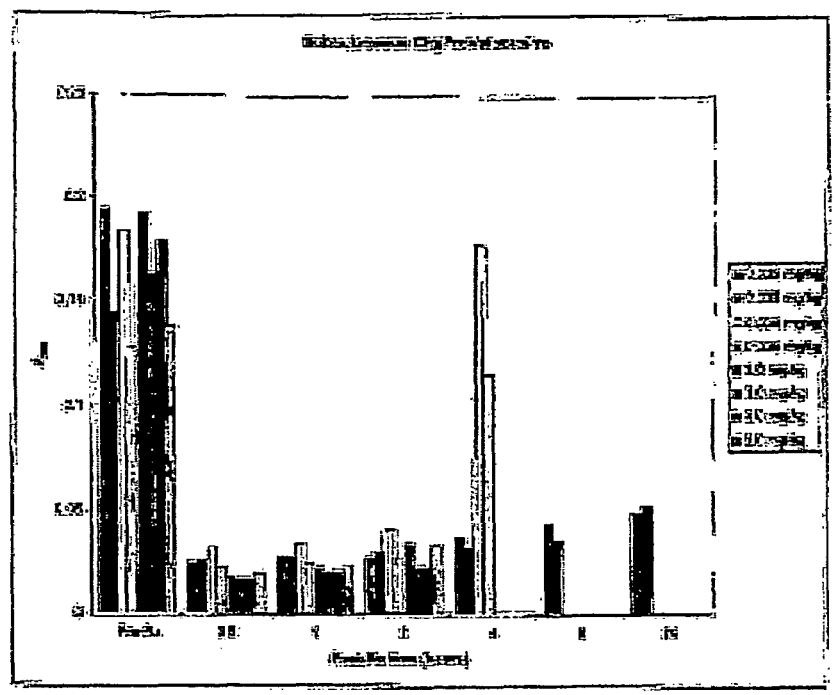
Figure 7. Serum DPP IV activity in rats as a function of time following three different doses of CHG-Pro-Val-boroPro given subcutaneously. Results demonstrate when compared to Figure 5. that CHG-Pro-Val-boroPro may be more active when given orally than when given subcutaneously.

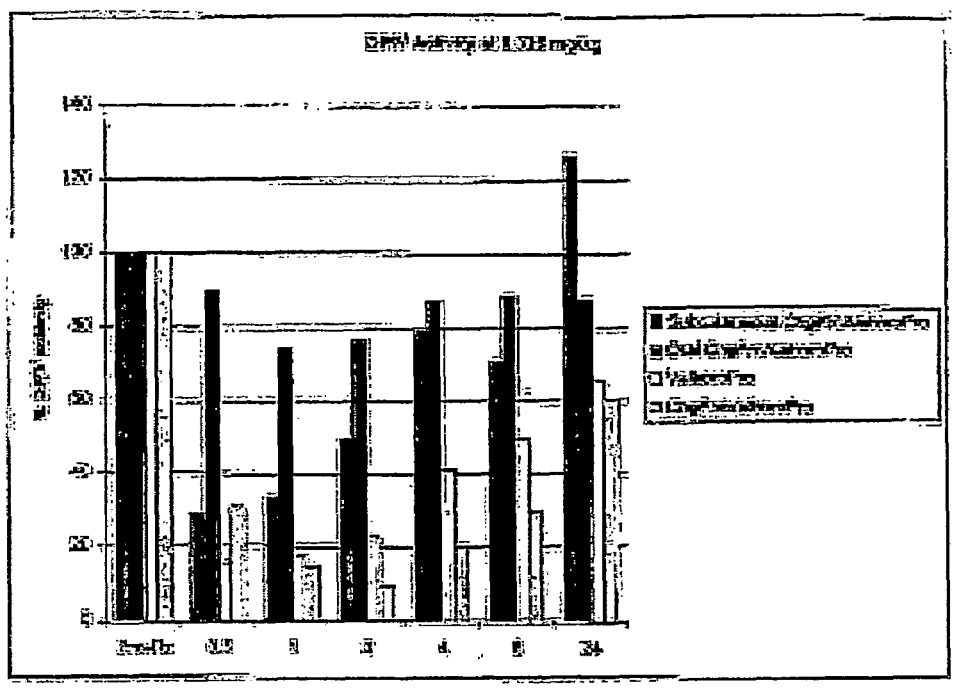

Figure 8. Serum DPP IV activity in rats as a function of time following a single oral dose of 0.025 mg/kg. Each bar represents the average of four rats. Results demonstrate that CHG-Pro-Val-boroPro outperforms Val-boroPro in inhibition serum DPP IV enzyme activity. Note that with CHG-Pro-Val-boroPro inhibition, although a little slower to develop, is greater and longer lasting than with Val-boroPro. Results also show that the prodrug form of Ala-boroPro, CHG-Pro-Ala-boroPro, chemically very simlar to CHG-Pro-Val-boroPro, is much less orally active.

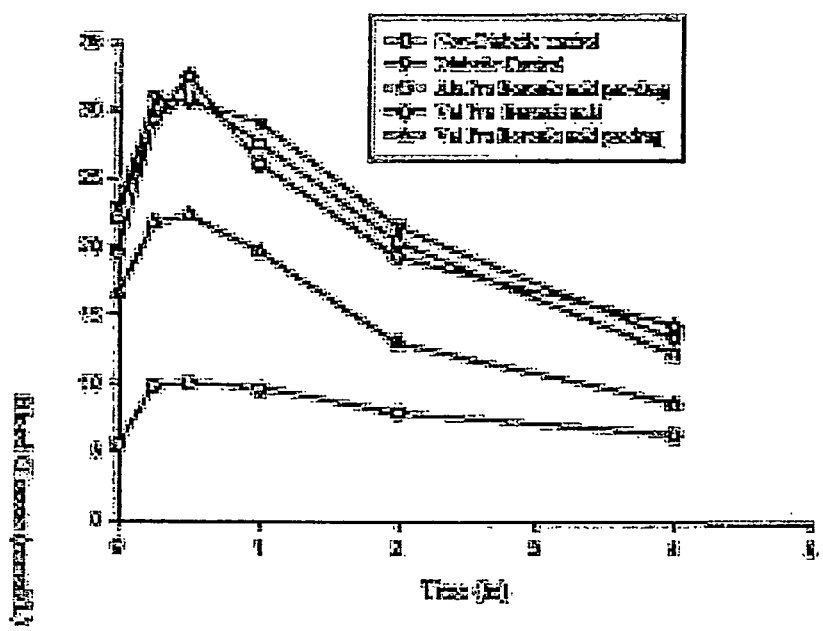
Figure 9. Oral glucose tolerance test (OGTT) in DB/DB mice given four hours post oral dose of test agents at 0.5 mg/kg Val-boroPro. Dose of CHG-Pro-Val-boroPro and CHG-Pro-Ala-boroPro calculated to be equivalent to 0.05 mg/kg of Val-boroPro.

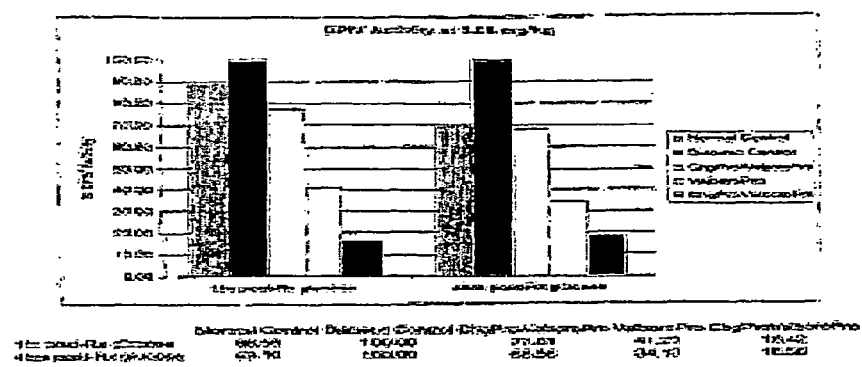
Figure 10. Serum DPP IV activity in rats as a function of time at 1hr and 4hr intervals following a single oral dose of 0.05 mg/kg. Each bar represents the average of four rats.

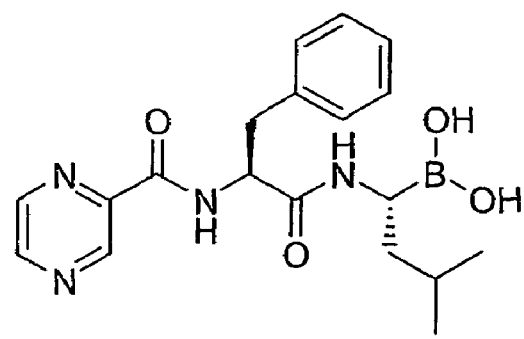
LDP 341
Millenium's proteasome inhibitor
in phase II clinical trials
R-Phe-Leu-B(OH)₂
Figure 11. Structure of Millenium's LDP 341 Proteosome Protease Inhibitor.

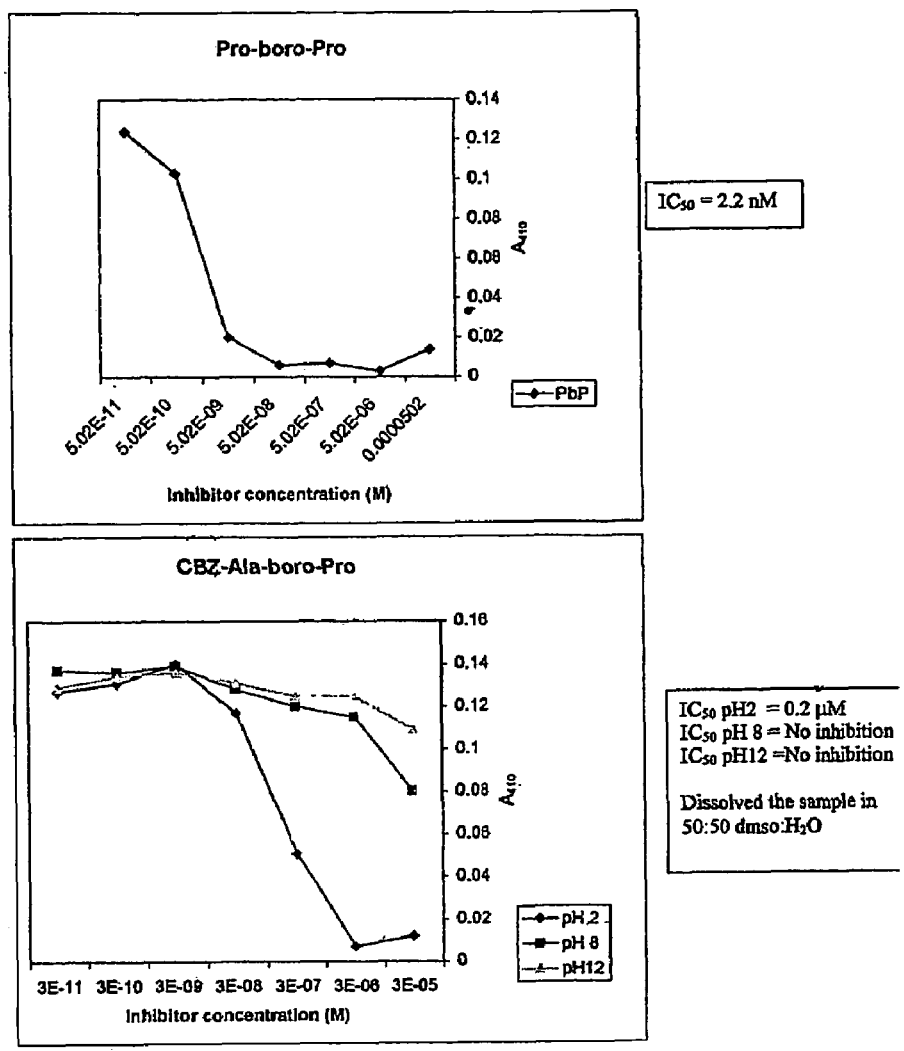
Figure 12. IC$_{50}$ concentration graphs of Pro-boro-Pro and CBZ-Ala-boro-Pro

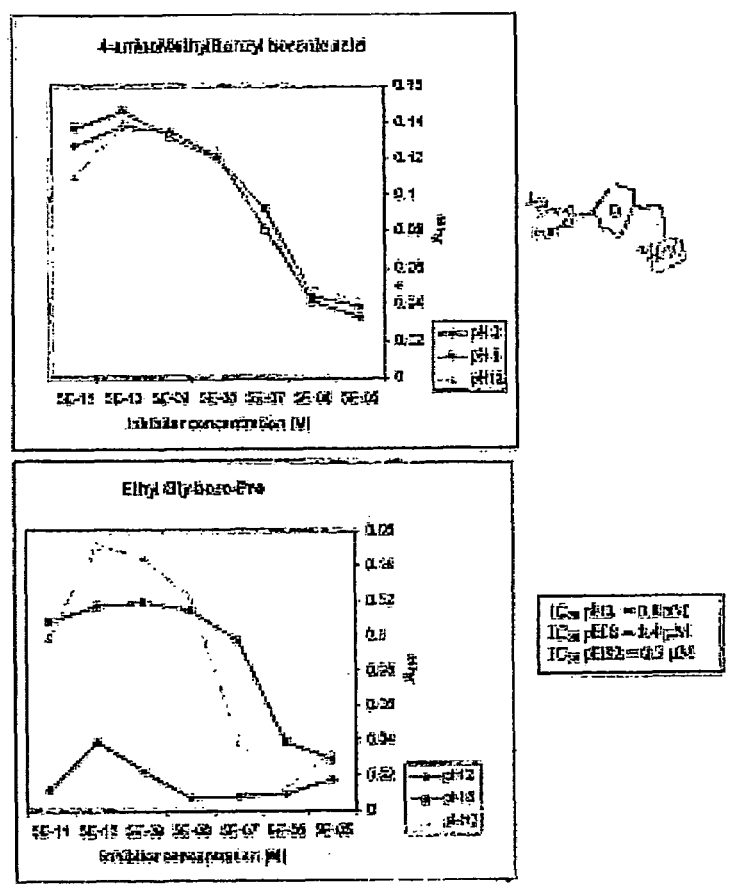
Figure 13. IC$_{50}$ pH dependance of 4-aminomethylbenzylboronic acid and ethyl Gly-boro-Pro

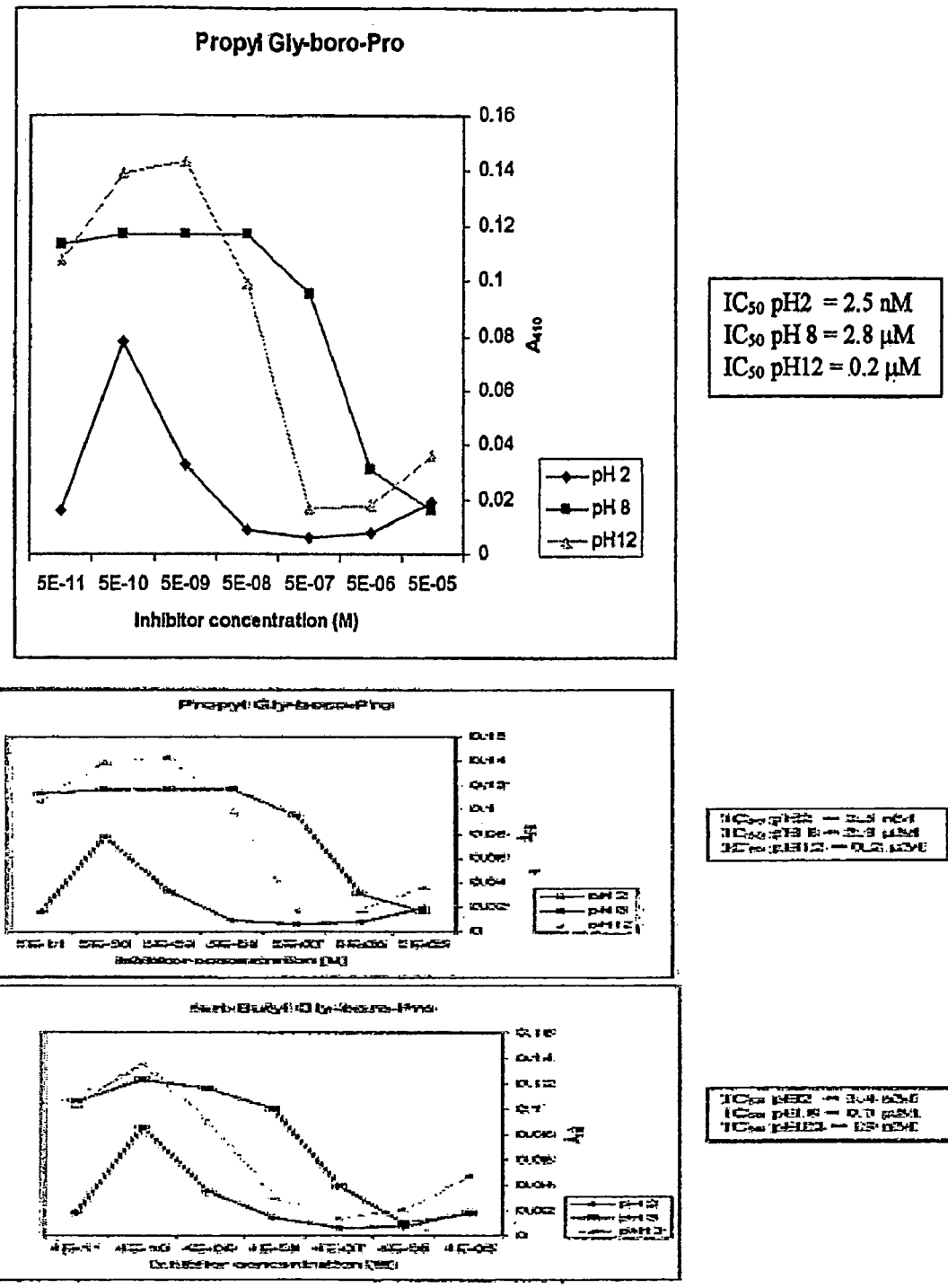
Figure 14. IC$_{50}$ pH dependance of propyl Gly-boroPro and t-butyl Gly-boroPro.

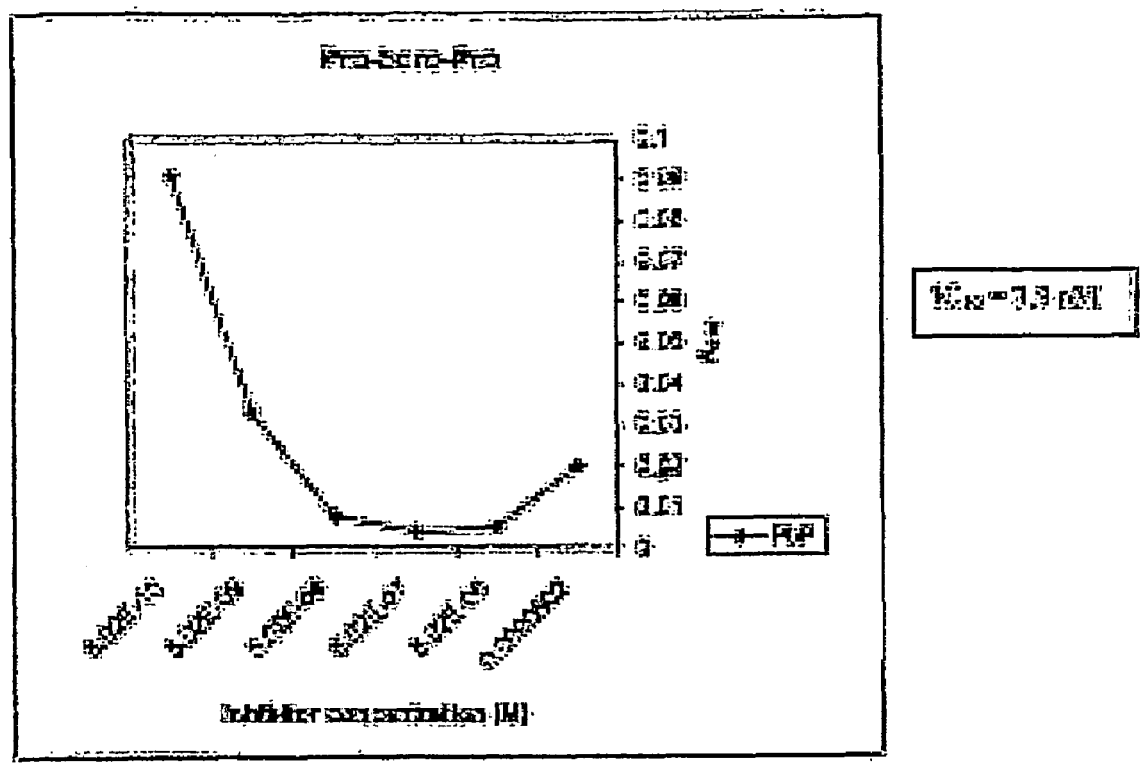
Figure 15. $IC_{50}$ concentration graph of Pro-boro-Pro.

Figure 16. Inhibition profile of AspProGlyboroPro against DPIV at selected pHs

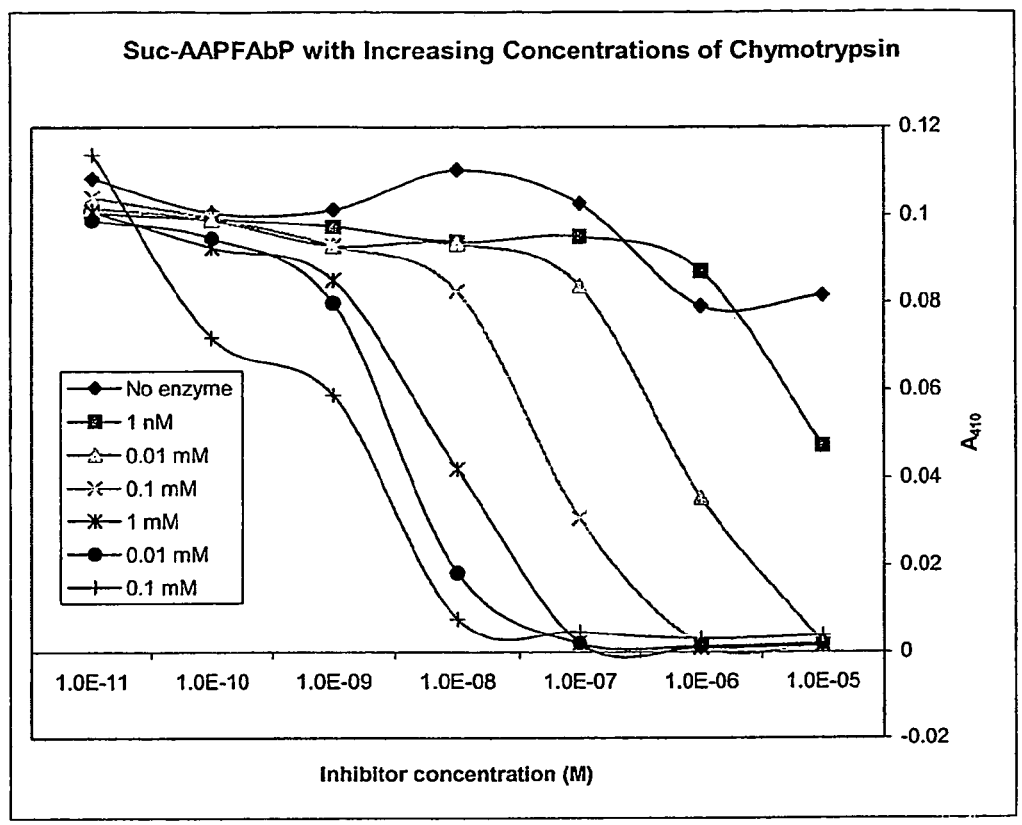
Figure 17. Inhibition profile of Suc-AlaAlaProPheAlaboroPro against chymotrpsin at selected pHs.

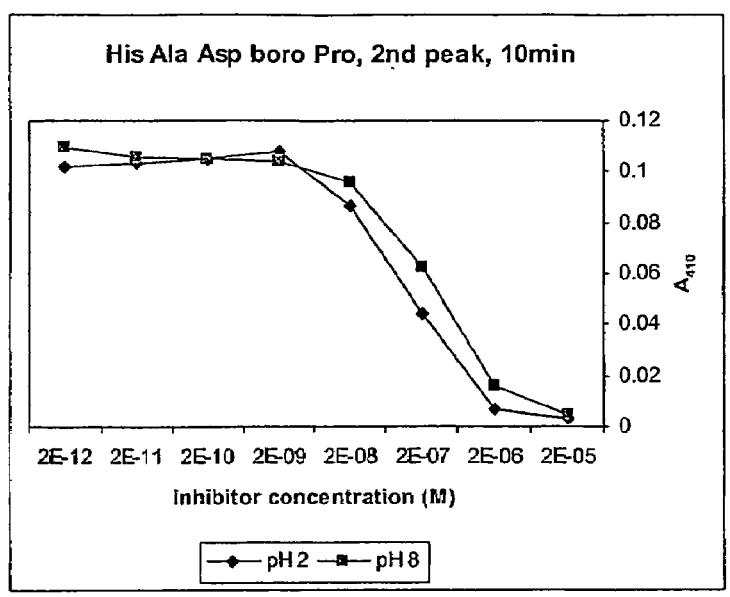
Figure 18a. Inhibition profile of HisAlaAspboroPro against DPIV at selected pHs at 10 minutes.

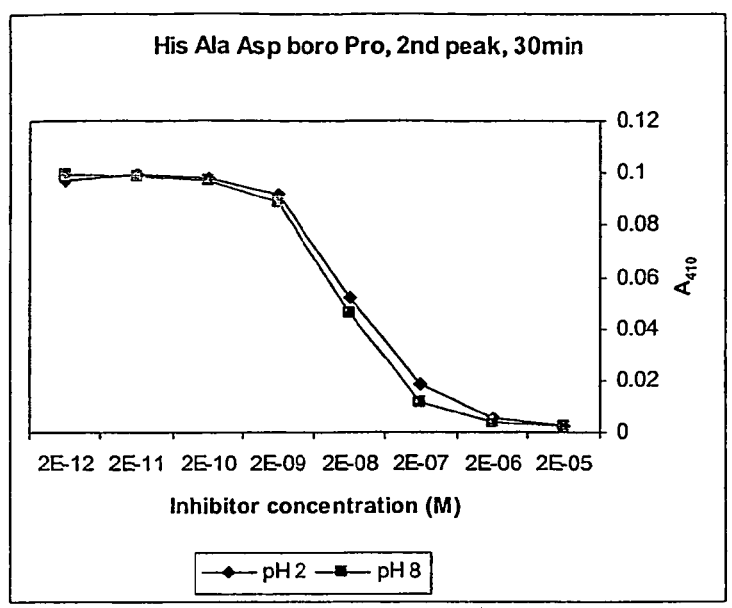
Figure 18b. Inhibition profile of HisAlaAspboroPro against DPIV at selected pHs at 30 minutes.

Figure 18c. Inhibition profile of HisAlaAspboroPro against DPIV at selected pHs at 1 hr.

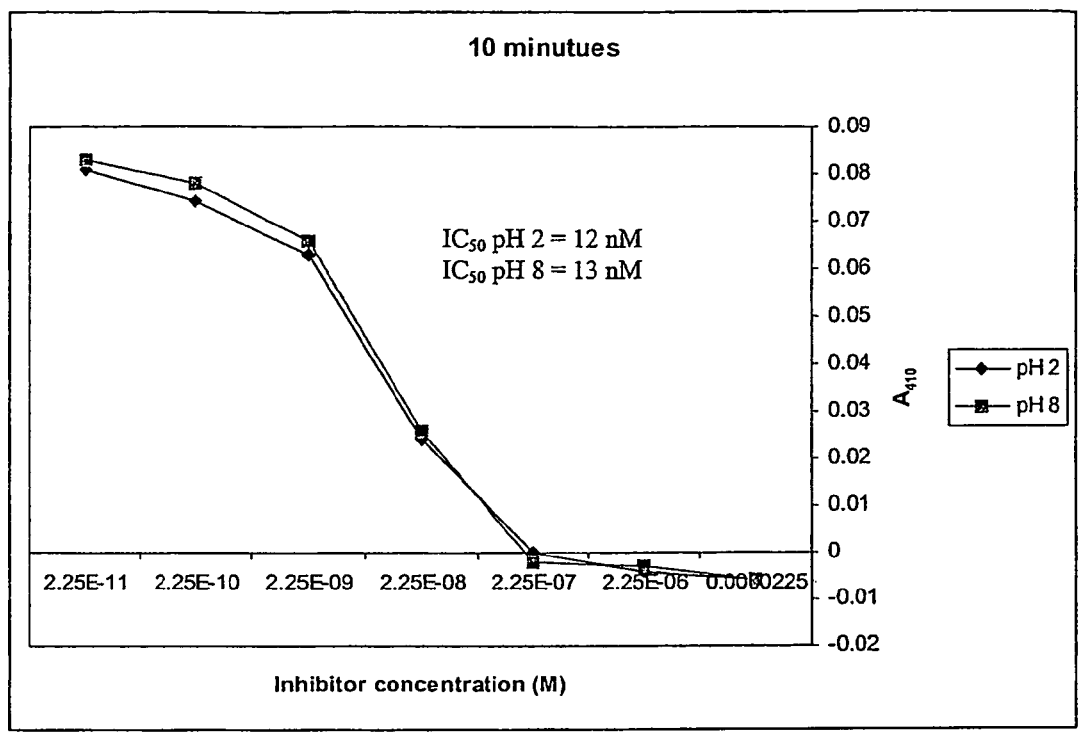
Figure 19a. Inhibition profile of PheProAlaboroPro against DPIV at selected pHs at 10 minutes
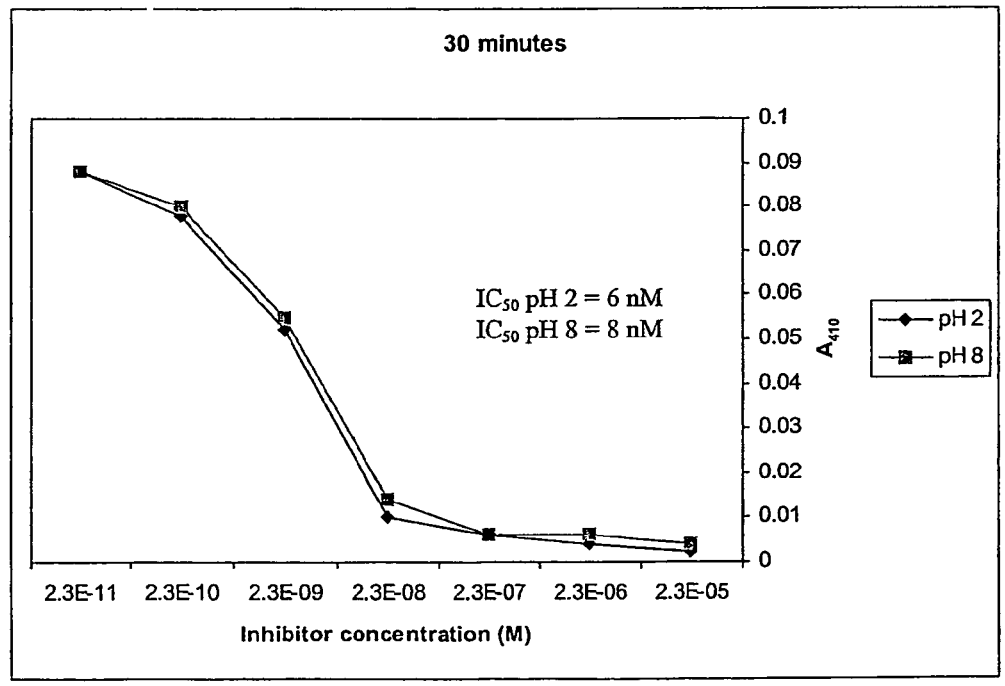
Figure 19b. Inhibition profile of PheProAlaboroPro against DPIV at selected pHs at 30 minutes Figure 19c. Inhibition profile of PheProAlaboroPro against DPIV at selected pHs at 1 hr Figure 19d. Inhibition profile of PheProAlaboroPro against DPIV at selected pHs at 2 hrs Figure 19e. Inhibition profile of PheProAlaboroPro against DPIV at selected pHs at 4 hrs Figure 19f. Inhibition profile of PheProAlaboroPro against DPIV at selected pHs at 8 hrs Figure 19g. Time resolved inhibitory potency of PheProAlaboroPro against DPIV at selected pHs.

Figure 20. Inhibition profile of LysProPheboroLeu against DPIV at selected pHs.

Figure 21. Inhibition profile of TyrProSerboroPro against DPIV at selected pHs.

Figure 22a. Inhibition profile of ChgAla-tBugboroPro against DPIV at selected pHs at 10 minutes.

Figure 22b. Inhibition profile of ChgAla-tBugboroPro against DPIV at selected pHs at 30 minutes.

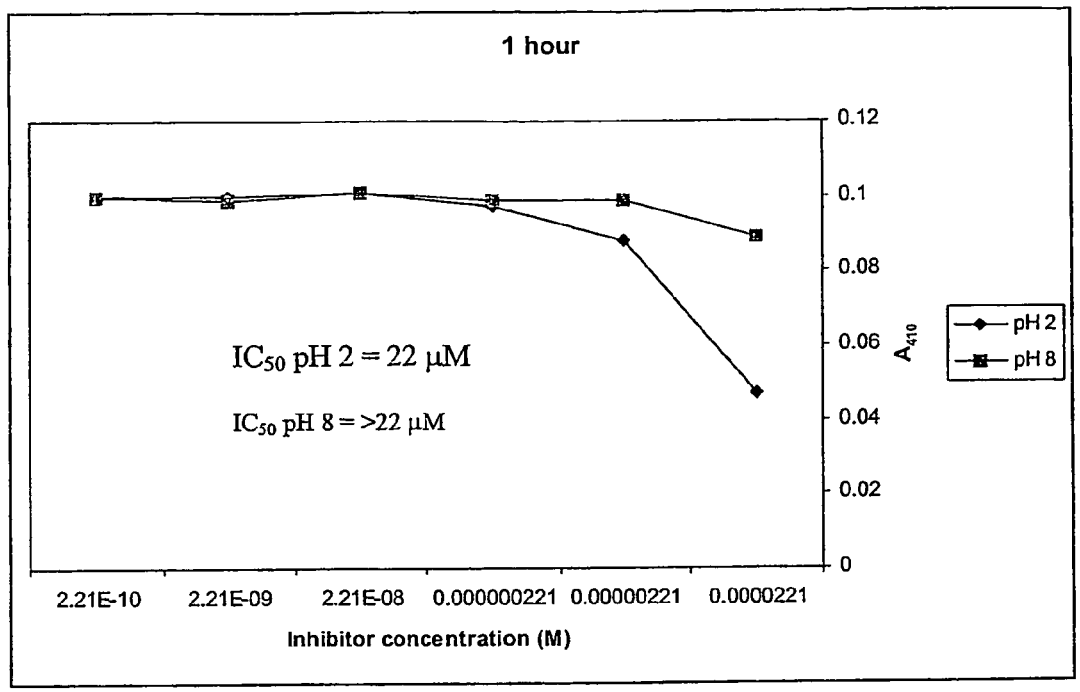
Figure 22c. Inhibition profile of ChgAla-tBugboroPro against DPIV at selected pHs at 1 hr.
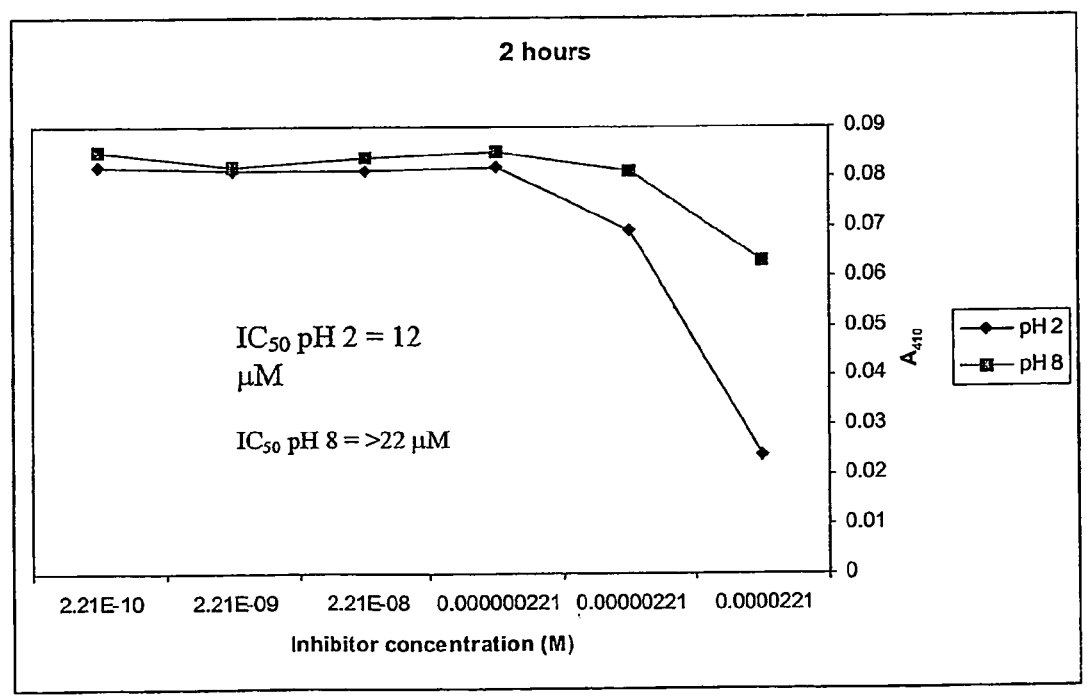
Figure 22d. Inhibition profile of ChgAla-tBugboroPro against DPIV at selected pHs at 2 hrs.

Figure 22e. Inhibition profile of ChgAla-tBugboroPro against DPIV at selected pHs at 4 hrs.

Figure 22f. Inhibition profile of ChgAla-tBugboroPro against DPIV at selected pHs at 8 hrs.

Figure 22g. Inhibition profile of ChgAla-tBugboroPro against DPIV at selected pHs at 24 hrs.

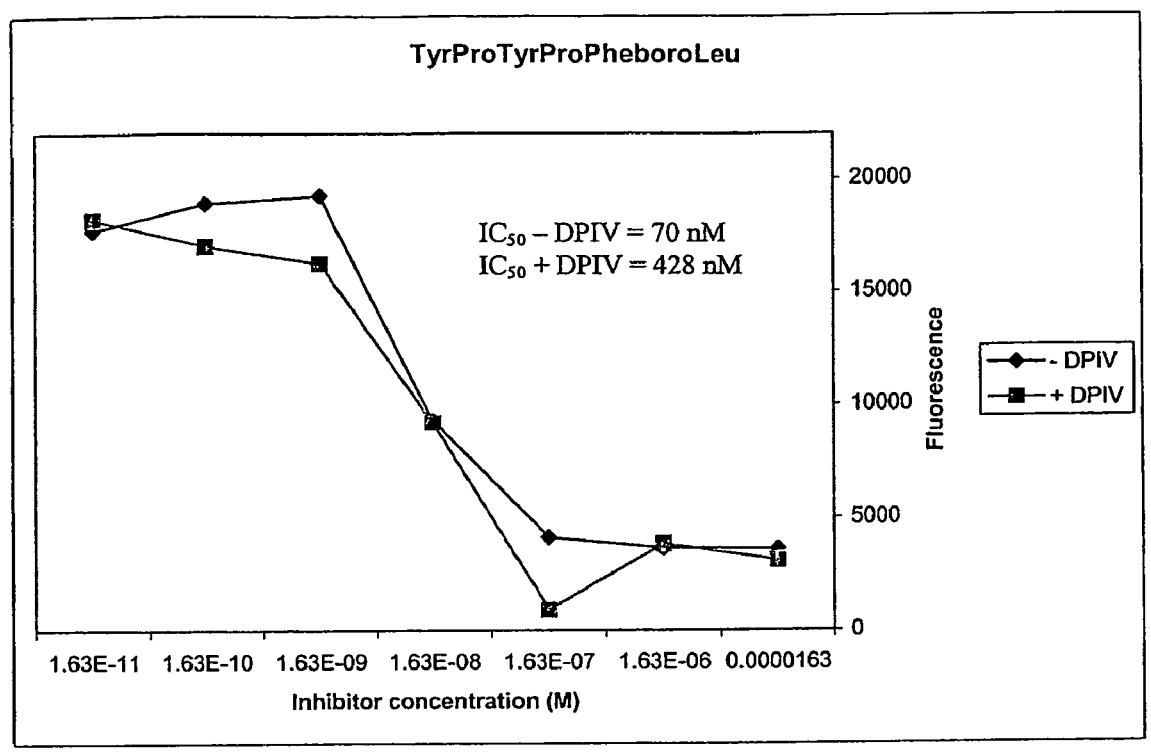
Figure 23. Inhibition profile of TyrProTyrProPheboroLeu against DPIV

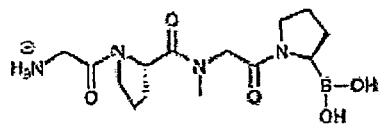
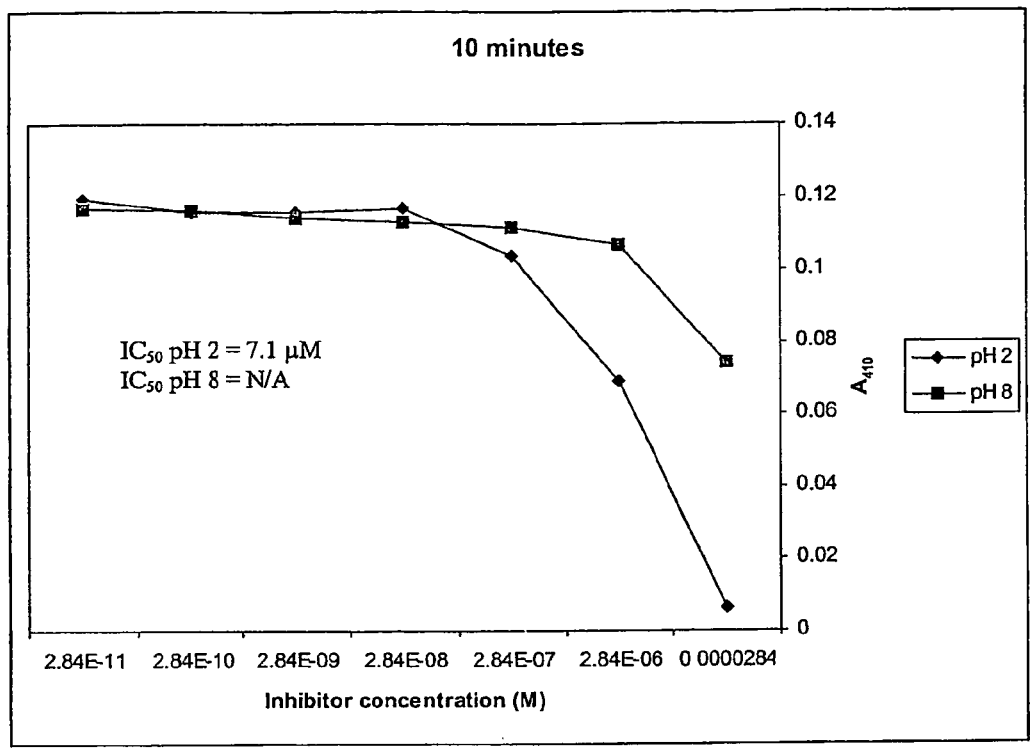
Figure 24 a. Inhibition Profile Of Glypro-N-Me-Gly-BoroPro Against DP IV At Selected pHs At 10 minutes
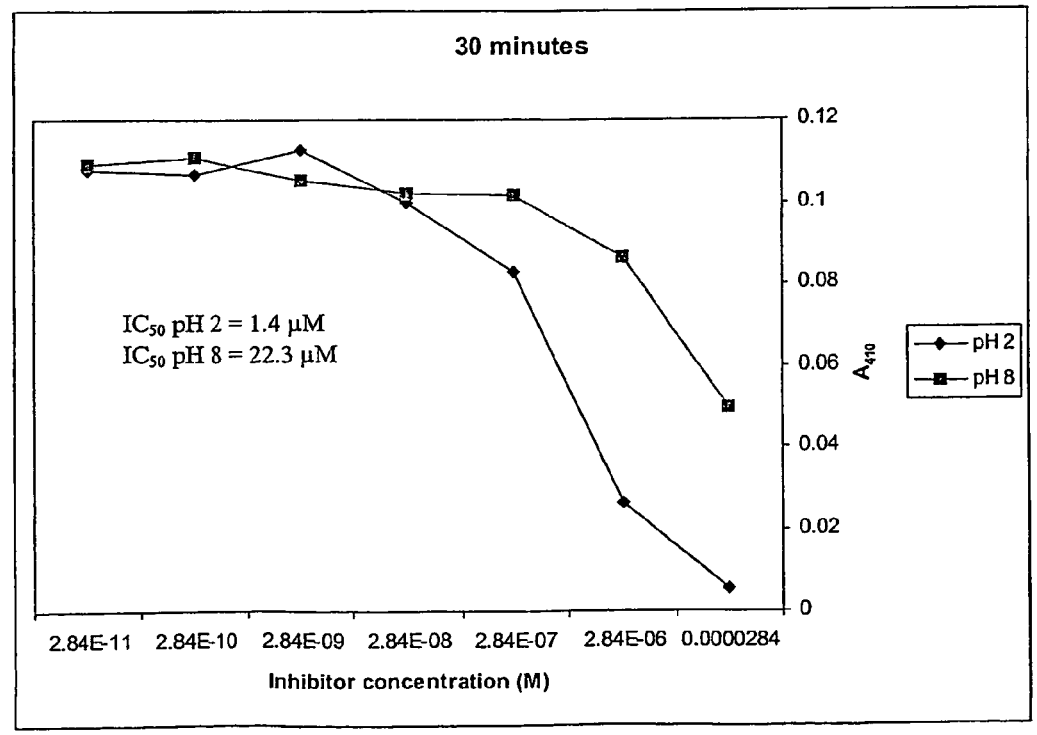

Figure 24b. Inhibition Profile Of Glypro-N-Me-Gly-BoroPro Against DP IV At Selected pHs At 30 minutes
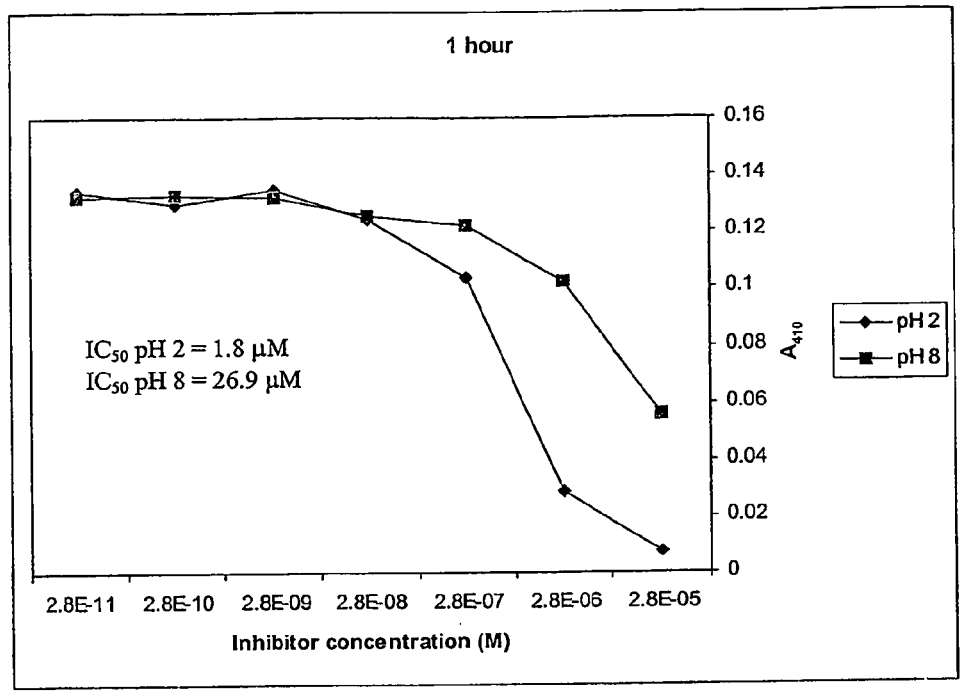
Figure 24 c. Inhibition Profile Of Glypro-N-Me-Gly-BoroPro Against DP IV At Selected pHs At 1 hour
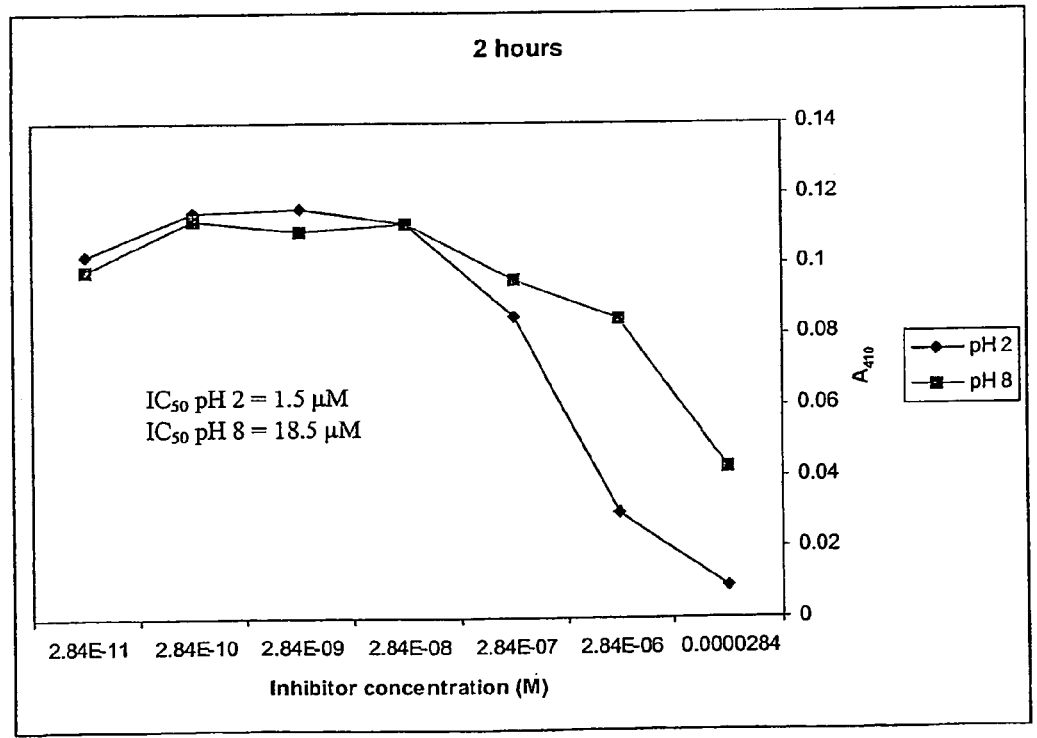
Figure 24d. Inhibition Profile Of Glypro-N-Me-Gly-BoroPro Against DP IV At Selected pHs At 2 hrs.

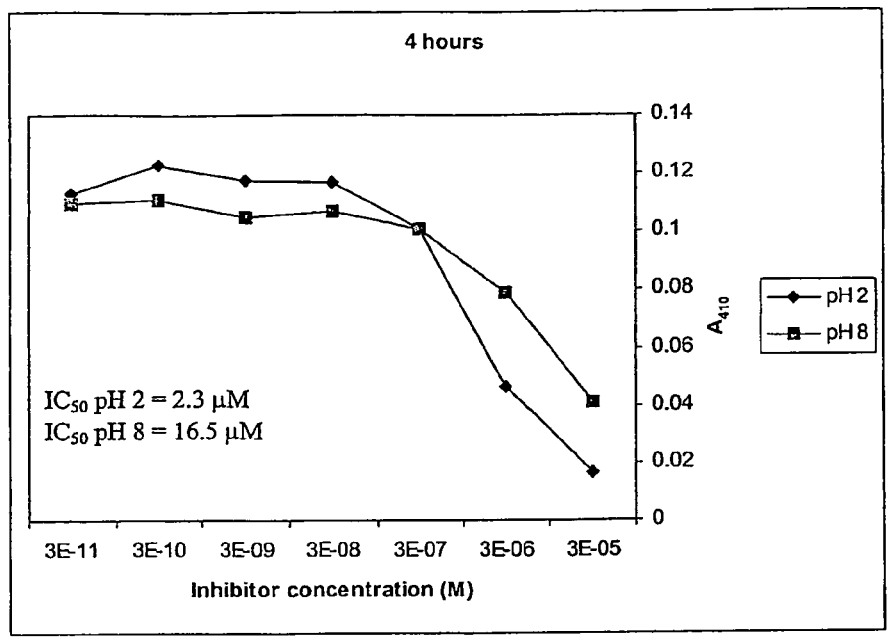
Figure 24e. Inhibition Profile Of Glypro-N-Me-Gly-BoroPro Against DP IV At Selected pHs At 4 hrs
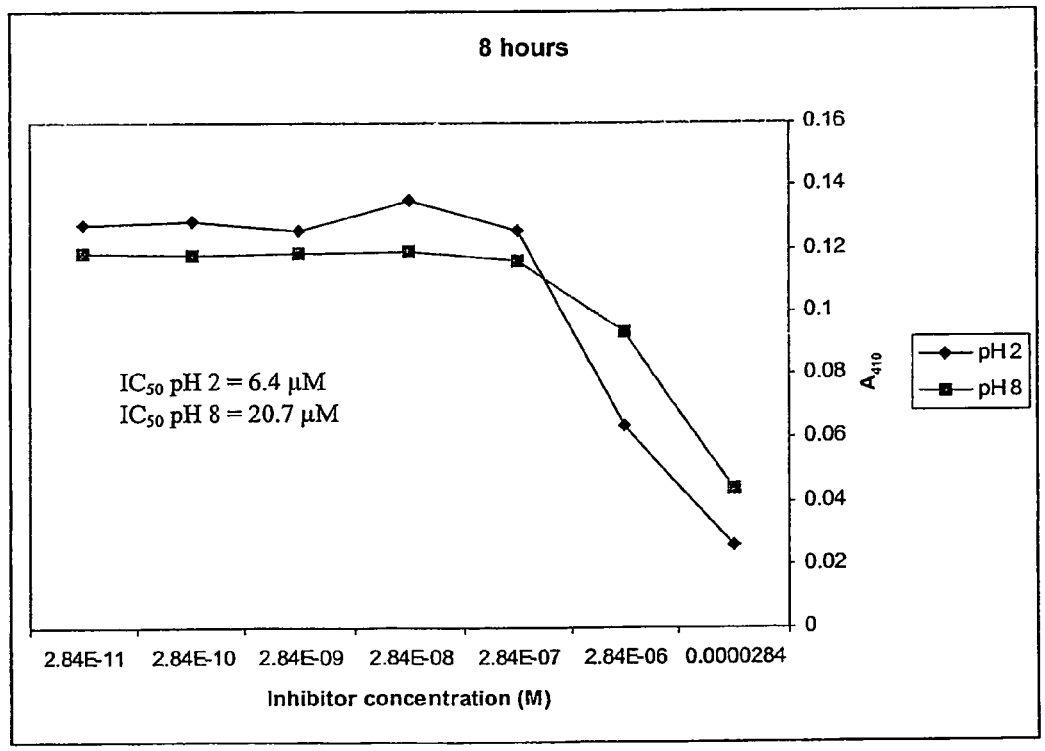
Figure 24f. Inhibition Profile Of Glypro-N-Me-Gly-BoroPro Against DP IV At Selected pHs At 8 hrs.

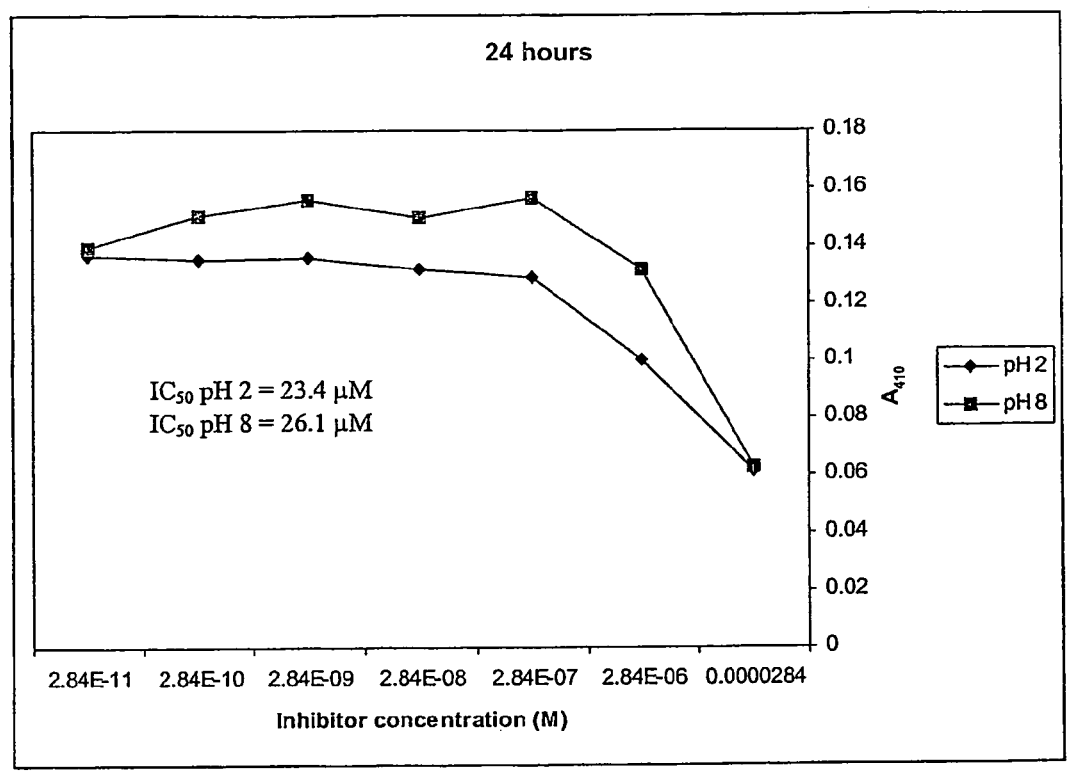
Figure 24g. Inhibition Profile Of Glypro-N-Me-Gly-BoroPro Against DP IV At Selected pHs At 24 hrs

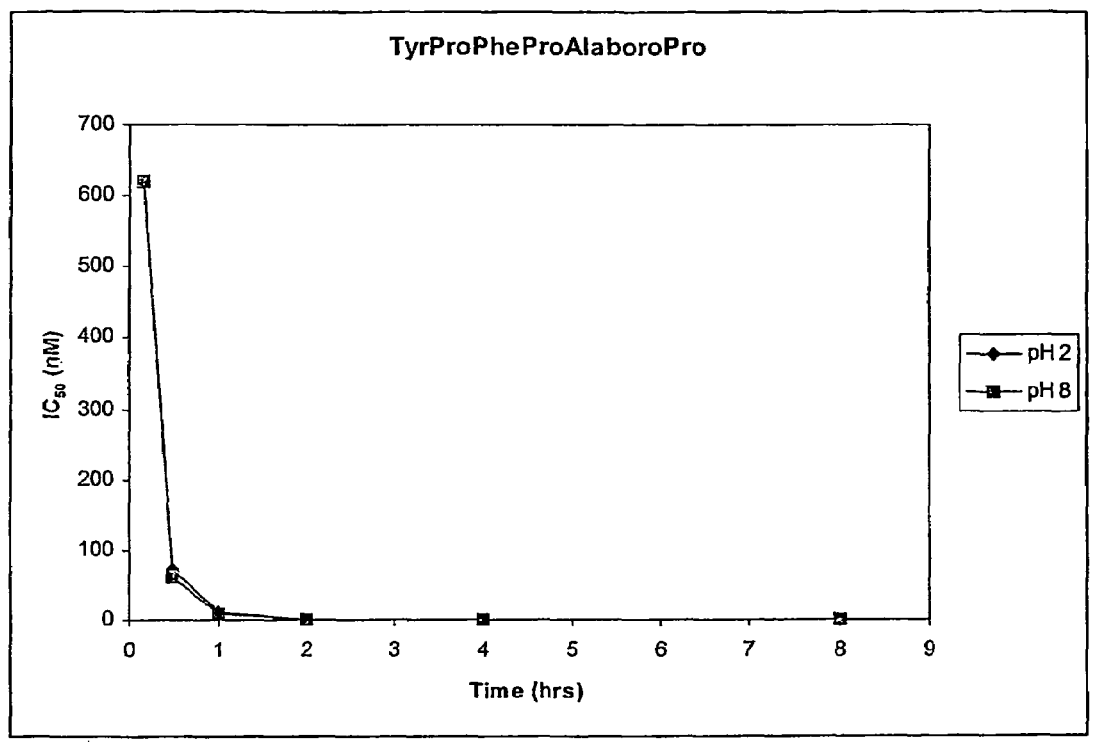
Figure 25. Inhibition profile of TyrProPheAlaboroPro against DP IV at selected pHs.

Figure 26. Inhibition profile of tBugProAlaboroPro against DP IV at selected pHs.

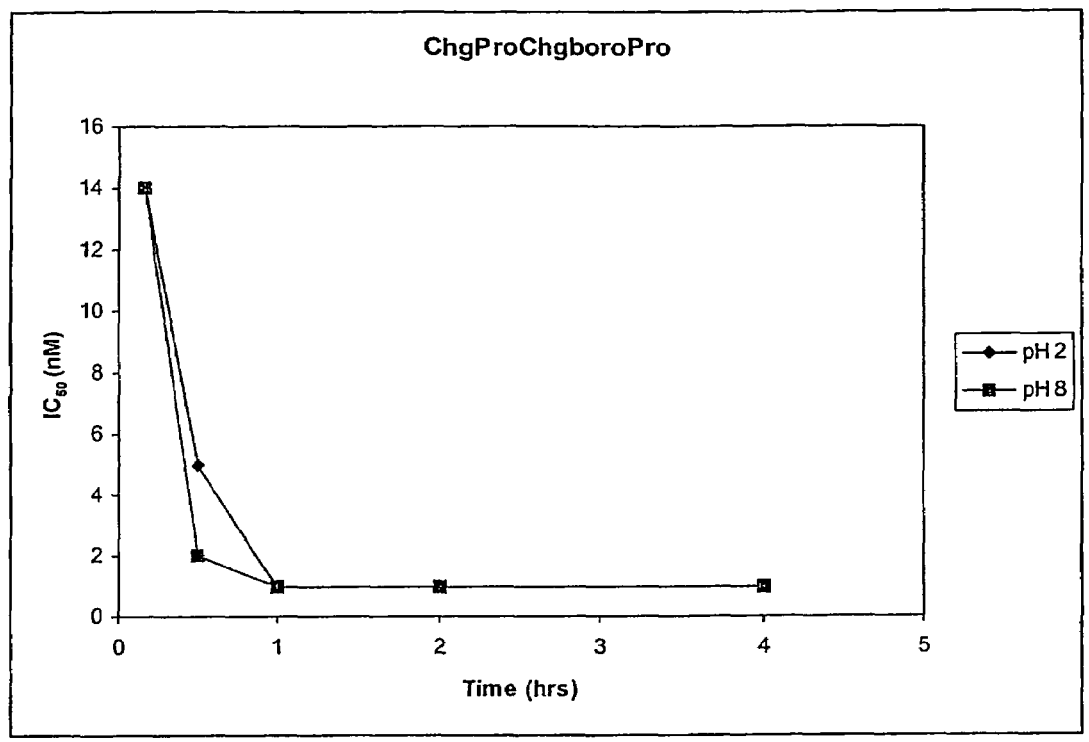
Figure 27. Inhibition profile of ChgProChgboroPro against DP IV at selected pHs.

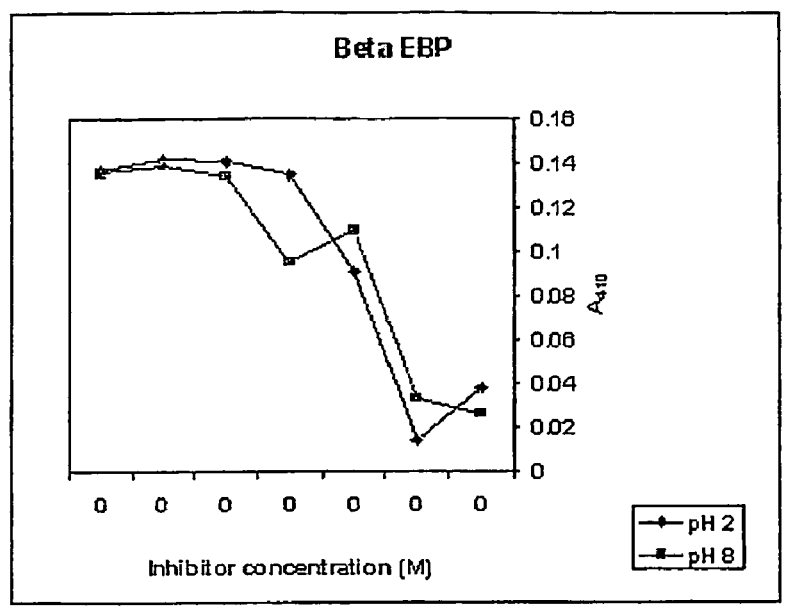
Figure 28. Inhibition profile of Beta EBP against DP IV at selected pHs.

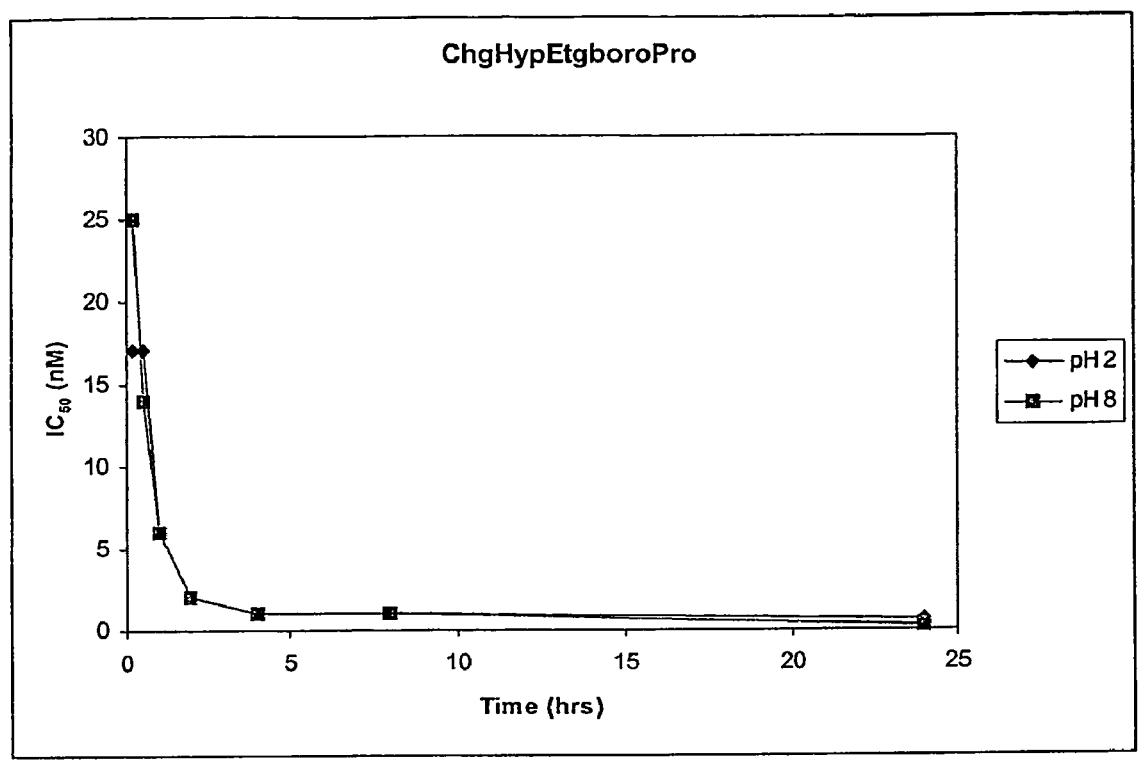
Figure 29. Inhibition profile of ChgHypEtgboroPro against DP IV at selected pHs.

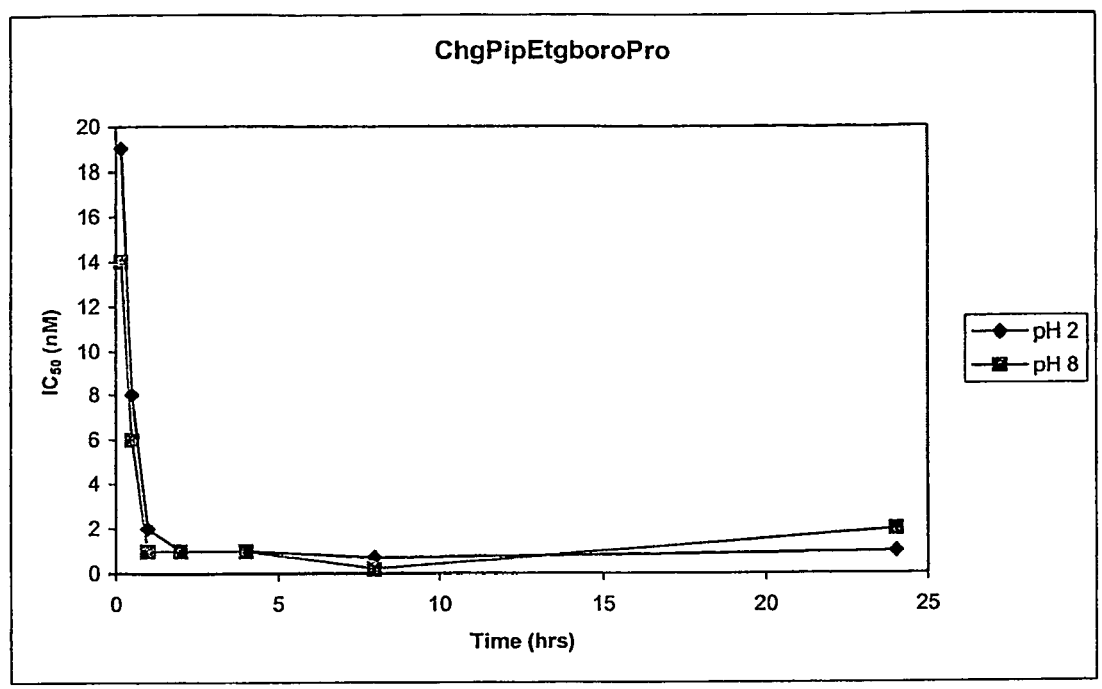
Figure 30. Inhibition profile of ChgPipEtgboroPro against DP IV at selected pHs.

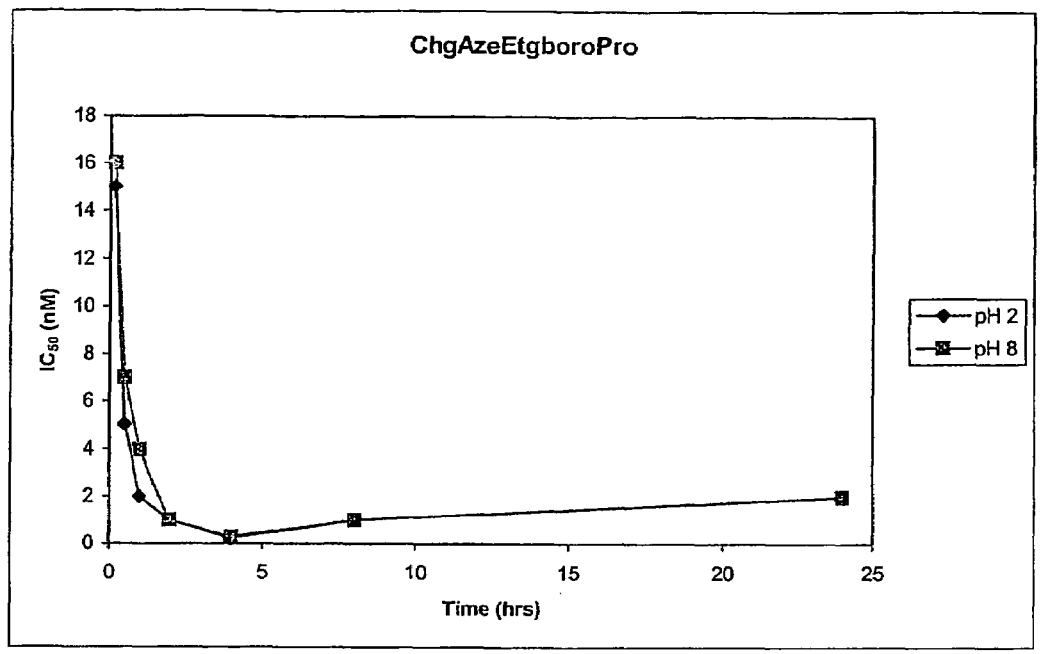
Figure 31. Inhibition profile of ChgAzeEtgboroPro against DP IV at selected pHs.
ChgAzeEtgboroPro =
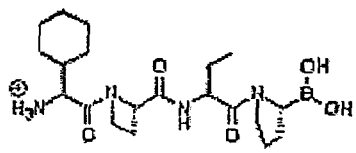

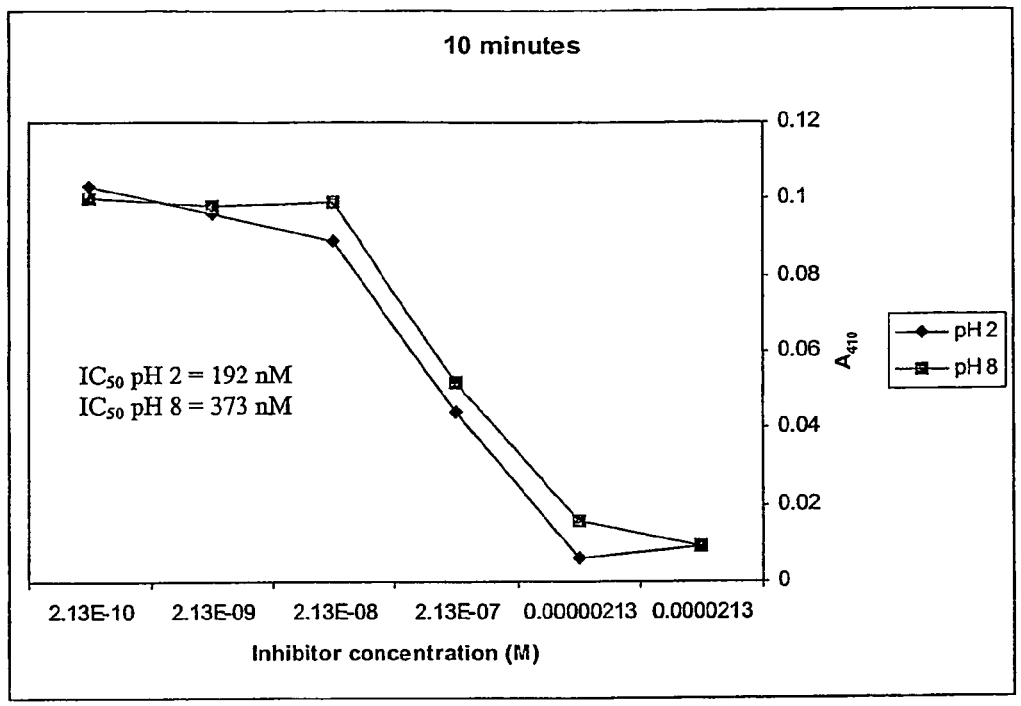
Figure 32a. Inhibition profile of ChgThz2EtgboroPro against DP IV at selected pHs at 10 minutes.
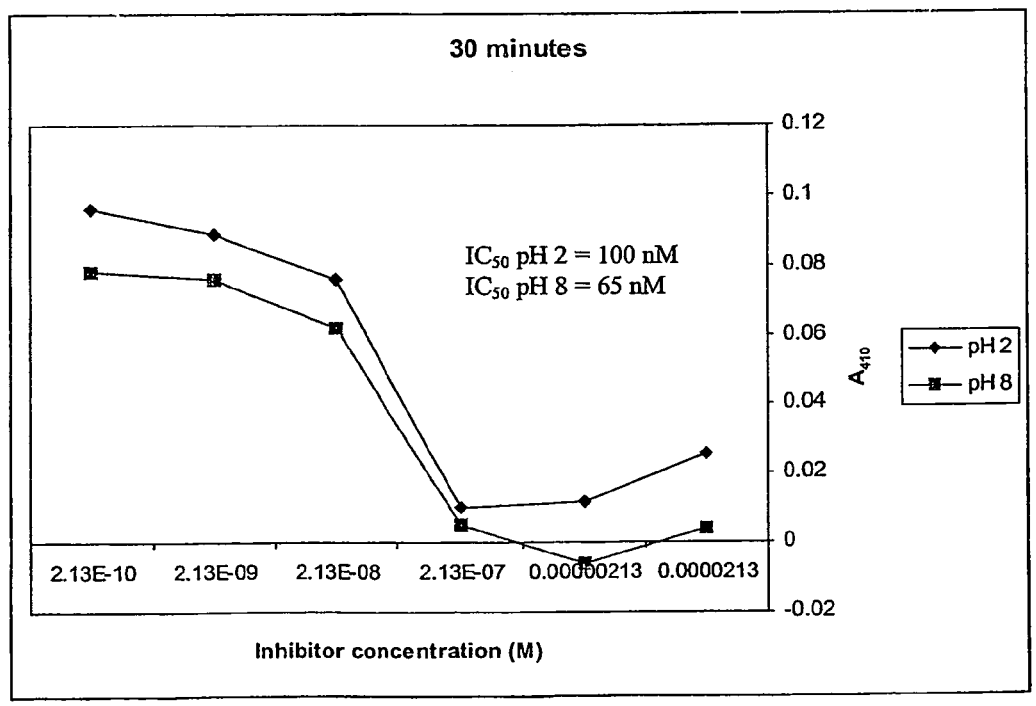
Figure 32b. Inhibition profile of ChgThz2EtgboroPro against DP IV at selected pHs at 30 minutes.

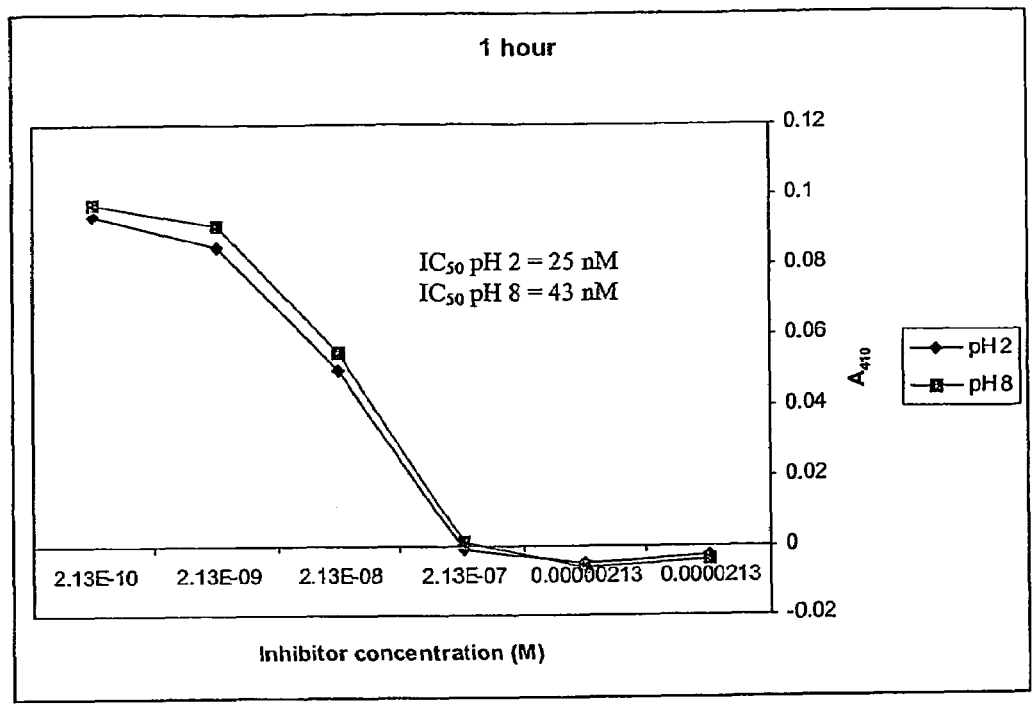
Figure 32c. Inhibition profile of ChgThz2EtgboroPro against DP IV at selected pHs at 1 hr.
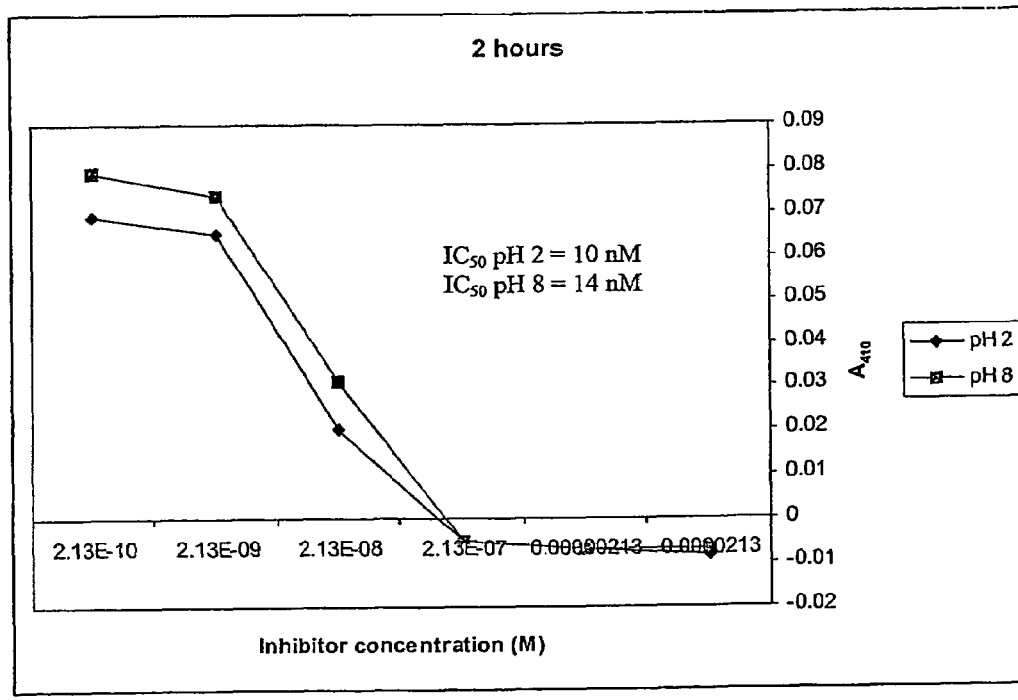
Figure 32d. Inhibition profile of ChgThz2EtgboroPro against DP IV at selected pHs at 2 hrs.

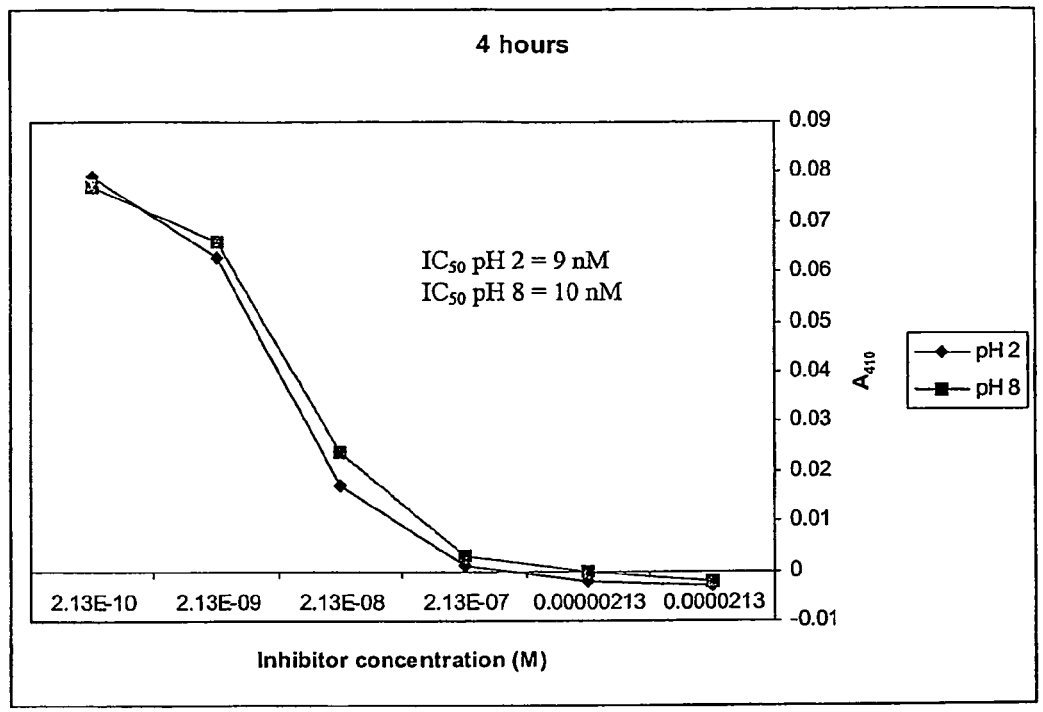
Figure 32e. Inhibition profile of ChgThz2EtgboroPro against DP IV at selected pHs at 4 hrs.
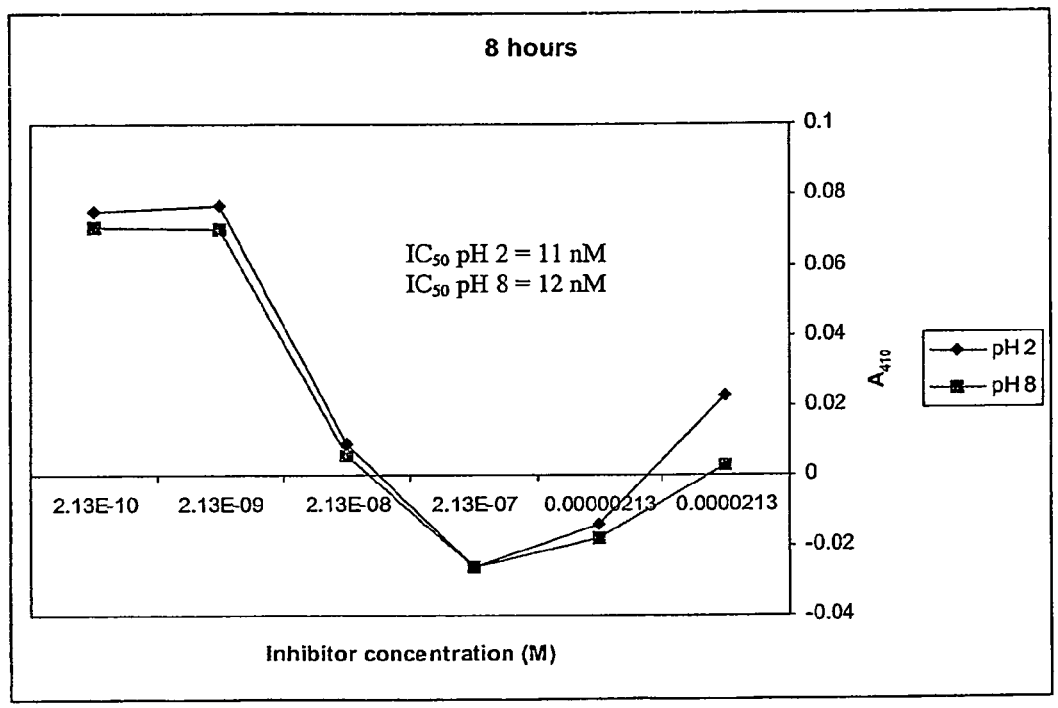
Figure 32f. Inhibition profile of ChgThz2EtgboroPro against DP IV at selected pHs at 8 hrs.

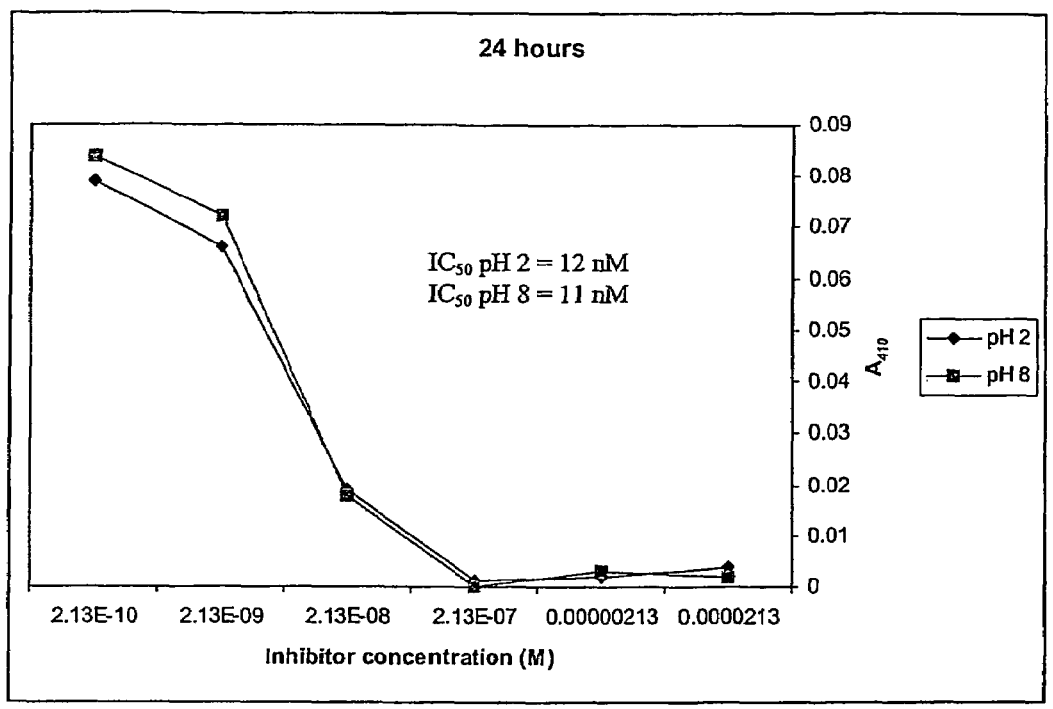
Figure 32g. Inhibition profile of ChgThz2EtgboroPro against DP IV at selected pHs at 24 hrs.
ChgThz2EtgboroPro = 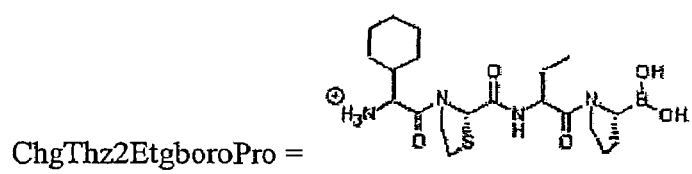

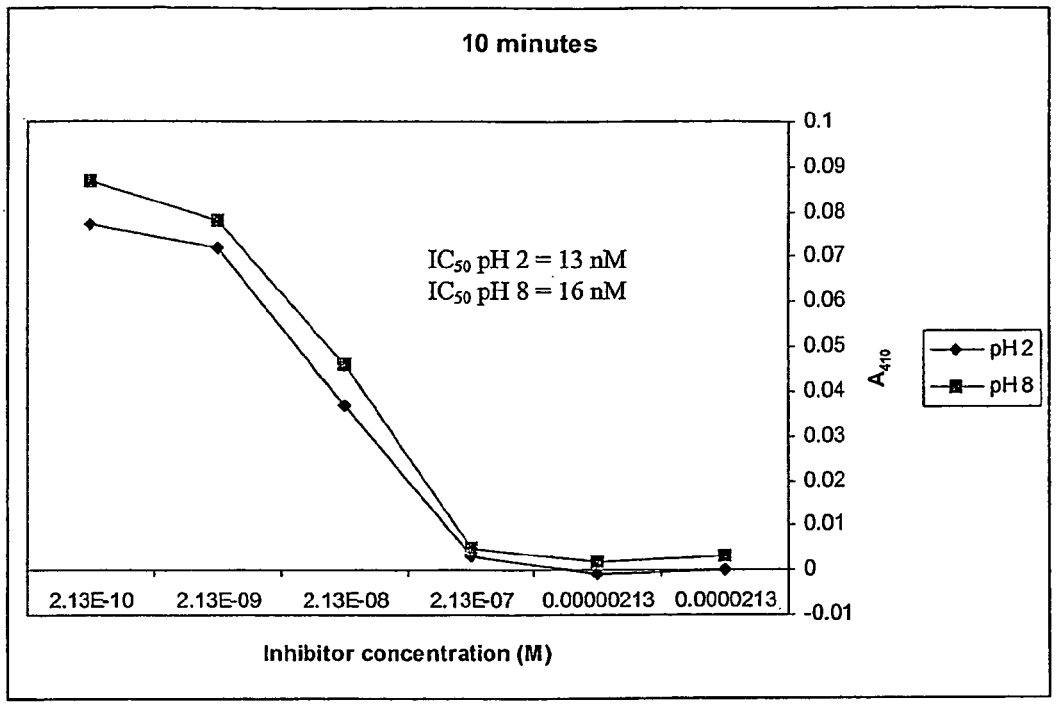
Figure 33a. Inhibition profile of ChgThz4EtgboroPro against DP IV at selected pHs at 10 minutes.
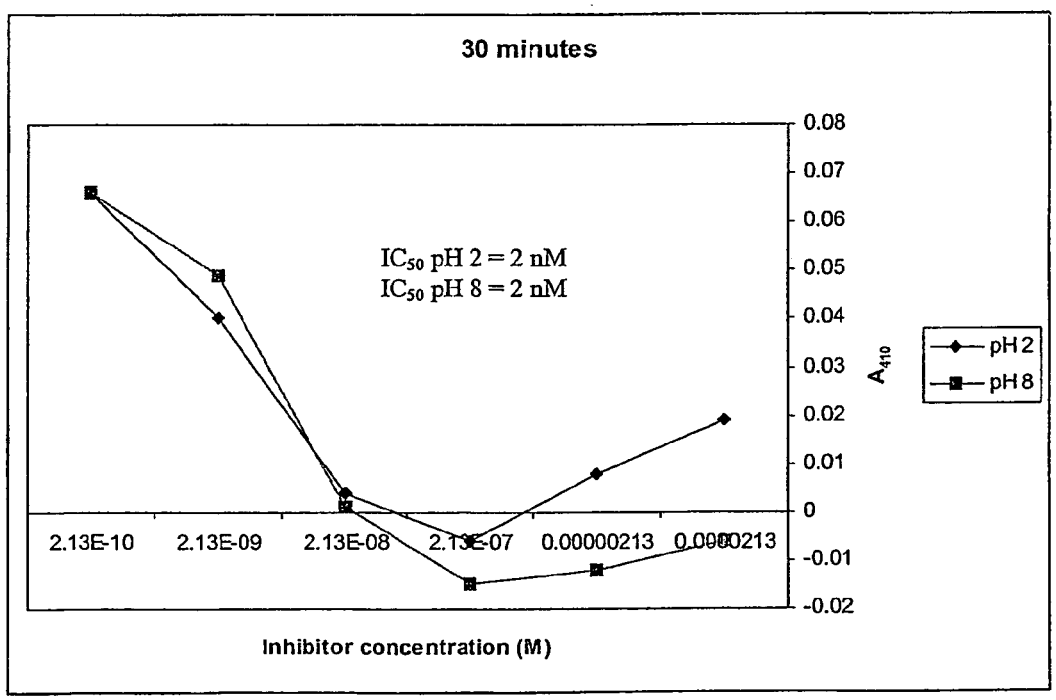
Figure 33b. Inhibition profile of ChgThz4EtgboroPro against DP IV at selected pHs at 30 minutes.

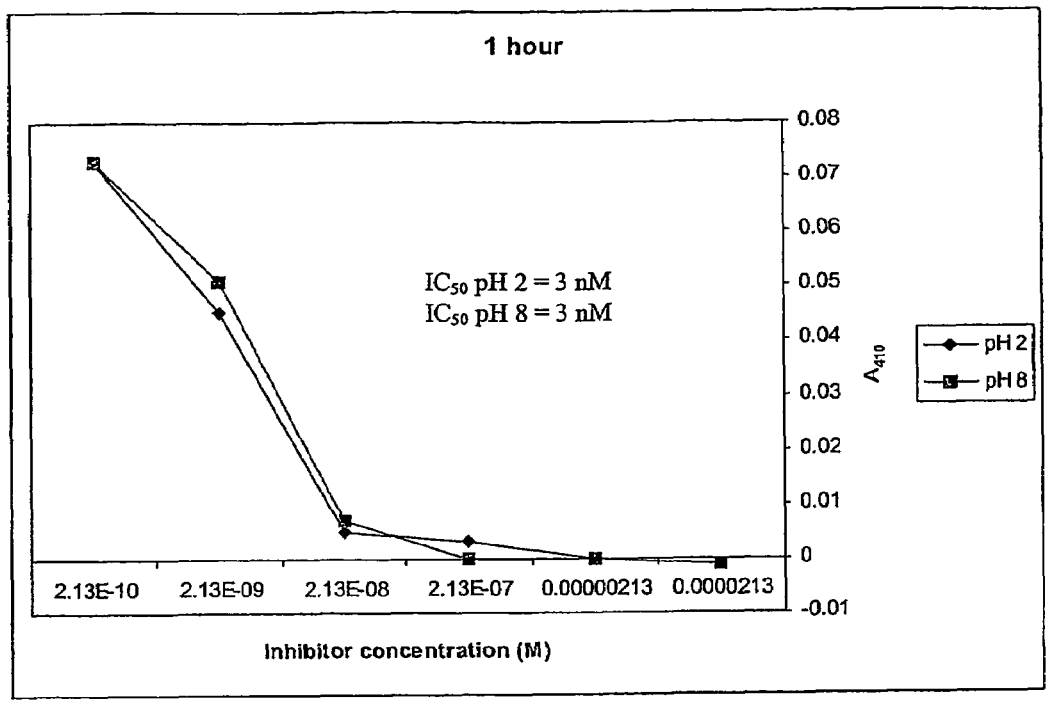
Figure 33c. Inhibition profile of ChgThz4EtgboroPro against DP IV at selected pHs at 1 hr.
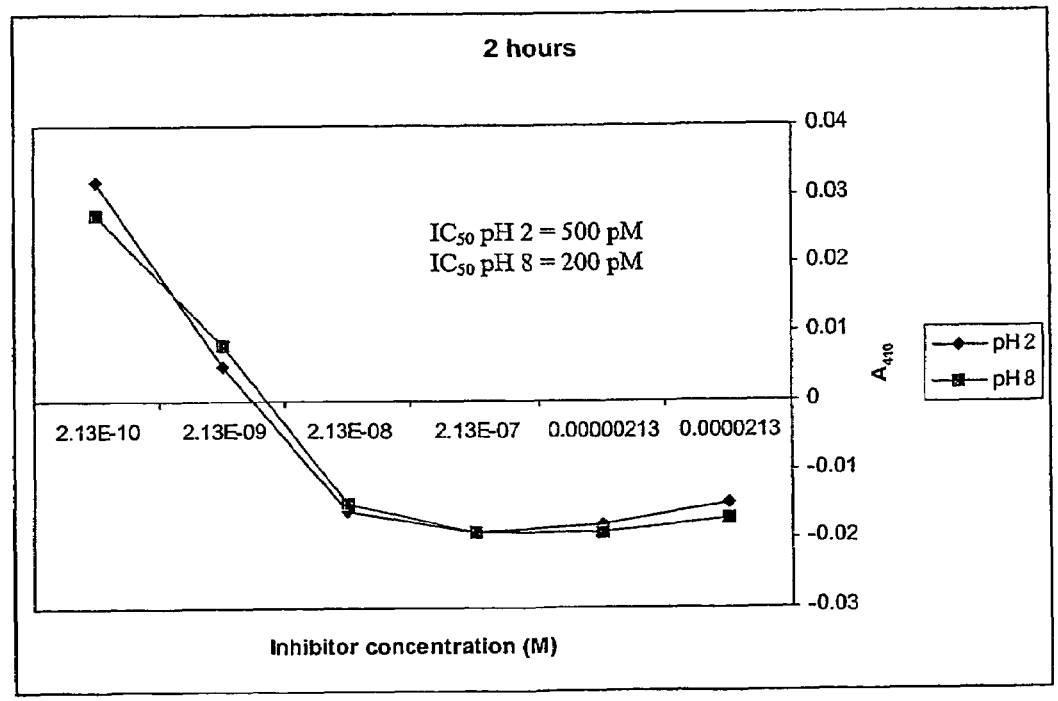
Figure 33d. Inhibition profile of ChgThz4EtgboroPro against DP IV at selected pHs at 2 hrs..

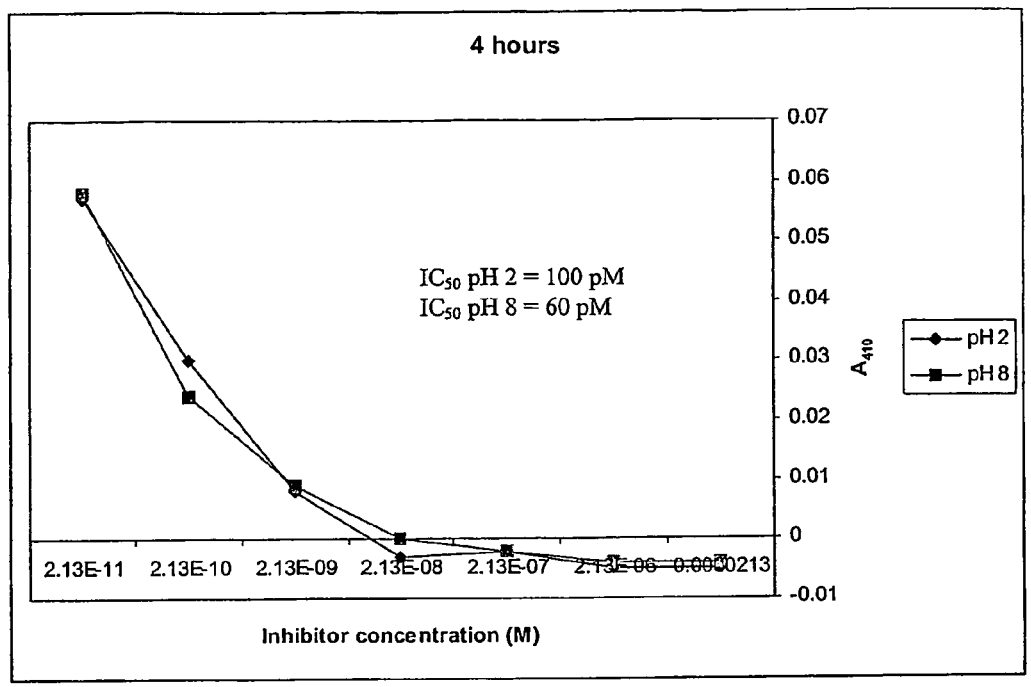
Figure 33e. Inhibition profile of ChgThz4EtgboroPro against DP IV at selected pHs at 4 hrs.
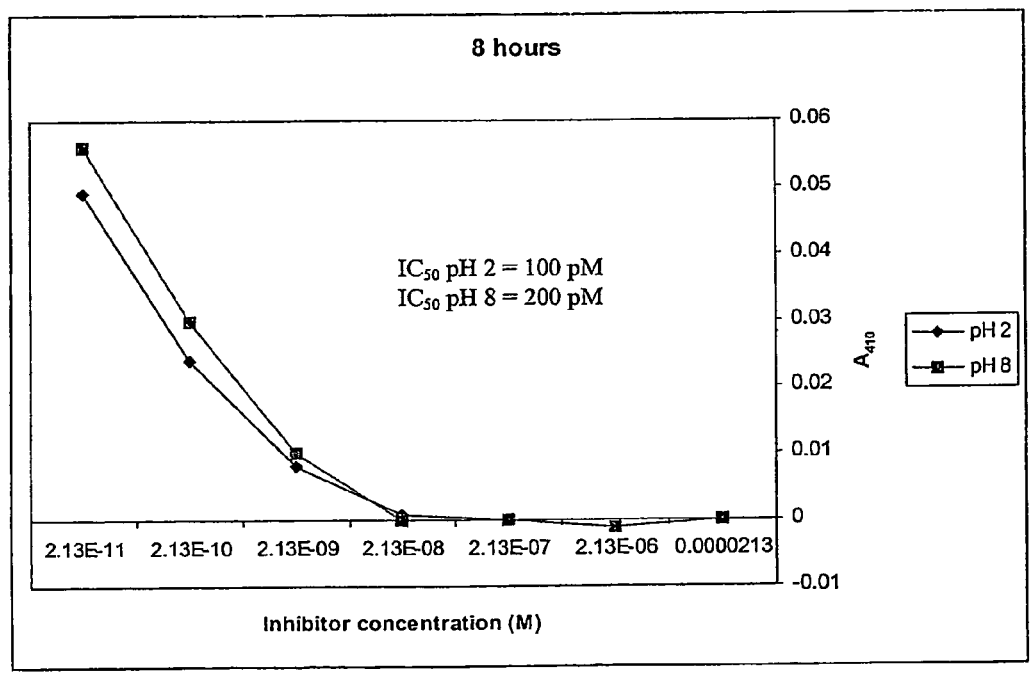
Figure 33f. Inhibition profile of ChgThz4EtgboroPro against DP IV at selected pHs at 8 hrs.
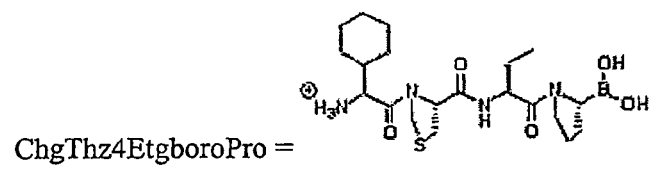
ChgThz4EtgboroPro =

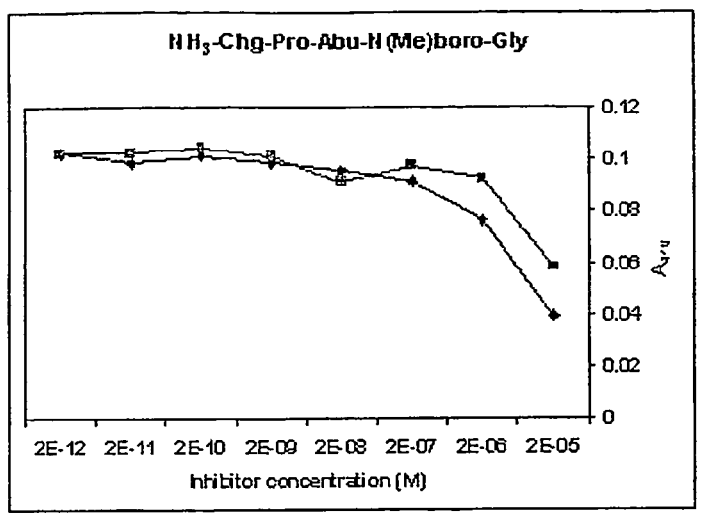
Figure 34. Inhibition profile of NH₃-ChgProAbuN(me)boroGly against DP IV at selected pHs
NH₃-ChgProAbuN(me)boroGly = 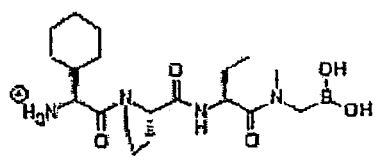

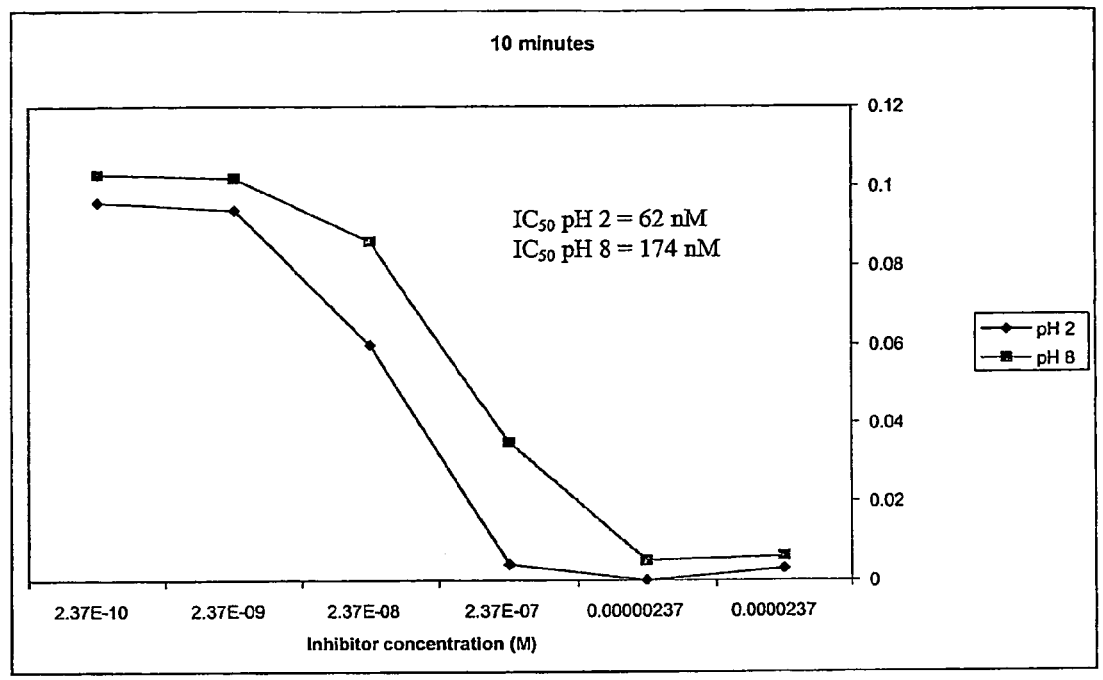
Figure 35a. Inhibition profile of HisAlaEtgboroPro against DP IV at selected pHs at 10 minutes.
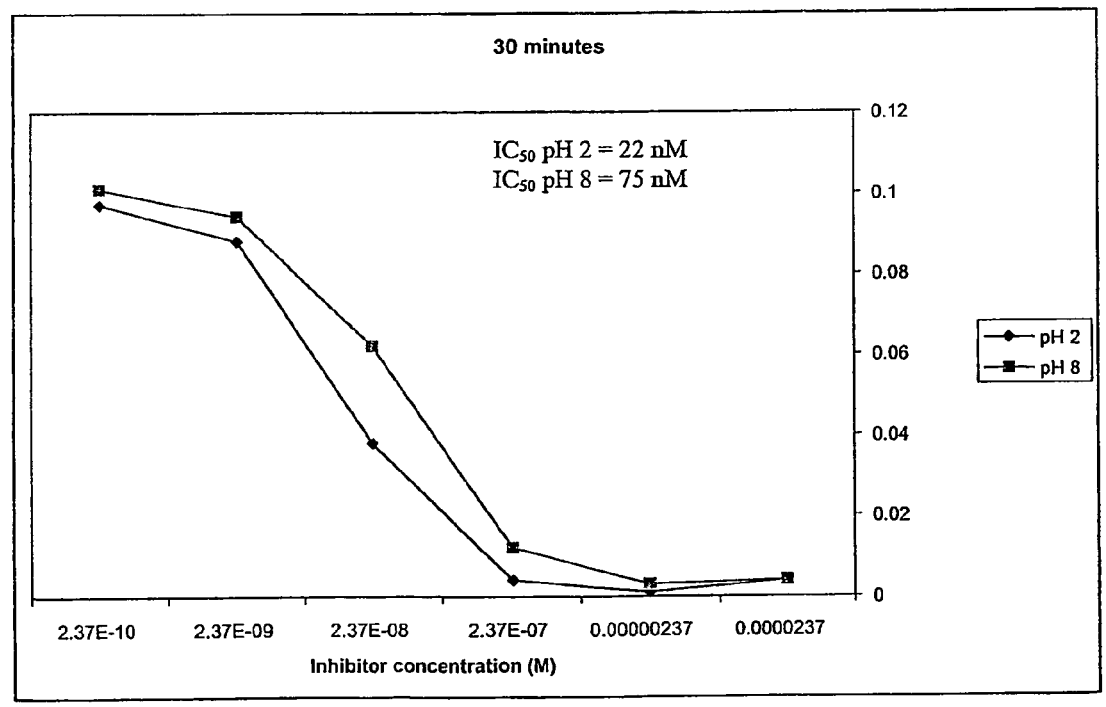
Figure 35b. Inhibition profile of HisAlaEtgboroPro against DP IV at selected pHs at 30 minutes.

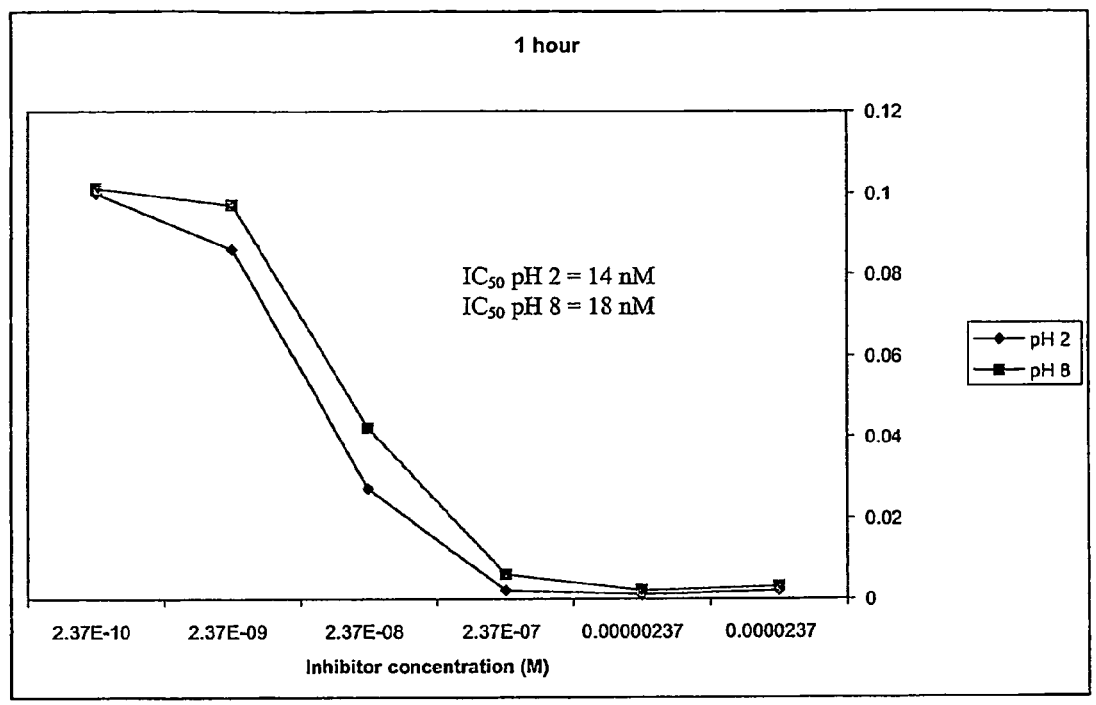
Figure 35c. Inhibition profile of HisAlaEtgboroPro against DP IV at selected pHs at 1 hr.
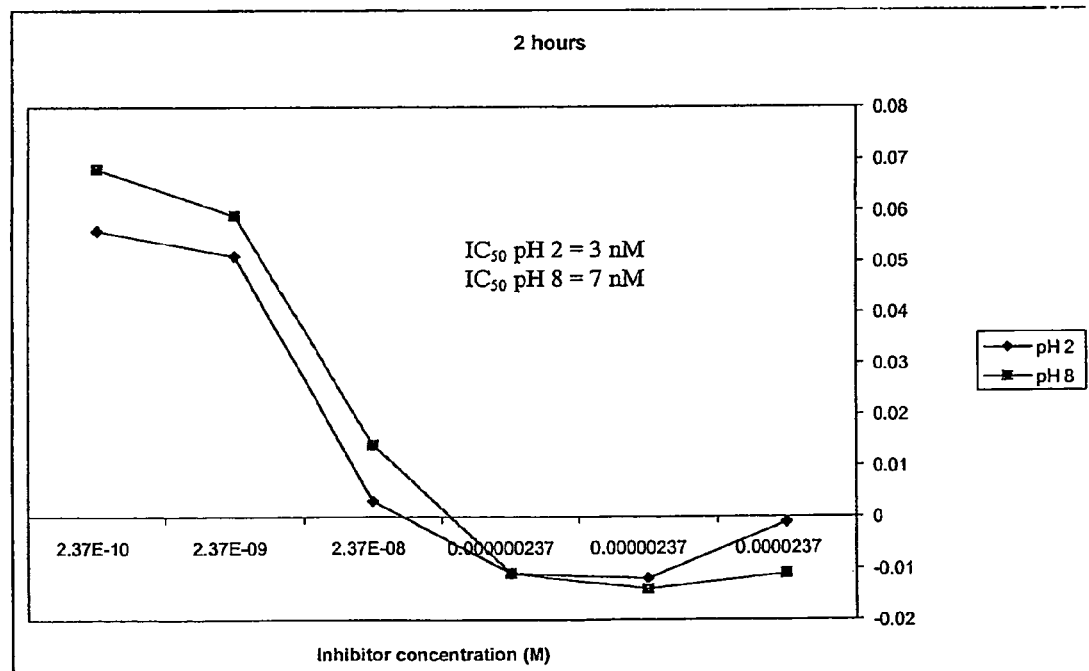
Figure 35d. Inhibition profile of HisAlaEtgboroPro against DP IV at selected pHs at 2 hrs.

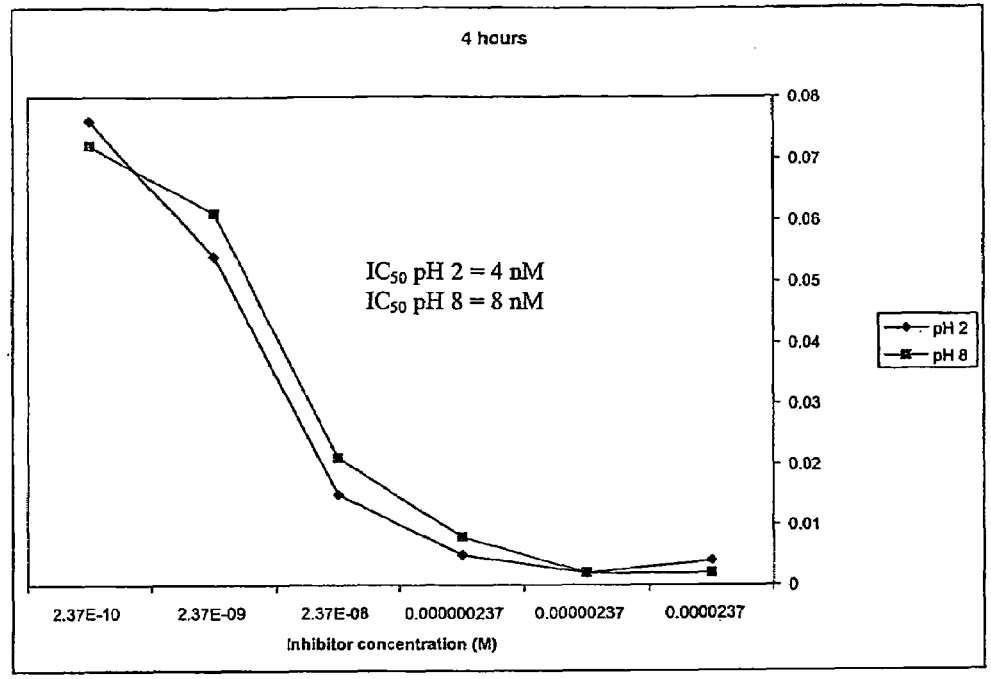
Figure 35e. Inhibition profile of HisAlaEtgboroPro against DP IV at selected pHs at 4 hrs.
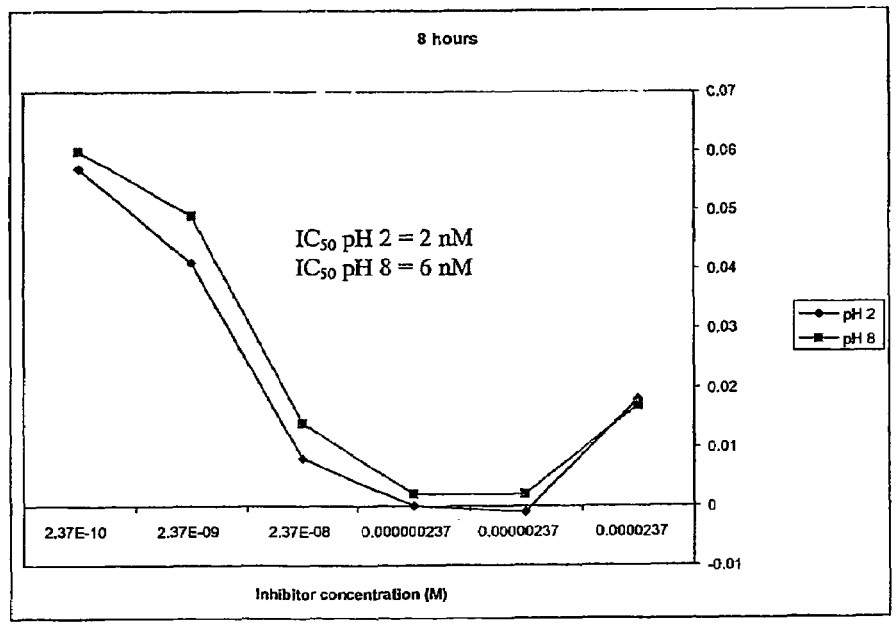
Figure 35f. Inhibition profile of HisAlaEtgboroPro against DP IV at selected pHs at 8 hrs.

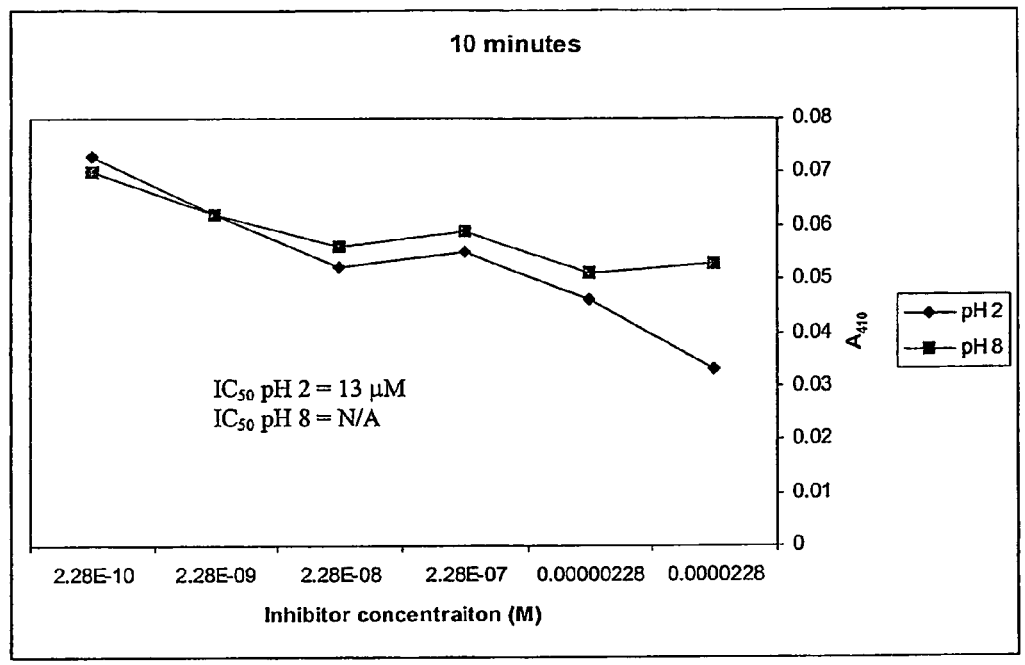
Figure 36a. Inhibition profile of ChgAib-EthylGly-boroPro against DP IV at selected pHs at 10 minutes.
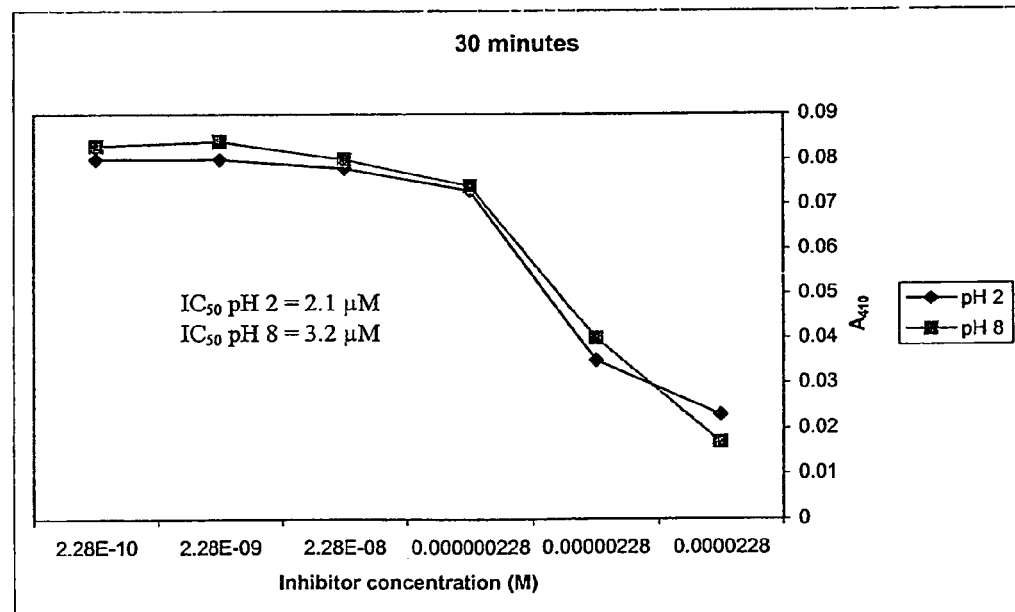
Figure 36b. Inhibition profile of ChgAib-EthylGly-boroPro against DP IV at selected pHs at 30 minutes.

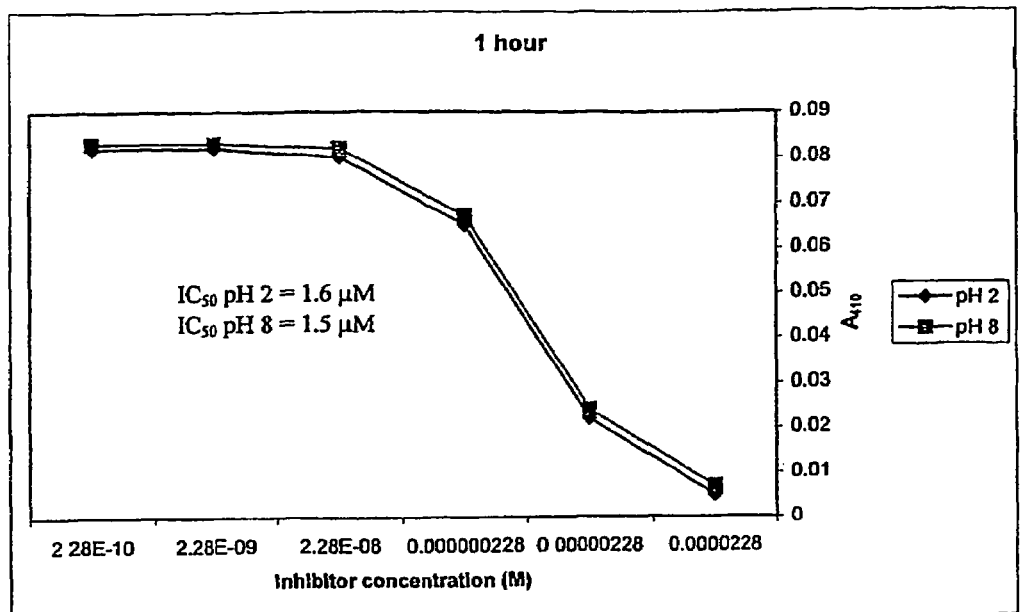
Figure 36c. Inhibition profile of ChgAib-EthylGly-boroPro against DP IV at selected pHs at 1 hr.
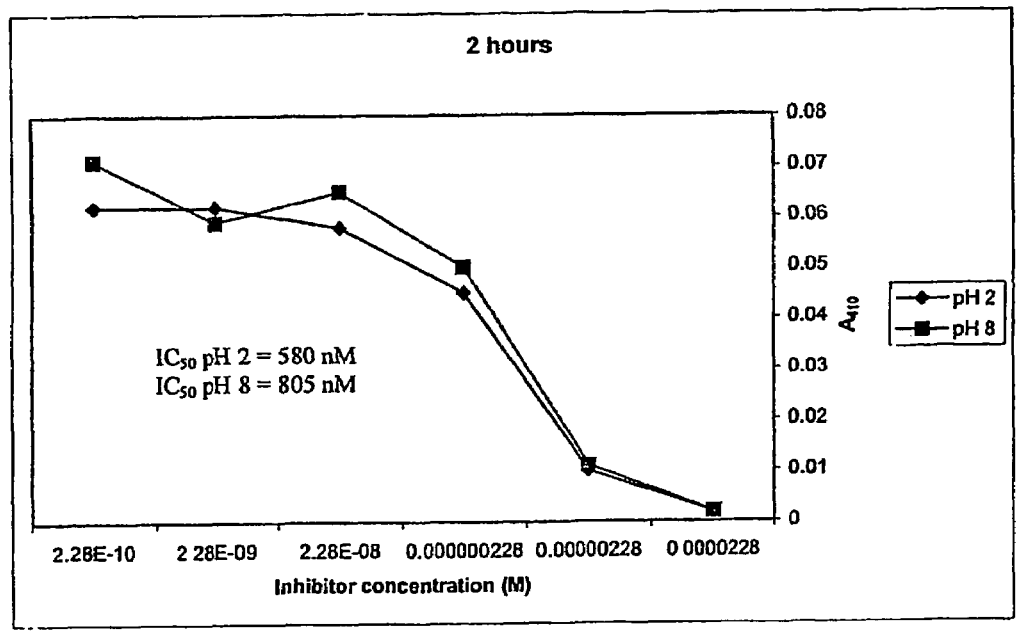
Figure 36d. Inhibition profile of ChgAib-EthylGly-boroPro against DP IV at selected pHs at 2 hrs.

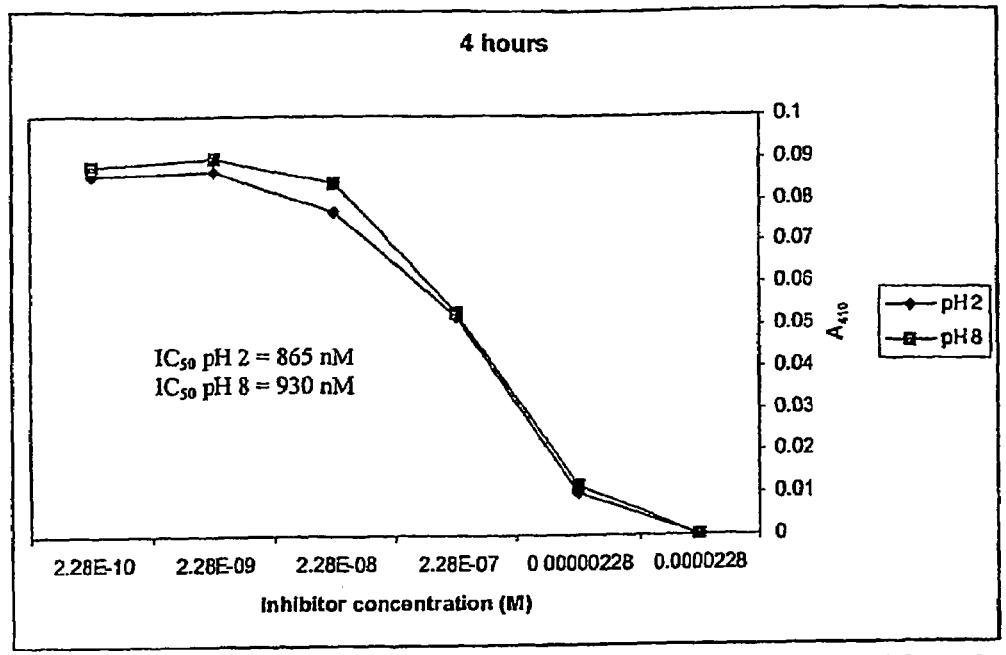
Figure 36e. Inhibition profile of ChgAib-EthylGly-boroPro against DP IV at selected pHs at 4 hrs.
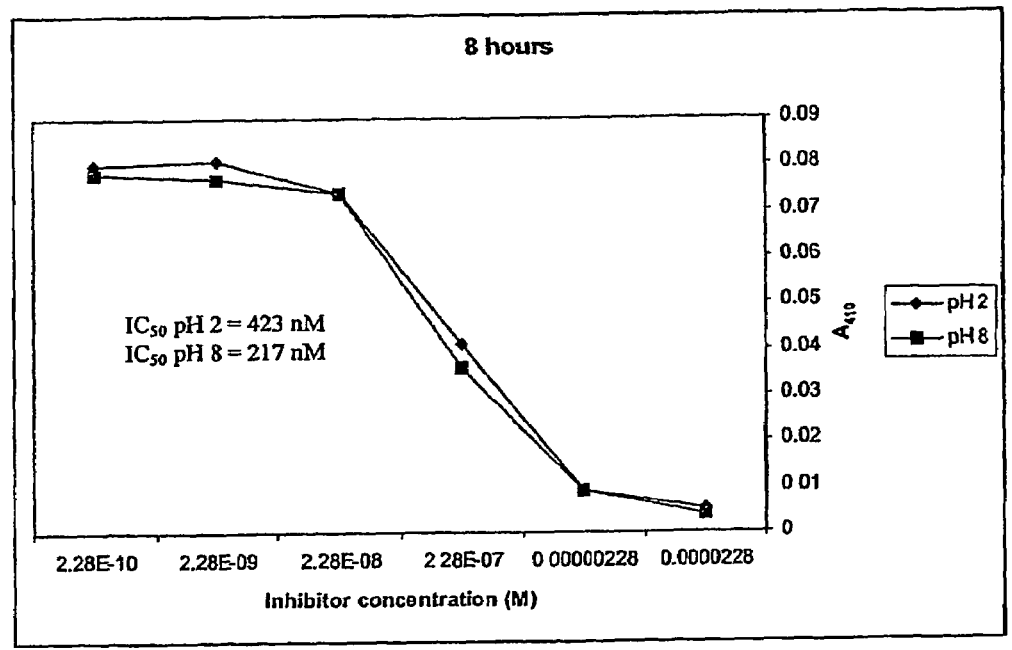
Figure 36f. Inhibition profile of ChgAib-EthylGly-boroPro against DP IV at selected pHs at 8 hrs.

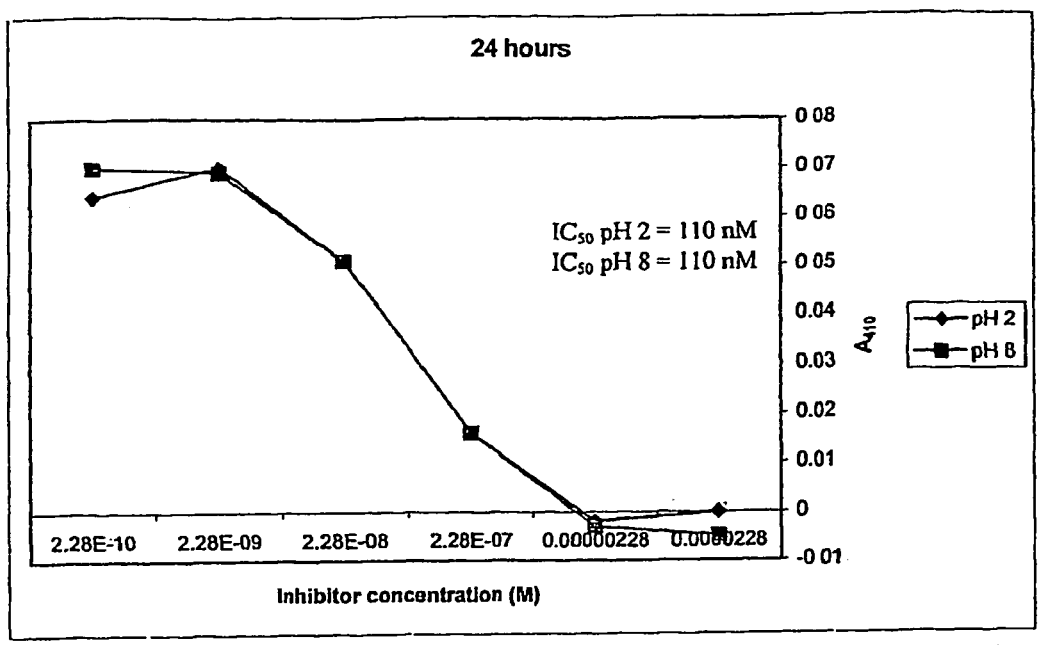
Figure 36g. Inhibition profile of ChgAib-EthylGly-boroPro against DP IV at selected pHs at 24 hrs.
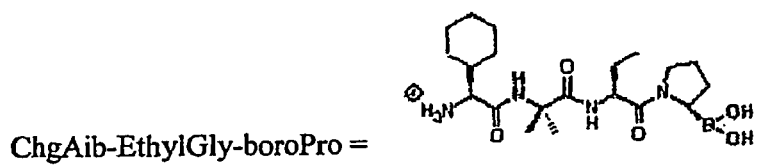
ChgAib-EthylGly-boroPro =

CHGPRO-TBUG-BOROALA
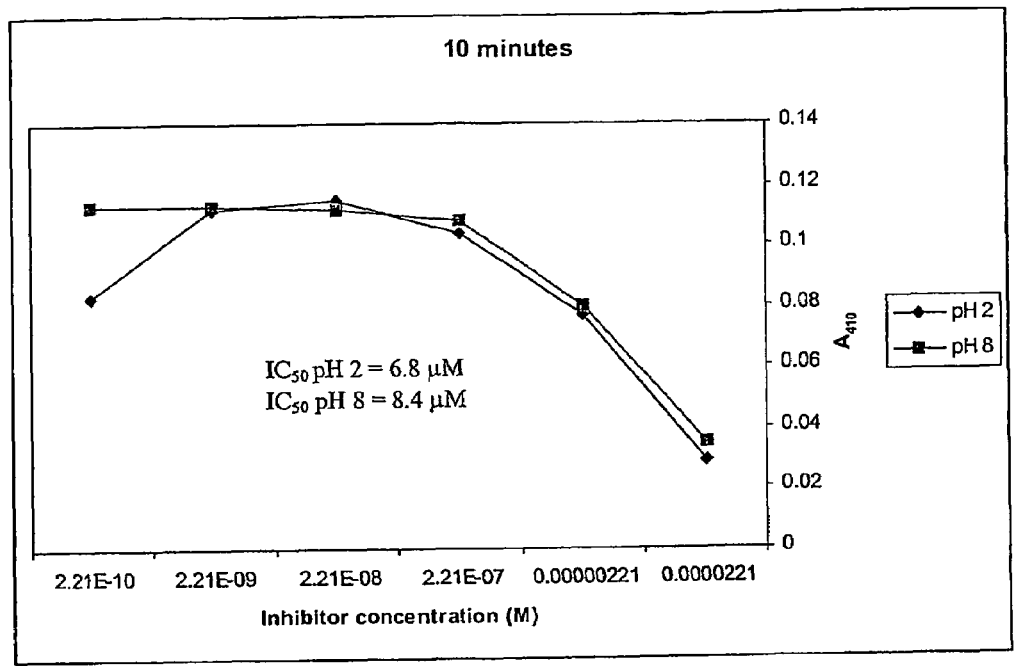
Figure 37a. Inhibition profile of ChgPro-tBug-boroAla against DP IV at selected pHs at 10 minutes.
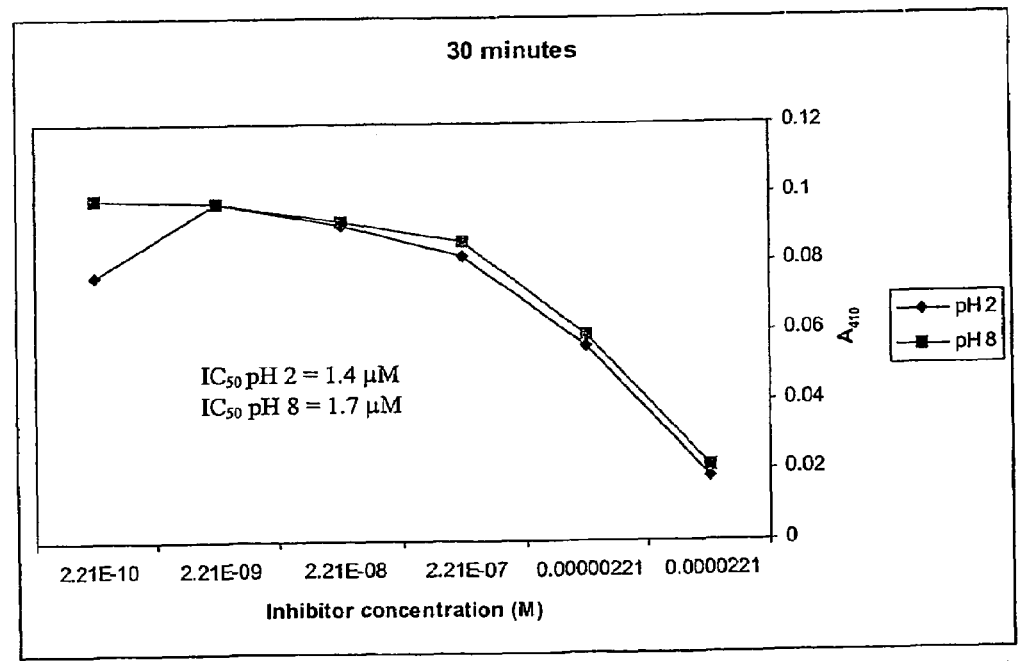
Figure 37b. Inhibition profile of ChgPro-tBug-boroAla against DP IV at selected pHs at 30 minutes.

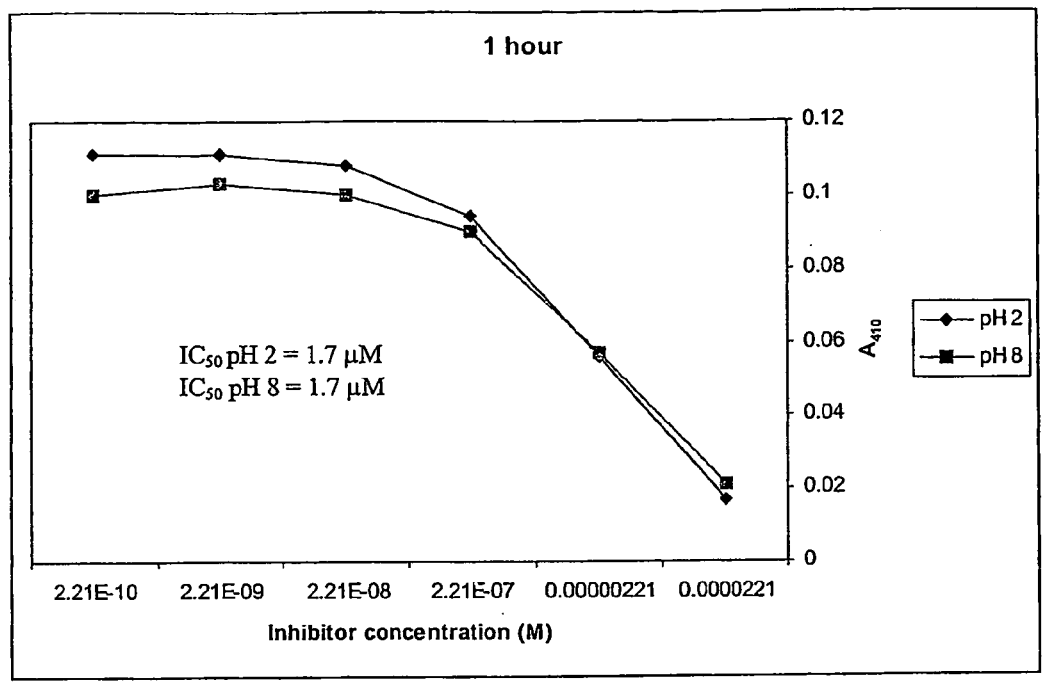
Figure 37c. Inhibition profile of ChgPro-tBug-boroAla against DP IV at selected pHs at 1 hr.
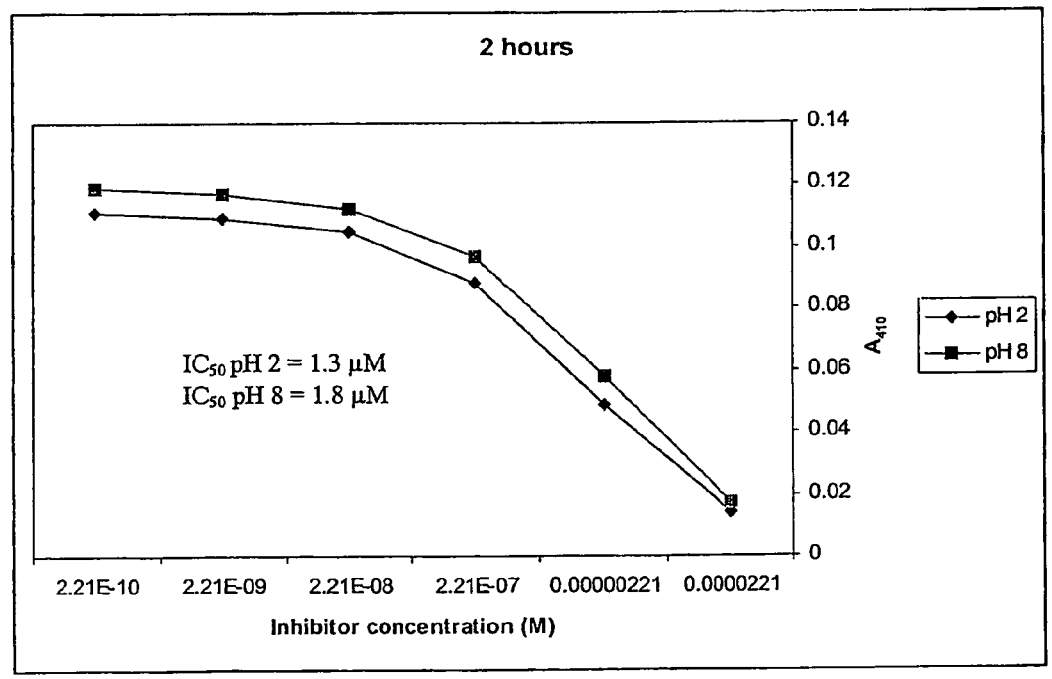
Figure 37d. Inhibition profile of ChgPro-tBug-boroAla against DP IV at selected pHs at 2 hrs.

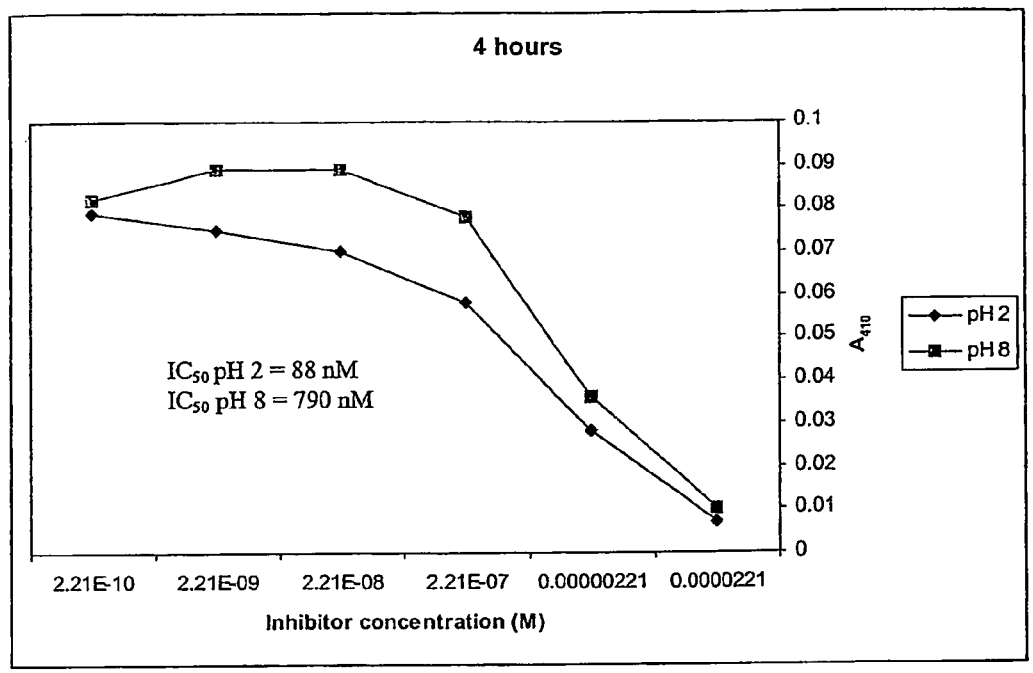
Figure 37e. Inhibition profile of ChgPro-tBug-boroAla against DP IV at selected pHs at 4hrs.
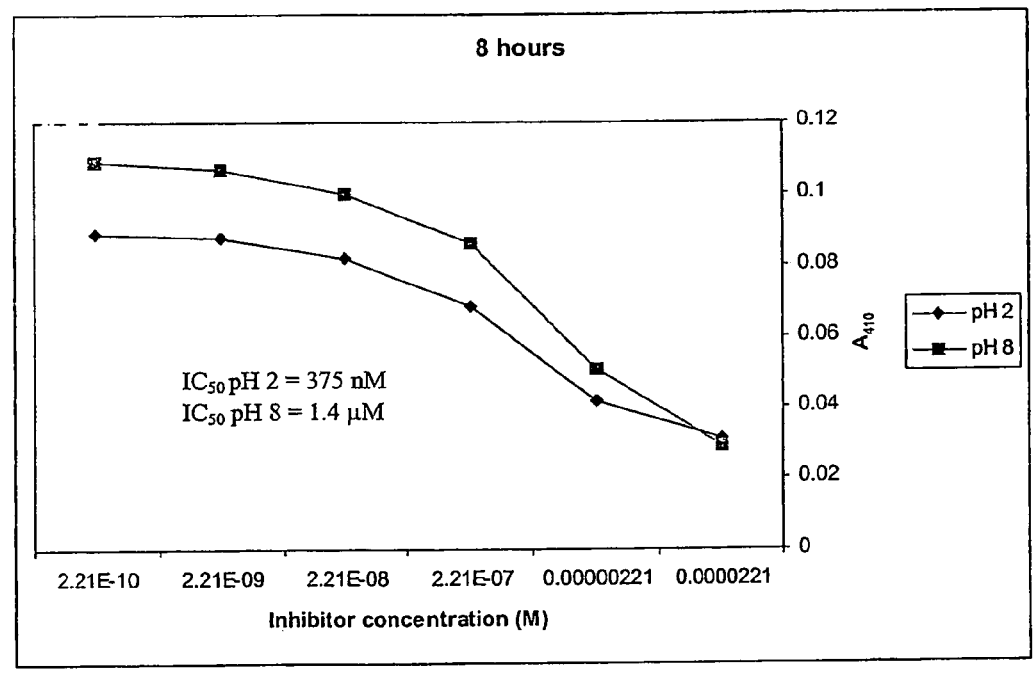
Figure 37f. Inhibition profile of ChgPro-tBug-boroAla against DP IV at selected pHs at 8hrs.

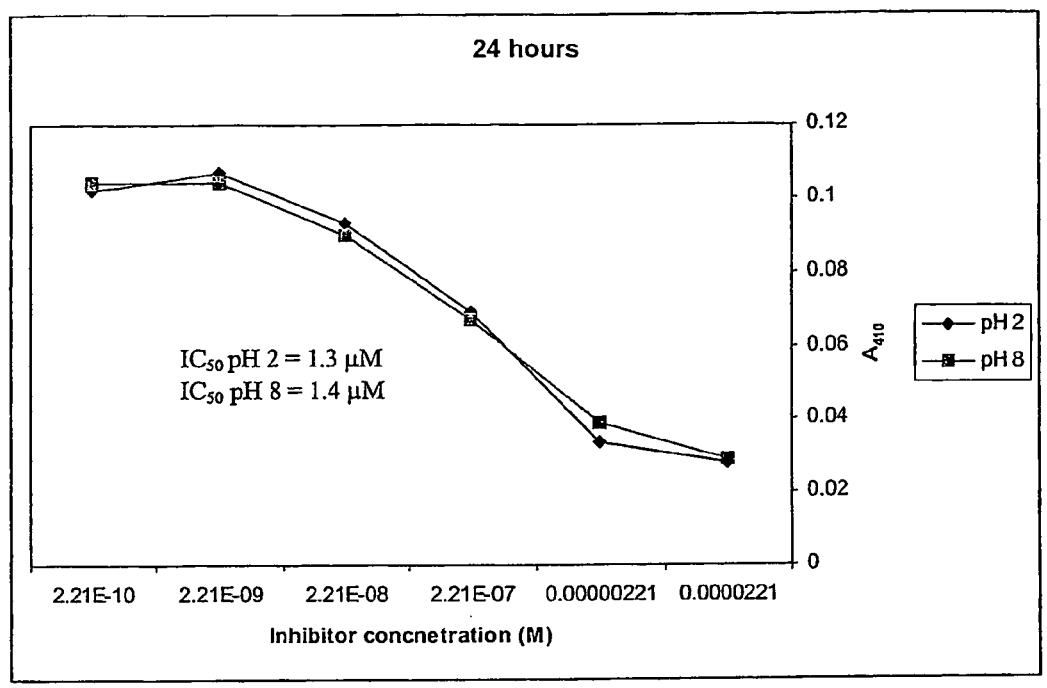
Figure 37g. Inhibition profile of ChgPro-tBug-boroAla against DP IV at selected pHs at 24 hrs.

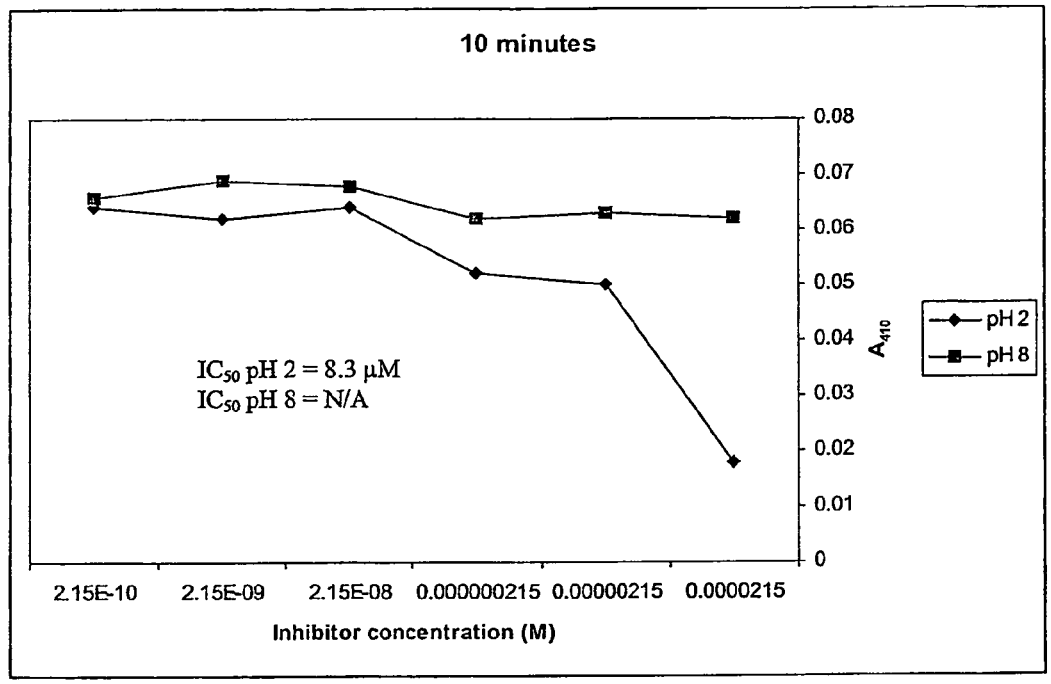
Figure 38a. Inhibition profile of ChgCpg-EthylGly-boroPro against DP IV at selected pHs at 10 minutes.
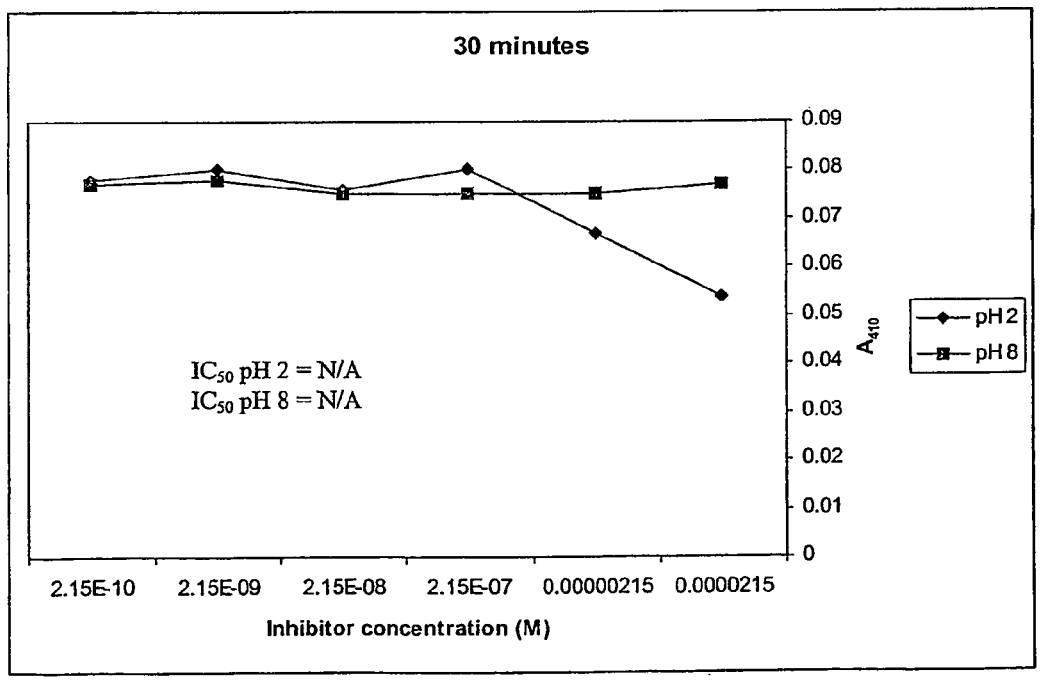
Figure 38b. Inhibition profile of ChgCpg-EthylGly-boroPro against DP IV at selected pHs at 30 minutes.

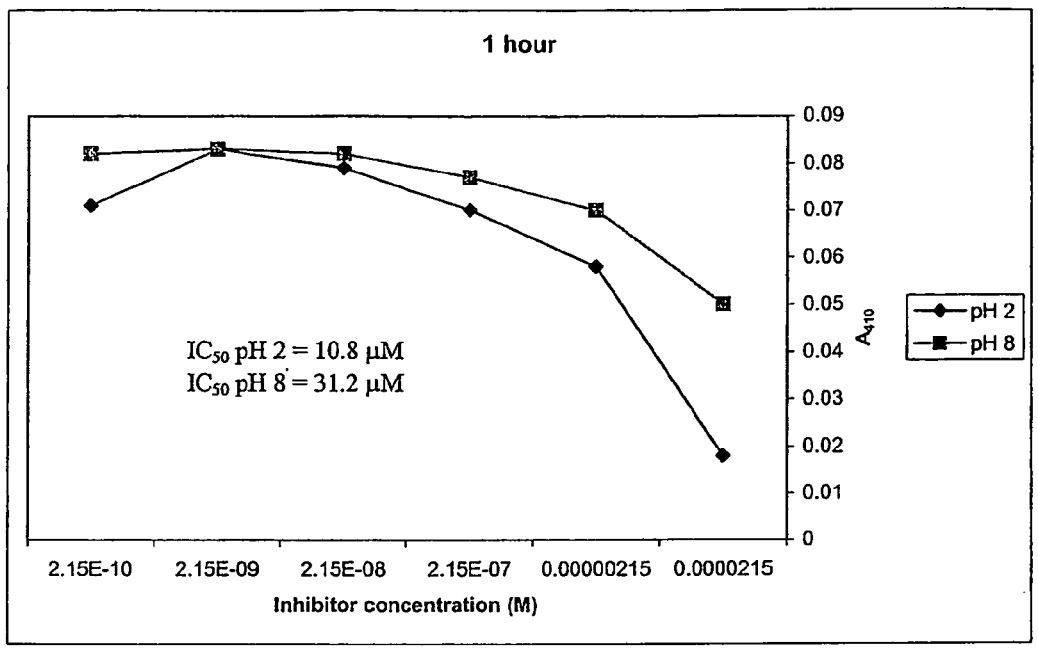
Figure 38c. Inhibition profile of ChgCpg-EthylGly-boroPro against DP IV at selected pHs at 1 hr.
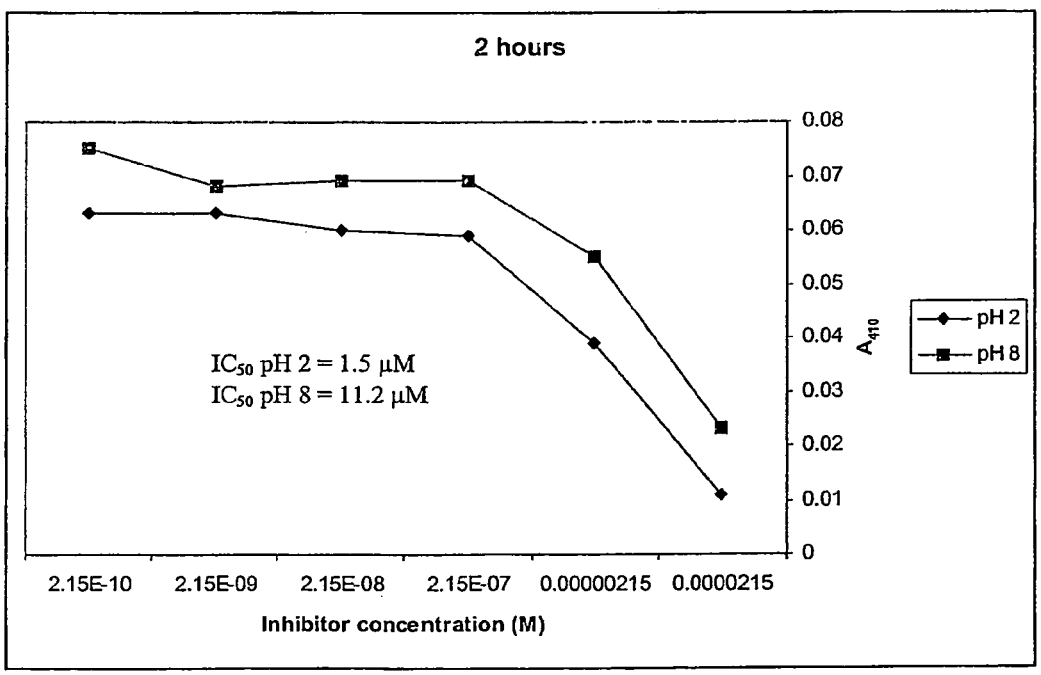
Figure 38d. Inhibition profile of ChgCpg-EthylGly-boroPro against DP IV at selected pHs at 2 hrs

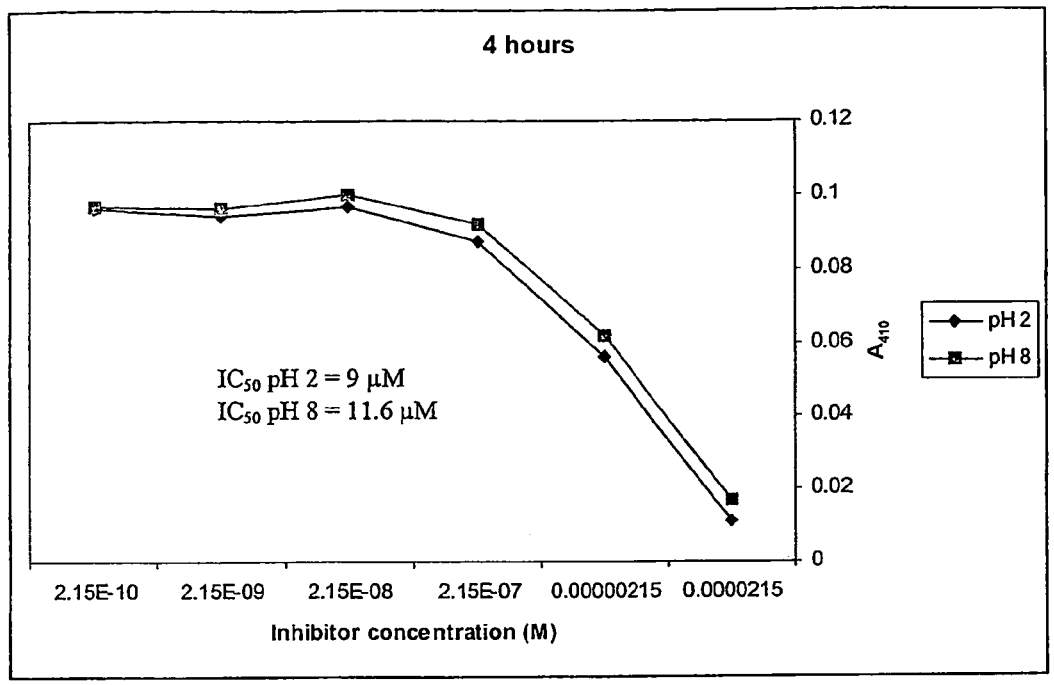
Figure 38e. Inhibition profile of ChgCpg-EthylGly-boroPro against DP IV at selected pHs at 4 hrs
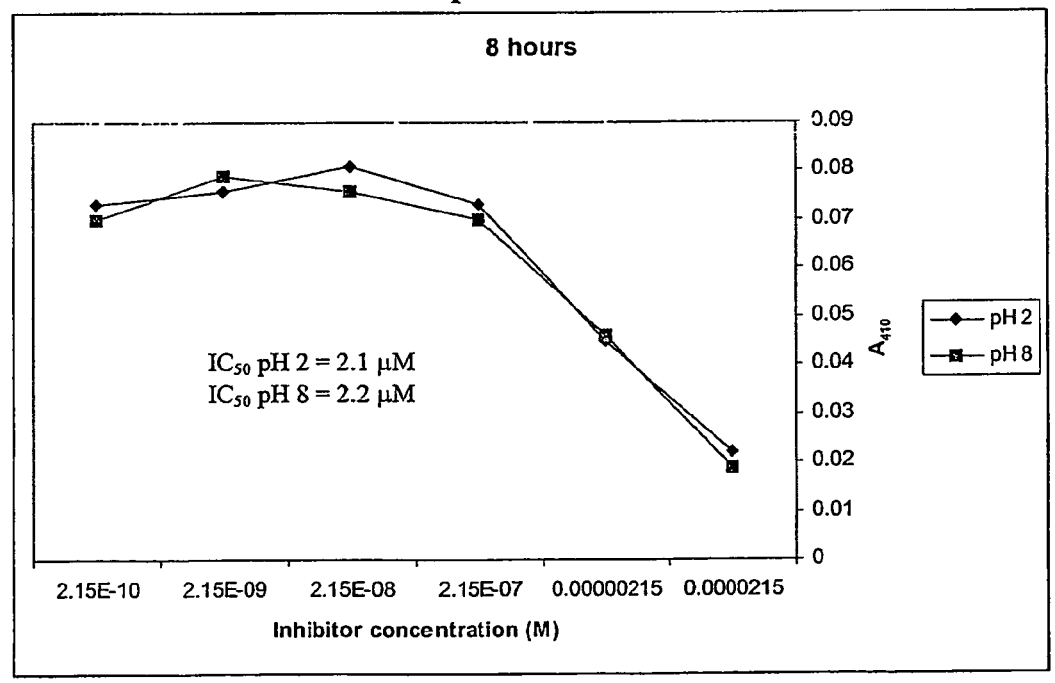
Figure 38f. Inhibition profile of ChgCpg-EthylGly-boroPro against DP IV at selected pHs at 8 hr

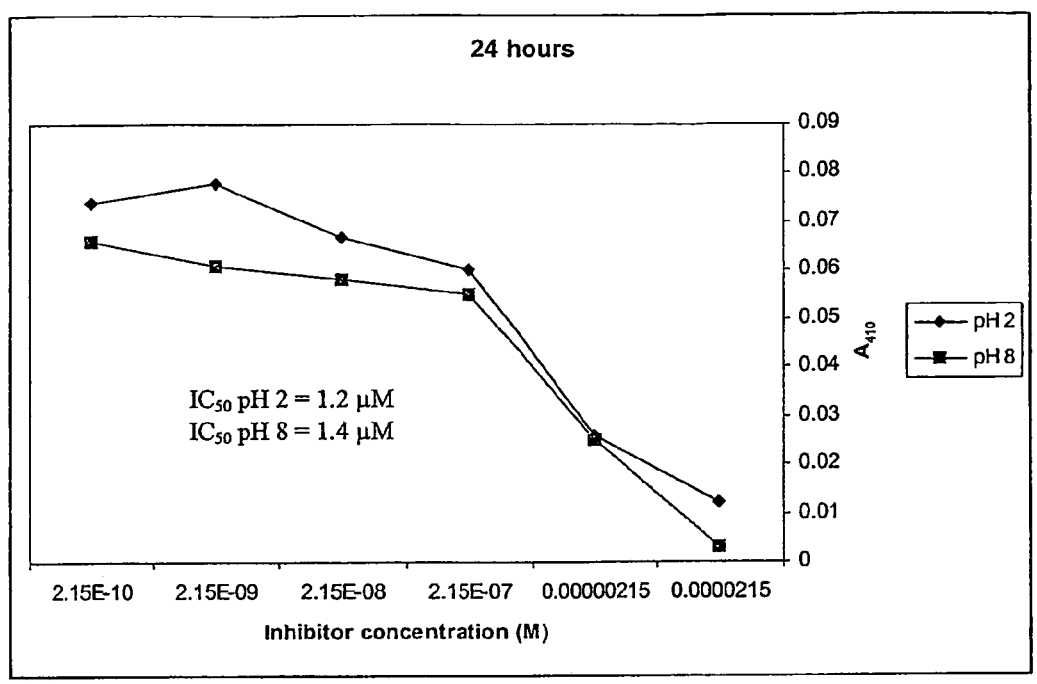
Figure 38g. Inhibition profile of ChgCpg-EthylGly-boroPro against DP IV at selected pHs at 24 hrs
ChgCpg-EthylGly-boroPro = 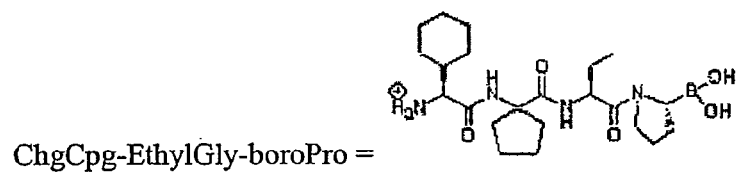

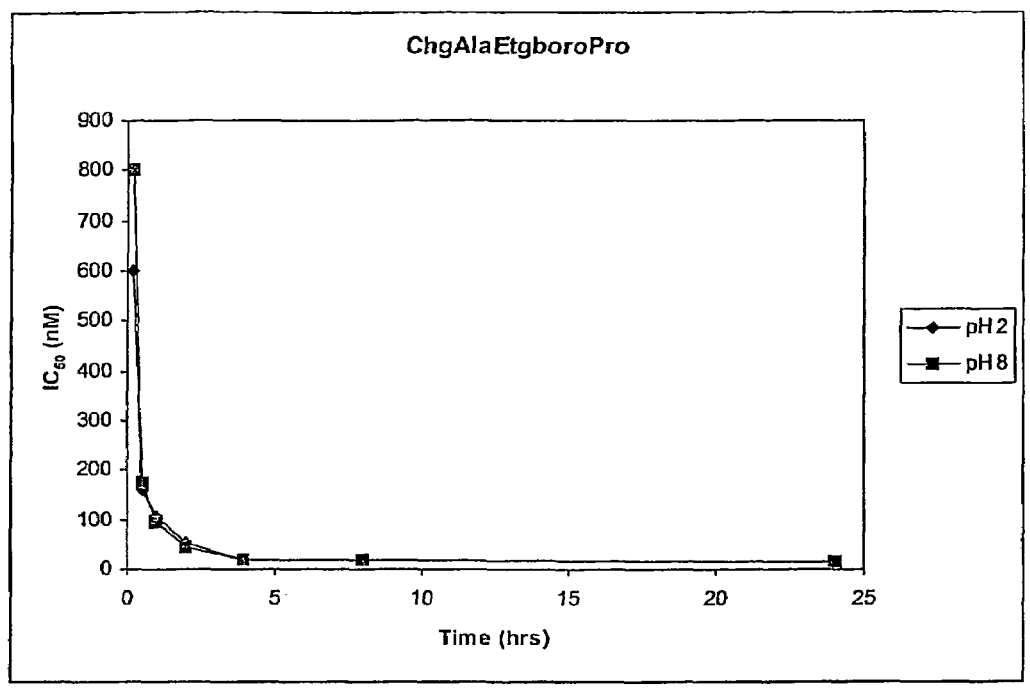
Figure 39. Inhibition profile of ChgAla-Etg-boroPro against DP IV at selected pHs.

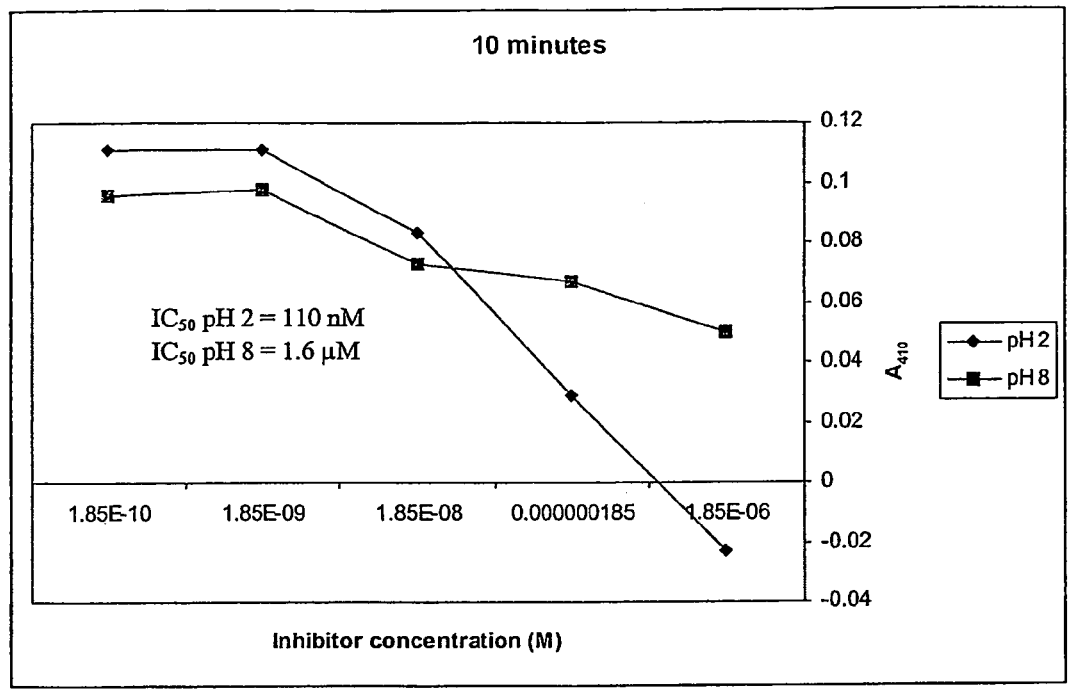
Figure 40a. Inhibition profile of Tyr-(D)-ProPheboroPro against DP IV at selected pHs at 10 minutes.
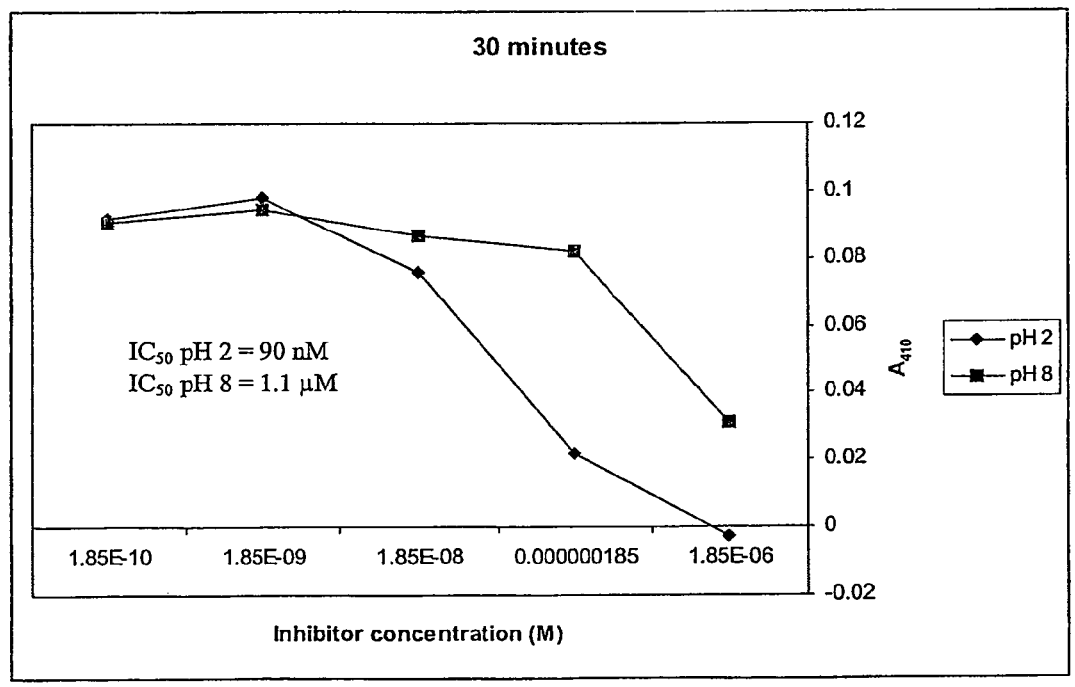
Figure 40b. Inhibition profile of Tyr-(D)-ProPheboroPro against DP IV at selected pHs at 30 minutes.

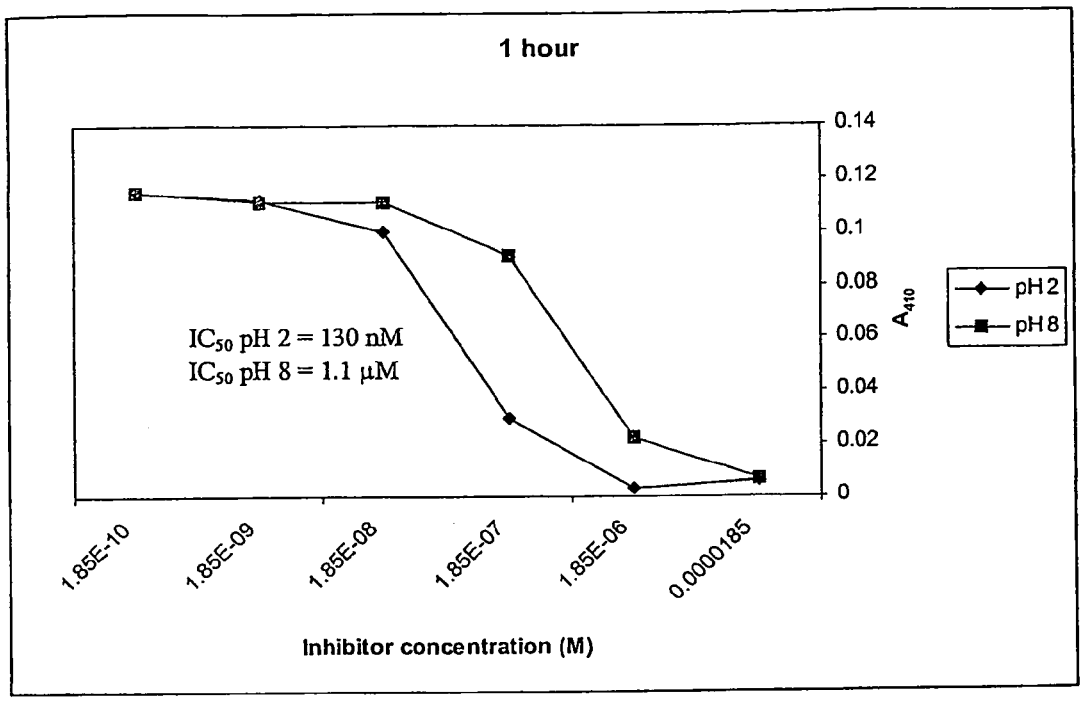
Figure 40c.  Inhibition profile of Tyr-(D)-ProPheboroPro against DP IV at selected pHs at 1 hr.
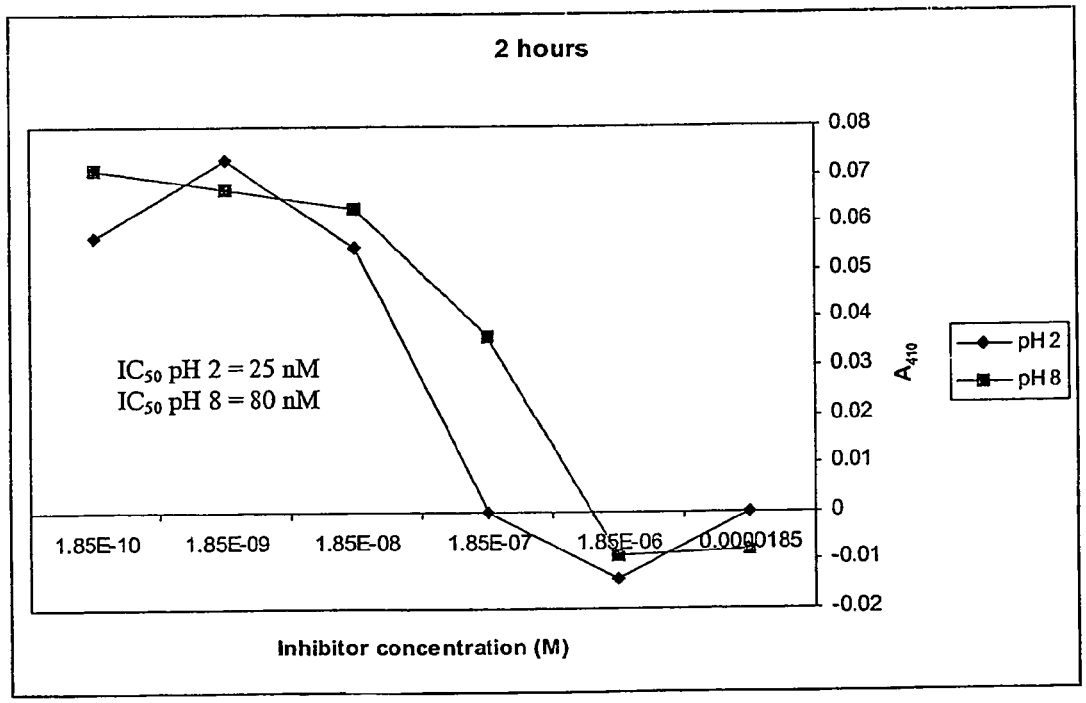
Figure 40d.  Inhibition profile of Tyr-(D)-ProPheboroPro against DP IV at selected pHs at 2 hrs.

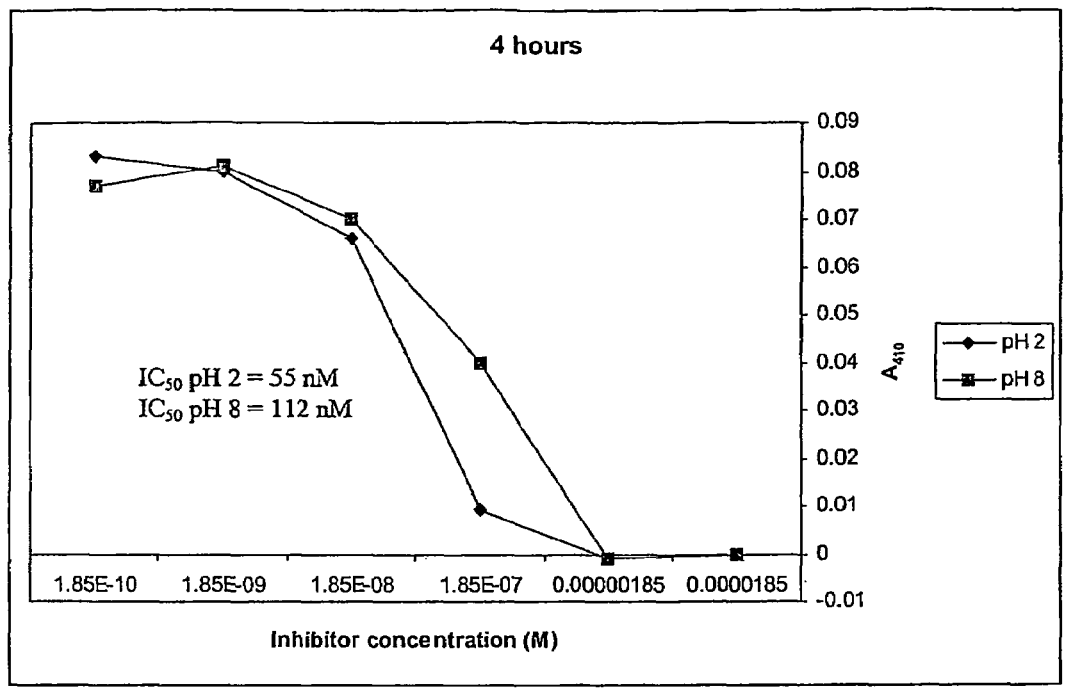
Figure 40e. Inhibition profile of Tyr-(D)-ProPheboroPro against DP IV at selected pHs at 4 hrs.
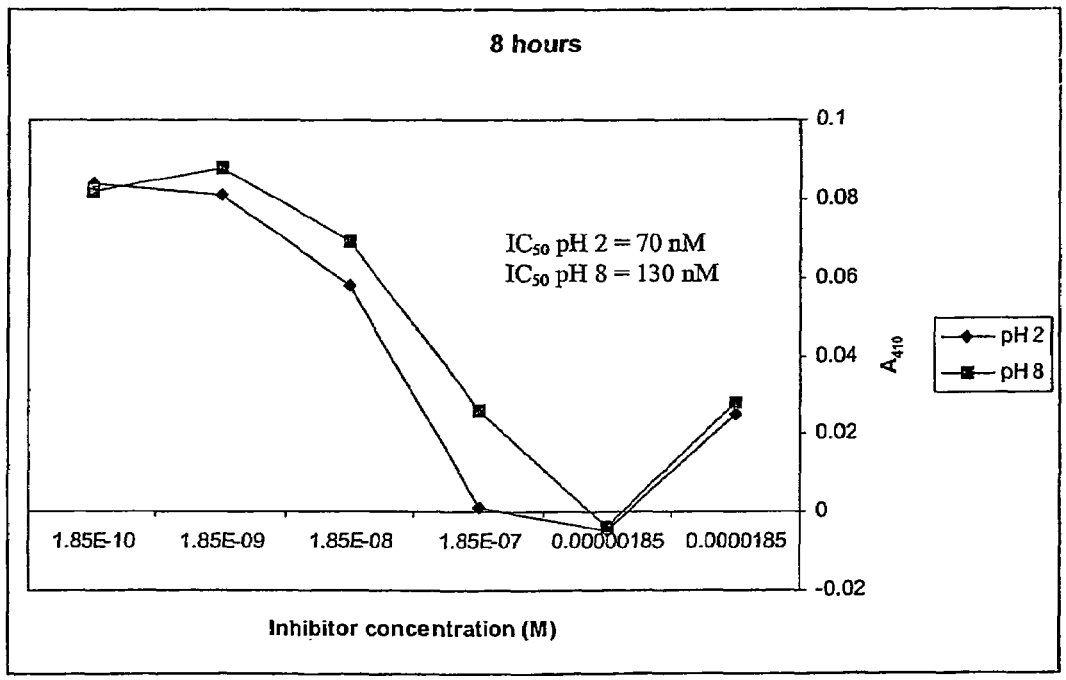
Figure 40f. Inhibition profile of Tyr-(D)-ProPheboroPro against DP IV at selected pHs at 8 hrs.

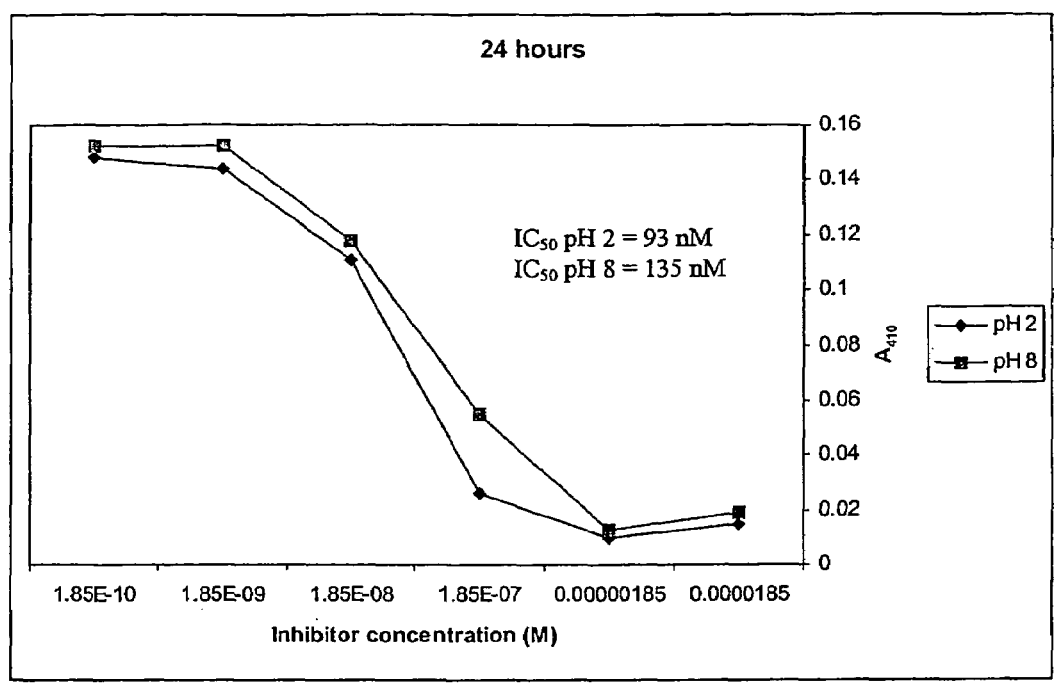
Figure 40g. Inhibition profile of Tyr-(D)-ProPheboroPro against DP IV at selected pHs at 24 hrs.
Tyr-(D)-ProPheboroPro = 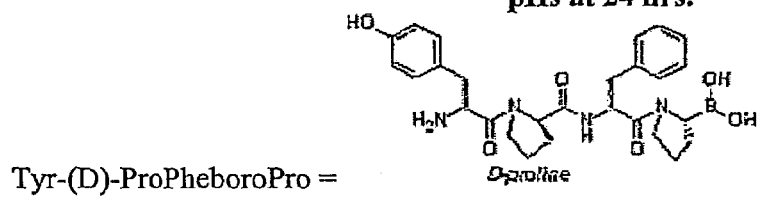

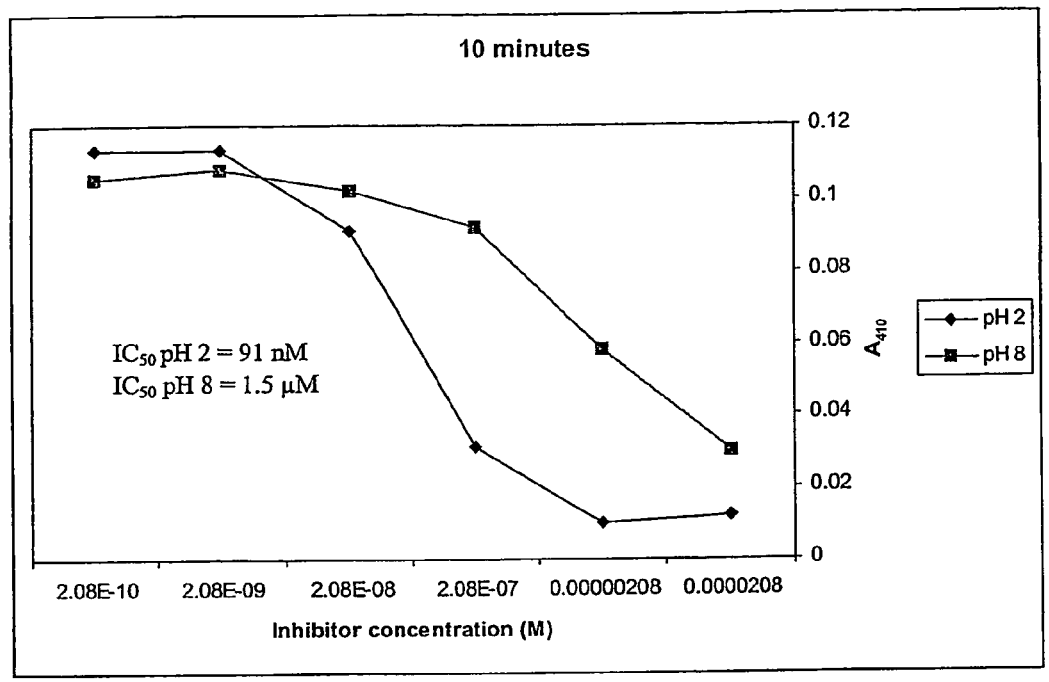
Figure 41a. Inhibition profile of ChgPro-tBug-boroPro against DP IV at selected pHs at 10 minutes.
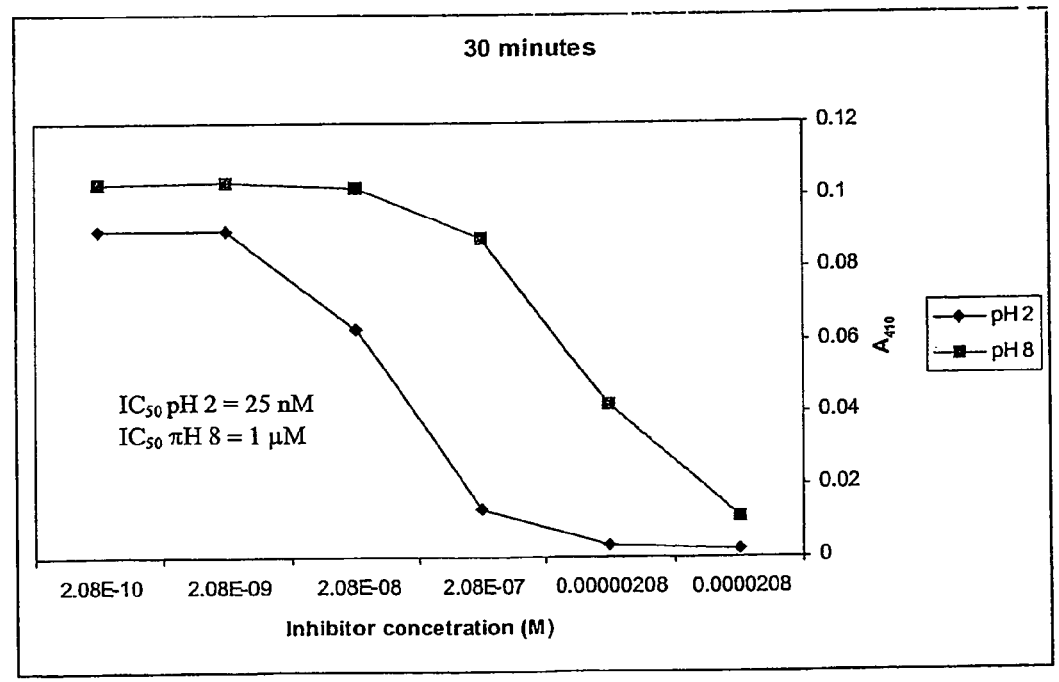
Figure 41b. Inhibition profile of ChgPro-tBug-boroPro against DP IV at selected pHs at 30 minutes.

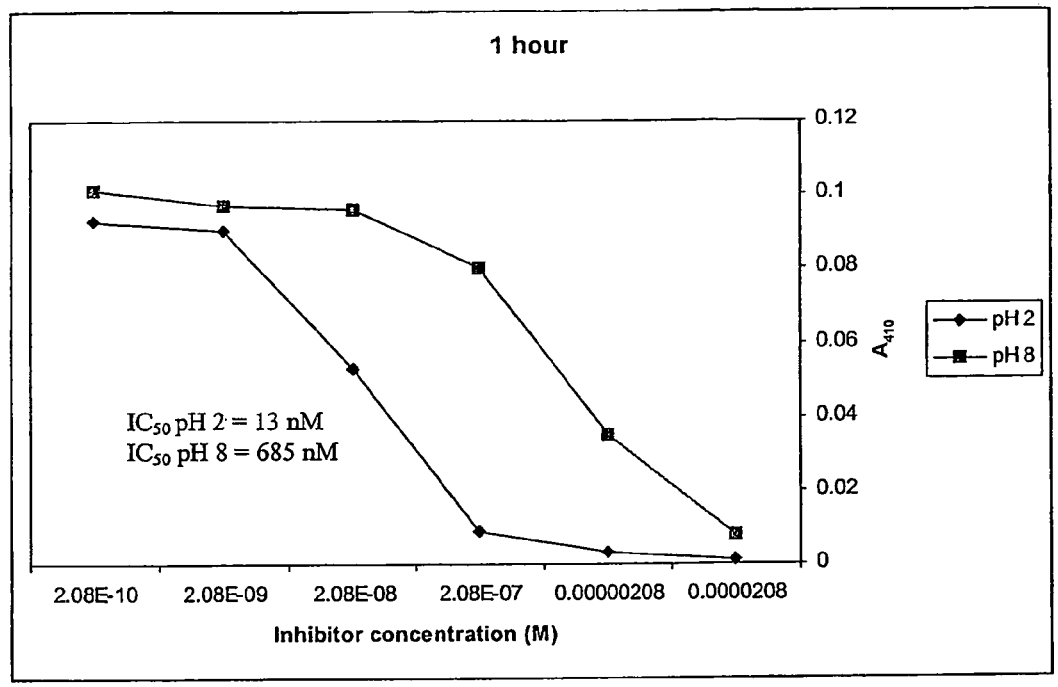
Figure 41c. Inhibition profile of ChgPro-tBug-boroPro against DP IV at selected pHs at 1 hr.
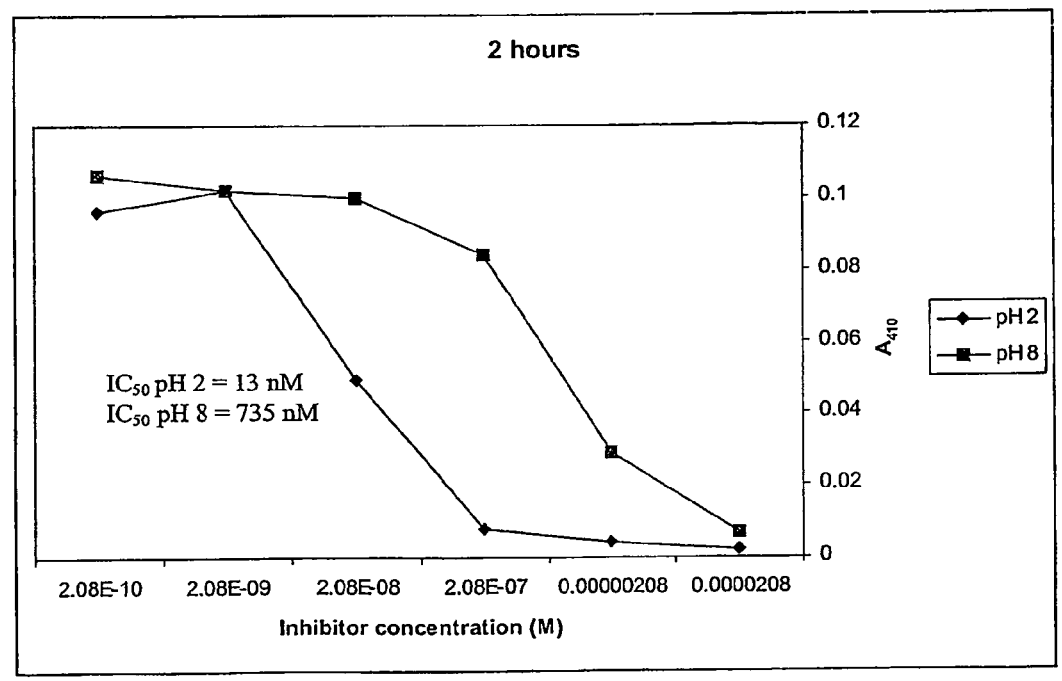
Figure 41d. Inhibition profile of ChgPro-tBug-boroPro against DP IV at selected pHs at 2 hrs.

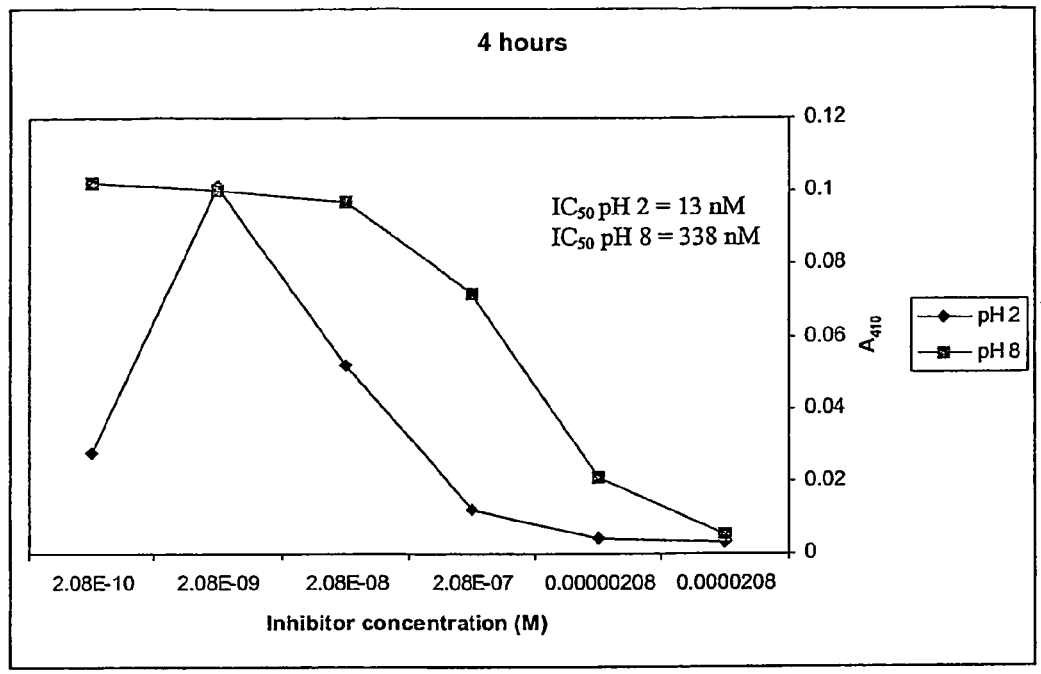
Figure 41e. Inhibition profile of ChgPro-tBug-boroPro against DP IV at selected pHs at 4 hrs.
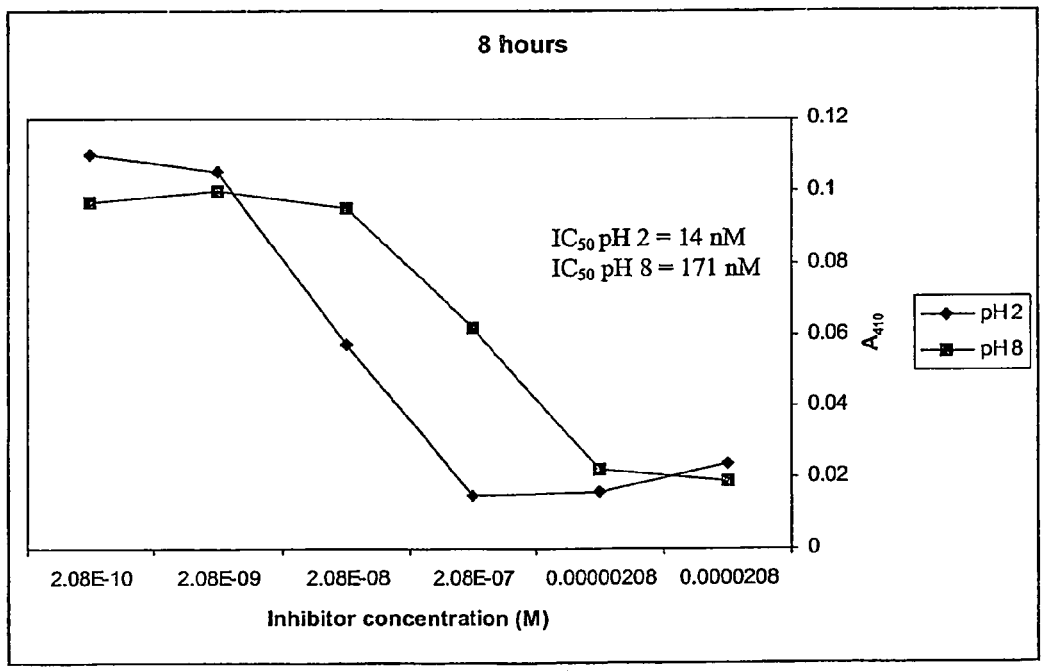
Figure 41f. Inhibition profile of ChgPro-tBug-boroPro against DP IV at selected pHs at 8 hrs.

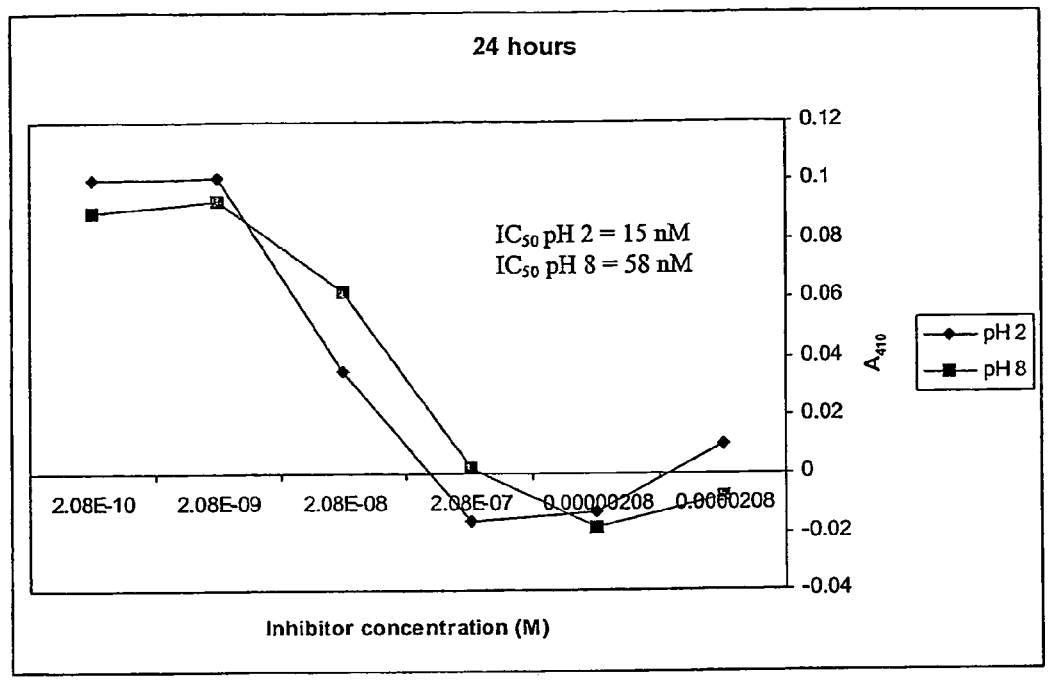
Figure 41g. Inhibition profile of ChgPro-tBug-boroPro against DP IV at selected pHs at 24 hrs.
ChgPro-tBug-boroPro = 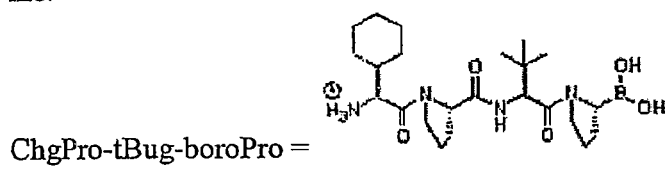

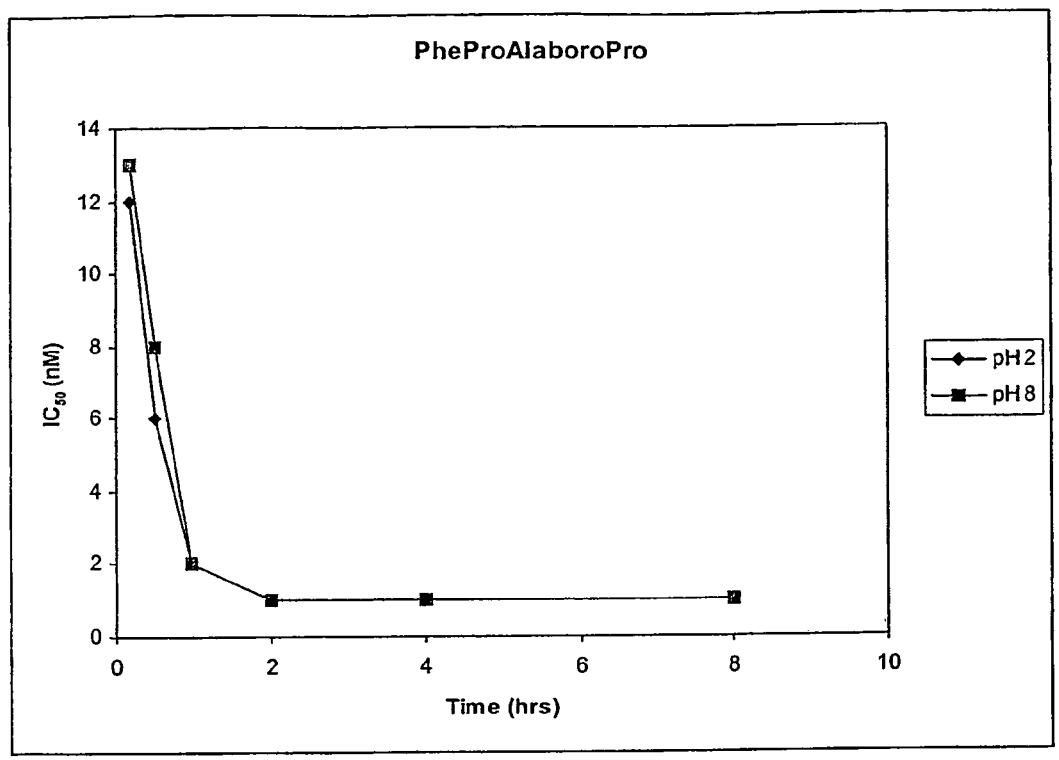
Figure 42.  Inhibition profile of PhePro-Ala-boroPro against DP IV at selected pHs.
PhePro-Ala-boroPro = 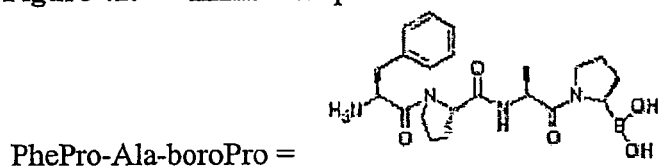

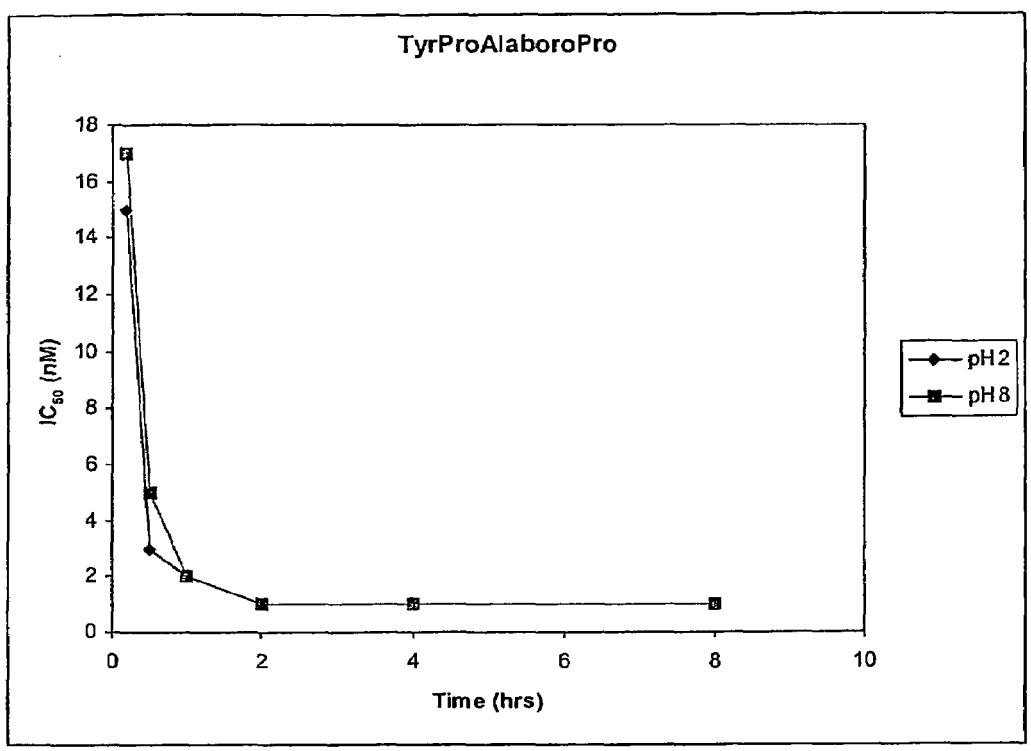
Figure 43. Inhibition profile of TyrProAlaboroPro against DP IV at selected pHs.
TyrProAlaboroPro = 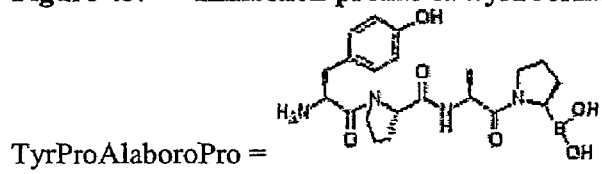

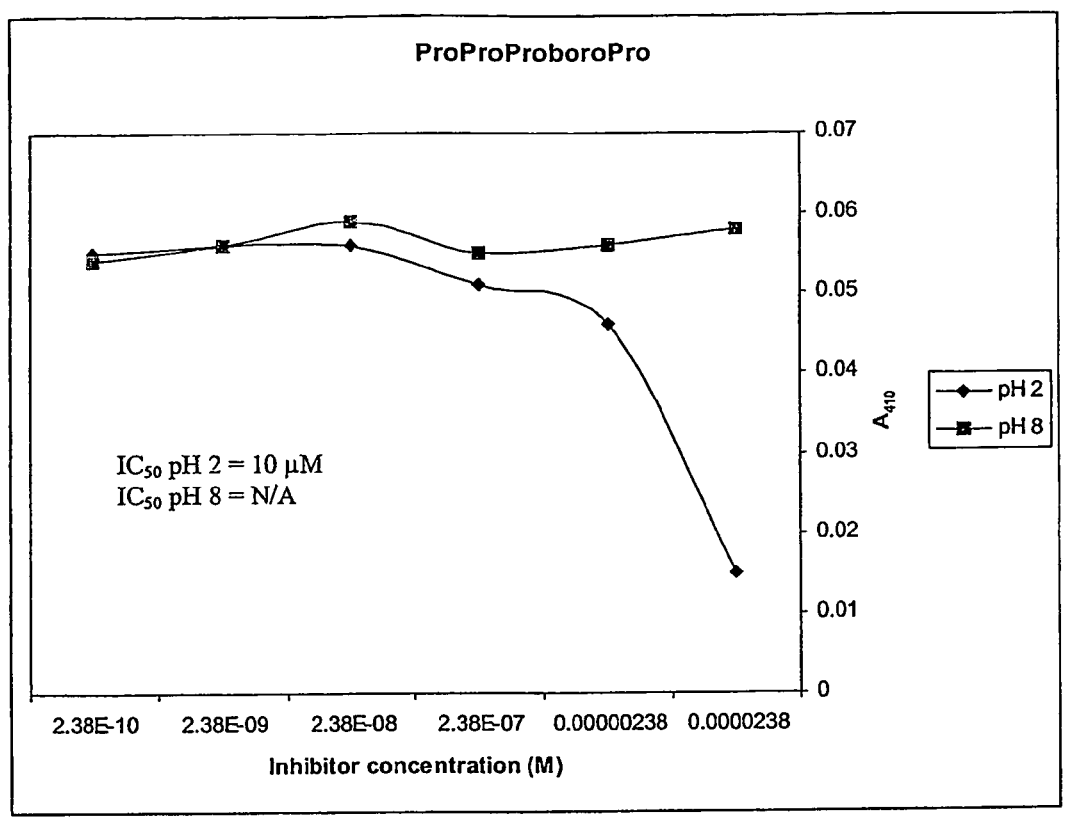
Figure 44. Inhibition profile of ProProProboroPro against DP IV at selected pHs.

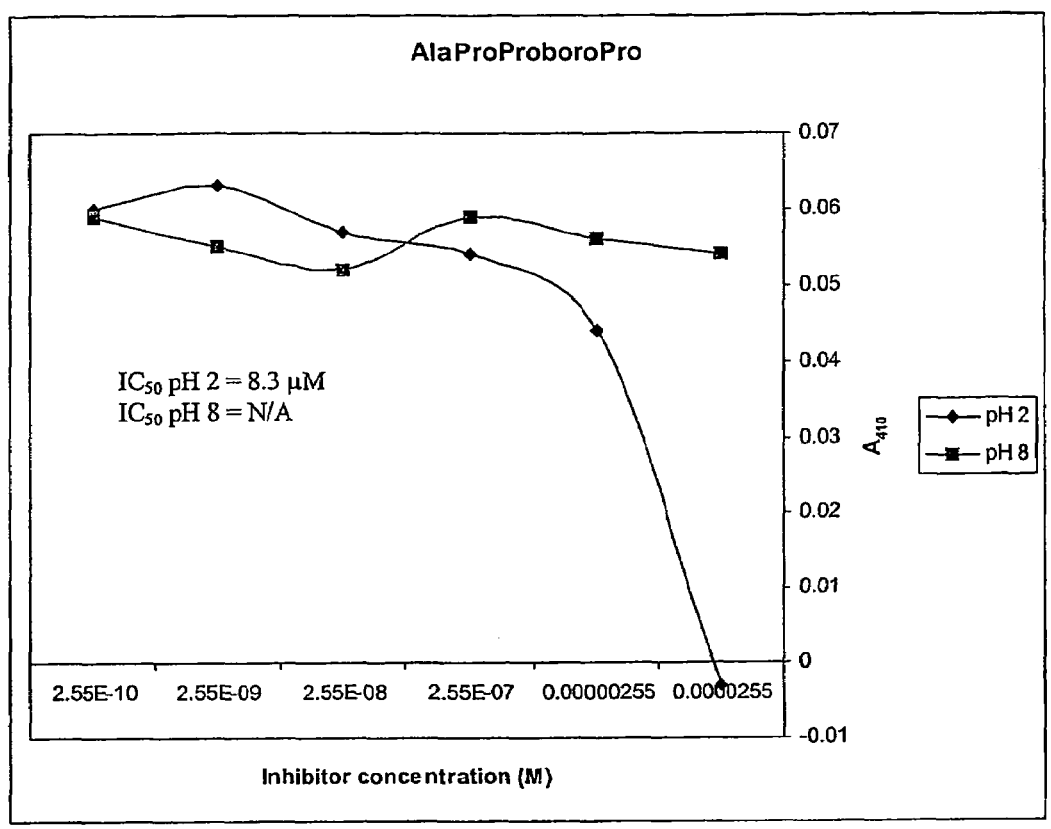
Figure 45.  Inhibition profile of AlaProProboroPro against DP IV at selected pHs.

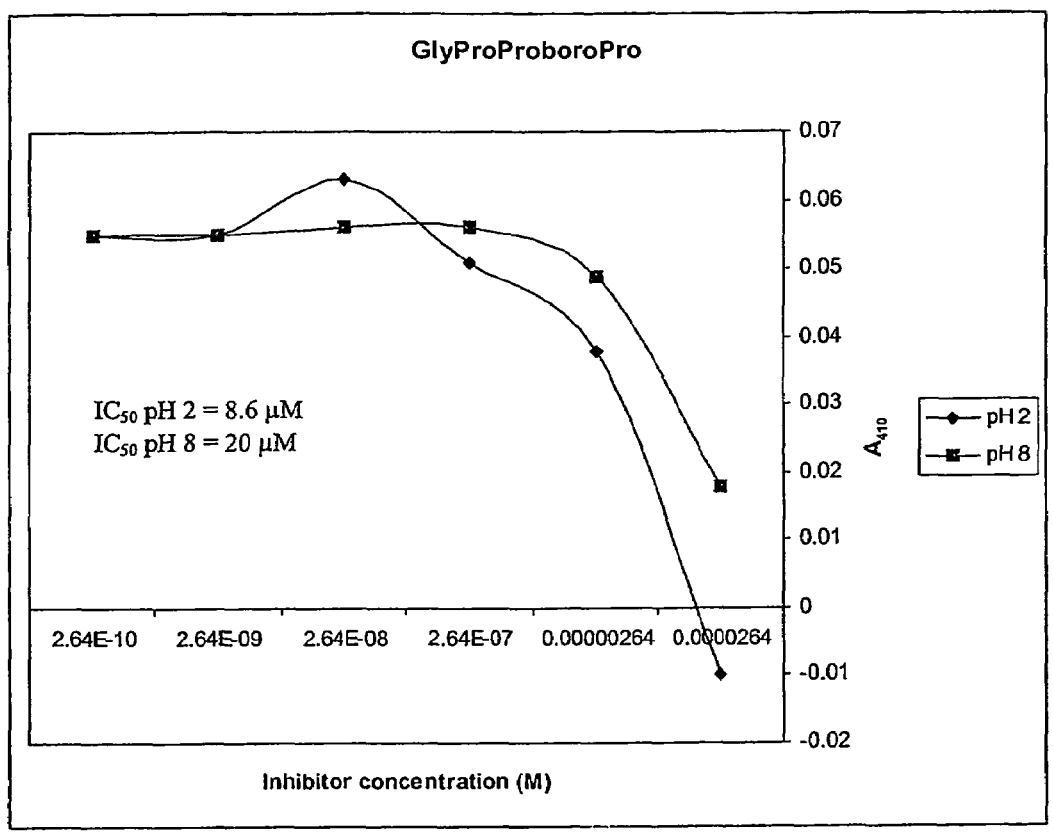
Figure 46. Inhibition profile of GlyProProboroPro against DP IV at selected pHs.

Figure 47 Smart drug compounds
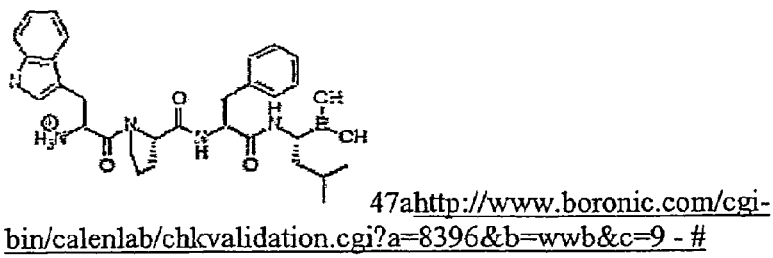
47a http://www.boronic.com/cgi-bin/calenlab/chkvalidation.cgi?a=8396&b=wwb&c=9 - #
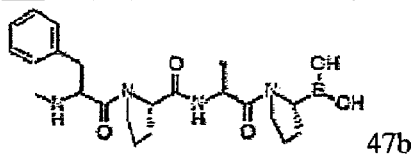
47b
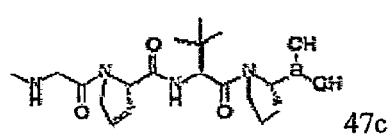
47c
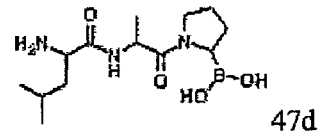
47d
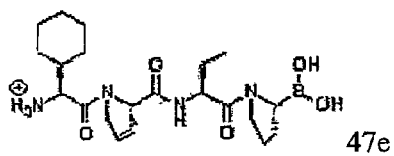
47e
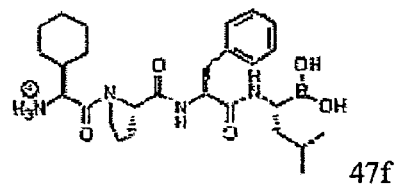
47f
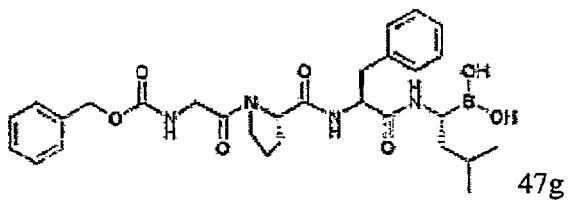
47g
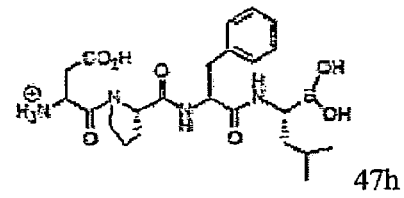
47h
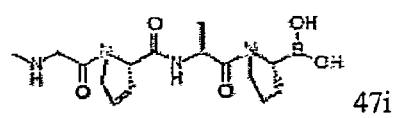
47i
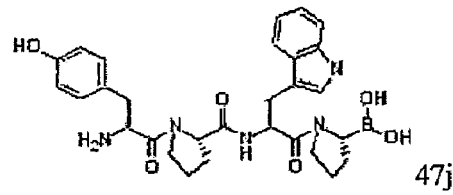
47j
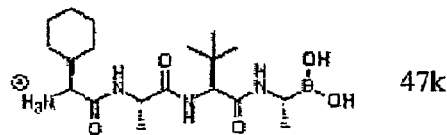
47k
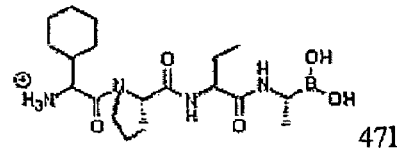
47l
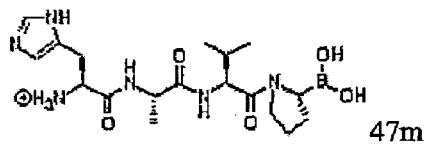
47m Figure 48    Smart drug compounds
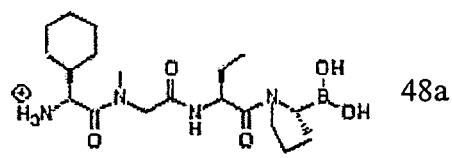 48a
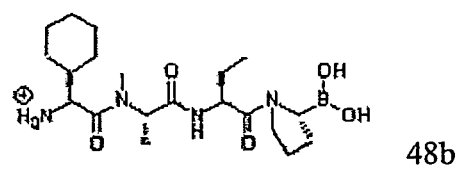 48b
http://www.boronic.com/cgi-bin/calenlab/chkvalidation.cgi?a=5468&b=wwb&c=9 - #
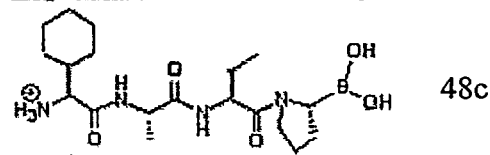 48c
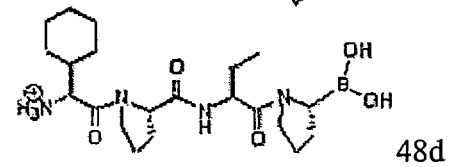 48d
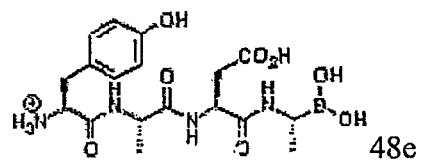 48e
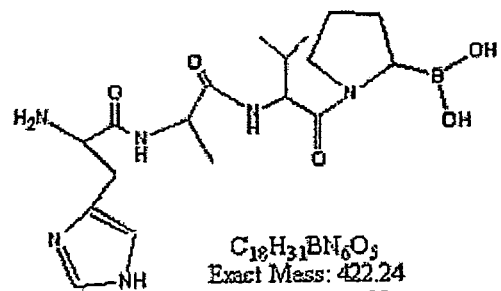
$C_{18}H_{31}BN_6O_5$
Exact Mass: 422.24
Mol. Wt.: 422.29
C, 51.20; H, 7.40; B, 2.56; N, 19.90; O, 18.94    48g
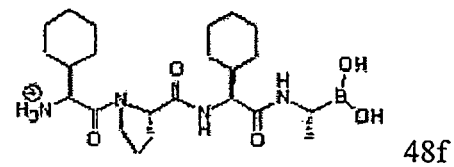 48f
BocProChgboroPro
48h
BocProAlaboroPro
48i
BocProValboroPro
48j Figure 49    Smart drug compounds
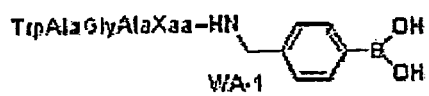
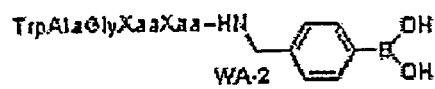
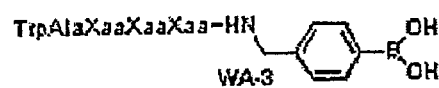
Xaa = all amino acids except Cys  47a1-3
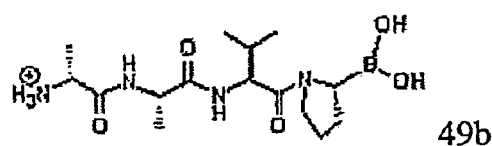
49b
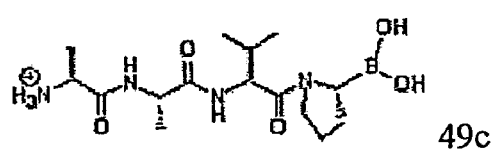
49c
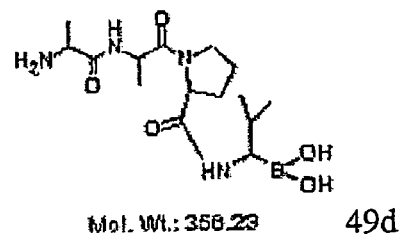
Mol. Wt.: 358.23   49d
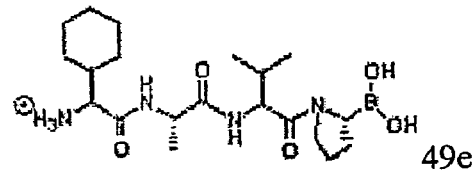
49e
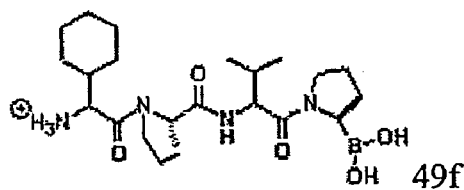
49f
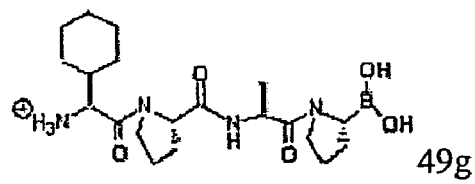
49g
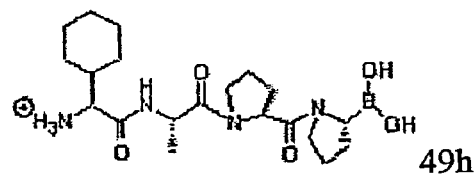
49h
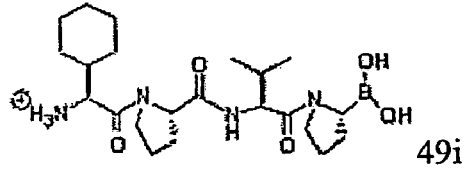
49i
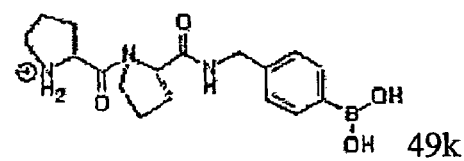
49k Figure 50 Smart drug compounds
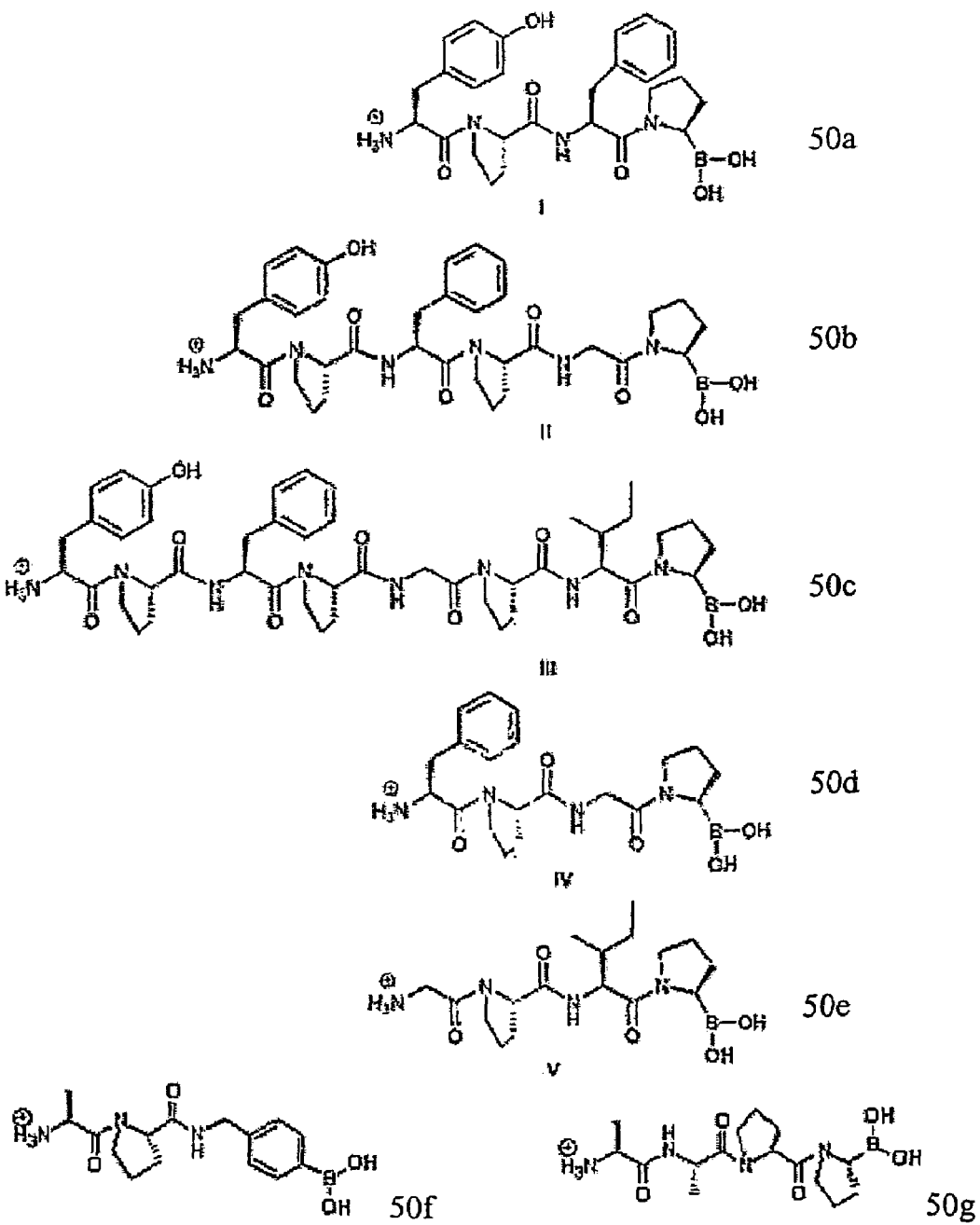
50a
50b
50c
50d
50e
50f  50g
Ac-Val-Ala-Pro-boroArg
50h

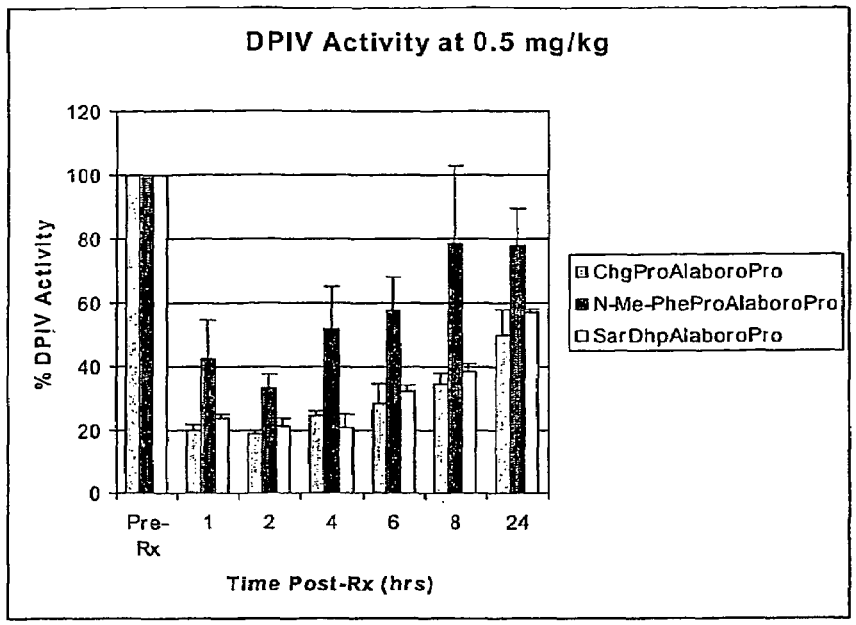
Figure 51a. In vivo time resolved inhibition of DPIV by ChgProAlaboroPro, N-Me-PheProAlaboroPro and SarDhpAlaboroPro at 0.5 mg/kg dosage level
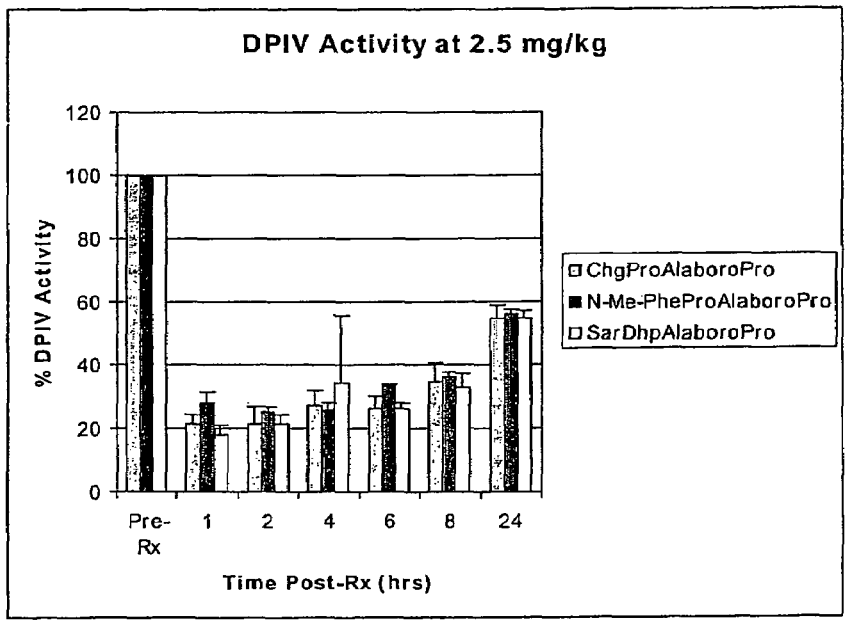
Figure 51b. In vivo time resolved inhibition of DPIV by ChgProAlaboroPro, N-Me-PheProAlaboroPro and SarDhpAlaboroPro at 2.5 mg/kg dosage level

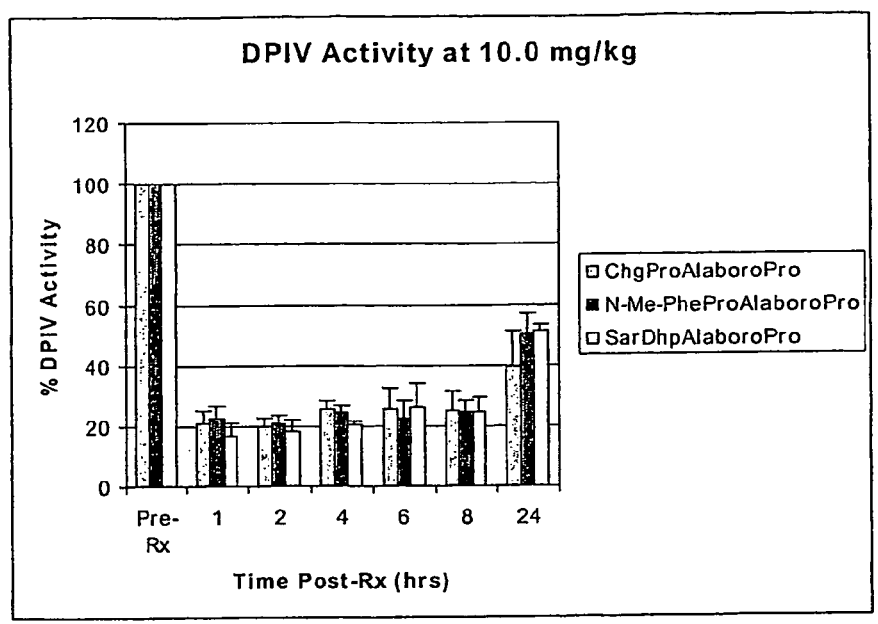
Figure 51c. In vivo time resolved inhibition of DPIV by ChgProAlaboroPro, N-Me-PheProAlaboroPro and SarDhpAlaboroPro at 10.0 mg/kg dosage level

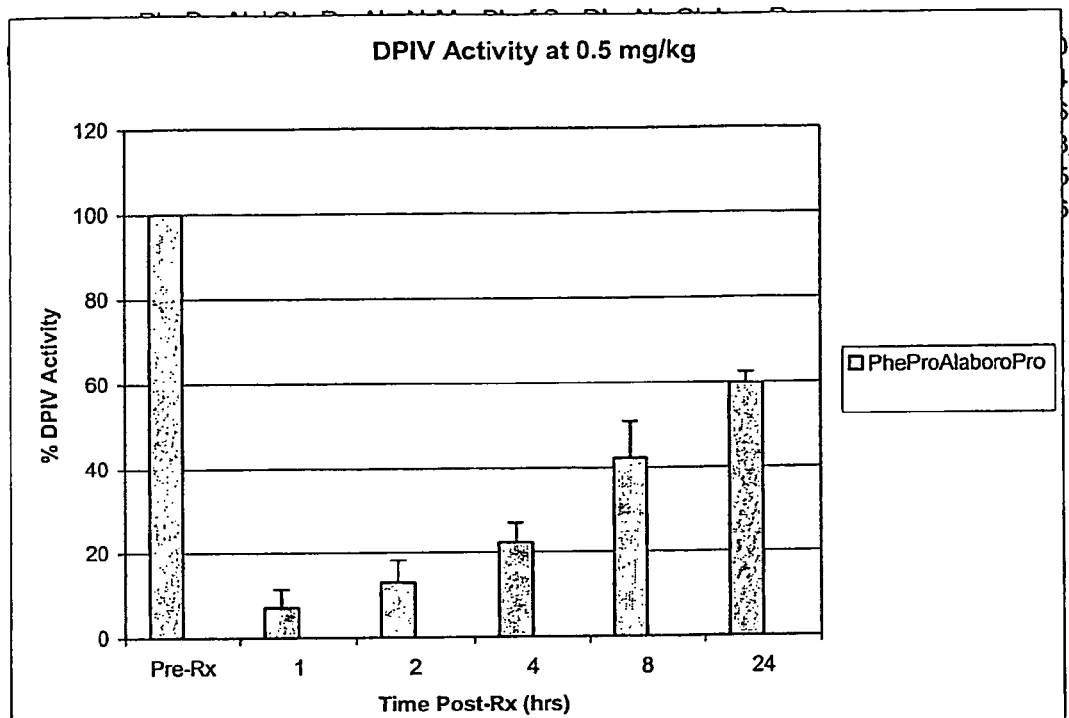
Figure 52a. In vivo time resolved inhibition of DPIV by PheProAlaboroPro at 0.5 mg/kg dosage level
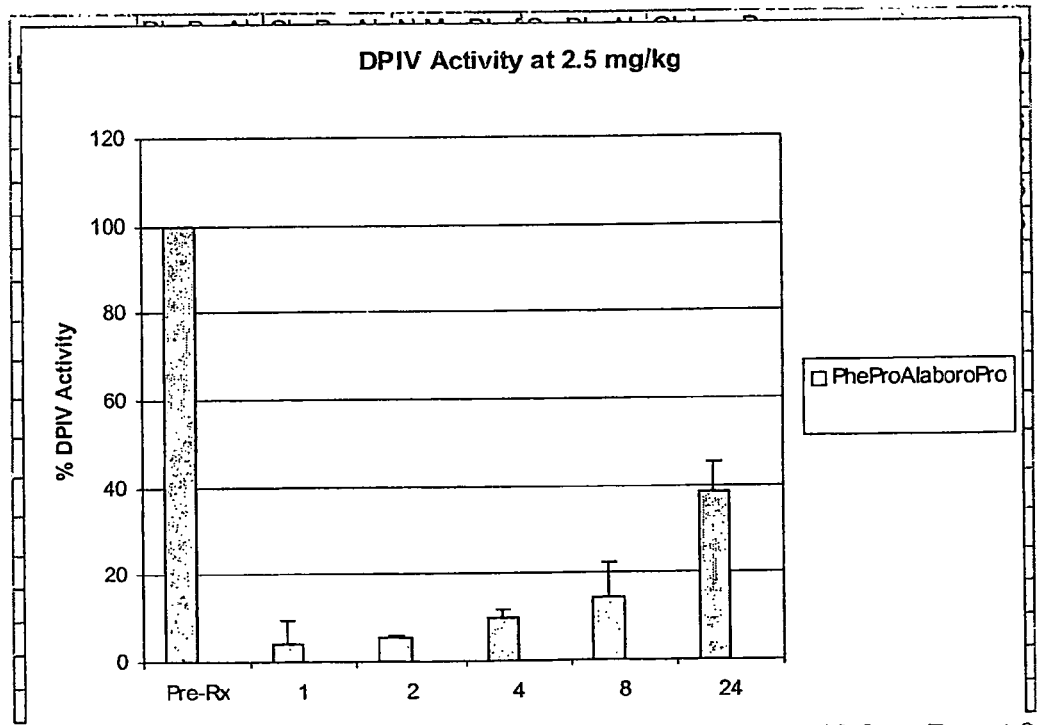
Figure 52b. In vivo time resolved inhibition of DPIV by PheProAlaboroPro at 0.5 mg/kg dosage level

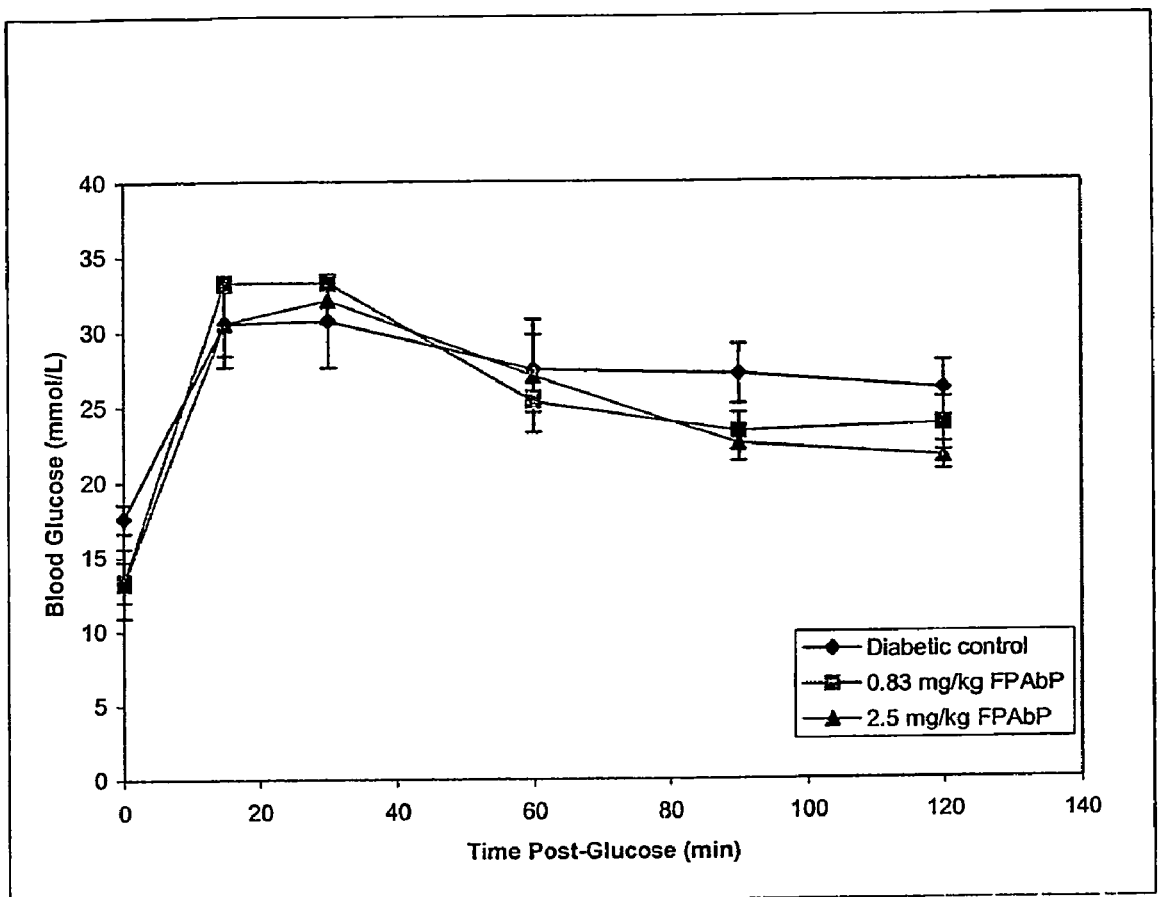
Figure 53. Blood glucose levels in diabetic mice following treatment with PheProAlaboroPro Figure 54. Inhibition profile of N-Me-PheProAlaboroPro against DPIV

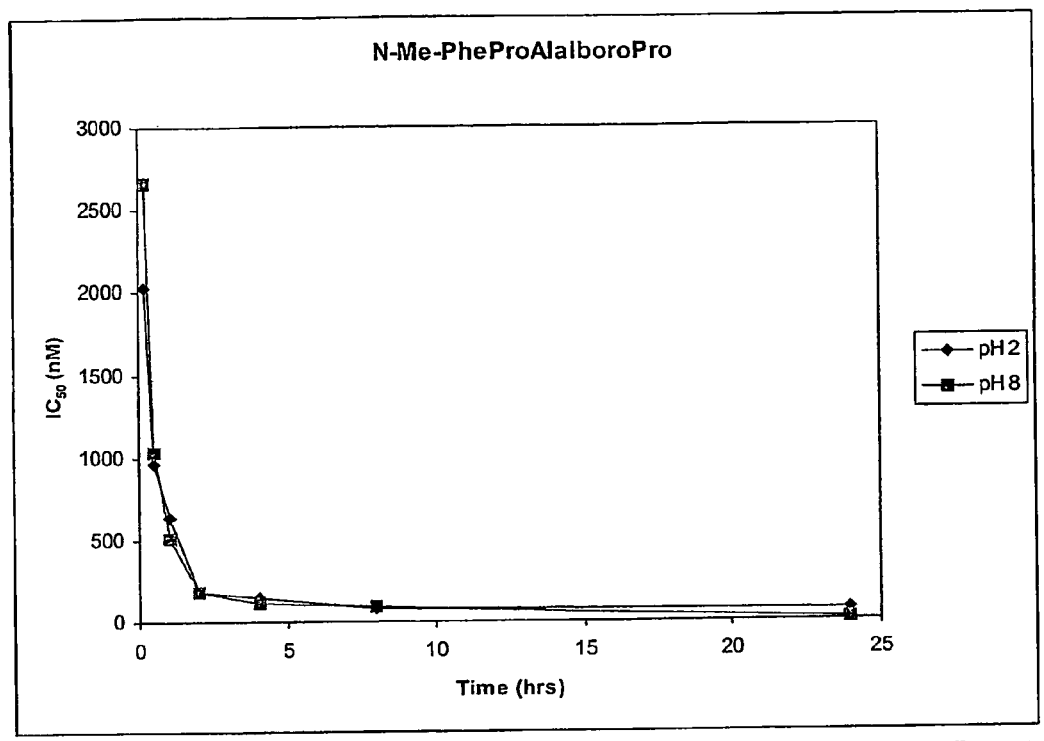
Figure 55  Time resolved inhibition of DPIV by N-Me-PheProAlaboroPro at selected pHs.

Figure 56a. Inhibition profile of SarDhpAlaboroPro against DPIV at selected pHs at 10 minutes Figure 56b. Inhibition profile of SarDhpAlaboroPro against DPIV at selected pHs at 30 minutes

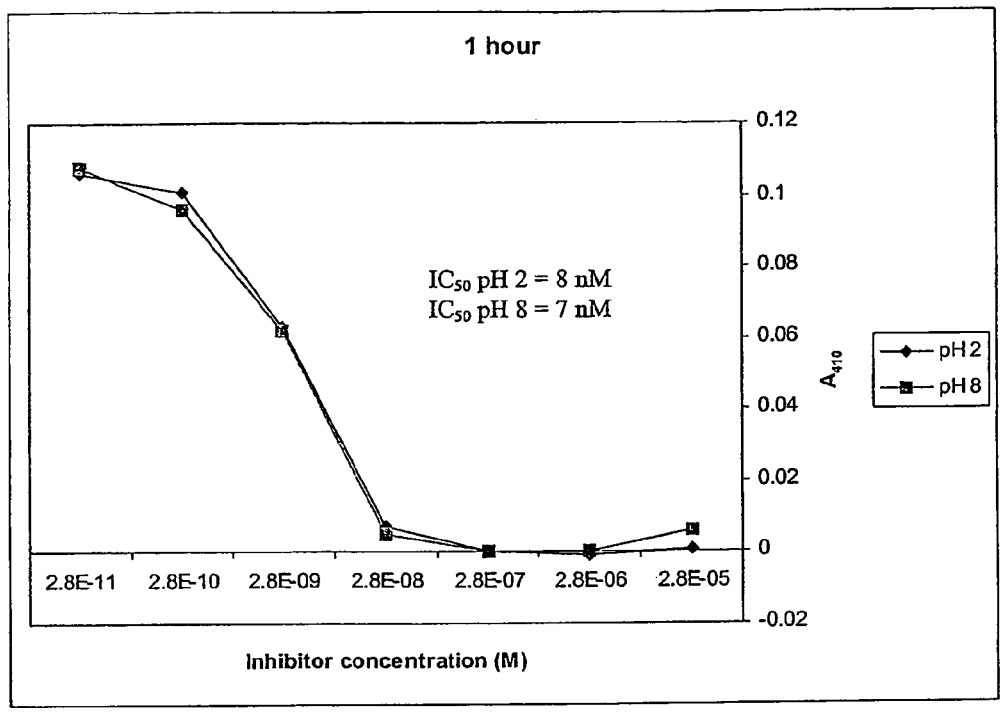
Figure 56c. Inhibition profile of SarDhpAlaboroPro against DPIV at selected pHs at 1 hr
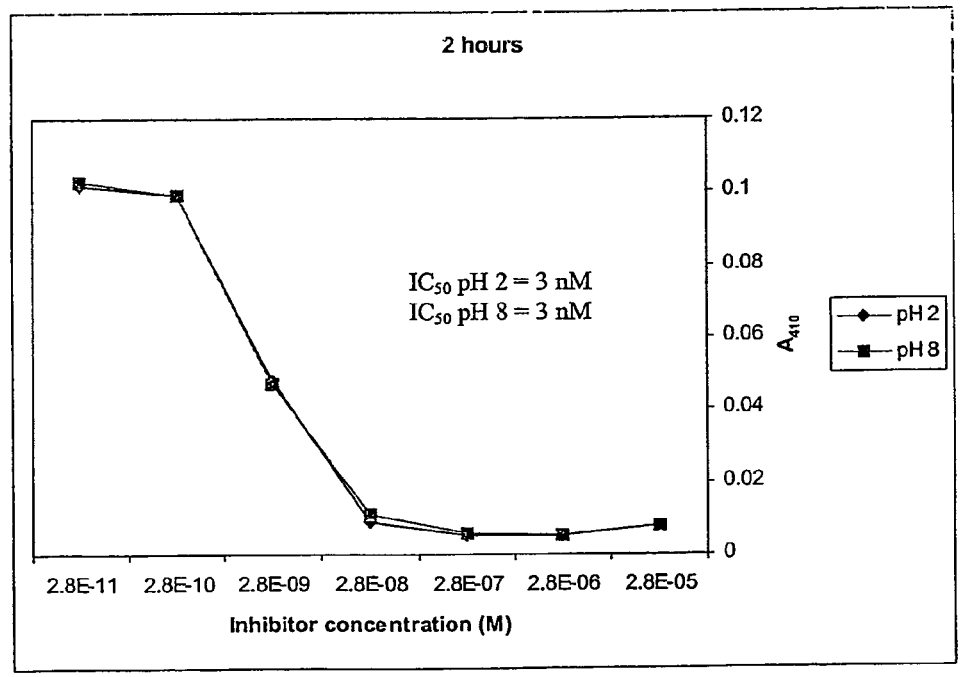
Figure 56d. Inhibition profile of SarDhpAlaboroPro against DPIV at selected pHs at 2 hrs Figure 56e. Inhibition profile of SarDhpAlaboroPro against DPIV at selected pHs at 4 hrs Figure 56f. Inhibition profile of SarDhpAlaboroPro against DPIV at selected pHs at 8 hrs Figure 56g. Inhibition profile of SarDhpAlaboroPro against DPIV at selected pHs at 24 hrs Figure 56h. Time resolved inhibitory SarDhpAlaboroPro against DPIV at selected pHs

Administration of DPP-IV Inhibitor (PheProAlaboroPro) to WildType (WT) and Double Incretin Receptor Knockout (DKO) Mice
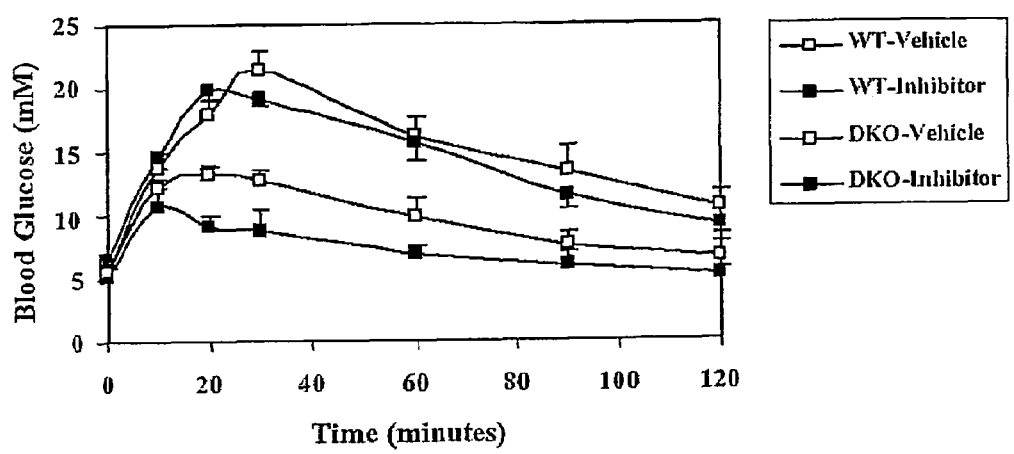
Inhibitor was administered orally (1.25mg/kg) 1 hour prior to oral glucose challenge.
Figure 57   In vivo activity of PheProAlaboroPro

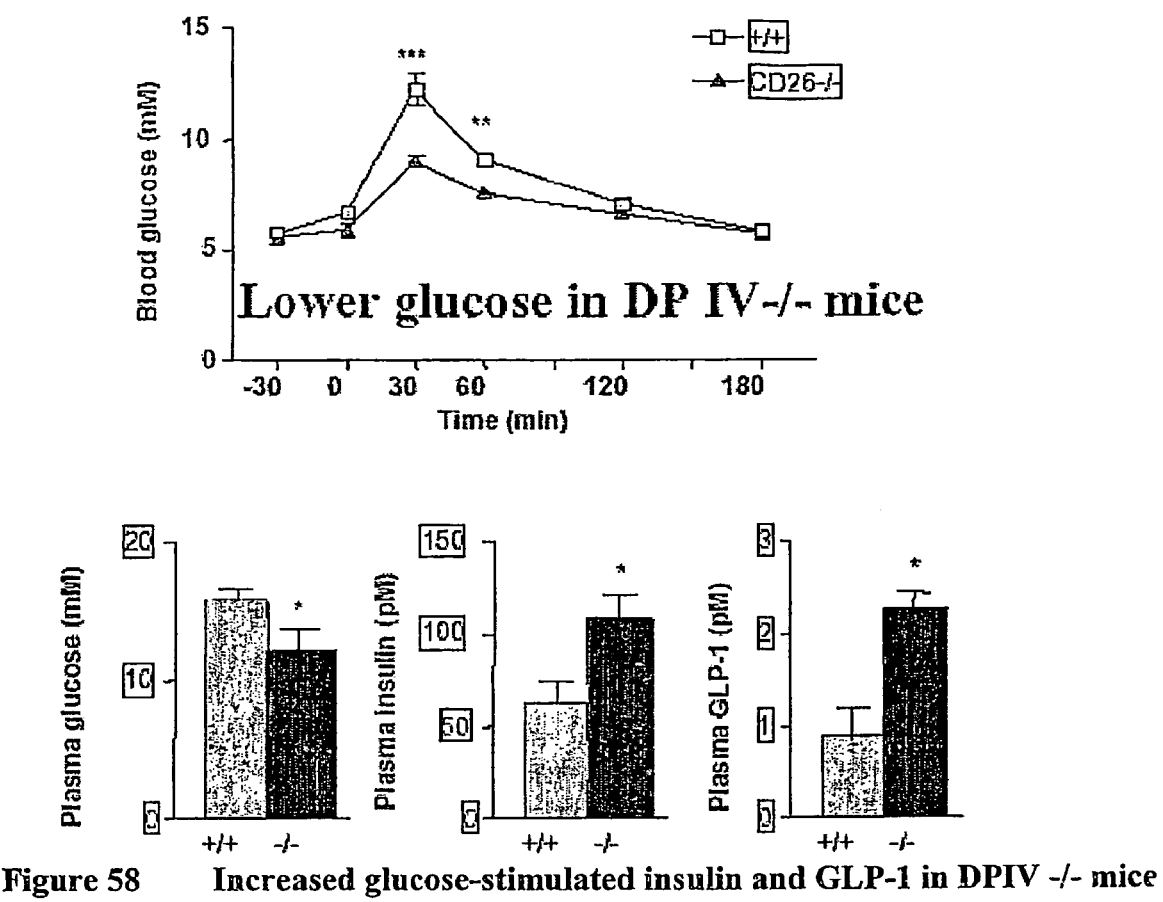
Figure 58　Increased glucose-stimulated insulin and GLP-1 in DPIV -/- mice

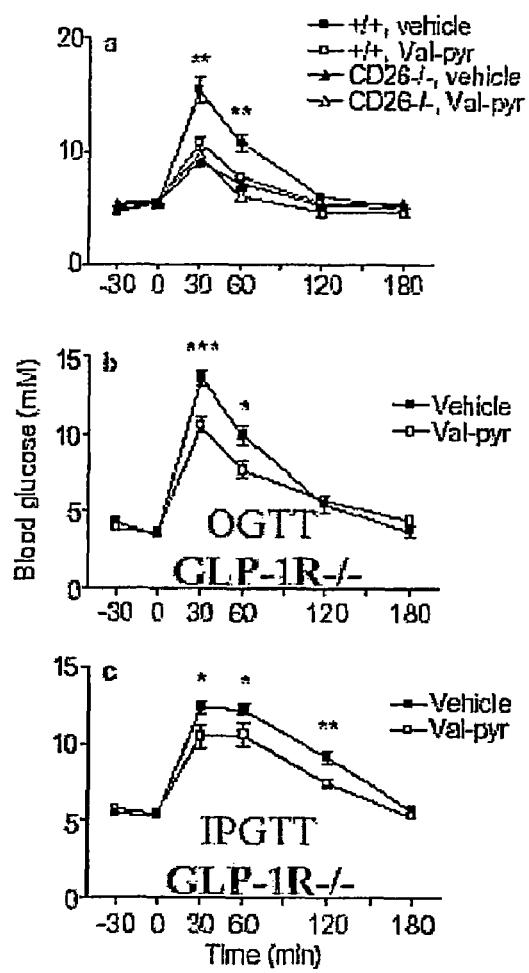
Figure 59 GLP-1 signaling is not required for action of DPIV inhibitors

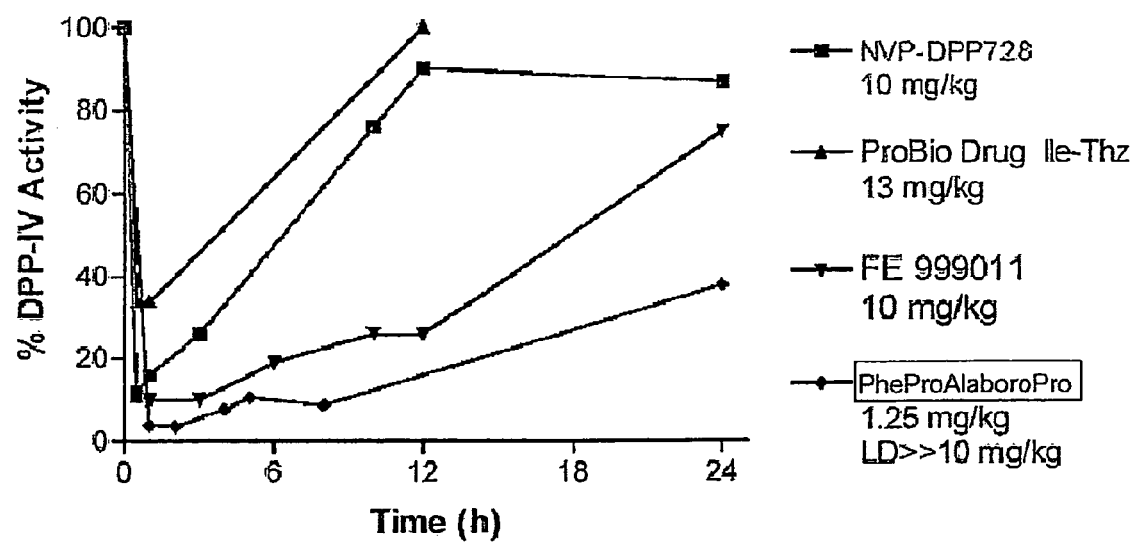
Figure 60 Comparisons of time resolved potencies of various DPIV inhibitors in mice

|  | Normal Control | Diabetic Control | ValboroPro | ChgProValboroPro |
|---|---|---|---|---|
| 0.05 mg/kg | | | | |
| 1hr post-Rx glucose | 88.56 | 100 | 41.29 | 16.42 |
| 4hrs post-Rx glucose | 69.16 | 100 | 34.13 | 18.56 |
| | | | | |
| 0.025 mg/kg | | | c | |
| 1hr Post Rx-Glucose | 82.65 | 100 | 47.49 | 34.70 |
| 4hrs Post Rx-Glucose | 89.95 | 100 | 39.23 | 24.40 |
| | | | | |
| 0.01 mg/kg | | | | |
| 1hr Post Rx-Glucose | 82.65 | 100.00 | 59.36 | 48.86 |
| 4hrs Post Rx-Glucose | 89.95 | 100.00 | 58.85 | 40.67 |
| | | | | |
| 0.0025 mg/kg | | | | |
| 1hr Post Rx-Glucose | 82.65 | 100.00 | 94.52 | 84.47 |
| 4hrs Post Rx-Glucose | 89.95 | 100.00 | 93.30 | 81.82 |

Figure 61  Comparison between ChgProValboroPro and ValboroPro in blocking DPP IV catalytic activity *in vivo* in mice.

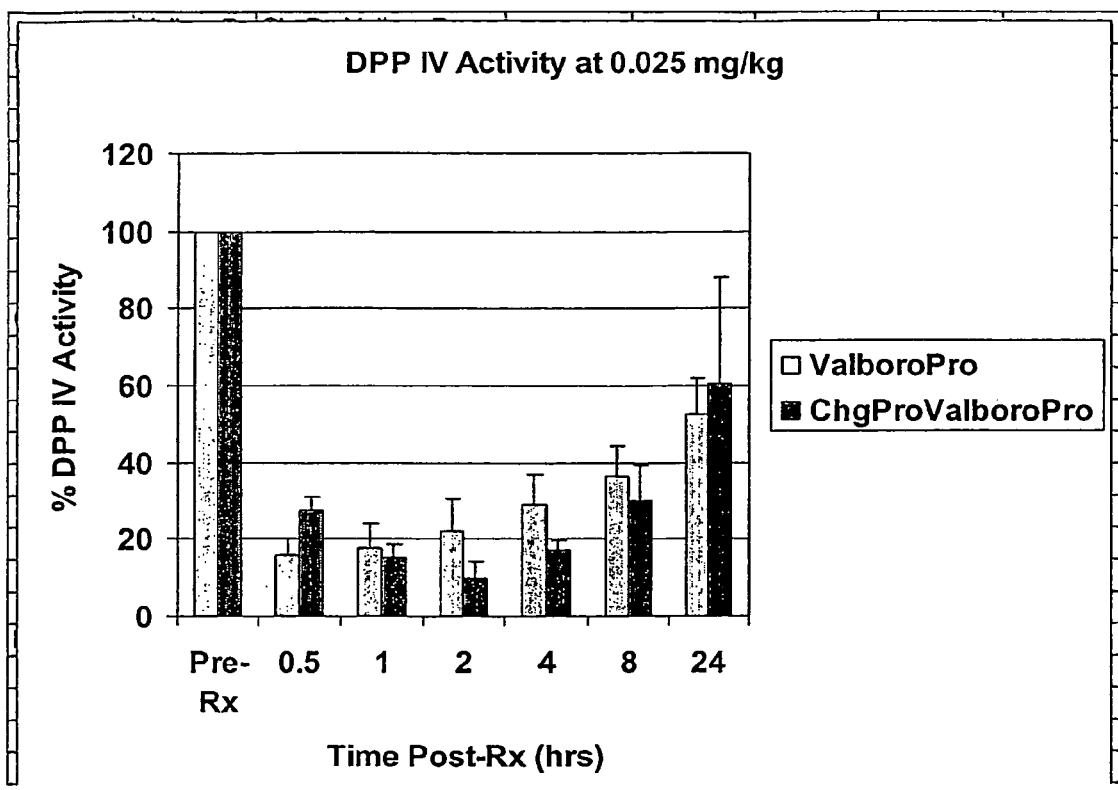
Figure 62   ChgProValboroPro is more potent, longer acting, and safer than ValboroPro in vivo in rats. Each bar represents the average of four animals

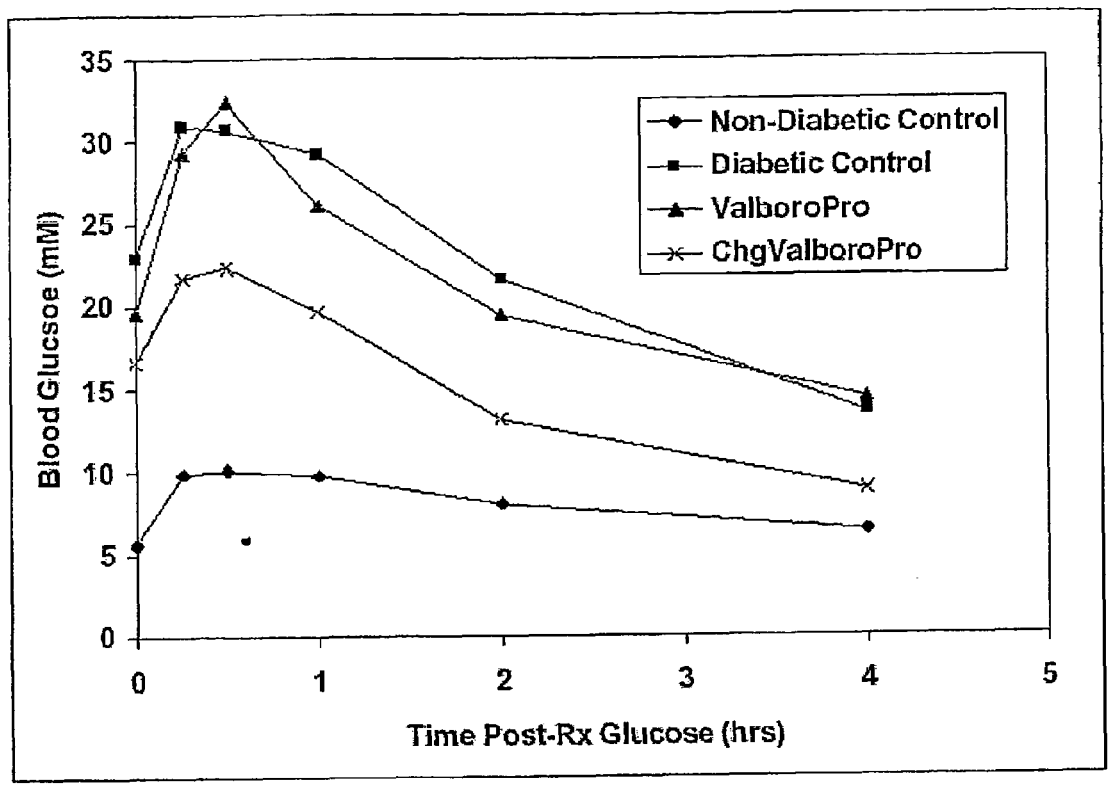
Figure 63   ChgProValboroPro performs better than ValboroPro in oral glucose tolerance tests in db/db mice at a single oral dose of 0.05 mg/kg. Test articles given three hours before oral glucose challenge at T = 0 on above graph. Each time point represents the average of five mice.

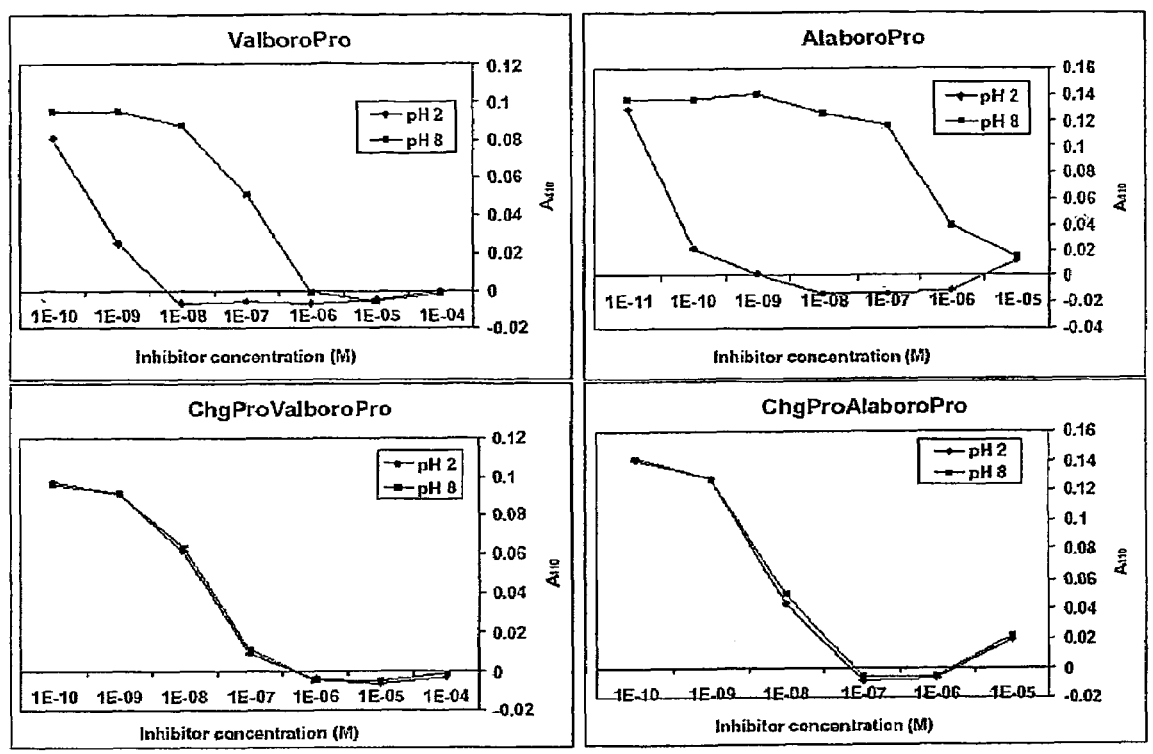
Figure 64 Smart prodrug molecule versions of potent DPP IV inhibitors exhibit increased potency at high pH and pH independence in in vitro DPP IV inhibition assays

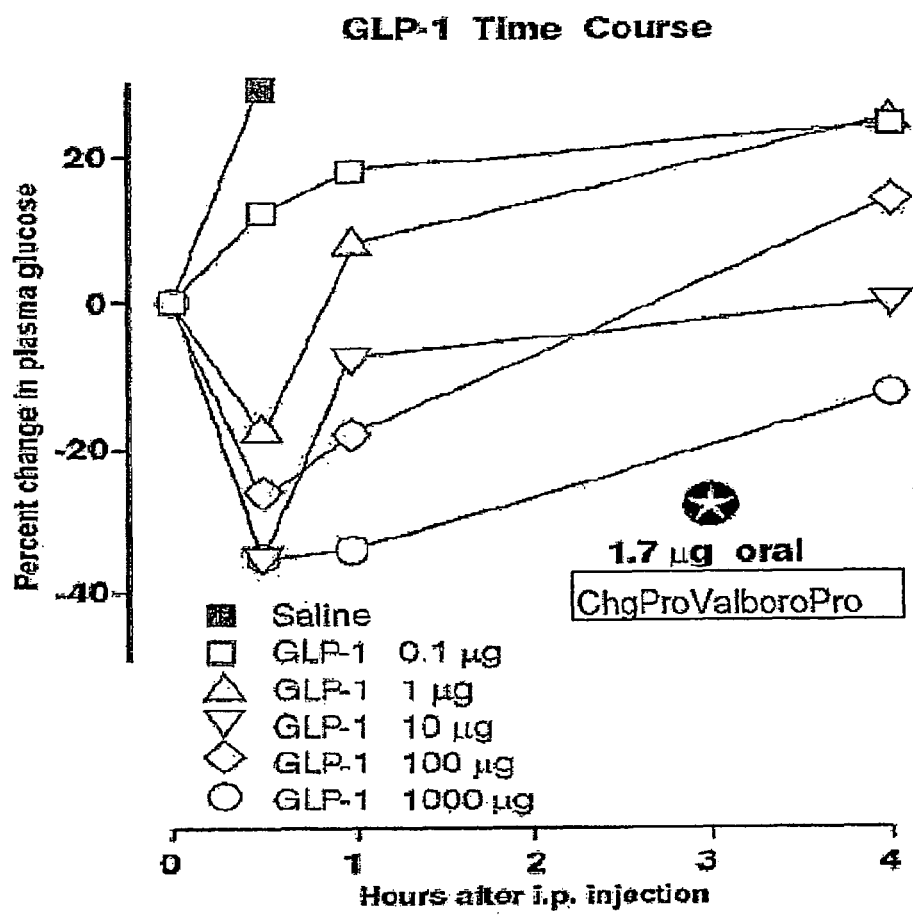
Figure 65  ChgProValboroPro outperforms GLP-1 in lowering fasting blood glucose in db/db mice. A dose of 1.7 mg corresponds to the 0.05 mg/kg dose.

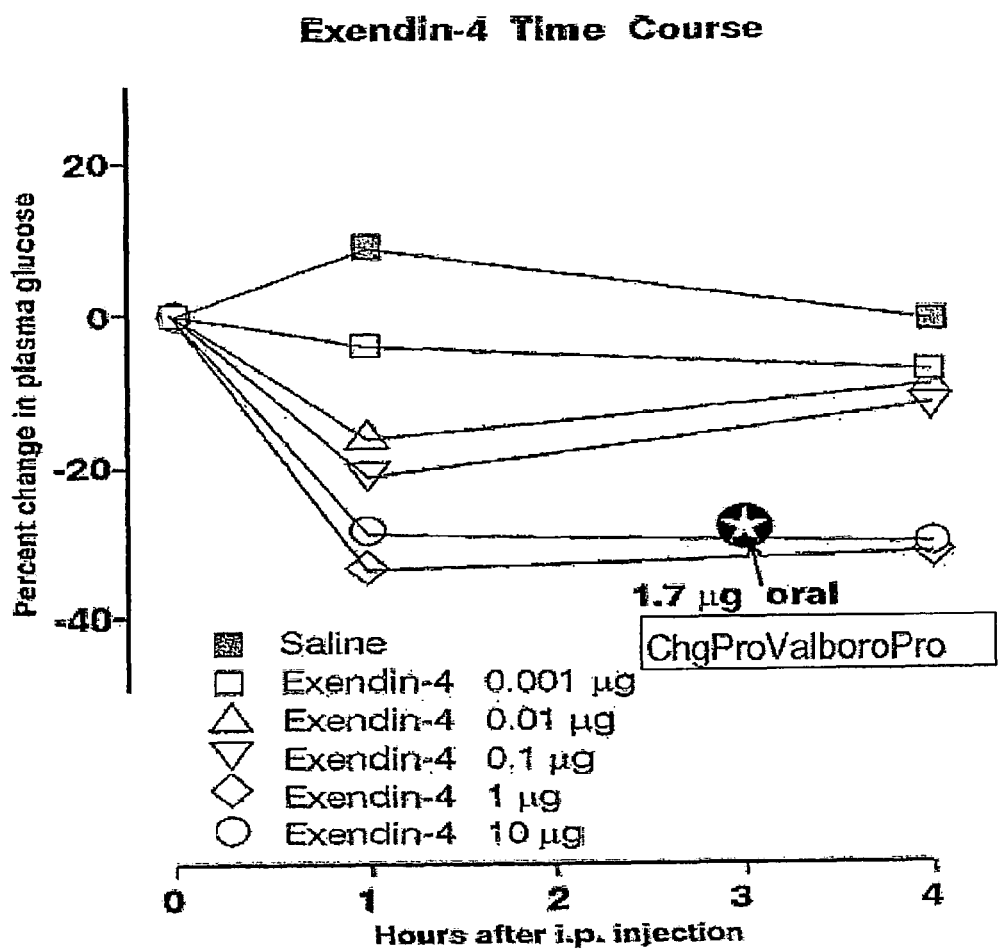

(Exendin-4 data from Fig. 1B in *Diabetes*, 48, 1028 (1999))

Figure 66  ChgProValboroPro is as effective as exendin-4 in lowering fasting blood glucose in diabetic mice. Exendin is in phase 3 clinical trials for the treatment of type 2 diabetes (Amylin). Exendin-4 is widely regarded as the most powerful agent currently know for lowering fasting blood glucose levels and for improving glycemic control in diabetics.

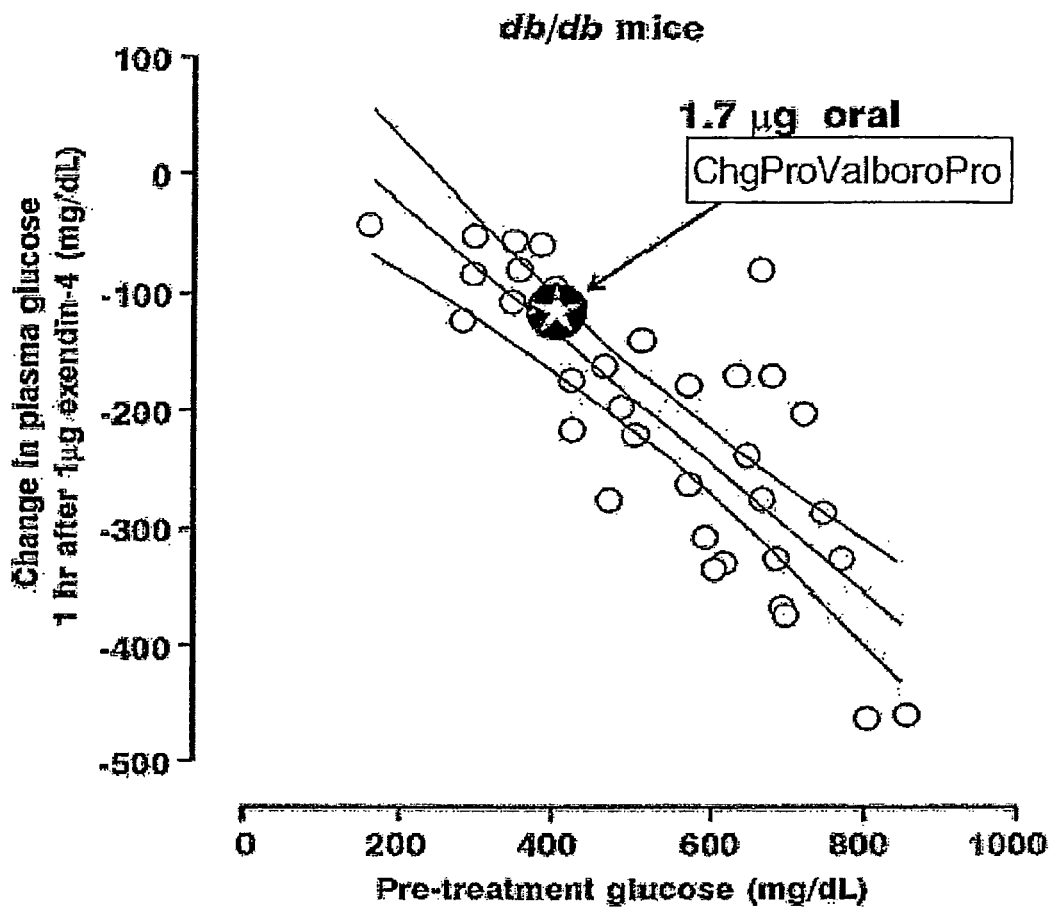
(Exendin-4 data from Fig. 2A in *Diabetes*, 48, 1028 (1999))
Figure 67  The greater the hyperglycemia the greater is the effect exendin-4 exerts in lowering fasting blood glucose. This shows that ChgProValboroPro does about what the highest dose of exendin-4 could be expected to do in the db/db mice to which ChgProValboroPro was given.

| Inhibitor | $K_i$ (pM) |
|---|---|
| Ala-boroPro | 26 (15) |
| Phe-boroPro | 61 (15) |
| Pro-boroPro | 73 (21) |
| Val-boroPro | 177 (32) |

Figure 68  $K_i$ values for DPIV inhibitors. $K_i$ values measured in 0.1 HEPES pH 8.0, 0.14 M NaCl at 23 C with 200 mM AlaPro-P-nitroanalide as the substrate. The numbers in the parentheses are the standard errors.

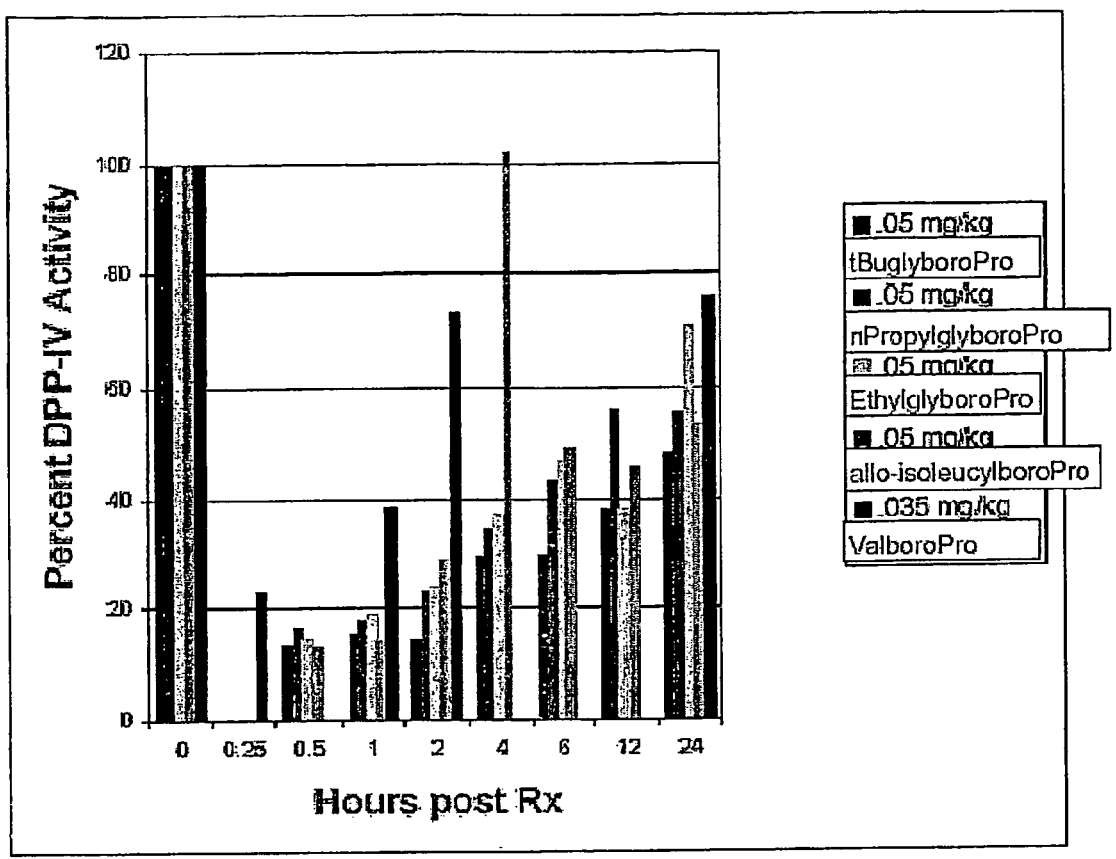
Figure 69  Activity profiles for selected DPIV inhibitors. $K_i$ values measured in 0.1 HEPES pH 8.0, 0.14 M NaCl at 23 C with 200 mM AlaPro-P-nitroanalide as the substrate. The numbers in the parentheses are the standard errors.

US 7,691,967 B2

SMART PRO-DRUGS OF SERINE PROTEASE INHIBITORS

This application is a national stage filing under 35 U.S.C. 371 of International Application PCT/US03/013561, filed Apr. 30, 2003, which designated the United States and which claims the benefit of U.S. provisional application No. 60/376,636, filed Apr. 30, 2002. The entire teachings of the referenced Applications are incorporated herein by reference. International Application PCT/US03/013561 was published under PCT Article 21(2) in English.

BACKGROUND OF THE INVENTION

Proteases are enzymes that cleave proteins at single, specific peptide bonds. Proteases can be classified into four generic classes: serine, thiol or cysteinyl, acid or aspartyl, and metalloproteases (Cuypers et al., J. Biol. Chem. 257:7086 (1982)). Proteases are essential to a variety of biological activities, such as digestion, formation and dissolution of blood clots, reproduction and the immune reaction to foreign cells and organisms. Aberrant proteolysis is associated with a number of disease states in man and other mammals. In many instances, it is beneficial to disrupt the function of one or more proteolytic enzymes in the course of therapeutically treating an animal.

The binding site for a peptide substrate consists of a series of "specificity subsites" across the surface of the enzyme. The term "specificity subsite" refers to a pocket or other site on the enzyme capable of interacting with a portion of a substrate for the enzyme. In discussing the interactions of peptides with proteases, e.g., serine and cysteine proteinases and the like, the present application utilizes the nomenclature of Schechter and Berger [(1967) Biochem. Biophys. Res. Commun. 27:157-162)]. The individual amino acid residues of a substrate or inhibitor are designated P1, P2, etc. and the corresponding subsites of the enzyme are designated S1, S2, etc, starting with the carboxy terminal residue produced in the cleavage reaction. The scissile bond of the substrate is amide bond between S1-S1' of the substrate. Thus, for the peptide Xaa1-Xaa2-Xaa3-Xaa4 which is cleaved between the Xaa3 and Xaa4 residues, the Xaa3 residue is referred to as the P1 residue and binds to the S1 subsite of the enzyme, Xaa2 is referred to as the P2 residue and binds to the S2 subsite, and so forth.

Dipeptidyl peptidase IV (DPIV), for example, is a serine protease which cleaves N-terminal dipeptides from a peptide chain containing, preferably, a proline residue in the penultimate position, e.g., in the P1 position. DPIV belongs to a group of cell-membrane-associated peptidases and, like the majority of cell-surface peptidases, is a type II integral membrane protein, being anchored to the plasma membrane by its signal sequence. DPIV is found in a variety of differentiated mammalian epithelia, endothelia and hemapoetic cells and tissues, including those of lymphoid origin where it is found specifically on the surface of CD4+ T cells. DPIV has been identified as the leukocyte differentiation marker CD26.

Proteosomes are serine proteases responsible for the majority of intracellular protein turnover in eukaryotic cells, including proteolytic degradation of damaged, oxidized or misfolded proteins, as well as processing or degradation of key regulatory proteins required for various cellular functions, such as, e.g., cell cycle progression. For example, the 26S proteosome is a multi-catalytic protease comprising at its catalytic core the 20s proteosome, a multi-subunit complex of approximately 700 kDa molecular weight. While serving an essential physiological role, the proteosome is also responsible for the inappropriate or accelerated protein degradation that occurs as a result or cause of pathological conditions in which normal cellular processes become disregulated. One notable example is cancer, in which the unregulated proteosome-mediated degradation of cell cycle regulatory proteins, including cyclins, cyclin dependent kinase inhibitors, and tumor suppressor genes, results in accelerated and uncontrolled mitosis, thereby promoting cancer growth and spread. (Goldberg et al. 1995 Chem. & Biol. 2:503-508; Coux et al. 1996 Annu. Rev. Biochem. 65:801-847; Deshaies 1995 Trends Cell Biol. 5:428-434). The inhibition of the proteosome enzymatic function holds promise in arresting or blunting the disease progression in disease states such as cancer or inflammation.

Proteosome inhibitors, e.g., lactacystin and its analogs, have been shown to block the development of the preerythrocytic and erythrocytic stages of *Plasmodium* spp, the malaria parasites. During both its hepatic and erythrocytic stages the parasite undergoes radical morphological changes and many rounds of replication, events that likely require proteosome activity. Lactacystin has been found to covalently modify the catalytic N-terminal threonines of the active sites of proteosomes, inhibiting the activity of all proteosomes examined, including those in mammalian cells, protozoa, and archeae. (Gantt et al. 1998 Antimicrob Agents Chemother. 42:2731-2738).

The human fibroblast activation protein (FAPα) is a $M_r$ 95,000 cell surface molecule originally identified with monoclonal antibody (mAb) F19 (Rettig et al. 1988 Proc. Natl. Acad. Sci. USA 85:3110-3114; Rettig et al. 1993 Cancer Res. 53:3327-3335). The FAPα cDNA codes for a type II integral membrane protein with a large extracellular domain, transmembrane segment, and short cytoplasmic tail (Scanlan et al. 1994 Proc. Natl. Acad. Sci. USA 91:5657-5661; WO 97/34927). FAPα shows 48% amino acid sequence identity to the T-cell activation antigen CD26, also known as dipeptidyl peptidase IV (DPP IV), a membrane-bound protein with dipeptidyl peptidase activity (Scanlan et al.). FAPα has enzymatic activity and is a member of the serine protease family, with serine 624 being critical for enzymatic function (WO 97/34927). Work using a membrane overlay assay revealed that FAPα dimers are able to cleave Ala-Pro-7-amino-4-trifluoromethyl coumarin, Gly-Pro-7-amino-4-trifluoromethyl coumarin, and Lys-Pro-7-amino-4-trifluoromethyl coumarin dipeptides (WO 97/34927).

FAPα is selectively expressed in reactive stromal fibroblasts of many histological types of human epithelial cancers, granulation tissue of healing wounds, and malignant cells of certain bone and soft tissue sarcomas. Normal adult tissues are generally devoid of detectable FAPα, but some foetal mesenchymal tissues transiently express the molecule. In contrast, most of the common types of epithelial cancers, including >90% of breast, non-small-cell lung, and colorectal carcinomas, contain FAPα-reactive stromal fibroblasts (Scanlan et al.). These FAPα+ fibroblasts accompany newly formed tumor blood vessels, forming a distinct cellular compartment interposed between the tumor capillary endothelium and the basal aspect of malignant epithelial cell clusters (Welt et al. 1994 J. Clin. Oncol. 12(6):1193-1203). While FAPα+ stromal fibroblasts are found in both primary and metastatic carcinomas, the benign and premalignant epithelial lesions tested (Welt et al.), such as fibroadenomas of the breast and colorectal adenomas, only rarely contain FAPα+ stromal cells. Based on the restricted distribution pattern of FAPα in normal tissues and its uniform expression in the supporting stroma of many malignant tumors, clinical trials with $^{131}$I-labeled mAb F19 have been initiated in patients with metastatic colon carcinomas (Welt et al.)

SUMMARY OF THE INVENTION

The present invention relates to prodrugs of protease inhibitors, such as inhibitors of proteosome, DPP IV, FAPα and the like. These "pro-inhibitors" are activated, i.e., cleaved by an "activating protease" to release an active inhibitor moiety in proximity to a "target protease". The identity of activating protease and target protease can be the same (such pro-inhibitors being refered to as "Target-Activated Smart Protease Inhibitors" or "TASPI") or different (e.g., "Target-Directed Smart Protease Inhibitors" or "TDSPI"). After activation of the pro-inhibitor, the active inhibitor moiety can self-inactivate by, e.g., intramolecular-cyclization or cis-trans isomerization.

These pro-inhibitors of the present invention exhibit surprising characterisitcs including improved potency, extended duration of action, improved stability, and/or a decrease in toxicity.

In certain preferred embodiments, the present invention provides pro-inhibitors which inhibit post-proline cleaving enzymes, such as inhibitors of dipeptidyl peptidase IV (DPP IV), as well as pharmaceutical compositions thereof, and methods for using such inhibitors. Such pro-inhibitors of the present invention can be used as part of treatments for a variety of disorders/conditions, such as those which are mediated by DPP IV. For instance, the subject inhibitors can be used to up-regulate GIP and GLP-1 activities, e.g., by increasing the half-life of those hormones, as part of a treatment for regulating glucose levels and/or metabolism, e.g., to reduce insulin resistance, treat hyperglycemia, hyperinsulinemia, obesity, hyperlipidemia, hyperlipoprotein-emia (such as chylomicrons, VLDL and LDL), and to regulate body fat and more generally lipid stores, and, more generally, for the improvement of metabolism disorders, especially those associated with diabetes, obesity and/or atherosclerosis.

While not wishing to bound by any particular theory, it is observed that compounds which inhibit DPP IV are, correlatively, able to improve glucose tolerance, though not necessarily through mechanisms involving DPP IV inhibition per se. Indeed, the applicant has previously demonstrated an effect in mice lacking a GLP-1 receptor suggesting that the subject method may not include a mechanism of action directly implicating GLP-1 itself, though it has not been ruled out that GLP-1 may have other receptors. However, in light of the correlation with DPP IV inhibition, in preferred embodiments, the subject method utilizes an agent with a Ki for DPP IV inhibition of 50.0 nm or less, more preferably of 10.0 nm or less, and even more preferably of 1.0, 0.1 or even 0.01 nM or less. Indeed, inhibitors with Ki values in the picomolar and even femtomolar range are contemplated. Thus, while certain of the pro-inhibitors described herein, for convenience, as "DPP IV inhibitors", it will be understood that such nomenclature is not intending to limit the subject invention to a particular mechanism of action.

Certain of the subject compounds have extended duration. Accordingly, in certain preferred embodiments, the inhibitor(s) is selected, and the amount of inhibitor formulated, to provide a dosage which inhibits serum DPP IV levels by at least 50 percent for at least 4 hours after a single dose, and even more preferably for at least 8 hours or even 12 or 16 hours after a single dose.

For instance, in certain embodiments the method involves administration of a DPP IV pro-inhibitor, preferably at a predetermined time(s) during a 24-hour period, in an amount effective to improve one or more aberrant indices associated with glucose metabolism disorders (e.g., glucose intolerance, insulin resistance, hyperglycemia, hyperinsulinemia and Type I and II diabetes).

In other embodiments, the method involves administration of a DPP IV pro-inhibitor in an amount effective to improve aberrant indices associated with obesity. Fat cells release the hormone leptin, which travels in the bloodstream to the brain and, through leptin receptors there, stimulates production of GLP-1. GLP-1, in turn, produces the sensation of being full. The leading theory is that the fat cells of most obese people probably produce enough leptin, but leptin may not be able to properly engage the leptin receptors in the brain, and so does not stimulate production of GLP-1. There is accordingly a great deal of research towards utilizing preparations of GLP-1 as an appetite suppressant. The subject method provides a means for increasing the half-life of both endogenous and ectopically added GLP-1 in the treatment of disorders associated with obesity.

In a more general sense, the present invention provides methods and pro-inhibitor compositions for altering the pharmokinetics of a variety of different polypeptide hormones by inhibiting the proteolysis of one or more peptide hormones by DPP IV or some other proteolytic activity. Post-secretory metabolism is an important element in the overall homeostasis of regulatory peptides, and the other enzymes involved in these processes may be suitable targets for pharmacological intervention by the subject method.

For example, the subject method can be used to increase the half-life of other proglucagon-derived peptides, such as glicentin (corresponding to PG 1-69), oxyntomodulin (PG 33-69), glicentin-related pancreatic polypeptide (GRPP, PG 1-30), intervening peptide-2 (IP-2, PG 111-122amide), and glucagon-like peptide-2 (GLP-2, PG 126-158).

GLP-2, for example, has been identified as a factor responsible for inducing proliferation of intestinal epithelium, See, for example, Drucker et al. (1996) PNAS 93:7911. The subject DPP IV pro-inhibitors can be used as part of a regimen for treating injury, inflammation or resection of intestinal tissue, e.g., where enhanced growth and repair of the intestinal mucosal epithelial is desired, such as in the treatment of Crohn's disease or Inflammatory Bowel Disease (IBD).

DPP IV has also been implicated in the metabolism and inactivation of growth hormone-releasing factor (GHRF). GHRF is a member of the family of homologous peptides that includes glucagon, secretin, vasoactive intestinal peptide (VIP), peptide histidine isoleucine (PHI), pituitary adenylate cyclase activating peptide (PACAP), gastric inhibitory peptide (GIP) and helodermin. Kubiak et al. (1994) Peptide Res 7:153. GHRF is secreted by the hypothalamus, and stimulates the release of growth hormone (GH) from the anterior pituitary. Thus, the subject method can be used to improve clinical therapy for certain growth hormone deficient children, and in clinical therapy of adults to improve nutrition and to alter body composition (muscle vs. fat). The subject method can also be used in veterinary practice, for example, to develop higher yield milk production and higher yield, leaner livestock.

Likewise, the DPP IV pro-inhibitors of the subject invention can be used to alter the plasma half-life of secretin, VIP, PHI, PACAP, GIP and/or helodermin. Additionally, the subject method can be used to alter the pharmacokinetics of Peptide YY and neuropeptide Y, both members of the pancreatic polypeptide family, as DPP IV has been implicated in the processing of those peptides in a manner which alters receptor selectivity.

In other embodiments, the subject DPP IV pro-inhibitors can be used to stimulate hematopoiesis.

In still other embodiments, the subject DPP IV pro-inhibitors can be used to inhibit growth or vascularization of transformed cells/tissues, e.g., to inhibit cell proliferation such as that associated with tumor growth and metastasis, and for inhibiting angiogenesis in an abnormal proliferative cell mass.

In yet other embodiments, the subject DPP IV pro-inhibitors can be used to reduce immunological responses, e.g., as an immunosuppressant.

In yet other examples, the DPP IV pro-inhibitors according to the present invention can be used to treat CNS maladies such as strokes, tumors, ischemia, Parkinson's disease, memory loss, hearing loss, vision loss, migraines, brain injury, spinal cord injury, Alzheimer's disease and amyotrophic lateral sclerosis (which has a CNS component). Additionally, the DPP IV pro-inhibitors can be used to treat disorders having a more peripheral nature, including multiplesclerosis and diabetic neuropathy.

Another aspect of the present invention relates to pharmaceutical compositions of the subject post-proline cleaving enzyme inhibitors, particularly DPP IV pro-inhibitors, and their uses in treating and/or preventing disorders which can be improved by altering the homeostasis of peptide hormones. In a preferred embodiment, such DPP IV pro-inhibitors have hypoglycemic and antidiabetic activities, and can be used in the treatment of disorders marked by aberrant glucose metabolism (including storage). In particular embodiments, the compositions of the subject methods are useful as insulinotropic agents, or to potentiate the insulinotropic effects of such molecules as GLP-1. In this regard, certain embodiments of the present compositions can be useful for the treatment and/or prophylaxis of a variety of disorders, including one or more of: hyperlipidemia, hyperglycemia, obesity, glucose tolerance insufficiency, insulin resistance and diabetic complications.

BRIEF DESCRIPTION OF THE FIGURES

FIG. 1 Structures of AlaboroPro and ProboroPro in alignment with CD26/DPP IV cleavable peptide substrate FIG. 2 pH dependent conformational equilibrium of Xaa-boroPro's.

FIG. 3 pH dependence of DPP IV inhibition by Val-boro-Pro (top left) and Ala-boroPro (top right) compared to the pH independence of the corresponding smart drugs. Inhibitors were incubated overnight in pH 2 or pH 8 solutions and then added directly to an enzyme assay solution at pH8.0.

FIG. 4 Examples of pH-dependent conformational equilibrium for different electron deficient functional groups.

FIG. 5 Cyclohexylglycine-Proline (or Proline analog)-Valine-boroProline

FIG. 6 Serum DPP IV activity in rats as a function of time following three different doses of CHG-Pro-Val-boroPro given orally. Results demonstrate that CHG-Pro-Val-boro-Pro is orally active.

FIG. 7 Serum DPP IV activity in rats as a function of time following three different doses of CHG-Pro-Val-boroPro given subcutaneously.

FIG. 8 Serum DPP IV activity in rats as a function of time following a single oral dose of 0.025 mg/kg.

FIG. 9 Oral glucose tolerance test (OGTT) in DB/DB mice given four hours post oral dose of test agents at 0.5 mg/kg Val-boroPro.

FIG. 10 Serum DPP IV activity in rats as a function of time at 1 hr and 4 hr intervals following a single oral dose of 0.05 mg/kg.

FIG. 11 Structure of Millenium's LDP 341 Proteosome Protease Inhibitor

FIG. 12 $IC_{50}$ concentration graphs of Pro-boro-Pro and CBZ-Ala-boro-Pro

FIG. 13 $IC_{50}$ pH dependance of 4-aminomethylbenzylboronic acid and ethyl Gly-boro-Pro FIG. 14 $IC_{50}$ pH dependance of propyl Gly-boroPro and t-butyl Gly-boroPro.

FIG. 15 $IC_{50}$ concentration graph of Pro-boro-Pro

FIG. 16 Inhibition profile of AspProGlyboroPro against DPP IV at selected pHs

FIG. 17 Inhibition profile of Suc-AlaAlaProPheAlaboroPro against chymotrpsin at selected pHs FIGS. 18a-c Inhibition profile of HisAlaAspboroPro against DPP IV at selected pHs at different time intervals FIGS. 19a-g. Time resolved inhibitory potency of PheProAlaboroPro against DPP IV at selected pHs FIG. 20. Inhibition profile of LysProPheboroLeu against DPP IV at selected pHs.

FIG. 21. Inhibition profile of TyrProSerboroPro against DPP IV at selected pHs.

FIGS. 22a-g Inhibition profile of ChgAla-tBugboroPro against DPP IV at selected pHs at different time intervals FIG. 23 Inhibition profile of TyrProTyrProPheboroLeu against DPP IV FIGS. 24a-g Inhibition profile of Glypro-N-Me-Gly-Boro-Pro against DPP IV at selected pHs at different time intervals FIG. 25 Inhibition profile of TyrProPheAlaboroPro against DP IV at selected pHs.

FIG. 26 Inhibition profile of tBugProAlaboroPro against DP IV at selected pHs.

FIG. 27 Inhibition profile of ChgProChgboroPro against DP IV at selected pHs.

FIG. 28 inhibition profile of Beta EBP against DP IV at selected pHs.

FIG. 29 Inhibition profile of ChgHypEtgboroPro against DP IV at selected pHs.

FIG. 30 Inhibition profile of ChgPipEtgboroPro against DP IV at selected pHs.

FIG. 31 Inhibition profile of ChgAzeEtgboroPro against DP IV at selected pHs.

FIGS. 32a-g Inhibition profile of ChgThz2EtgboroPro against DP IV at selected pHs at different time intervals FIGS. 33a-f Inhibition profile of ChgThz4EtgboroPro against DP IV at selected pHs at different time intervals FIG. 34 Inhibition profile of NH3-ChgProAbuN(me)boro-Gly against DP IV at selected pHs FIGS. 35a-f Inhibition profile of HisAlaEtgboroPro against DP IV at selected pHs at different time intervals FIGS. 36a-g Inhibition profile of ChgAib-EthylGly-boro-Pro against DP IV at selected pHs at different time intervals FIGS. 37a-g Inhibition profile of ChgPro-tBug-boroAla against DP IV at selected pHs at different time intervals FIGS. 38a-g Inhibition profile of ChgCpg-EthylGly-boro-Pro against DP IV at selected pHs at different time intervals FIG. 39 Inhibition profile of ChgAla-Etg-boroPro against DP IV at selected pHs FIGS. 40a-g Inhibition profile of Tyr-(D)-ProPheboroPro against DP IV at selected pHs at different time intervals FIGS. 41a-g Inhibition profile of ChgPro-tBug-boroPro against DP IV at selected pHs at different time intervals FIG. 42 Inhibition profile of PhePro-Ala-boroPro against DP IV at selected pHs.

FIG. 43 Inhibition profile of TyrProAlaboroPro against DP IV at selected pHs.

FIG. 44 Inhibition profile of ProProProboroPro against DP IV at selected pHs.

FIG. 45 Inhibition profile of AlaProProboroPro against DP IV at selected pHs.

FIG. 46 Inhibition profile of GlyProProboroPro against DP IV at selected pH

FIG. 47 Smart drug compounds

FIG. 48 Smart drug compounds

FIG. 49 Smart drug compounds

FIG. 50 Smart drug compounds

FIGS. 51*a-c* In vivo time resolved inhibition of DPP IV by ChgProAlaboroPro, N-Me-PheProAlaboroPro and SarDhpAlaboroPro at different dosage levels FIGS. 52*a,b* In vivo time resolved inhibition of DPP IV by PheProAlaboroPro at different dosage levels FIG. 53 Blood glucose levels in diabetic mice following treatment with PheProAlaboroPro FIG. 54. Inhibition profile of N-Me-PheProAlaboroPro against DPP IV FIG. 55 Time resolved inhibition of DPP IV by N-Me-PheProAlaboroPro at selected pHs.

FIGS. 56*a-h*. Inhibition profile of SarDhpAlaboroPro against DPP IV at selected pHs at different times FIG. 57 In vivo activity of PheProAlaboroPro FIG. 58 Increased glucose-stimulated insulin and GLP-1 in DPP IV −/− mice FIG. 59 GLP-1 signaling is not required for action of DPP IV inhibitors FIG. 60 Comparisons of time resolved potencies of various DPP IV inhibitors in mice FIG. 61 Comparison between ChgProValboroPro and Val-boroPro in blocking DPP IV catalytic activity in vivo in mice.

FIG. 62 ChgProValboroPro is more potent, longer acting, and safer than ValboroPro in vivo in rats. Each bar represents the average of four animals FIG. 63 ChgproValboroPro performs better than Valboro-Pro in oral glucose tolerance tests in db/db mice at a single oral dose of 0.05 mg/kg. Test articles given three hours before oral glucose challenge at T=0 on above graph. Each time point represents the average of five mice.

FIG. 64 Smart pro-inhibitor molecule versions of potent DPP IV inhibitors exhibit increased potency at high pH and pH independence in in vitro DPP IV inhibition assays FIG. 65 ChgProValboroPro outperforms GLP-1 in lowering fasting blood glucose in db/db mice. A dose of 1.7 mg corresponds to the 0.05 mg/kg dose.

FIG. 66 ChgProValboroPro is as effective as exendin-4 in lowering fasting blood glucose in diabetic mice.

FIG. 67 The greater the hyperglycemia the greater is the effect exendin-4 exerts in lowering fasting blood glucose.

FIG. 68 Ki values for DPP IV inhibitors.

FIG. 69 Activity profiles for selected DPP IV inhibitors.

DETAILED DESCRIPTION OF THE INVENTION

I. Overview

Dipeptide boronic acid inhibitors of the type Xaa-boroPro, where Xaa refers to any natural or non-naturally occurring amino acid, and boroPro refers to the analog of proline in which the C-terminal carboxylate has been replaced by a boronyl group (FIG. 1), are very potent inhibitors of dipeptidyl amino peptidase type IV (DPP IV). However, these inhibitors undergo a pH dependent conformational equilibration between an open chain conformer and cyclic conformer (FIG. 2). The open chain form predominates under acidic condition while the cyclic form predominates at neutral and basic conditions. The open chain form is the one active as an enzyme inhibitor; the cyclic form is substantially inactive as an enzyme inhibitor. Similar reversible intraconversions occur with other dipeptide inhibitors, such as nitriles, aldehydes, etc, when the dipeptide includes a free amino terminus. The net result of the cyclization reaction, which can occur at physiological pH's, is to reduce the effectiveness, potency and duration of action of these molecules as enzyme inhibitors and also therefore decrease their attractiveness as potential drugs.

The rates of inter-conversion between open and cyclic forms, and the equilibrium constant ($K_{eq}$=[cyclic]/[open]) depend in part on pH. For example a boroAlanine, boroLeucine, boroArginine, or any natural or non-naturaly occurring amino acid having a boronyl group in place of its C-terminal carboxylate will also undergo cyclization when incorporated into dipeptide or dipeptide-like structures (such as $NH_2$-Xaa-boroAla, $NH_2$-Xaa-boroLeu, $NH_2$-Xaa-boroArg), although the intrinsic rates and equilibrium position will differ. The $T_{1/2}$ for the inter-conversion reaction may vary from a few seconds to minutes when boroXaa is boroGly or boroAla, to hours when it is boroPro. (Pro-boroPro has $T_{1/2}$ of 2 & 8 hours respectively for the cyclization and uncyclization reactions). The equilibrium constant $K_{eq}$ can vary from 0.01 to 0.001 (in favor of the open conformer) at pH 2.0 to 100 to 1000 (in favor of the cyclic conformer) at pH 7.2 (i.e., physiological pH). FIG. 3 illustrates this phenomenon for Ala-boroPro, Pro-boroPro and Val-boroPro as it demonstrates that all three molecules are more effective as inhibitors of DPP IV when pre-incubated at low pH than at high pH. Importantly, the molecules have a relatively low rates of decomposition, even under conditions in which the inactivae conformer is present as the predominates. The inhibitory activity of the open chain conformer can be restored if the molecules incubated at high pH are re-equilibrated in low pH buffer for a time sufficient to re-establish the low pH equilibrium. The time required to restore full activity varies from several hours to several days.

In certain embodiments of the present invention, dipeptide and dipeptide-like transition state analogue inhibitors with other electron deficient functional groups in place of the boronyl group will also exhibit similar reversible cyclization reactions with consequent attenuation of their potency. These include, for example nitriles (CN), aldehydes (CHO), trifluoromethylketones ($COCF_3$), and alpha keto amides (CO-$CONH_2$) (FIG. 4). In addition, the reversible self-inactivation phenomenon may also be attributable, although possibly to a lesser degree, to cis/trans isomerization, especially for dipeptides and dipeptide-like transition state analogue inhibitors which include proline at P1 position. Thus, though the details may vary considerably from one electrophilic transition state mimetic to another, the cyclization or cis-trans isomerization reaction can nonetheless be expected in each case to reduce the effectiveness of the corresponding inhibitors relative to what the effectiveness would be if cyclization or cis-trans isomerization did not occur. The reduction in effectiveness, i.e. the ratio of $K_i$'s of the active inhibitor to the self-inactivated inhibitor, can vary from factors of as little as two or so, to many thousands and even greater.

In certain preferred embodiments of the present invention, the deficiency, or handicap, of the dipeptide transition state structures as enzyme inhibitors owing to the cyclization reaction is eliminated, while at the same time making use of the cyclization reaction to further improve the specificity, safety and shel-life of these entities as drugs. The new molecules of the invention have highly desirable attributes that in combination are unprecedented, and which therefore represent a wholly new class of molecules that we term "smart" protease inhibitors. These attributes include a non-inhibitory prodrug that release a "hyper"-active inhibitor in the vicinity of the target enzyme which, when it diffuses away from the target enzyme, will cyclize and therefore inactivate itself.

II. Definitions

For convenience, certain terms employed in the specification, examples, and appended claims are collected here.

A. Chemical Submoieties

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

'Acyl' refers to a group suitable for acylating a nitrogen atom to form an amide or carbamate, a carbon atom to form a ketone, a sulfur atom to form a thioester, or an oxygen atom to form an ester group, e.g.+a hydrocarbon attached to a —C(═O)— moiety. Preferred acyl groups include benzoyl, acetyl, tert-butyl acetyl, pivaloyl, and trifluoroacetyl. More preferred acyl groups include acetyl and benzoyl. The most preferred acyl group is acetyl.

The term 'acylamino' is art-recognized and preferably refers to a moiety that can be represented by the general formula:

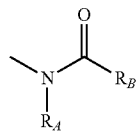

wherein $R_A$ and $R_B$ each independently represent hydrogen or a hydrocarbon substituent, such as alkyl, heteroalkyl, aryl, heteroaryl, carbocyclic aliphatic, and heterocyclic aliphatic.

The terms 'amine' and 'amino' are art-recognized and refer to both unsubstituted and substituted amines as well as quaternary ammonium salts, e.g., as can be represented by the general formula:

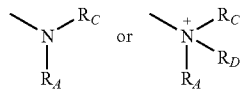

wherein $R_A$, $R_C$, and $R_D$ each independently represent hydrogen or a hydrocarbon substituent, or $R_A$ and $R_C$ taken together with the N atom to which they are attached complete a heterocycle having from 4 to 8 atoms in the ring structure. In preferred embodiments, none of $R_A$, $R_C$, and $R_D$ is acyl, e.g., $R_A$, $R_C$, and $R_D$ are selected from hydrogen, alkyl, heteroalkyl, aryl, heteroaryl, carbocyclic aliphatic, and heterocyclic aliphatic. The term 'alkylamine' as used herein means an amine group, as defined above, having at least one substituted or unsubstituted alkyl attached thereto. Amino groups that are positively charged (e.g., $R_D$ is present) are referred to as 'ammonium' groups. In amino groups other than ammonium groups, the amine is preferably basic, e.g., its conjugate acid has a $pK_a$ above 7.

The terms 'amido' and 'amide' are art-recognized as an amino-substituted carbonyl, such as a moiety that can be represented by the general formula:

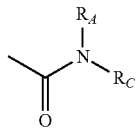

wherein $R_A$ and $R_C$ are as defined above. In certain embodiments, the amide will include imides.

'Alkyl' refers to a saturated or unsaturated hydrocarbon chain having 1 to 18 carbon atoms, preferably 1 to 12, more preferably 1 to 6, more preferably still 1 to 4 carbon atoms. Alkyl chains may be straight (e.g., n-butyl) or branched (e.g., sec-butyl, isobutyl, or t-butyl). Preferred branched alkyls have one or two branches, preferably one branch. Preferred alkyls are saturated. Unsaturated alkyls have one or more double bonds and/or one or more triple bonds. Preferred unsaturated alkyls have one or two double bonds or one triple bond, more preferably one double bond. Alkyl chains may be unsubstituted or substituted with from 1 to 4 substituents. Preferred alkyls are unsubstituted. Preferred substituted alkyls are mono-, di-, or trisubstituted. Preferred alkyl substituents include halo, haloalkyl, hydroxy, aryl (e.g., phenyl, tolyl, alkoxyphenyl, alkyloxycarbonylphenyl, halophenyl), heterocyclyl, and heteroaryl.

The terms 'alkenyl' and 'alkynyl' refer to unsaturated aliphatic groups analogous in length and possible substitution to the alkyls described above, but that contain at least one double or triple bond, respectively.

When not otherwise indicated, the terms alkyl, alkenyl and alkynyl preferably refer to lower alkyl, alkenyl and lower alkynyl groups, respectively, e.g., having from 1-8 carbons.

The terms 'alkoxyl' and 'alkoxy' as used herein refer to an —O-alkyl group. Representative alkoxyl groups include methoxy, ethoxy, propyloxy, tert-butoxy, and the like. An 'etheR is two hydrocarbons covalently linked by an oxygen. Accordingly, the substituent of a hydrocarbon that renders that hydrocarbon an ether can be an alkoxyl, or another moiety such as —O-aryl, —O-heteroaryl, —O-heteroalkyl, —O-aralkyl, —O-heteroaralkyl, —O-carbocylic aliphatic, or —O-heterocyclic aliphatic.

An 'alkylseleno' or 'selenoalkyl' refers to a -Se-alkyl group. 'Selenoethers' more broadly refers to two hydrocarbon groups linked by a selenium atom. Accordingly, the substituent of a hydrocarbon that renders that hydrocarbon a selenoether can be an alkylseleno, or another moiety such as -Se-aryl, -Se-heteroaryl, -Se-heteroalkyl, -Se-aralkyl, -Se-heteroaralkyl, -Se-carbocylic aliphatic, or -Se-heterocyclic aliphatic.

The term 'alkylthio' refers to an —S-alkyl group. Representative alkylthio groups include methylthio, ethylthio, and the like. 'ThioetheR refers to a sulfur atom bound to two hydrocarbon substituents, e.g., an ether wherein the oxygen is replaced by sulfur. Thus, a thioether substituent on a carbon atom refers to a hydrocarbon-substituted sulfur atom substituent, such as alkylthio or arylthio, etc.

The term 'aralkyl', as used herein, refers to an alkyl group substituted with an aryl group.

'Aryl ring' refers to an aromatic hydrocarbon ring system. Aromatic rings are monocyclic or fused bicyclic ring systems, such as phenyl, naphthyl, etc. Monocyclic aromatic rings contain from about 5 to about 10 carbon atoms, preferably from 5 to 7 carbon atoms, and most preferably from 5 to 6 carbon atoms in the ring. Bicyclic aromatic rings contain from 8 to 12 carbon atoms, preferably 9 or 10 carbon atoms in the ring. The term 'aryl' also includes bicyclic ring systems wherein only one of the rings is aromatic, e.g., the other ring is cycloalkyl, cycloalkenyl, or heterocyclyl. Aromatic rings may be unsubstituted or substituted with from 1 to about 5 substituents on the ring. Preferred aromatic ring substituents include: halo, cyano, lower alkyl, heteroalkyl, haloalkyl, phenyl, phenoxy, or any combination thereof. More preferred substituents include lower alkyl, cyano, halo, and haloalkyl.

'Biohydrolyzable amide' refers to an amide moiety that is cleaved (e.g., to form a hydroxyl and a carboxylic acid) under physiological conditions. Physiological conditions include the acidic and basic environments of the digestive tract (e.g., stomach, intestines, etc.), enzymatic cleavage, metabolism, and other biological processes, and preferably refer to physiological conditions in a vertebrate, such as a mammal.

'Biohydrolyzable esteR refers to an ester moiety that is cleaved (e.g., to form a hydroxyl and a carboxylic acid) under physiological conditions. Physiological conditions include the acidic and basic environments of the digestive tract (e.g., stomach, intestines, etc.), enzymatic cleavage, metabolism, and other biological processes, and preferably refer to physiological conditions in a vertebrate, such as a mammal.

'Biohydrolyzable imide' refers to an imide moiety that is cleaved (e.g., to form a hydroxyl and a carboxylic acid) under physiological conditions. Physiological conditions include the acidic and basic environments of the digestive tract (e.g., stomach, intestines, etc.), enzymatic cleavage, metabolism, and other biological processes, and preferably refer to physiological conditions in a vertebrate, such as a mammal.

'Carbocyclic aliphatic ring' refers to a saturated or unsaturated hydrocarbon ring. Carbocyclic aliphatic rings are not aromatic. Carbocyclic aliphatic rings are monocyclic, or are fused, spiro, or bridged bicyclic ring systems. Monocyclic carbocyclic aliphatic rings contain from about 4 to about 10 carbon atoms, preferably from 4 to 7 carbon atoms, and most preferably from 5 to 6 carbon atoms in the ring. Bicyclic carbocyclic aliphatic rings contain from 8 to 12 carbon atoms, preferably from 9 to 10 carbon atoms in the ring. Carbocyclic aliphatic rings may be unsubstituted or substituted with from 1 to 4 substituents on the ring. Preferred carbocyclic aliphatic ring substituents include halo, cyano, alkyl, heteroalkyl, haloalkyl, phenyl, phenoxy or any combination thereof. More preferred substituents include halo and haloalkyl. Preferred carbocyclic aliphatic rings include cyclopentyl, cyclohexyl, cyclohexenyl, cycloheptyl, and cyclooctyl. More preferred carbocyclic aliphatic rings include cyclohexyl, cycloheptyl, and cyclooctyl.

The term 'carbonyl' is art-recognized and includes such moieties as can be represented by the general formula:

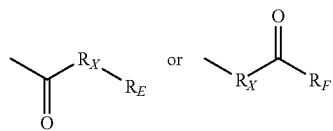

wherein $R_x$ is a bond or represents an oxygen or a sulfur, and $R_E$ represents a hydrogen, hydrocarbon substituent, or a pharmaceutically acceptable salt, $R_F$ represents a hydrogen or hydrocarbon substituent. Where $R_X$ is an oxygen and $R_E$ or $R_F$ is not hydrogen, the formula represents an 'esteR. Where $R_X$ is an oxygen, and $R_E$ is as defined above, the moiety is referred to herein as a carboxyl group, and particularly when $R_E$ is a hydrogen, the formula represents a 'carboxylic acid'. Where $R_X$ is an oxygen, and $R_F$ is hydrogen, the formula represents a 'formate'. In general, where the oxygen atom of the above formula is replaced by sulfur, the formula represents a 'thiocarbonyl' group. Where $R_X$ is a sulfur and $R_E$ or $R_F$ is not hydrogen, the formula represents a 'thioester.' Where $R_X$ is a sulfur and $R_E$ is hydrogen, the formula represents a 'thiocarboxylic acid.' Where $R_X$ is a sulfur and $R_F$ is hydrogen, the formula represents a 'thioformate.' On the other hand, where $R_X$ is a bond, $R_E$ is not hydrogen, and the carbonyl is bound to a hydrocarbon, the above formula represents a 'ketone' group. Where $R_X$ is a bond, $R_E$ is hydrogen, and the carbonyl is bound to a hydrocarbon, the above formula represents an 'aldehyde' or 'formyl' group.

'Ci alkyl' is a heteroalkyl chain having i member atoms. For example, C4 alkyls contain four carbon member atoms. C4 alkyls containing may be saturated or unsaturated with one or two double bonds (cis or trans) or one triple bond. Preferred C4 alkyls are saturated. Preferred unsaturated C4 alkyl have one double bond. C4 alkyl may be unsubstituted or substituted with one or two substituents. Preferred substituents include lower alkyl, lower heteroalkyl, cyano, halo, and haloalkyl.

'Halogen' refers to fluoro, chloro, bromo, or iodo substituents. Preferred halo are fluoro, chloro and bromo; more preferred are chloro and fluoro.

'Haloalkyl' refers to a straight, branched, or cyclic hydrocarbon substituted with one or more halo substituents. Preferred haloalkyl are C1-C12; more preferred are C1-C6; more preferred still are C1-C3. Preferred halo substituents are fluoro and chloro. The most preferred haloalkyl is trifluoromethyl.

'Heteroalkyl' is a saturated or unsaturated chain of carbon atoms and at least one heteroatom, wherein no two heteroatoms are adjacent. Heteroalkyl chains contain from 1 to 18 member atoms (carbon and heteroatoms) in the chain, preferably 1 to 12, more preferably 1 to 6, more preferably still 1 to 4. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Prefer-red unsaturated heteroalkyl have one or two double bonds or one triple bond, more preferably one double bond. Heteroalkyl chains may be unsubstituted or substituted with from 1 to about 4 substituents unless otherwise specified. Preferred heteroalkyl are unsubstituted. Preferred heteroalkyl substituents include halo, aryl (e.g., phenyl, tolyl, alkoxyphenyl, alkoxycarbonylphenyl, halophenyl), heterocyclyl, heteroaryl. For example, alkyl chains substituted with the following substituents are heteroalkyl: alkoxy (e.g., methoxy, ethoxy, propoxy, butoxy, pentoxy), aryloxy (e.g., phenoxy, chlorophenoxy, tolyloxy, methoxyphenoxy, benzyloxy, alkoxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkoxycarbonylphenylthio), amino (e.g., amino, mono- and di-C1-C3 alkylamino, methylphenylamino, methylbenzylamino, C1-C3 alkylamido, carbamamido, ureido, guanidino).

'Heteroatom' refers to a multivalent non-carbon atom, such as a boron, phosphorous, silicon, nitrogen, sulfur, or oxygen atom, preferably a nitrogen, sulfur, or oxygen atom. Groups containing more than one heteroatom may contain different heteroatoms.

'Heteroaryl ring' refers to an aromatic ring system containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 in the ring. Bicyclic heteroaromatic rings contain from 8 to 12 member atoms, preferably 9 or 10 member atoms in the ring. The term 'heteroaryl' also includes bicyclic ring systems wherein only one of the rings is aromatic, e.g., the other ring is cycloalkyl, cycloalkenyl, or heterocyclyl. Heteroaromatic rings may be unsubstituted or substituted with from 1 to about 4 substituents on the ring. Preferred heteroaromatic ring substituents include halo, cyano, lower alkyl, heteroalkyl, haloalkyl, phenyl, phenoxy or any combination thereof. Preferred heteroaromatic rings include thienyl, thiazolyl, oxazolyl, pyrrolyl, purinyl, pyrimidyl, pyridyl, and furanyl. More preferred heteroaromatic rings include thienyl, furanyl, and pyridyl.

'Heterocyclic aliphatic ring' is a non-aromatic saturated or unsaturated ring containing carbon and from 1 to about 4 heteroatoms in the ring, wherein no two heteroatoms are adjacent in the ring and preferably no carbon in the ring attached to a heteroatom also has a hydroxyl, amino, or thiol group attached to it. Heterocyclic aliphatic rings are monocyclic, or are fused or bridged bicyclic ring systems. Monocyclic heterocyclic aliphatic rings contain from about 4 to about 10 member atoms (carbon and heteroatoms), preferably from 4 to 7, and most preferably from 5 to 6 member atoms in the ring. Bicyclic heterocyclic aliphatic rings contain from 8 to 12 member atoms, preferably 9 or 10 member atoms in the ring. Heterocyclic aliphatic rings may be unsubstituted or substituted with from 1 to about 4 substituents on the ring. Preferred heterocyclic aliphatic ring substituents include halo, cyano, lower alkyl, heteroalkyl, haloalkyl, phenyl, phenoxy or any combination thereof. More preferred substituents include halo and haloalkyl. Heterocyclyl groups include, for example, thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, hydantoin, oxazoline, imidazolinetrione, triazolinone, quinoline, phthalazine, naphthyridine, quinoxaline, quinazoline, quinoline, pteridine, carbazole, carboline, phenanthridine, acridine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. Preferred heterocyclic aliphatic rings include piperazyl, morpholinyl, tetrahydrofuranyl, tetrahydropyranyl and piperidyl. Heterocycles can also be polycycles.

The term 'hydroxyl' means —OH.

'Lower alkyl' refers to an alkyl chain comprised of 1 to 4, preferably 1 to 3 carbon member atoms, more preferably 1 or 2 carbon member atoms. Lower alkyls may be saturated or unsaturated. Preferred lower alkyls are saturated. Lower alkyls may be unsubstituted or substituted with one or about two substituents. Preferred substituents on lower alkyl include cyano, halo, trifluoromethyl, amino, and hydroxyl. Throughout the application, preferred alkyl groups are lower alkyls. In preferred embodiments, a substituent designated herein as alkyl is a lower alkyl. Likewise, 'lower alkenyl' and 'lower alkynyl' have similar chain lengths.

'Lower heteroalkyl' refers to a heteroalkyl chain comprised of 1 to 4, preferably 1 to 3 member atoms, more preferably 1 to 2 member atoms. Lower heteroalkyl contain one or two non-adjacent heteroatom member atoms. Preferred lower heteroalkyl contain one heteroatom member atom. Lower heteroalkyl may be saturated or unsaturated. Preferred lower heteroalkyl are saturated. Lower heteroalkyl may be unsubstituted or substituted with one or about two substituents. Preferred substituents on lower heteroalkyl include cyano, halo, trifluoromethyl, and hydroxyl.

'Mi heteroalkyl' is a heteroalkyl chain having i member atoms. For example, M4 heteroalkyls contain one or two non-adjacent heteroatom member atoms. M4 heteroalkyls containing 1 heteroatom member atom may be saturated or unsaturated with one double bond (cis or trans) or one triple bond. Preferred M4 heteroalkyl containing 2 heteroatom member atoms are saturated. Preferred unsaturated M4 heteroalkyl have one double bond. M4 heteroalkyl may be unsubstituted or substituted with one or two substituents. Preferred substituents include lower alkyl, lower heteroalkyl, cyano, halo, and haloalkyl.

'Member atom' refers to a polyvalent atom (e.g., C, O, N, or S atom) in a chain or ring system that constitutes a part of the chain or ring. For example, in cresol, six carbon atoms are member atoms of the ring and the oxygen atom and the carbon atom of the methyl substituent are not member atoms of the ring.

As used herein, the term 'nitro' means —NO$_2$.

'Phenyl' is a six-membered monocyclic aromatic ring that may or may not be substituted with from 1 to 5 substituents. The substituents may be located at the ortho, meta or para position on the phenyl ring, or any combination thereof. Preferred phenyl substituents include: halo, cyano, lower alkyl, heteroalkyl, haloalkyl, phenyl, phenoxy or any combination thereof. More preferred substituents on the phenyl ring include halo and haloalkyl. The most preferred substituent is halo.

The terms 'polycyclyl' and 'polycyclic group' refer to two or more rings (e.g., cycloalkyls, cycloalkenyls, heteroaryls, aryls and/or heterocyclyls) in which two or more member atoms of one ring are member atoms of a second ring. Rings that are joined through non-adjacent atoms are termed 'bridged' rings, and rings that are joined through adjacent atoms are 'fused rings'.

As used herein, the term "solvate" refers to a complex of variable stoichiometry formed by a solute or a salt or pharmaceutically functional derivative thereof and a solvent. Such solvents for the purpose of the invention should not interfere with the biological activity of the solute. Examples of solvents include, but are not limited to water, methanol, ethanol, and acetic acid. Preferably the solvent used is a pharmaceutically acceptable solvent. Examples of pharmaceutically acceptable solvents include water, ethanol, and acetic acid.

The term 'sulfhydryl' means —SH, and the term 'sulfonyl' means —SO$_2$—.

The term 'sulfamoyl' is art-recognized and includes a moiety represented by the general formula:

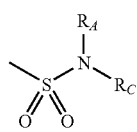

in which $R_A$ and $R_C$ are as defined above.

The term 'sulfate' is art-recognized and includes a moiety that can be represented by the general formula:

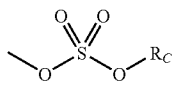

in which R$_C$ is as defined above.

The term 'sulfonamido' is art-recognized, and includes a moiety represented by the general formula:

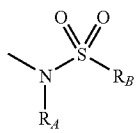

in which R$_A$ and R$_B$ are as defined above.

The terms 'sulfoxido' and 'sulfinyl', as used herein, are art-recognized and include a moiety represented by the general formula:

in which R$_A$ is as defined above.

A 'substitution' or 'substituent' on a small organic molecule generally refers to a position on a multi-valent atom bound to a moiety other than hydrogen, e.g., a position on a chain or ring exclusive of the member atoms of the chain or ring. Such moieties include those defined herein and others as are known in the art, for example, halogen, alkyl, alkenyl, alkynyl, azide, haloalkyl, hydroxyl, carbonyl (such as carboxyl, alkoxycarbonyl, formyl, ketone, or acyl), thiocarbonyl (such as thioester, thioacetate, or thioformate), alkoxyl, phosphoryl, phosphonate, phosphinate, amine, amide, amidine, imine, cyano, nitro, azido, sulfhydryl, alkylthio, sulfate, sulfonate, sulfamoyl, sulfonamido, sulfonyl, silyl, ether, cycloalkyl, heterocyclyl, heteroalkyl, heteroalkenyl, and heteroalkynyl, heteroaralkyl, aralkyl, aryl or heteroaryl. It will be understood by those skilled in the art that certain substituents, such as aryl, heteroaryl, polycyclyl, alkoxy, alkylamino, alkyl, cycloalkyl, heterocyclyl, alkenyl, alkynyl, heteroalkyl, heteroalkenyl, and heteroalkynyl, can themselves be substituted, if appropriate. This invention is not intended to be limited in any manner by the permissible substituents of organic compounds. It will be understood that 'substitution' or 'substituted with' includes the implicit proviso that such substitution is in accordance with permitted valence of the substituted atom and the substituent, and that the substitution results in a stable compound, e.g., which does not spontaneously undergo transformation such as by rearrangement, cyclization, elimination, hydrolysis, etc.

As used herein, the definition of each expression, e.g., alkyl, m, n, etc., when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl, and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The term "amino-terminal protecting group" as used herein, refers to terminal amino protecting groups that are typically employed in organic synthesis, especially peptide synthesis. Any of the known categories of protecting groups can be employed, including acyl protecting groups, such as acetyl, and benzoyl; aromatic urethane protecting groups, such as benzyloxycarbonyl; and aliphatic urethane protecting groups, such as tert-butoxycarbonyl. See, for example, The Peptides, Gross and Mienhoffer, eds., Academic Press, New York (1981), Vol. 3, pp. 3-88; and Green, T. W. & Wuts, P. G. M., Protective Groups in Organic Synthesis, 2nd edition, John Wiley and Sons, Inc., New York (1991). Preferred protecting groups include aryl-, aralkyl-, heteroaryl- and heteroarylalkyl-carbonyl and sulfonyl moieties.

For purposes of this invention, the chemical elements are identified in accordance with the Periodic Table of the Elements, CAS version, Handbook of Chemistry and Physics, 67th Ed., 1986-87, inside cover. Also for purposes of this invention, the term 'hydrocarbon' is contemplated to include all permissible compounds or moieties having at least one carbon-hydrogen bond. In a broad aspect, the permissible hydrocarbons include acyclic and cyclic, branched and unbranched, carbocyclic and heterocyclic, aromatic and non-aromatic organic compounds which can be substituted or unsubstituted.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts can be formed with an appropriate optically active acid or base, followed by resolution of the diastereomers thus formed by fractional crystallization or chromatographic means well known in the art, and subsequent recovery of the purified enantiomers. Enantiomers may also be separated using a 'chiral column', i.e., by chromatographically separating the enantiomers using chiral molecules bound to a solid support.

Contemplated equivalents of the compounds described above include compounds which otherwise correspond thereto, and which have the same useful properties thereof, wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

B. General Terms

The term "amino acid analog" refers to a compound structurally similar to a naturally occurring amino acid wherein either the C-terminal carboxy group, the N-terminal amino group or side-chain functional group has been chemically modified. For example, aspartic acid-(beta-methyl ester) is an amino acid analog of aspartic acid; N-ethylglycine is an amino acid analog of glycine; or alanine carboxamide is an amino acid analog of alanine.

The term "$ED_{50}$" means the dose of a drug that produces 50% of its maximum response or effect.

The terms "gastrointestinal inflammation", "inflammatory bowel disease", and "inflammation of the gastrointestinal tract" are used interchangeably herein to mean inflammation of any portion of the gastrointestinal tract, from the esophagus to the sigmoid flexure or the termination of the colon in the rectum. The inflammation can be acute, but, generally, the composition of this invention is used to treat chronic conditions.

The term "healthcare providers" refers to individuals or organizations that provide healthcare services to a person, community, etc. Examples of "healthcare providers" include doctors, hospitals, continuing care retirement communities, skilled nursing facilities, subacute care facilities, clinics, multispecialty clinics, freestanding ambulatory centers, home health agencies, and HMO's.

The term "$IC_{50}$" means the dose of a drug that inhibits a biological activity by 50%.

The term "$LD_{50}$" means the dose of a drug that is lethal in 50% of test subjects.

A "single oral dosage formulation" is a dosage which provides an amount of drug to produce a serum concentration at least as great as the $EC_{50}$ for that drug, but less than the $LD_{50}$. Another measure for a single oral dosage formulation is that it provides an amount of drug necessary to produce a serum concentration at least as great as the $IC_{50}$ for that drug, but less than the $LD_{50}$. By either measure, a single oral dosage formulation is preferably an amount of drug which produces a serum concentration at least 10 percent less than the $LD_{50}$, and even more preferably at least 50 percent, 75 percent or even 90 percent less than the drug's the $LD_{50}$. A "patient" or "subject" to be treated by the subject method can mean either a human or non-human subject.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the pro-inhibitors of the present invention from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) RingeRs solution; (19) ethyl alcohol; (20) phosphate buffer solutions; and (21) other non-toxic compatible substances employed in pharmaceutical formulations.

The term "pharmaceutically acceptable salts" in these instances refers to the relatively non-toxic, inorganic and organic base addition salts of compounds of the present invention.

The term "pharmaceutically functional derivative" refers to any pharmaceutically acceptable derivative of a pro-inhibitor of the present invention, for example, an ester or an amide, which upon administration to a mammal is capable of providing (directly or indirectly) the pro-inhibitor. Such derivatives are recognizable to those skilled in the art, without undue experimentation. Nevertheless reference is made to the teaching of Burger's Medicinal Chemistry and Drug Discovery, 5th Edition, Vol 1.

As used herein the term "physiological conditions" refers to temperature, pH, ionic strength, viscosity, and like biochemical parameters which are compatible with a viable organism, and/or which typically exist intracellularly in a viable mammalian cell The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. For instance, the phrase "N-terminal protecting group" or "amino-protecting group" as used herein refers to various amino-protecting groups which can be employed to protect the N-terminus of an amino acid or peptide against undesirable reactions. Examples of suitable groups include acyl protecting groups such as, to illustrate, formyl, dansyl, acetyl, benzoyl, trifluoroacetyl, succinyl and methoxysuccinyl; aromatic urethane protecting groups as, for example, benzyloxycarbonyl (Cbz); and aliphatic urethane protecting groups such as t-butoxycarbonyl (Boc) or 9-Fluorenylmethoxycarbonyl (FMOC). The field of protecting group chemistry has been reviewed (Greene, T. W.; Wuts, P. G. M. *Protective Groups in Organic Synthesis*, $2^{nd}$ ed.; Wiley: New York, 1991).

The term "reversible conformation-dependent inactivation" refers to conformational changes that occur under physiological conditions, such as pH-dependent conformation changes, that result in two conformers having different potency for inhibition of a target protease. Preferably, one of the conformers (the "inactive conformer") has less than 50 percent of the inhibitory activity of active conformers, and even more preferably less than 25, 10, 5 or even 1 percent. To further illustrate, in the case of reversible pH-dependent cyclization, the cyclic conformer preferably has a Ki (inhibitory constant) for inhibiting the target protease at least 5 times greater than the linear conformer, and even more preferably at least 10, 100, 1000 or even 10,000 times greater.

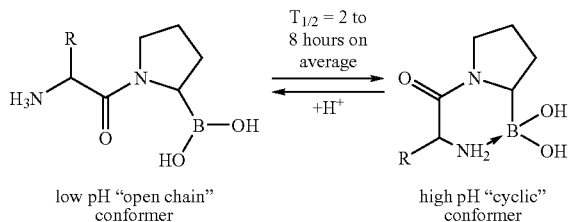

low pH "open chain" conformer ⇌ high pH "cyclic" conformer $T_{1/2}$ = 2 to 8 hours on average The term "shelf-life" typically refers to the time period for which the performance characteristics of a pro-inhibitor remain at peak. As used herein, the term "$T_{90}$" refers to the amount of time it takes for a preparation of the subject pro-inhibitor to degrade to the point that it has 90 percent of the activity of the starting sample, e.g., a diminishment of 10 percent. Likewise, the term "$T_{50}$" refers to the amount of time it takes for a preparation of the subject pro-inhibitor to degrade to the point that it has 50 percent of the activity of the starting sample, e.g., a diminishment of 50 percent. The shelf-life, whether reported as $T_{90}$ or $T_{50}$, for a given pharmaceutical preparation of a pro-inhibitor is the measured for the preparation as it is packaged for use by a healthcare provider or patient.

The term "small" as defined herein refers to a group of 10 atoms or less.

The term "statistically significant" as used herein means that the obtained results are not likely to be due to chance fluctuations at the specified level of probability. The two most commonly specified levels of significance are 0.05 (p=0.05) and 0.01 (p=0.01). The level of significance equal to 0.05 and 0.01 means that the probability of error is 5 out of 100 and 1 out of 100, respectively. With regard to purported differences herein, e.g., improved potency, shelf-life, etc., it will be understood that such differences are at least statistically significant.

As used herein the term "substantially soluble" refers to pro-inhibitors which can be dissolved in inhalant propeller mixture to form a substantially clear to hazy solution which will not separate into layers or form a precipitate when left unagitated for a minimum of 24 hours at room temperature.

By "transdermal patch" is meant a system capable of delivery of a drug to a patient via the skin, or any suitable external surface, including mucosal membranes, such as those found inside the mouth. Such delivery systems generally comprise a flexible backing, an adhesive and a drug retaining matrix, the backing protecting the adhesive and matrix and the adhesive holding the whole on the skin of the patient. On contact with the skin, the drug-retaining matrix delivers pro-inhibitor to the skin, the drug then passing through the skin into the patient's system.

The term "quaternizing agent" refers to a chemical compound which converts a nitrogen atom with fewer than four substituents to a positively charged nitrogen atom with four substituents. Examples of "quaternizing agents" include lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others.

The term "therapeutic index" refers to the therapeutic index of a drug defined as $LD_{50}/ED_{50}$.

A "therapeutically effective amount" of a compound, e.g., such as a dipeptidyl peptidase inhibitor of the present invention, with respect to the subject method of treatment, refers to an amount of the compound(s) in a preparation which, when administered as part of a desired dosage regimen (to a mammal, preferably a human) brings alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

A "therapeutically effective daily dosage" of a compound, e.g., such as a pro-inhibitor of the present invention, with respect to the subject method of treatment, refers to an amount of the compound(s) in a preparation which, when administered as part of a desired daily dosage regimen (to a mammal, preferably a human) brings alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

III. Exemplary Compounds

In certain embodiments, the subject invention provides "pro-inhibitors" represented by the general formula (I) or a solvate, pharmaceutically functional derivative or pharmaceutically acceptable salt thereof:

$$A\text{-}G \qquad (I)$$

wherein
  A represents an "address moiety", e.g., a peptidyl moiety which is a substrate for an activating protease;
  A and G are covalently linked by a bond that is cleaved by the activating protease; and
  G represents an "inhibitor moiety", e.g., which inhibits the proteolytic activity of a target protease, wherein, the inhibitor moiety G, when cleaved from A by the activating serine protease, undergoes reversible conformation-dependent inactivation (such as intramolecular cyclization or cis/trans isomerization), and/or inhibits the target protease with a Ki of 100 nM or less.

In preferred embodiments, the address moiety A represents a C-terminally linked peptide or peptide analog, e.g., of 2-10 amino acid residues, more preferably 2-4 residues, which is a substrate for the activating enzyme. In certain preferred embodiments, A is a dipeptidyl or tripepidyl moiety. In certain embodiments, A is derived from naturally occurring amino acids or analogs thereof, and in certain preferred embodiments, at least one residue of A is a non-naturally occurring amino acid analog.

In certain preferred embodiments, such as when the address moiety A is a substrate of DPP IV, the amino terminus of the peptide or peptide analog is blocked with an amino-terminal protecting group, preferably a lower alkyl such as a methyl group.

In preferred embodiments, the inhibitor moiety G is a dipeptidyl moiety and a electrophilic functional group that can form a covalent adduct with a residue in the active site of a protease replacing the carboxyl terminus of the dipeptidyl moiety. For instance, the inhibitor moiety G can be represented in the general formula (II):

$$Xaa_1\text{-}Xaa_2\text{-}W \qquad (II)$$

wherein
   Xaa1 and Xaa2 each independently represent an amino acid residue, e.g., from naturally occurring amino acids or analogs thereof;
   W represents a functional group which reacts with an active site residue of the targeted protease to form a covalent adduct, as for example, —CN, —CH=NR$_5$,

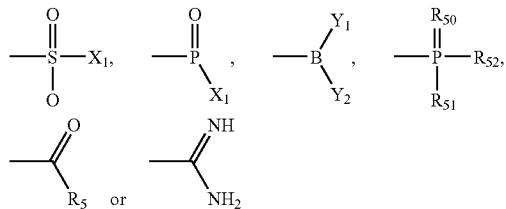

R$_5$ represents H, an alkyl, an alkenyl, an alkynyl, —C(X$_1$)(X$_2$)X$_3$, —(CH$_2$)m-R$_6$, —(CH$_2$)n-OH, —(CH$_2$)n-O-alkyl, —(CH$_2$)n-O-alkenyl, —(CH$_2$)n-O-alkynyl, —(CH$_2$)n-O—(CH$_2$)m-R$_6$, —(CH$_2$)n-SH, —(CH$_2$)n-S-alkyl, —(CH$_2$)n-S-alkenyl, —(CH$_2$)n-S-alkynyl, —(CH$_2$)n-S—(CH$_2$)m-R$_6$, —C(O)C(O)NH$_2$, —C(O)C(O)OR$_7$;
   R$_6$ represents, independently for each occurrence, a substituted or unsubstituted aryl, aralkyl, cycloalkyl, cycloalkenyl, or heterocycle;
   R$_7$ represents, independently for each occurrence, hydrogen, or a substituted or unsubstituted alkyl, alkenyl, aryl, aralkyl, cycloalkyl, cycloalkenyl, or heterocycle; and
   Y$_1$ and Y$_2$ can independently or together be OH, or a group capable of being hydrolyzed to a hydroxyl group, including cyclic derivatives where Y$_1$ and Y$_2$ are connected via a ring having from 5 to 8 atoms in the ring structure (such as pinacol or the like),
   R$_{50}$ represents O or S;
   R$_{51}$ represents N$_3$, SH$_2$, NH$_2$, NO$_2$ or —OR$_7$;
   R$_{52}$ represents hydrogen, a lower alkyl, an amine, —OR$_7$, or a pharmaceutically acceptable salt, or R$_{51}$ and R$_{52}$ taken together with the phosphorous atom to which they are attached complete a heterocyclic ring having from 5 to 8 atoms in the ring structure
   X$_1$ represents a halogen;
   X$_2$ and X$_3$ each represent a hydrogen or a halogen;
   m is zero or an integer in the range of 1 to 8; and n is an integer in the range of 1 to 8.

The pro-inhibitors of the present invention do not themselves undergo cyclization or other forms of reversible conformation-dependent inactivation, and can be constructed such that they do not inhibit the selected target enzyme, or other enzymes to any significant extent, before being cleaved by the activating protease. That is, the pro-inhibitors are themselves inactive, but produce an active conformer of the inhibitor moiety G in the body when the address moiety A is removed pro-inhibitor.

However, the molecules of the invention are more than just prodrugs as conventionally understood and defined. The "active" component of a conventional prodrug, when released from the precursor prodrug, does not differ chemically or functionally from the "active" component as it would be prepared in a non-prodrug embodiment. In contrast, the inhibitor moieties G, when released from the pro-inhibitor A-G, are all predominantly found as the active conformer.

For example, an inhibitory moiety that is subject to reversible pH-dependent inactivation is produced as the open chain conformer, even though it is released within the body at physiological pH (i.e., ~7.2), a pH that would normally strongly favor the cyclic inactive conformer. If released in the vicinity of the target enzyme, as is intended by the pro-inhibitor design, the inhibitor moieties G will have a higher apparent potency relative to the inhibitor moiety administered alone, as the latter route of administration of the inhibitor will result in substantially greater amounts of the inactive cyclic conformer as a consequence to the equilibration between the active and inactive conformers at physiological pH. This is especially true at higher pH values, but some amount of cyclic structure is also present even at lower pH values for separately prepared inhibitors G.

A second feature that makes the pro-inhibitor molecules of the current invention different from typical prodrugs is that the inhibitor moiety, after being generated in the active conformer near the target, undergoes the reversible conformation-dependent inactivation over time, e.g., as it diffuses away from the target enzyme, thereby reducing the possibility of deleterious sideeffects that may result from inhibition of enzymes occurring in other parts of the patient. This combination of being released in a "hyper" or "super-active," open-chain form in the vicinity of the target enzyme together with this "programmed" deactivation mechanism makes the molecules of the invention more specific, effective, and safer (i.e., having fewer side effects) than the inhibitor moiety used on its own.

In certain embodiments, the inhibitor moiety G is a dipeptidyl moiety, e.g., derived from naturally occurring amino acids or amino acid analogs.

In certain embodiments, the inhibitor moiety G is an inhibitor of a target protease which, when cleaved from proinhibitor by the activating protease, inhibits the target protease with a K$_i$ of 100 nM ($10^{-7}$M) or less, and even more preferably, a Ki less than equal to 25 nM, 10 nM ($10^{-8}$M), 1 nM ($10^{-9}$M), or 0.1 nM ($10^{-10}$M). In certain embodiments, K$_i$'s of less than $10^{-11}$M and even $10^{-12}$M have been measured or estimated for the subject inhibitor moieties.

In certain embodiments, the K$_i$ for the inactive conformer is at least 5 times greater than the K$_i$ for the active conformer of the inhibitor moiety, and even more preferably at least 100, 1000 or even 10,000 times greater.

In certain preferred embodiments, the equilibrium constant (K$_{eq}$) for the reversible conformation-dependent inactivation, such as a cyclization reaction, is at least 5:1 in favor of the inactive conformer, and even more preferably 10:1, 100:1 or even 1,000:1.

In certain preferred embodiments, the therapeutic index for the pro-inhibitor is at least 2 times greater than the therapeutic index for the inhibitor moiety alone, and even more preferably 5, 10, 50 or even 100 times greater.

For many of the subject pro-inhibitors, another improvement over the inhibitor moiety itself is increased stability in pharmaceutical preparations, such as in solution, oils or solid formulations. Such stability can be expressed in terms of shelf-life. In certain preferred embodiments, the subject pro-inhibitor has a T$_{90}$ of at least 7 days, and even more preferably of at least 20, 50, 100 or even 200 days. In certain preferred embodiments, the subject pro-inhibitor has a T$_{50}$ of at least 20 days, and even more preferably of at least 50, 100, 200 or even 400 days. In certain preferred embodiments, the subject pro-inhibitor has a T$_{90}$ as a solid, single oral dosage formulation of at least 20, 50, 100 or even 200 days. In certain preferred embodiments, the subject pro-inhibitor has a T$_{90}$ as a liquid, single dosage suspension of at least 20, 50, 100 or even 200 days.

Preferred pharmaceutical preparations of the subject pro-inhibitors are substantially pyrogen-free. For example, in certain preferred embodiments, the endotoxin concentration of the subject preparation, as assayed by the via the gel-clot method (as a limits test with comparison to the maximum allowed FDA limit, as stated in appendix E of the Endotoxin Guidance), is less than 10 EU/mL or EU/single dosage formulation, and even more preferably less than 5, 1, or even 0.1 EU/mL or EU/single dosage formulation.

In certain embodiments, a single administration of the pro-inhibitor, such as bolus injection, oral dosage or inhaled dosage, can produce a sustained in vivo effect, such as to provide a therapeutically effective amount ($\geq ED_{50}$ concentration) of the inhibitor moiety G for a period of at least 4 hours, and even more preferably at least 8, 12 or even 16 hours.

In certain preferred embodiments, the released inhibitor moiety G, and particularly the inactive conformer, has half-life (e.g., relative to decomposition into lower molecular weight fragments and/or irreversible conformers) in serum or other biologically relevant fluid of greater than 10 hours, and even more preferably a half-life greater than 24, 48 or 120 hours. Such half-life can be measured by determining, for example, the amount of active conformer that can be generated when the sample is shifted to conditions that reverse the conformation-dependent inactivation. For instance, a sample incubated at pH 7.2—which favors the inactive conformer, can be shifted to low pH to determine the relative levels of inhibitor activity over a period of time.

Formulations of the present invention include those especially formulated for oral, buccal, parental, transdermal, inhalation, intranasal, transmucosal, implant, or rectal administration.

In certain preferred embodiments, the subject pro-inhibitors are orally available, and can be provided in the form of solid dosage formulations suitable for oral administration to a human patient.

In certain preferred embodiments, the subject pro-inhibitors are transdermally active, and can be provided in the form of topical cream or suspension or a transdermal patch.

Another aspect of the invention provides a pharmaceutical package including one or more of the subject pro-inhibitors, and instructions (written and/or pictorial) describing the administration of the formulation to a patient. Merely to illustrate, exemplary packages are appropriately dosed and include instructions for one or more of: treatment or prophylaxis of metabolic disorders, gastrointestinal disorders, viral disorders, inflammatory disorders, diabetes, obesity, hyperlipidemia, dermatological or mucous membrane disorders, psoriasis, intestinal distress, constipation, autoimmune disorders, encephalomyelitis, complement mediated disorders, glomerulonepritis, lipodystrophy; tissue damage, psychosomatic, depressive, and neuropsychiatric disorders, HIV infection, allergies, inflammation, arthritis, transplant rejection, high blood pressure, congestive heart failure, tumors, and stress-induced abortions.

Preferably, the package includes the one or more pro-inhibitors provided as a single oral dosage formulation.

Where the pro-inhibitor includes one more chiral centers, in preferred embodiments, the pro-inhibitor is provided as at least 75 mol percent of the eutomer (relative to the distomer) of that pro-inhibitor, and even more preferably at least 85, 90, 95 or even 99 mol percent. Generally, the eutomer with the L-enatiomer (with respect to the Cα carbon) of an amino acid or amino acid analog.

In certain embodiments, the pro-inhibitor is a tetrapeptidyl moiety represented in the general formula (III):

$$Xaa'_1\text{-}Xaa''_2\text{-}Xaa_1\text{-}Xaa_2\text{-}W \qquad (III)$$

wherein $Xaa'_1$, $Xaa''_2$, $Xaa_1$ and $Xaa_2$ each independently represent an amino acid residue, e.g., from naturally occurring amino acids or analogs thereof;

W represents a functional group which reacts with an active site residue of the targeted protease to form a covalent adduct, as for example, —CN, —CH=NR$_5$,

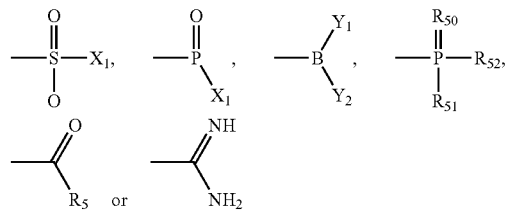

$R_5$ represents H, an alkyl, an alkenyl, an alkynyl, —C(X$_1$)(X$_2$)X$_3$, —(CH$_2$)m-R$_6$, —(CH$_2$)n-OH, —(CH$_2$)n-O-alkyl, —(CH$_2$)n-O-alkenyl, —(CH$_2$)n-O-alkynyl, —(CH$_2$)n-O—(CH$_2$)m-R$_6$, —(CH$_2$)n-SH, —(CH$_2$)n-S-alkyl, —(CH$_2$)n-S-alkenyl, —(CH$_2$)n-S-alkynyl, —(CH$_2$)n-S—(CH$_2$)m-R$_6$, —C(O)C(O)NH$_2$, —C(O)C(O)OR$_7$;

$R_6$ represents, independently for each occurrence, a substituted or unsubstituted aryl, aralkyl, cycloalkyl, cycloalkenyl, or heterocycle;

$R_7$ represents, independently for each occurrence, hydrogen, or a substituted or unsubstituted alkyl, alkenyl, aryl, aralkyl, cycloalkyl, cycloalkenyl, or heterocycle; and $Y_1$ and $Y_2$ can independently or together be OH, or a group capable of being hydrolyzed to a hydroxyl group, including cyclic derivatives where $Y_1$ and $Y_2$ are connected via a ring having from 5 to 8 atoms in the ring structure (such as pinacol or the like), $R_{50}$ represents O or S;

$R_{51}$ represents N$_3$, SH$_2$, NH$_2$, NO$_2$ or —OR$_7$;

$R_{52}$ represents hydrogen, a lower alkyl, an amine, —OR$_7$, or a pharmaceutically acceptable salt, or $R_{51}$ and $R_{52}$ taken together with the phosphorous atom to which they are attached complete a heterocyclic ring having from 5 to 8 atoms in the ring structure $X_1$ represents a halogen;

$X_2$ and $X_3$ each represent a hydrogen or a halogen;

m is zero or an integer in the range of 1 to 8; and n is an integer in the range of 1 to 8.

In certain preferred embodiments, $Xaa'_1$ includes an amino-terminal protecting group.

In certain preferred embodiments, $Xaa'_1$, is an amino acid analog having a tetrasubsituted Cβ carbon, e.g., a carbon having four subistituents none of which is a hydrogen. For instance, $Xaa'_1$, can be an amino acid analog represented in the general formula:

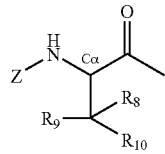

wherein: $R_8$ and $R_9$ each independently represent a lower alkyl or a halogen; $R_{10}$ represents a lower alkyl, an aryl, a hydroxyl group or —$(CH_2)_m$—COOH; Z represents a hydrogen or an amino terminal protecting group; and m=0, 1 or 2. In certain preferred embodiments, $R_8$ and $R_9$ each independently represents a lower alkyl, more preferably methyl, ethyl or propyl, and even more preferably a methyl. In certain preferred embodiments, $R_{10}$ represents a lower alkyl, more preferably methyl, ethyl or propyl, and even more preferably a methyl. In other preferred embodiments, $R_{10}$ represents an aryl, such as phenyl or hydroxyphenyl (preferably para-hydroxy). In yet other preferred embodiments, $R_{10}$ represents a hydroxyl group. In certain preferred embodiments, $R_{10}$ represents —$(CH_2)_m$—COOH, where m=0, 1 or 2, and preferably where m is 0 or 1.

In general, the subject pro-inhibitors can be divided into two distinct types on the basis of whether they are activated by the same, or by a different enzyme as the target enzyme of the inhibitor moiety. The first type will be referred to as Type 1 or Target-Activated Smart Protease Inhibitors (TASPI), the second as Type 2 or Target-Directed Smart Protease Inhibitors (TDSPI). Both embodiments of the pro-inhibitors provide for the specific delivery of the active component, e.g., in a "hyper-active" form to the targeted enzyme, and for attenuation of the inhibitor activity as the inhibitor moiety diffuses away from the target enzyme, and therefore for advantages in specificity, potency and safety compared to the inhibitor moiety itself in pure form.

TDSPIs of the present invention offer the additional prospects for tissue, or cellular specific inhibition of targeted enzymes. In other words TDSPIs offer the prospect of inhibiting a given enzyme in one given cell or tissue type but not in another. For example, every cell of the body contains a proteosome protease complex. Inhibition of proteasome function has a number of practical therapeutic and prophylactic applications. However, it is difficult to provide for inhibition of proteosome activity in a cell- or tissue-type selective manner. In certain embodiments of the current invention, TDSPIs can be constructed to deliver a proteosome inhibitor moiety in selective manner by usng a pro-inhibitor having an address moiety for a protease that is expressed in or adjacent to the intended target cells or tissue. To illustrate, it can be activated by FAP or Prostate Specific Antigen (PSA) and the resulting inhibitor moiety G is an inhibitor of the proteosome.

In preferred embodiments of TDSPIS, the address moiety A is not an efficient substrate for the target protease. For instance, as a substrate, address moiety A preferably has a turnover number as a substrate for the target protease of less than 1/second, and even more preferably less than 0.1/second, 0.001/second or even 0.0001/second.

In certain embodiments of the subject pro-inhibitors, the address moiety is a substrate for an activating protease selected from amongst serine proteases, cysteine proteases and metalloproteases. Likewise, the inhibitor moiety can be an dipeptidyl inhibitor for a target protease selected from serine proteases, cysteine proteases and metalloproteases. In certain preferred embodiments, the target protease is a serine proteases.

The pro-inhibitors of the present invention can be designed to work with target and activating serine proteases including, but not limited to, dipeptidyl peptidase-11 (DPP-XI), dipeptidyl peptidase IV (DPP IV), dipeptidyl peptidase (DPP VI), dipeptidyl peptidase 9 (DPP IX), aminopeptidase P, fibroblast activating protein alpha (seprase), prolyl tripeptidyl peptidase, prolyl oligopeptidase (endoproteinase Pro-C), attractin (soluble dipeptidyl-aminopeptidase), acylaminoacyl-peptidase (N-acylpeptide hydrolase; fMet aminopeptidase) and lysosomal Pro-X carboxypeptidase (angiotensinase C, prolyl carboxypeptidase).

The pro-inhibitors of the present invention can be designed to work with target and activating metalloproteases including membrane Pro-X carboxypeptidase (carboxypeptidase P), angiotensin-converting enzyme (Peptidyl-dipeptidase A multipeptidase], collagenase I (interstitial collagenase; matrix metalloproteinase 1; MMP-1; Mcol-A), ADAM 10 (alpha-secretase, myelin-associated disintegrin metalloproteinase), neprilysin (atriopeptidase; CALLA; CD10; endopeptidase 24.1 1; enkephalinase), Macrophage elastase (metalloelastase; matrix metalloproteinase 12; MMP-12], Matrilysin (matrix metalloproteinase 7; MMP-7), and neurolysin (endopeptidase 24.16; microsomal endopeptidase; mitochondrial oligopeptidase).

In certain preferred embodiments, the activating protease is a post-prolyl cleaving protease, such as selected from the group consisting of DPP IV, DPP II, Prolyl oligopeptidase (PO), Fibroblast Activating Protein (FAP), and prolyl carboxypeptidase. In certain embodiments where the post-prolyl cleaving protease is an endopeptidase, the amino terminus of A is blocked with an amino-terminal protecting group, preferably a lower alkyl such as a methyl group.

In other embodiments, the activating protease is selected from the group consisting of thrombin (Factor X), matriptase, falcipain, prostate specific antigen (PSA), and proteases homologous thereto.

In certain preferred embodiments, the target protease is a post-prolyl cleaving protease, such as selected from the group consisting of DPP IV, DPP II, Prolyl oligopeptidase (PO), Fibroblast Activating Protein (FAP), and prolyl carboxypeptidase.

In certain preferred embodiments, the subject pro-inhibitor is represented in the general formula (IV):

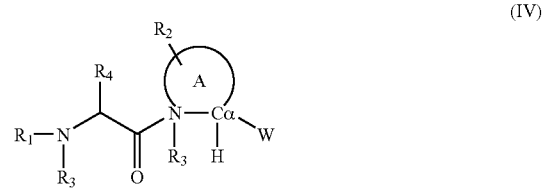

wherein
A represents a 4-8 membered heterocycle including the N and the Cα carbon; W represents a functional group which reacts with an active site residue of the targeted protease to form a covalent adduct, as for example, —CN, —CH=NR$_5$,

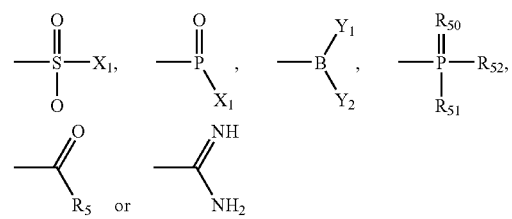

$R_1$ represents a C-terminally linked peptide or peptide analog which is a substrate for an activating enzyme;

R$_2$ is absent or represents one or more substitutions to the ring A, each of which can independently be a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —(CH$_2$)$_m$—R$_6$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$_6$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$_6$;

R$_3$ represents, independently for each occurrence, a hydrogen or a substituent which does not conjugate the electron pair of the the nitrogen from which it pends, such as a lower alkyl;

R$_4$ represents hydrogen or a small hydrophobic group such as a halogen, a lower alkyl, a lower alkenyl, or a lower alkynyl;

R$_5$ represents H, an alkyl, an alkenyl, an aLknyl, —C(X$_1$)(X$_2$)X$_3$, —(CH$_2$)m-R$_6$, —(CH$_2$)n-OH, —(CH$_2$)n-O-alkyl, —(CH$_2$)n-O-alkenyl, —(CH$_2$)n-O-alkynyl, —(CH$_2$)n-O—(CH$_2$)m-R$_6$, —(CH$_2$)n-SH, —(CH$_2$)n-S-alkyl, —(CH$_2$)n-S-alkenyl, —(CH$_2$)n-S-alkynyl, —(CH$_2$)n-S—(CH$_2$)m-R$_6$, —C(O)C(O)NH$_2$, —C(O)C(O)OR$_7$;

R$_6$ represents, for each occurrence, a substituted or unsubstituted aryl, aralkyl, cycloalkyl, cycloalkenyl, or heterocycle;

R$_7$ represents, for each occurrence, hydrogen, or a substituted or unsubstituted alkyl, alkenyl, aryl, aralkyl, cycloalkyl, cycloalkenyl, or heterocycle; and Y$_1$ and Y$_2$ can independently or together be OH, or a group capable of being hydrolyzed to a hydroxyl group, including cyclic derivatives where Y$_1$ and Y$_2$ are connected via a ring having from 5 to 8 atoms in the ring structure (such as pinacol or the like), R$_{50}$ represents O or S;

R$_{51}$ represents N$_3$, SH$_2$, NH$_2$, NO$_2$ or —OR$_7$;

R$_{52}$ represents hydrogen, a lower alkyl, an amine, —OR$_7$, or a pharmaceutically acceptable salt, or R$_{51}$ and R$_{52}$ taken together with the phosphorous atom to which they are attached complete a heterocyclic ring having from 5 to 8 atoms in the ring structure X$_1$ represents a halogen;

X$_2$ and X$_3$ each represent a hydrogen or a halogen;

m is zero or an integer in the range of 1 to 8; and n is an integer in the range of 1 to 8.

In certain preferred embodiments, R$_2$ is absent, or represents a small hydrophobic group.

In certain embodiments, the protease inhibitor is represented in the general formula (V):

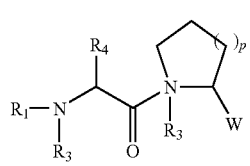

(V)

where R$_1$, R$_3$, R$_4$ and W are as defined above, and p is an integer from 1 to 3. In certain preferred embodiments, p is 1, and R$_3$ is a hydrogen in each occurrence.

In certain preferred embodiments of the subject pro-inhibitor structures II-V above, W represents:

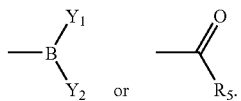

In certain preferred embodiments, R$_5$ is a hydrogen or —C(X$_1$)(X$_2$)X$_3$, wherein X$_1$ is a fluorine, and X$_2$ and X$_3$, if halogens, are also fluorine.

In certain preferred embodiments of the subject pro-inhibitor structures IV and V, R$_4$ is a lower alkyl.

In certain preferred embodiments of the subject pro-inhibitor structures IV and V, R$_4$ represents a sidechain of an amino acid residue selected from the group consisting of Gly, Ala, Val, Ser, Thr, Ile and Leu.

In certain preferred embodiments of the subject pro-inhibitor structures IV and V, R$_4$ represents a sidechain of an amino acid residue represented in the general formula:

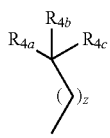

wherein

R$_{4a}$ and R$_{4b}$ each independently represent a hydrogen, lower alkyl, heteroalkyl, cycloalkyl, heterocycloalkyl, aryl, heteroaryl, alkoxyl, carboxyl, carboxamide, carbonyl, or cyano, with the caveat that either both or neither of R$_{4a}$ and R$_{4b}$ are hydrogen;

R$_{4c}$ represents a halogen, an amine, an alkyl, heteroalkyl, cycloalkyl, heterocycloalkyl, aryl, heteroaryl, alkoxyl, carboxyl, carboxamide, carbonyl, or cyano; and z is zero or an integer in the range of 0 to 3.

In certain preferred embodiments of the subject pro-inhibitor structures IV and V, R$_4$ represents a sidechain of an amino acid residue represented in the general formula:

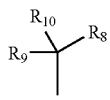

wherein: R$_8$ and R$_9$ each independently represent a lower alkyl or a halogen; R$_{10}$ represents a lower alkyl, an aryl, a hydroxyl group or —(CH$_2$)$_m$—COOH. In certain preferred embodiments, R$_8$ and R$_9$ each independently represents a lower alkyl, more preferably methyl, ethyl or propyl, and even more preferably a methyl. In certain preferred embodiments, R$_{10}$ represents a lower alkyl, more preferably methyl, ethyl or propyl, and even more preferably a methyl. In other preferred embodiments, R$_{10}$ represents an aryl, such as phenyl or hydroxyphenyl (preferably para-hydroxy). In yet other preferred embodiments, R$_{10}$ represents a hydroxyl group. In certain preferred embodiments, R$_{10}$ represents —(CH$_2$)$_m$—COOH, where m=0, 1 or 2, and preferably where m is 0 or 1.

In certain preferred embodiments of the subject pro-inhibitor structures IV and V, R$_1$ is a peptidyl moiety which is a substrate for a post-proline cleaving enzyme.

IV. Pharmaceutical Compositions

While it is possible for a compound of the present invention to be administered alone, it is preferable to administer the compound as a pharmaceutical formulation (composition). Protease inhibitors according to the invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

Thus, one aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) administration by inhalation, for example, aerosols, nebulizers, or dry powders; (3) parenteral administration, for example, by subcutaneous, intramuscular or intravenous injection as, for example, a sterile solution or suspension; (4) topical application, for example, as a cream, ointment or spray applied to the skin; (5) ophthalmic administration; or (6) intravaginal or intrarectal administration, for example, as a pessary, cream or foam. However, in certain embodiments the subject compounds may be simply dissolved or suspended in sterile water. In certain embodiments, the pharmaceutical preparation is non-pyrogenic, i.e., does not elevate the body temperature of a patient.

Another aspect of the invention provides for a method for preparing such pharmaceutical composition by combining the protease inhibitor prodrug and a pharmaceutically acceptable inert carrier, in a single dosage formulation. Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

Medicaments which may be administered in inhalant or aerosol formulations according to the invention include protease inhibitor prodrugs useful in inhalation therapy which may be presented in a form which is soluble or substantially soluble in the selected propellant system.

The particle size of the particulate medicament should be such as to permit inhalation of substantially all of the medicament into the lungs upon administration of the aerosol formulation and will thus desirably be less than 20 microns, preferably in the range 1 to 10 microns, e.g. 1 to 5 microns. The particle size of the medicament may be reduced by conventional means, for example by milling or micronisation.

The final aerosol formulation desirably contains 0.005-10% w/w, preferably 0.005-5% w/w, especially 0.01-1.0% w/w, of medicament relative to the total weight of the formulation.

It is desirable that the formulations of the invention contain no components which may provoke the degradation of stratospheric ozone. In particular it is desirable that the formulations are substantially free of chlorofluorocarbons such as $CCl_3F$, $CCl_2F_2$ and $CF_3CCl_3$. As used herein "substantially free" means less than 1% w/w based upon the propellant system, in particular less than 0.5%, for example 0.1% or less.

Administration of medicament may be indicated for the treatment of mild, moderate or severe acute or chronic symptoms or for prophylactic treatment. It will be appreciated that the precise dose administered will depend on the age and condition of the patient, the particular particulate medicament used and the frequency of administration and will ultimately be at the discretion of the attendant physician. When combinations of medicaments are employed the dose of each component of the combination will in general be that employed for each component when used alone. Typically, administration may be one or more times, for example from 1 to 8 times per day, giving for example 1, 2, 3 or 4 puffs each time. Preferably, administration may be one time per day.

For administration, the drug is suitably inhaled from a nebulizer, from a pressurized metered dose inhaler or as a dry powder from a dry powder inhaler (e.g. sold as TURBU-HALER®) or from a dry powder inhaler utilizing gelatin, plastic or other capsules, cartridges or blister packs.

A diluent or carrier, generally non-toxic and chemically inert to the medicament e.g. lactose, dextran, mannitol, glucose or any additives that will give the medicament a desired taste, can be added to the powdered medicament.

The micronized mixture may be suspended or dissolved in a liquid propellant mixture which is kept in a container that is sealed with a metering valve and fitted into a plastic actuator. The propellants used may be halocarbons of different chemical formulae. The most frequently used halocarbon propellants are trichlorofluoromethane (propellant 11), dichlorodifluoromethane (propellant 12), dichlorotetrafluoroethane (propellant 114), tetrafluoroethane (propellant 134a) and 1,1-difluoroethane (propellant 152a). Low concentrations of a surfactant such as sorbitan trioleate, lecithin, disodium dioctylsulphosuccinate or oleic acid may also be used to improve the physical stability.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions; and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides).

Depot injectable formulations are also prepared by entrapping the drug in liposomes or microemulsions that are compatible with body tissue.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the protease inhibitor prodrug in the proper medium. Absorption enhancers can also be used to increase the flux of the protease inhibitor prodrugs across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the protease inhibitor prodrug.

Formulations of the present invention which are suitable for vaginal administration also include pessaries, tampons, creams, gels, pastes, foams or spray formulations containing such carriers as are known in the art to be appropriate.

The amount of active ingredient which can be combined with a carrier material to produce a single dosage form will vary depending upon the host being treated and the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

When the compounds of the present invention are administered as pharmaceuticals, to humans and animals, they can be given alone or as a pharmaceutical composition containing, for example, 0.1 to 99.5% (more preferably, 0.5 to 90%) of active ingredient in combination with a pharmaceutically acceptable carrier.

In preferred embodiments, the subject compositions are sterile and pyrogen free.

V. Pharmaceutical Packages and Manufacture

One aspect of the present invention provides a packaged pharmaceutical comprising one or more pro-inhibitors of the present invention formulated in a pharmaceutically acceptable excipient, in association with instructions (written and/or pictorial) describing the recommended dosage and/or administration of the formulation to a patient. Such instructions may include details for treating or preventing a diseases, and optionally, warnings of possible side effects and drug-drug or drug-food interactions.

Another aspect of the invention relates to the use of the subject pro-inhibitors in the manufacture of a medicament for the treatment of a disorder for which inhibition of the target protease of the inhibitor moiety G provides a therapeutic benefit to a patient. Exemplary disorders are enumerated below.

Yet another aspect of the invention relates to a method for conducting a pharmaceutical business, which includes:

a. manufacturing one or more of the subject pro-inhibitors; and b. marketing to healthcare providers the benefits of using the preparation to treat or prevent any of the diseases or indications cited herein.

In certain embodiments, the subject business method can include providing a distribution network for selling the preparation. It may also include providing instruction material to patients or physicians for using the preparation to treat and prevent any of the diseases or indications cited herein.

VI. Methods of Use

A. Post-Proline Cleaving Enzymes

Certain embodiments of the subject pro-inhibitors can include inhibitor moieties that provide therapeutic compounds for treatment of disorders in mammals which can be treated (alleviated or reduced) by inhibition DPP IV, DPP II, Prolyl oligopeptidase (PO), Fibroblast Activating Protein (FAP), or prolyl carboxypeptidase activities of the mammal.

In certain embodiments, the subject pro-inhibitors can include a inhibitor moiety for DPP IV. In such embodiments, the subject pro-inhibitors can be used to regulate the proteolysis of such polypeptide factors as GLP-1, GIP, GLP-2, GRP, vasoactive intestinal peptide, peptide histidine methionine, PYY, substance P, β-casomorphine, NPY, PACAP38, prolactin, chorionic gonadotropin, aprotinin, corticotropin-like intermediate lobe peptide, pituitary adenylyl cyclase-activating peptide, (Tyr)melanostatin, LD78β(3-70), RANTES, eotaxin procolipase, enterostatin, vasostatin 1, endomorphin, morphiceptin, stromal cell derived factor, macrophage-derived chemokine, granulocyte chemotactic protein-2, and GHRH/GRF.

Accordingly, DPP IV-direced pro-inhibitors can be used to treat a a variety of metabolic, gastrointestinal, viral, and inflammatory diseases, including, but not limited to, diabetes, obesity, hyperlipidemia, dermatological or mucous membrane disorders, psoriasis, intestinal distress, constipation, autoimmune disorders such as encephalomyelitis, complement mediated disorders such as glomerulonepritis, lipodystrophy, and tissue damage, psychosomatic, depressive, and neuropsychiatric disease such as anxiety, depression, insomnia, schizophrenia, epilepsy, spasm, and chronic pain, HIV infection, allergies, inflammation, arthritis, transplant rejection, high blood pressure, congestive heart failure, tumors, and stress-induced abortions, for example cytokine-mediated murine abortions.

Certain of the subject DPP IV pro-inhibitors can promote satiety, weight loss, and the antidiabetic effects of GLP-1

Certain of the subject DPP IV pro-inhibitors may be useful for treating intestinal insufficiencies and mucous membrane disorders.

(i). Regulating Blood Glucose Levels

Certain pro-inhibitors of the present invention have the ability to lower blood glucose levels, to relieve obesity, to alleviate impaired glucose tolerance, to inhibit hepatic glucose neogenesis, and to lower blood lipid levels and to inhibit aldose reductase. They are thus useful for the prevention and/or therapy of hyperglycemia, obesity, hyperlipidemia, diabetic complications (including retinopathy, nephropathy, neuropathy, cataracts, coronary artery disease and arteriosclerosis) and furthermore for obesity-related hypertension and osteoporosis.

Diabetes mellitus is a disease characterized by hyperglycemia occurring from a relative or absolute decrease in insulin secretion, decreased insulin sensitivity or insulin resistance. The morbidity and mortality of this disease result from vascular, renal, and neurological complications. An oral glucose tolerance test is a clinical test used to diagnose diabetes. In an oral glucose tolerance test, a patient's physiological response to a glucose load or challenge is evaluated. After ingesting the glucose, the patient's physiological response to the glucose challenge is evaluated. Generally, this is accomplished by determining the patient's blood glucose levels (the concentration of glucose in the patient's plasma, serum or whole blood) for several predetermined points in time.

In one embodiment, the present invention provides a method for agonizing the action of GLP-1. It has been determined that isoforms of GLP-1 (GLP-1 (7-37) and GLP-1(7-36)), which are derived from preproglucagon in the intestine and the hind brain, have insulinotropic activity, i.e., they modulate glucose metabolism. DPP IV cleaves the isoforms to inactive peptides. Thus, in certain embodiments, inhibitor(s) of the present invention can agonize insulinotropic activity by interfering with the degradation of bioactive GLP-1 peptides.

(ii). Agonism of the Effects of Other Peptide Homones

In another embodiment, certain of the subject pro-inhibitors can be used to agonize the activity of peptide hormones, e.g., GLP-2, GIP and NPY.

To illustrate further, the present invention provides a method for agonizing the action of GLP-2. It has been determined that GLP-2 acts as a trophic agent, to promote growth of gastrointestinal tissue. The effect of GLP-2 is marked particularly by increased growth of the small bowel, and is therefore herein referred to as an "intestinotrophic" effect. DPP IV is known to cleave GLP-2 into a biologically inactive peptide. Thus, in one embodiment, inhibition of DPP IV interferes with the degradation of GLP-2, and thereby increases the plasma half-life of that hormone.

In still other embodiments, the subject method can be used to increase the half-life of other proglucagon-derived peptides, such as glicentin, oxyntomodulin, glicentin-related pancreatic polypeptide (GRPP), and/or intervening peptide-2 (IP-2). For example, glicentin has been demonstrated to cause proliferation of intestinal mucosa and also inhibits a peristalsis of the stomach, and has thus been elucidated as useful as a therapeutic agent for digestive tract diseases, thus leading to the present invention.

Thus, in one aspect, the present invention relates to therapeutic and related uses of pro-inhibitors for promoting the growth and proliferation of gastrointestinal tissue, most particularly small bowel tissue. For instance, the subject method can be used as part of a regimen for treating injury, inflammation or resection of intestinal tissue, e.g., where enhanced growth and repair of the intestinal mucosal epithelial is desired.

With respect to small bowel tissue, such growth is measured conveniently as a increase in small bowel mass and length, relative to an untreated control. The effect of subject inhibitors on small bowel also manifests as an increase in the height of the crypt plus villus axis. Such activity is referred to herein as an "intestinotrophic" activity. The efficacy of the subject method may also be detectable as an increase in crypt cell proliferation and/or a decrease in small bowel epithelium apoptosis. These cellular effects may be noted most significantly in relation to the jejunum, including the distal jejunum and particularly the proximal jejunum, and also in the distal ileum. A compound is considered to have "intestinotrophic effect" if a test animal exhibits significantly increased small bowel weight, increased height of the crypt plus virus axis, or increased crypt cell proliferation or decreased small bowel epithelium apoptosis when treated with the compound (or genetically engineered to express it themselves). A model suitable for determining such gastrointestinal growth is described by U.S. Pat. No. 5,834,428.

In general, patients who would benefit from either increased small intestinal mass and consequent increased small bowel mucosal function are candidates for treatment by the subject method. Particular conditions that may be treated include the various forms of sprue including celiac sprue which results from a toxic reaction to □-gliadin from wheat, and is marked by a tremendous loss of villae of the bowel; tropical sprue which results from infection and is marked by partial flattening of the villae; hypogammaglobulinemic sprue which is observed commonly in patients with common variable immunodeficiency or hypogammaglobulinemia and is marked by significant decrease in villus height. The therapeutic efficacy of the treatment may be monitored by enteric biopsy to examine the villus morphology, by biochemical assessment of nutrient absorption, by patient weight gain, or by amelioration of the symptoms associated with these conditions. Other conditions that may be treated by the subject method, or for which the subject method may be useful prophylactically, include radiation enteritis, infectious or post-infectious enteritis, regional enteritis (Crohn's disease), small intestinal damage due to toxic or other chemotherapeutic agents, and patients with short bowel syndrome.

More generally, the present invention provides a therapeutic method for treating digestive tract diseases. The term "digestive tract" as used herein means a tube through which food passes, including stomach and intestine. The term "digestive tract diseases" as used herein means diseases accompanied by a qualitative or quantitative abnormality in the digestive tract mucosa, which include, e.g., ulceric or inflammatory disease; congenital or acquired digestion and absorption disorder including malabsorption syndrome; disease caused by loss of a mucosal barrier function of the gut; and protein-losing gastroenteropathy. The ulceric disease includes, e.g., gastric ulcer, duodenal ulcer, small intestinal ulcer, colonic ulcer and rectal ulcer. The inflammatory disease include, e.g., esophagitis, gastritis, duodenitis, enteritis, colitis, Crohn's disease, proctitis, gastrointestinal Behcet, radiation enteritis, radiation colitis, radiation proctitis, enteritis and medicamentosa. The malabsorption syndrome includes the essential malabsorption syndrome such as disaccharide-decomposing enzyme deficiency, glucose-galactose malabsorption, fractose malabsorption; secondary malabsorption syndrome, e.g., the disorder caused by a mucosal atrophy in the digestive tract through the intravenous or parenteral nutrition or elemental diet, the disease caused by the resection and shunt of the small intestine such as short gut syndrome, cul-de-sac syndrome; and indigestible malabsorption syndrome such as the disease caused by resection of the stomach, e.g., dumping syndrome.

The term "therapeutic agent for digestive tract diseases" as used herein means the agents for the prevention and treatment of the digestive tract diseases, which include, e.g., the therapeutic agent for digestive tract ulcer, the therapeutic agent for inflammatory digestive tract disease, the therapeutic agent for mucosal atrophy in the digestive tract and the therapeutic agent for digestive tract wound, the amelioration agent for the function of the digestive tract including the agent for recovery of the mucosal barrier function and the amelioration agent for digestive and absorptive function. The ulcers include digestive ulcers and erosions, acute ulcers, namely, acute mucosal lesions.

The subject method, because of promoting proliferation of intestinal mucosa, can be used in the treatment and prevention of pathologic conditions of insufficiency in digestion and absorption, that is, treatment and prevention of mucosal atrophy, or treatment of hypoplasia of the digestive tract tissues and decrease in these tissues by surgical removal as well as improvement of digestion and absorption. Further, the subject method can be used in the treatment of pathologic mucosal conditions due to inflammatory diseases such as enteritis, Crohn's disease and ulceric colitis and also in the treatment of reduction in function of the digestive tract after operation, for example, in damping syndrome as well as in the treatment of duodenal ulcer in conjunction with the inhibition of peristalsis of the stomach and rapid migration of food from the stomach to the jejunum. Furthermore, glicentin can effectively be used in promoting cure of surgical invasion as well as in improving functions of the digestive tract. Thus, the present invention also provides a therapeutic agent for atrophy of the digestive tract mucosa, a therapeutic agent for wounds in the digestive tract and a drug for improving functions of the digestive tract which comprise glicentin as active ingredients.

Likewise, certain of the DPP IV pro-inhibitors of the subject invention can be used to alter the plasma half-life of secretin, VIP, PHL PACAP, GIP and/or helodermin. Additionally, the subject method can be used to alter the pharmacokinetics of Peptide YY and neuropeptide Y, both members of the pancreatic polypeptide family, as DPP IV has been implicated in the processing of those peptides in a manner which alters receptor selectivity.

Neuropeptide Y (NPY) is believed to act in the regulation vascular smooth muscle tone, as well as regulation of blood pressure. NPY also decreases cardiac contractility. NPY is also the most powerful appetite stimulant known (Wilding et al., (1992) *J Endocrinology* 132:299-302). The centrally evoked food intake (appetite stimulation) effect is predominantly mediated by NPY Y1 receptors and causes increase in body fat stores and obesity (Stanley et al., (1989) *Physiology and Behavior* 46:173-177).

According to the present invention, a method for treatment of anorexia comprises administering to a host subject an effective amount of an inhibitor(s) to stimulate the appetite and increase body fat stores which thereby substantially relieves the symptoms of anorexia.

A method for treatment of hypotension comprises administering to a host subject an effective amount of an inhibitor(s) of the present invention to mediate vasoconstriction and increase blood pressure which thereby substantially relieves the symptoms of hypotension.

DPP IV has also been implicated in the metabolism and inactivation of growth hormone-releasing factor (GHRF). GHRF is a member of the family of homologous peptides that includes glucagon, secretin, vasoactive intestinal peptide (VIP), peptide histidine isoleucine (PHI), pituitary adenylate cyclase activating peptide (PACAP), gastric inhibitory peptide (GIP) and helodermin. Kubiak et al. (1994) *Peptide Res* 7:153. GHRF is secreted by the hypothalamus, and stimulates the release of growth hormone (GH) from the anterior pituitary. Thus, the subject method can be used to improve clinical therapy for certain growth hormone deficient children, and in clinical therapy of adults to improve nutrition and to alter body composition (muscle vs. fat). The subject method can also be used in veterinary practice, for example, to develop higher yield milk production and higher yield, leaner livestock.

B. Proteosome Inhibitors

In other embodiments, the subject pro-inhibitors produce inhibitor moieties that are potent and highly selective proteasome inhibitors and can be employed to inhibit proteasome function. Inhibition of proteasome function has a number of practical therapeutic and prophylactic applications. However, because the proteosome is ubiquitous to living cells, there is a desire to provide embodiments of the subject pro-inhibitor that release a proteasome inhibitor using an address moiety that is cleaved at or in proximity to the intended target cells. For instance, the proteosome pro-inhibitors embodiments can include address moieties that are substrates for proteases that are expressed in tumors or other cells which are undergoing unwanted proliferation, or expressed in the tissue surrounding the tumor or other target proliferating cells. For instance, the address moiety can be a substrate for a protease expressed in the stromal layer adjacent a tumor.

In certain embodiments, the proteosome pro-inhibitors of the present invention provide a method of reducing the rate of degradation of p53 and other tumor suppressors. Such pro-inhibitors are contemplated as possessing important practical application in treating cell proliferative diseases, such as cancer, restenosis and psoriasis.

In certain embodiments, proteasome pro-inhibitors can be used to inhibit the processing of internalized cellular or viral antigens into antigenic peptides that bind to MHC-I molecules in an animal, and are therefore useful for treating autoimmune diseases and preventing rejection of foreign tissues, such as transplanted organs or grafts.

Finally, the present invention relates to the use of proteasome pro-inhibitors for treating specific conditions in animals that are mediated or exacerbated, directly or indirectly, by proteasome functions. These conditions include inflammatory conditions, such as tissue rejection, organ rejection, arthritis, infection, dermatoses, inflammatory bowel disease, asthma, osteoporosis, osteoarthritis and autoimmune disease such as lupus and multiple sclerosis; cell proliferative diseases, such as cancer, psoriasis and restenosis; and accelerated muscle protein breakdown that accompanies various physiological and pathological states and is responsible to a large extent for the loss of muscle mass (atrophy) that follows nerve injury, fasting, fever, acidosis, and certain endocrinopathies.

Compounds of the present invention inhibit the growth of cancer cells. Thus, the compounds can be employed to treat cancer, psoriasis, restenosis or other cell proliferative diseases in a patient in need thereof.

By the term "treatment of cancer" or "treating cancer" is intended description of an activity of compounds of the present invention wherein said activity prevents or alleviates or ameliorates any of the specific phenomena known in the art to be associated with the pathology commonly known as "cancer." The term "cancer" refers to the spectrum of pathological symptoms associated with the initiation or progression, as well as metastasis, of malignant tumors. By the term "tumor" is intended, for the purpose of the present invention, a new growth of tissue in which the multiplication of cells is uncontrolled and progressive. The tumor that is particularly relevant to the invention is the malignant tumor, one in which the primary tumor has the properties of invasion or metastasis or which shows a greater degree of anaplasia than do benign tumors.

Thus, "treatment of cancer" or "treating cancer" refers to an activity that prevents, alleviates or ameliorates any of the primary phenomena (initiation, progression, metastasis) or secondary symptoms associated with the disease. Cancers that are treatable are broadly divided into the categories of carcinoma, lymphoma and sarcoma Examples of carcinomas that can be treated by the composition of the present invention include, but are not limited to: adenocarcinoma, acinic cell adenocarcinoma, adrenal cortical carcinomas, alveoli cell carcinoma, anaplastic carcinoma, basaloid carcinoma, basal cell carcinoma, bronchiolar carcinoma, bronchogenic carcinoma, renaladinol carcinoma, embryonal carcinoma, anometroid carcinoma, fibrolamolar liver cell carcinoma, follicular carcinomas, giant cell carcinomas, hepatocellular carcinoma, intraepidermal carcinoma, intraepithelial carcinoma, leptomanigio carcinoma, medullary carcinoma, melanotic carcinoma, menigual carcinoma, mesometonephric carcinoma, oat cell carcinoma, squamal cell carcinoma, sweat gland carcinoma, transitional cell carcinoma, and tubular cell carcinoma. Sarcomas that can be treated by the composition of the present invention include, but are not limited to: amelioblastic sarcoma, angiolithic sarcoma, botryoid sarcoma, endometrial stroma sarcoma, ewing sarcoma, fascicular sarcoma, giant cell sarcoma, granulositic sarcoma, immunoblastic sarcoma, juxaccordial osteogenic sarcoma, coppices sarcoma, leukocytic sarcoma (leukemia), lymphatic sarcoma (lympho sarcoma), medullary sarcoma, myeloid sarcoma (granulocitic sarcoma), austiogenci sarcoma, periosteal sarcoma, reticulum cell sarcoma (histiocytic lymphoma), round cell sarcoma, spindle cell sarcoma, synovial sarcoma, and telangiectatic audiogenic sarcoma. Lymphomas that can be treated by the composition of the present invention include, but are not limited to: Hodgkin's disease and lymphocytic lymphomas, such as Burkitt's lymphoma, NPDL, NML, NH and diffuse lymphomas.

In other embodiments, certain of the proteosome pro-inhibitors employed in the practice of the present invention are capable of preventing this activation of NF-kB. Blocking NF-kB activity is contemplated as possessing important practical application in various areas of medicine, e.g., inflammation, sepsis, AIDS, and the like.

In certain embodiments, the compounds of the present invention can be formulated in topical form for treatment of skin disorders selected from psoriasis, dermatitis, Lichen planus, acne, and disorders marked by hyperproliferation of skin cells.

In certain embodiments, the compounds of the present invention can be formulated in topical form for treatment of uncontrolled hair growth.

C. Hematopoietic Agonists

In still another aspect, the present invention provides a method for stimulating hematopoietic cells in culture or in vivo. In certain embodiments, the subject DPP IV pro-inhibitors include an address moiety that is a substrate for a protease that is expressed in bone marrow.

According to one aspect of the invention, a method for stimulating hematopoietic cells in vitro is provided. The method involves (1) contacting the hematopoietic cells with a sufficient amount of an DPP IV pro-inhibitor to increase the number of hematopoietic cells and/or the differentiation of such hematopoietic cells relative to the number and differentiation of hematopoietic cells.

One important aspect of the invention involves restoring or preventing a deficiency in hematopoietic cell number in a subject. Such deficiencies can arise, for example, from genetic abnormalities, from disease, from stress, from chemotherapy (e.g. cytotoxic drug treatment, steroid drug treatment, immunosuppressive drug treatment, etc.) and from radiation treatment.

The pro-inhibitors of the invention can be administered alone, or in combination with additional agents for treating the condition, e.g., a different agent which stimulates activation or proliferation of said lymphocytes or hematopoietic cells. For example, the pro-inhibitors can be administered in conjunction with exogenous growth factors and cytokines which are specifically selected to achieve a particular outcome. For example, if it is desired to stimulate a particular hematopoietic cell type, then growth factors and cytokines which stimulate proliferation and differentiation of such cell type are used. Thus, it is known that interleukins-1, 2, 3, 4, 5, 6, 7, 9, 10, 11, 12, 13 and 17 are involved in lymphocyte differentiation. Interleukins 3 and 4 are involved in mast cell differentiation. Granulocyte macrophage colony stimulating factor (GMCSF), interleukin-3 and interleulin-5 are involved in the eosinophil differentiation. GMCSF, macrophage colony stimulating factor (MCSF) and IL-3 are involved in macrophage differentiation. GMCSF, GCSF and IL-3 are involved in neutrophil differentiation. GMSCF, IL-3, IL-6, IL-11 and TPO are involved in platelet differentiation. Flt3 Ligand is involved in dendritic cell growth. GMCSF, IL-3, and erythropoietin are involved in erythrocyte differentiation. Finally, the self-renewal of primitive, pluripotent progenitor cells capable of sustaining hematopoiesis requires SCF, Flt3 Ligand, G-CSF, IL-3, IL-6 and IL-11. Various combinations for achieving a desired result will be apparent to those of ordinary skill in the art.

VII. Exemplary Synthetic Schemes

Scheme 1. Synthetic scheme for ProPro benzyl amino boronic acid

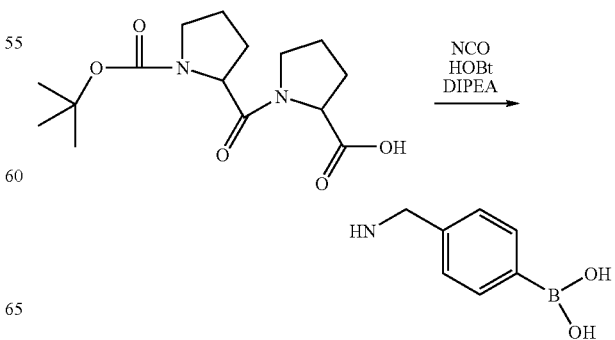

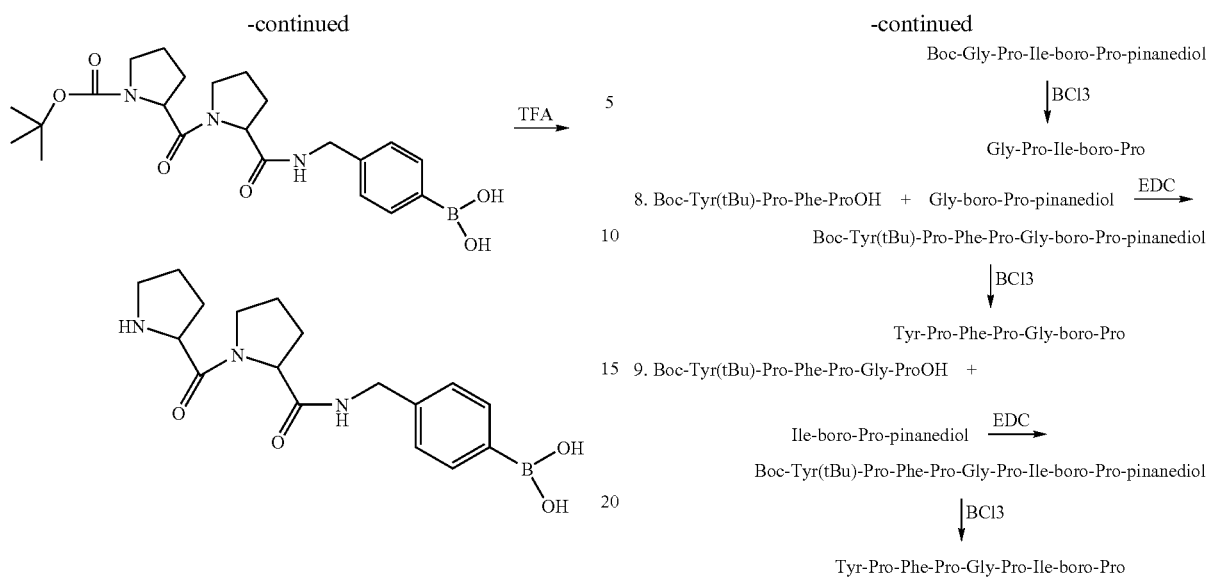

Scheme 2. Synthetic scheme for Casomorphin prodrugs

1. Boc-Tyr(tBu)OH + boro-Pro-pinanediol →(HATU)
   Boc-Tyr(tBu)boro-Pro-pinanediol
   ↓ BCl3
   Tyr-boro-Pro 2. Boc-Phe-OH + boro-Pro-pinanediol →(HATU)
   Boc-Phe-boro-Pro-pinanediol
   ↓ BCl3
   Phe-boro-Pro 3. Boc-Gly-OH + boro-Pro-pinanediol →(HATU)
   Boc-Gly-boro-Pro-pinanediol
   ↓ BCl3
   Gly-boro-Pro 4. Boc-Ile-OH + boro-Pro-pinanediol →(HATU)
   Boc-Ile-boro-Pro-pinanediol
   ↓ BCl3
   Ile-boro-Pro 5. Boc-Tyr(tBu)-PrOH + Phe-boro-Pro-pinanediol →(EDC)
   Boc-Tyr(tBu)-Pro-Phe-boro-Pro-pinanediol
   ↓ BCl3
   Tyr-Pro-Phe-boro-Pro 6. Boc-Phe-ProOH + Gly-boro-Pro-pinanediol →(EDC)
   Boc-Phe-Pro-Gly-boro-Pro-pinanediol
   ↓ BCl3
   Phe-Pro-Gly-boro-Pro 7. Boc-Gly-ProOH + Ile-boro-Pro-pinanediol →(EDC)
   Boc-Gly-Pro-Ile-boro-Pro-pinanediol
   ↓ BCl3
   Gly-Pro-Ile-boro-Pro 8. Boc-Tyr(tBu)-Pro-Phe-ProOH + Gly-boro-Pro-pinanediol →(EDC)
   Boc-Tyr(tBu)-Pro-Phe-Pro-Gly-boro-Pro-pinanediol
   ↓ BCl3
   Tyr-Pro-Phe-Pro-Gly-boro-Pro 9. Boc-Tyr(tBu)-Pro-Phe-Pro-Gly-ProOH +
   Ile-boro-Pro-pinanediol →(EDC)
   Boc-Tyr(tBu)-Pro-Phe-Pro-Gly-Pro-Ile-boro-Pro-pinanediol
   ↓ BCl3
   Tyr-Pro-Phe-Pro-Gly-Pro-Ile-boro-Pro Scheme 3. Synthetic scheme for Ala-Ala-Pro-boroVal -continued
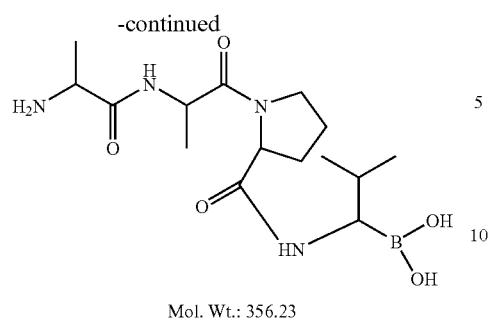
Mol. Wt.: 356.23
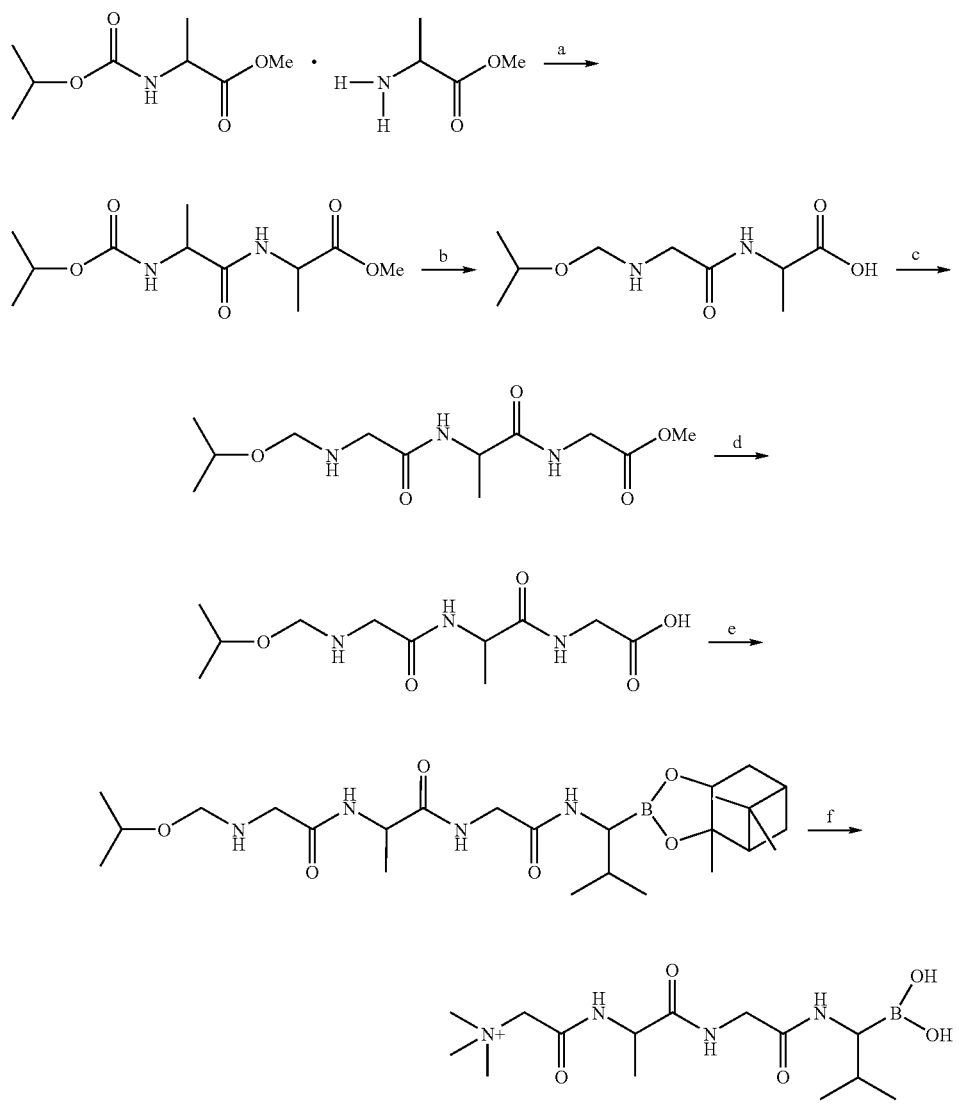
Reaction Conditions:
a) HOBt, EDCl, DIPEA, DMF, rt.
b) LiOH, THF:H2O (1:1).
c) H-gly-OMe, HOBt, EDCl, DIPEA, DMF, rt
d) LiOH, THF:H2O (1:1).
e) HATU, DMF, ValBoropinanediolester, N2 atm, rt
f) BCl3, -78° C.

Scheme 5. Synthetic scheme for His-Ala-Val-boroPro
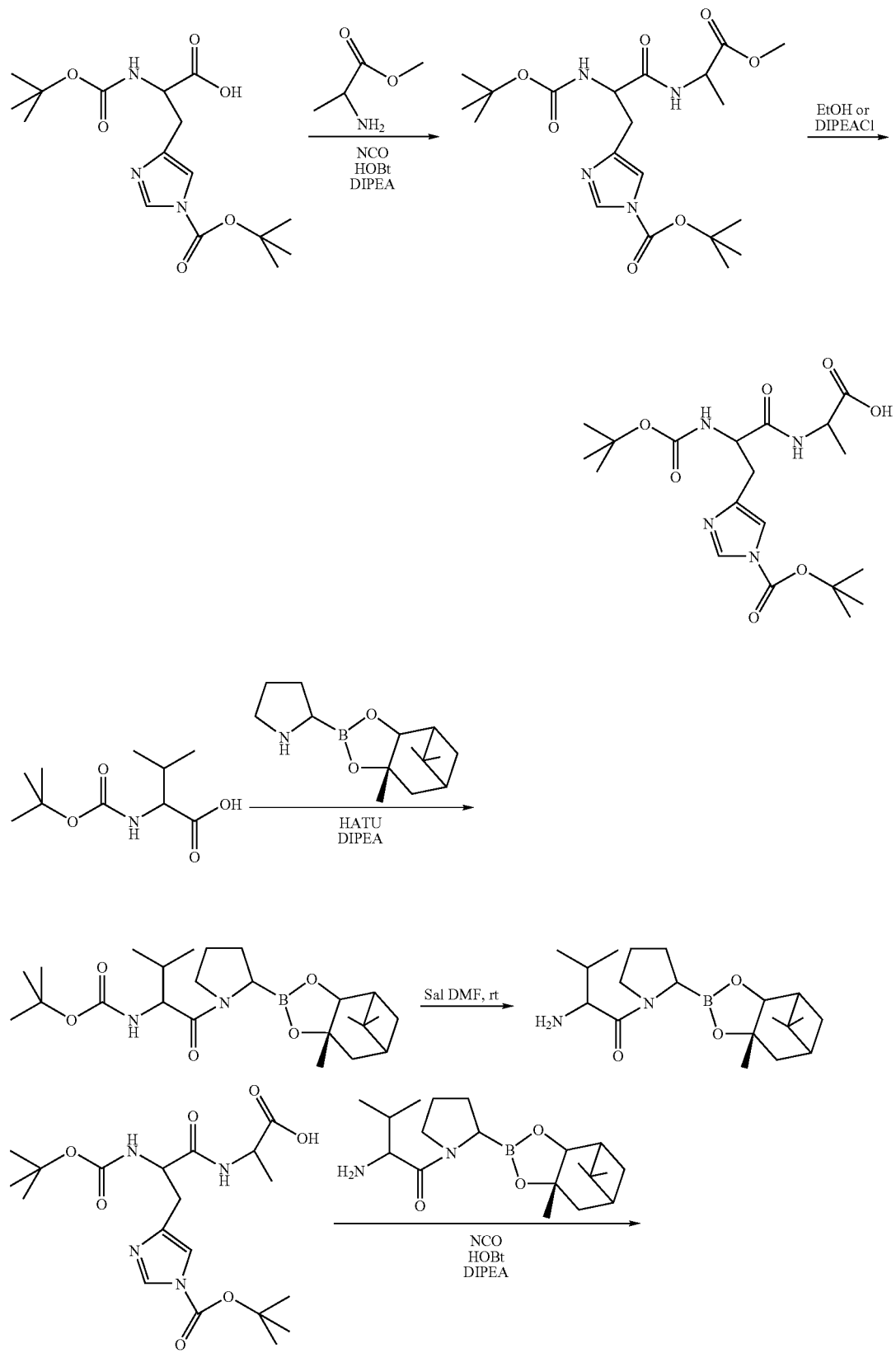

-continued
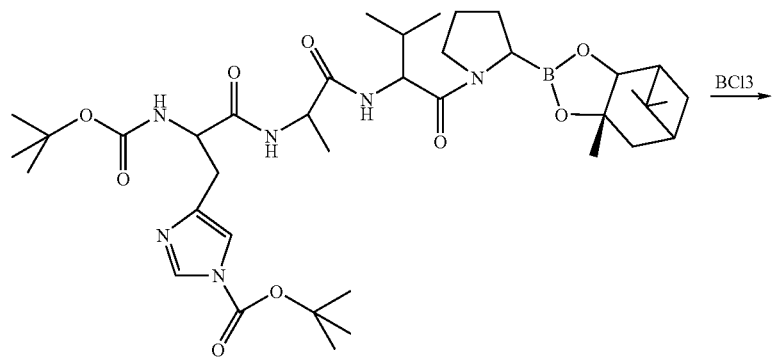
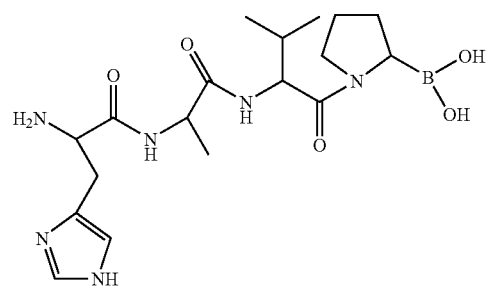
$C_{15}F_{31}ET_2O_4$
Exact Mass 422.24
Mol. Wt.: 422.20
O, 51.20, H, 1.40; S, 245; M, 19.90; O, 15.94
Scheme 6. Synthetic scheme for tBugProAlaboroPro
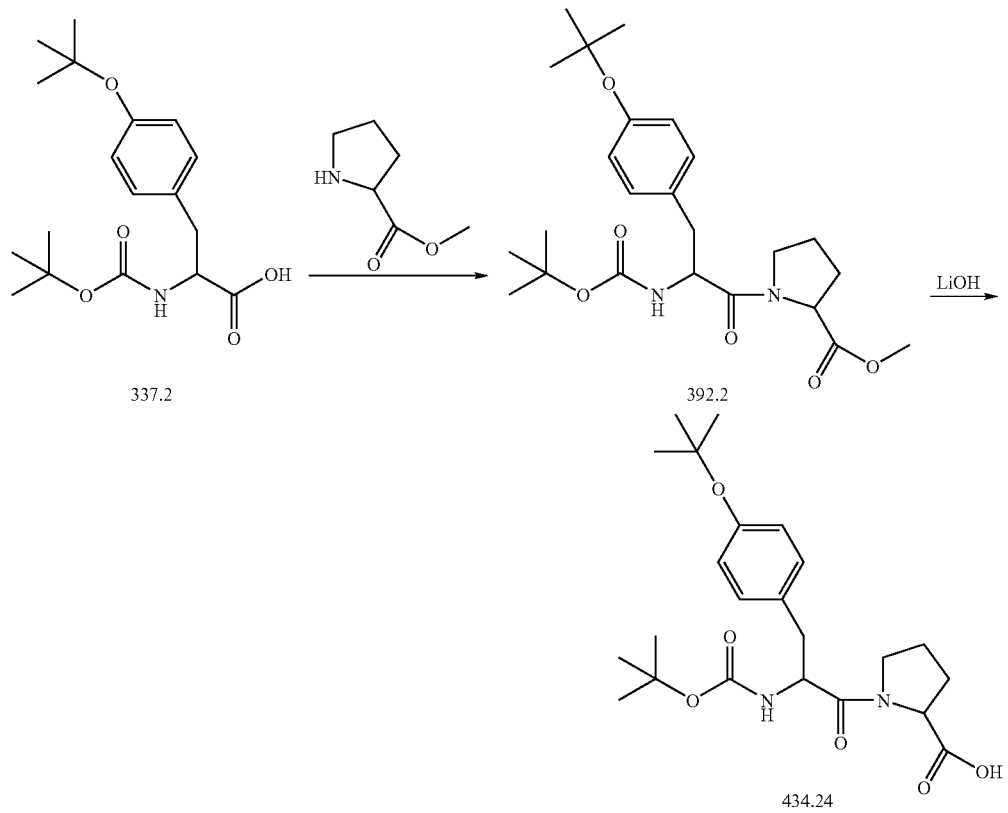

-continued
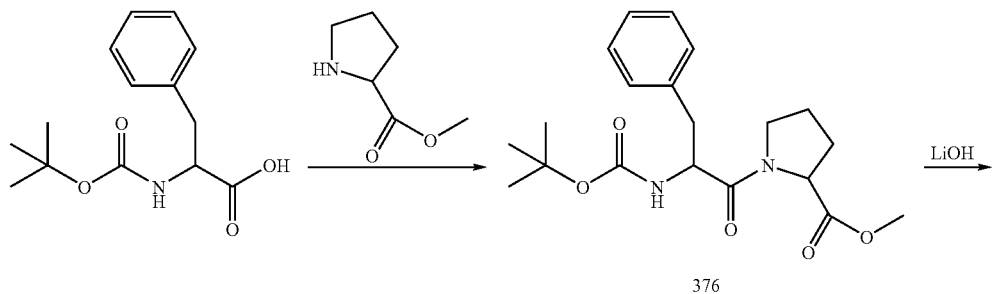
376
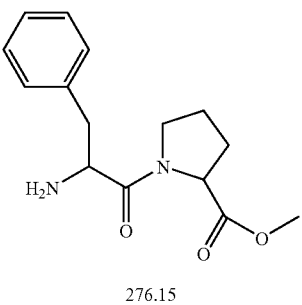
276.15
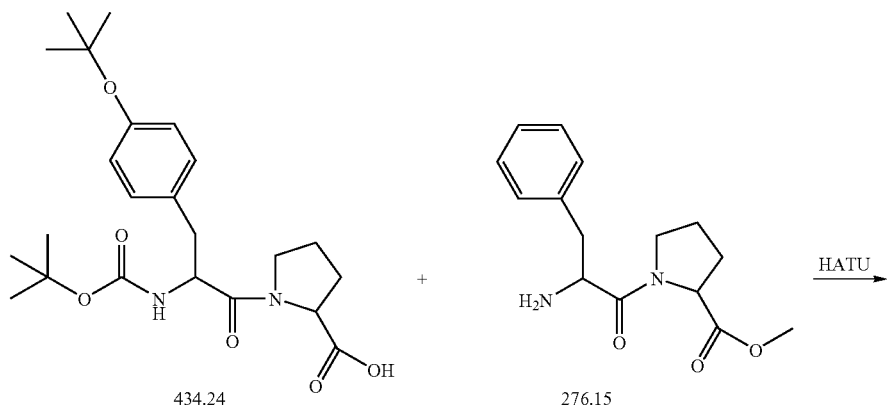
434.24    276.15
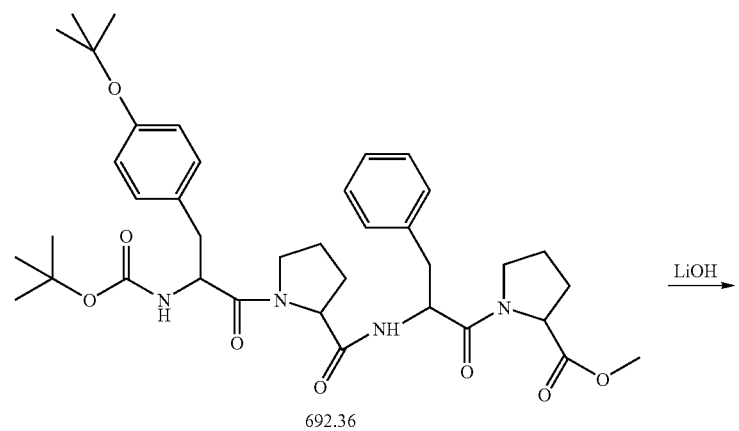
692.36

-continued
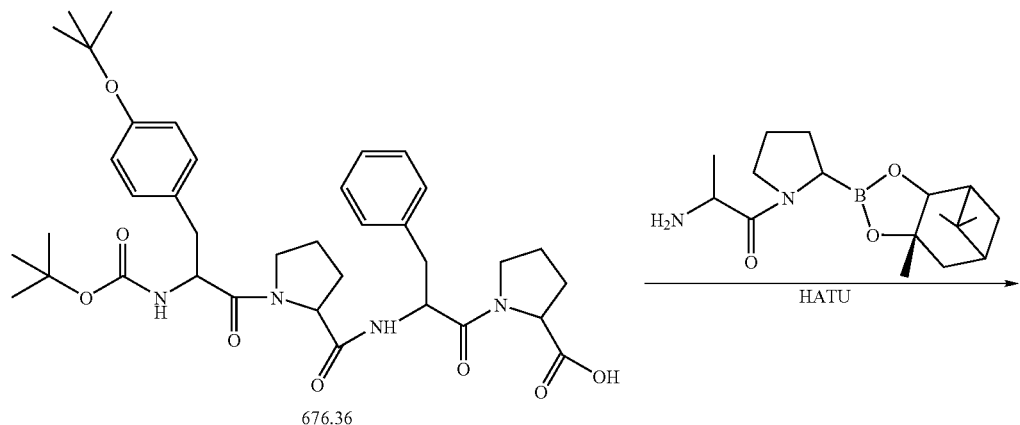
676.36
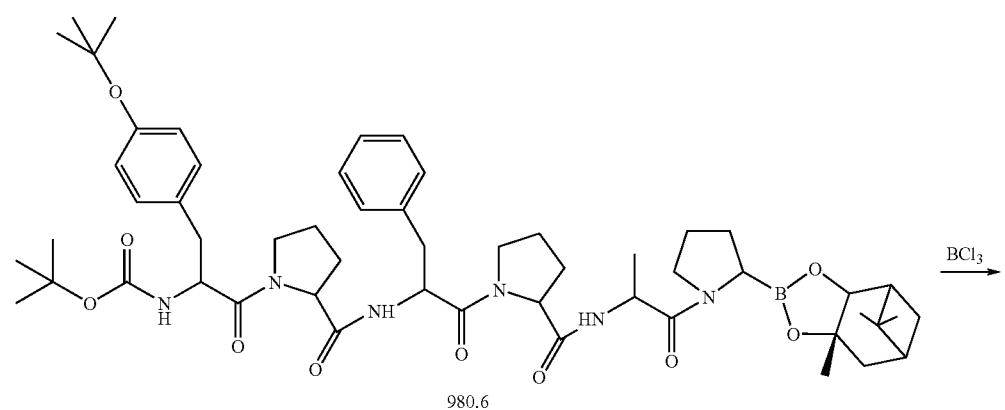
980.6
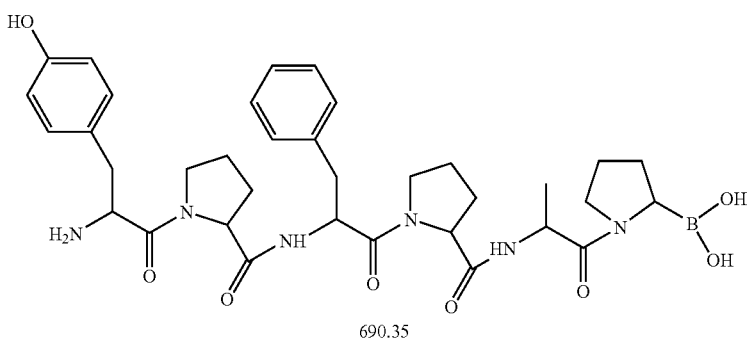
690.35
Scheme 7. Synthetic scheme for Beta EBP
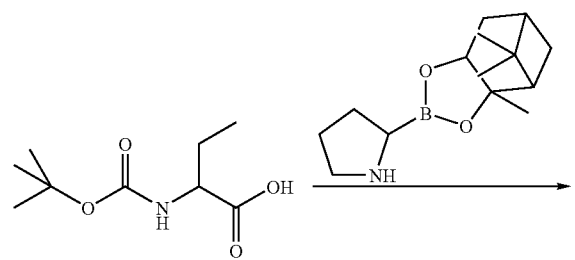

-continued
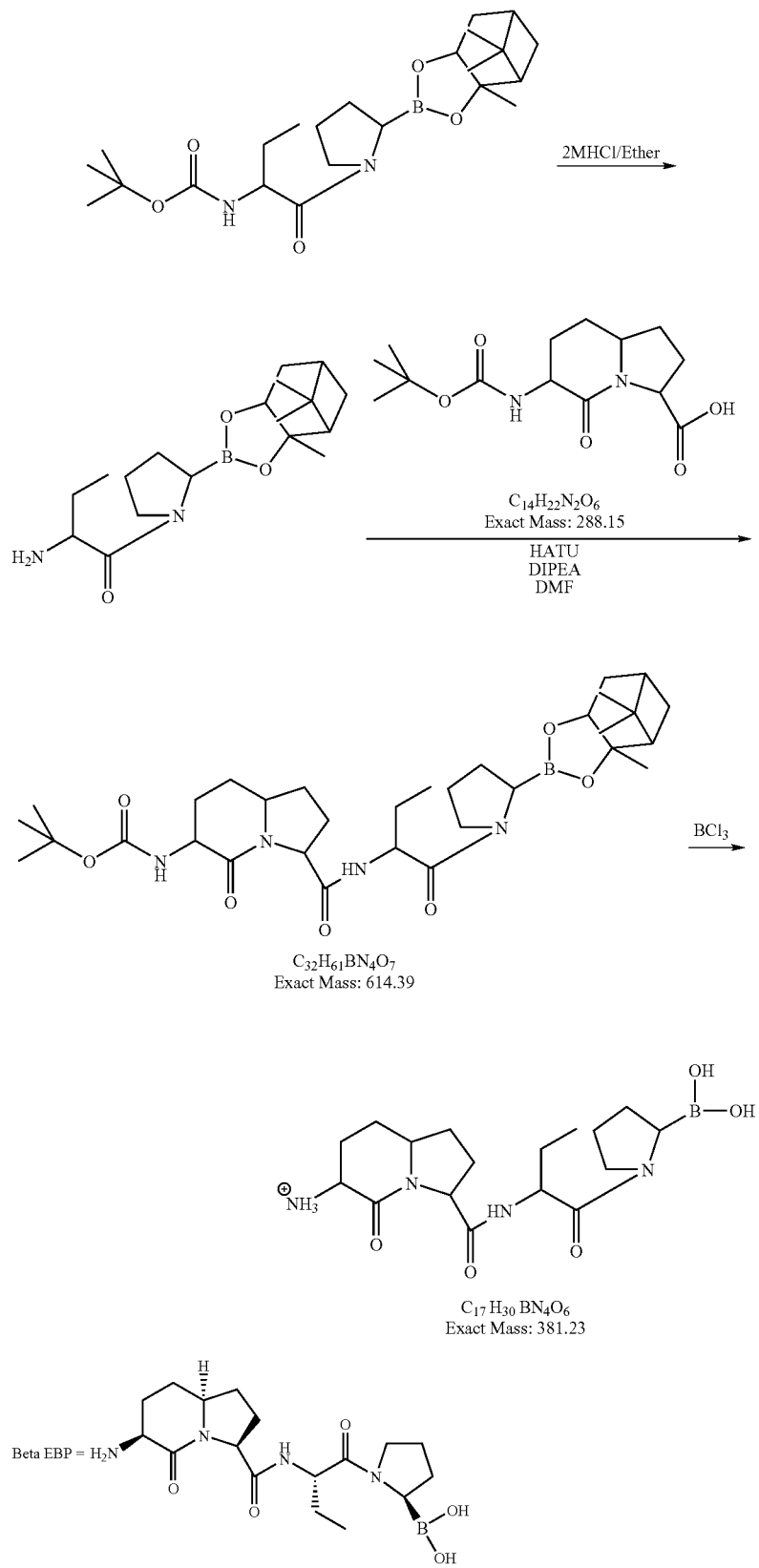

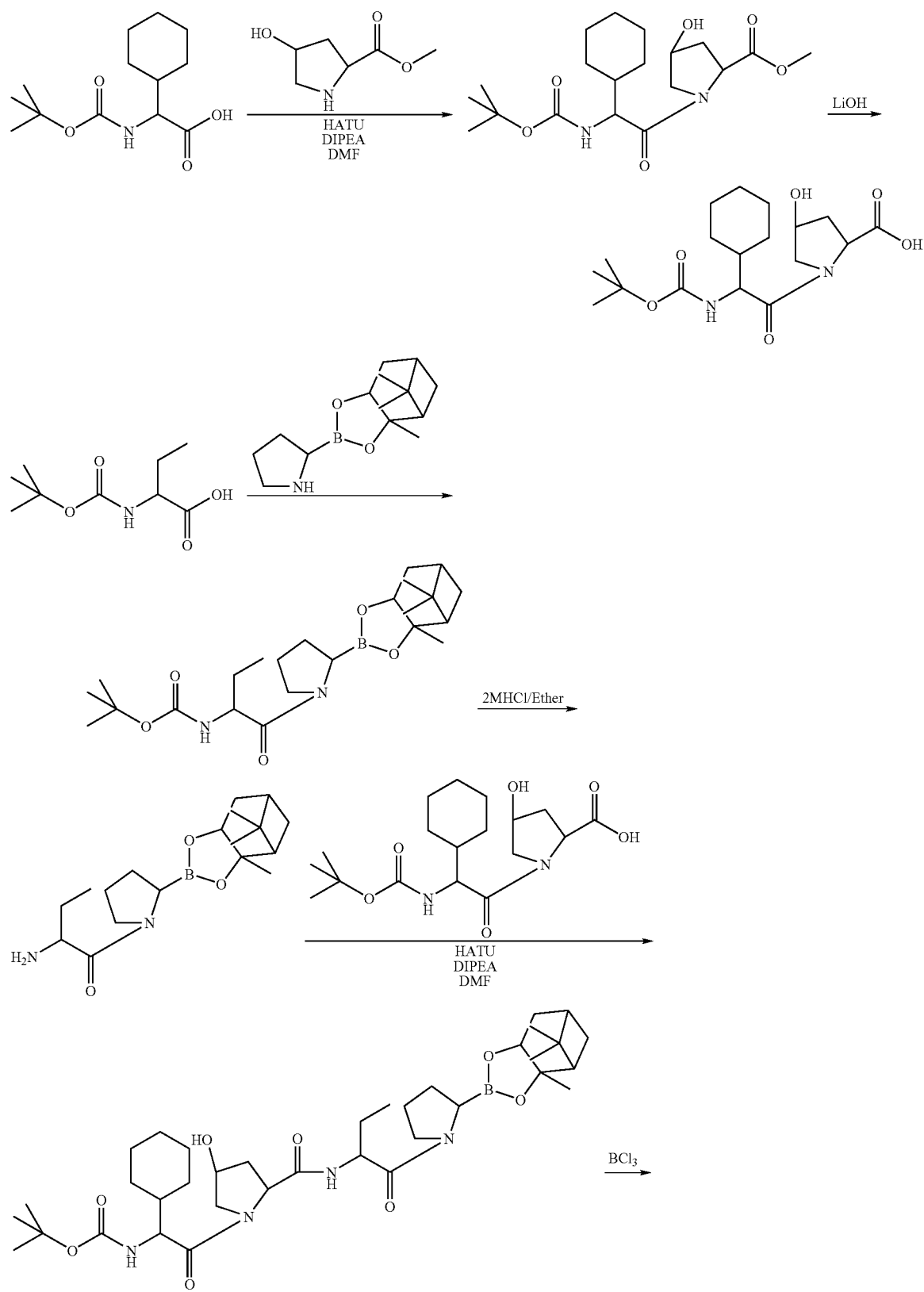

-continued
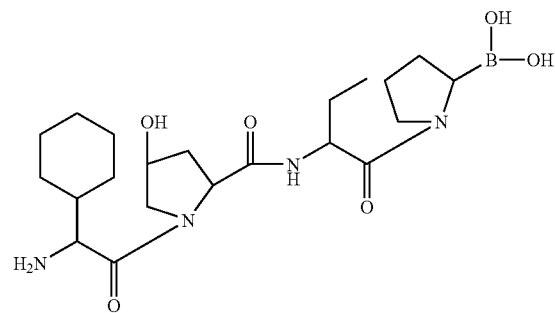
Scheme 9. Synthetic scheme for ChgPro-tBug-boroAla
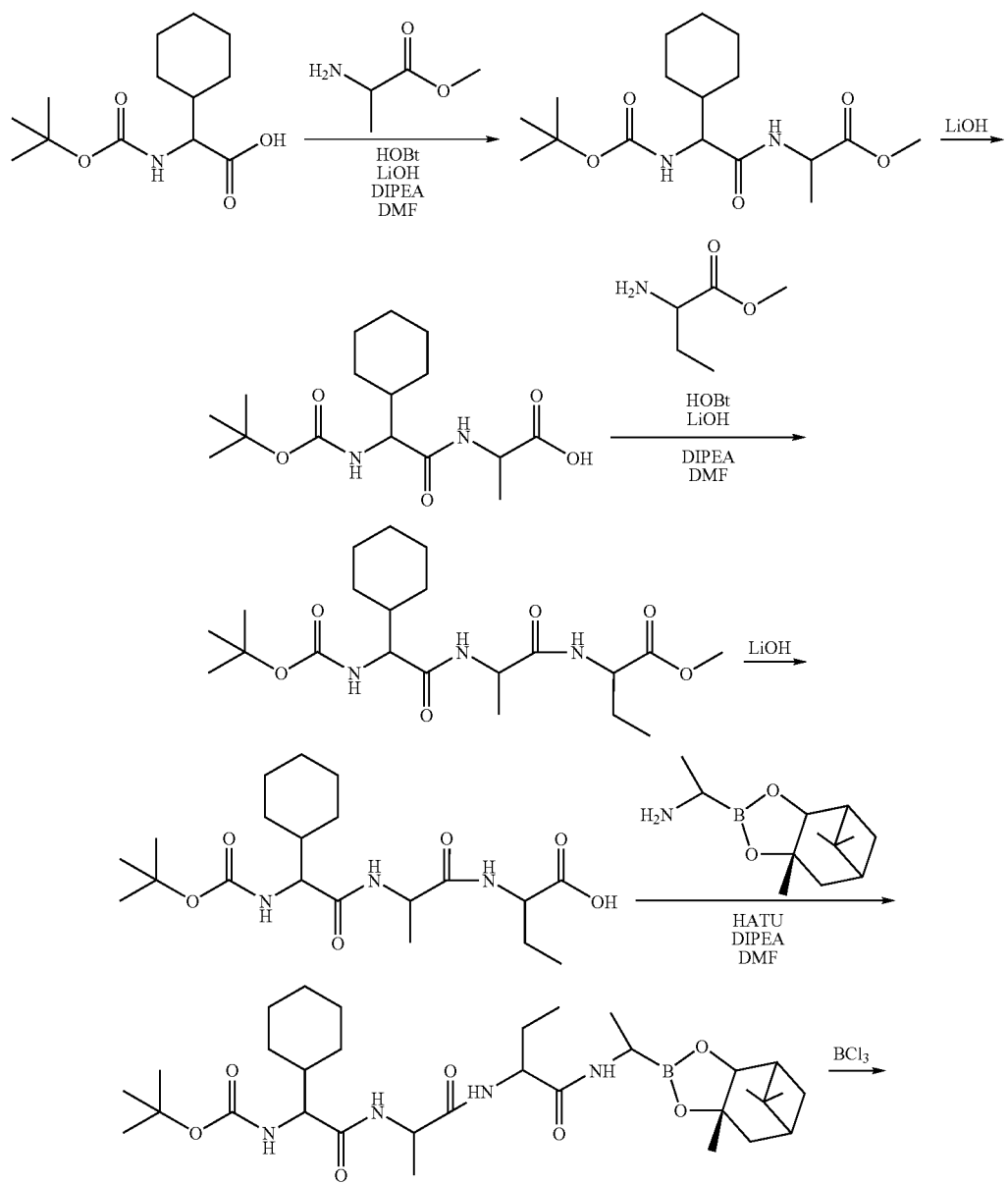

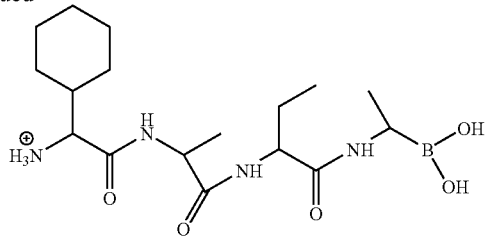
C₁₅H₃₁BN₄O₉
Exact Mass: 366.26
Mol. Wt.: 365.29
C,52.28; H, 8.89; B,261; H,145.4; O,267.6
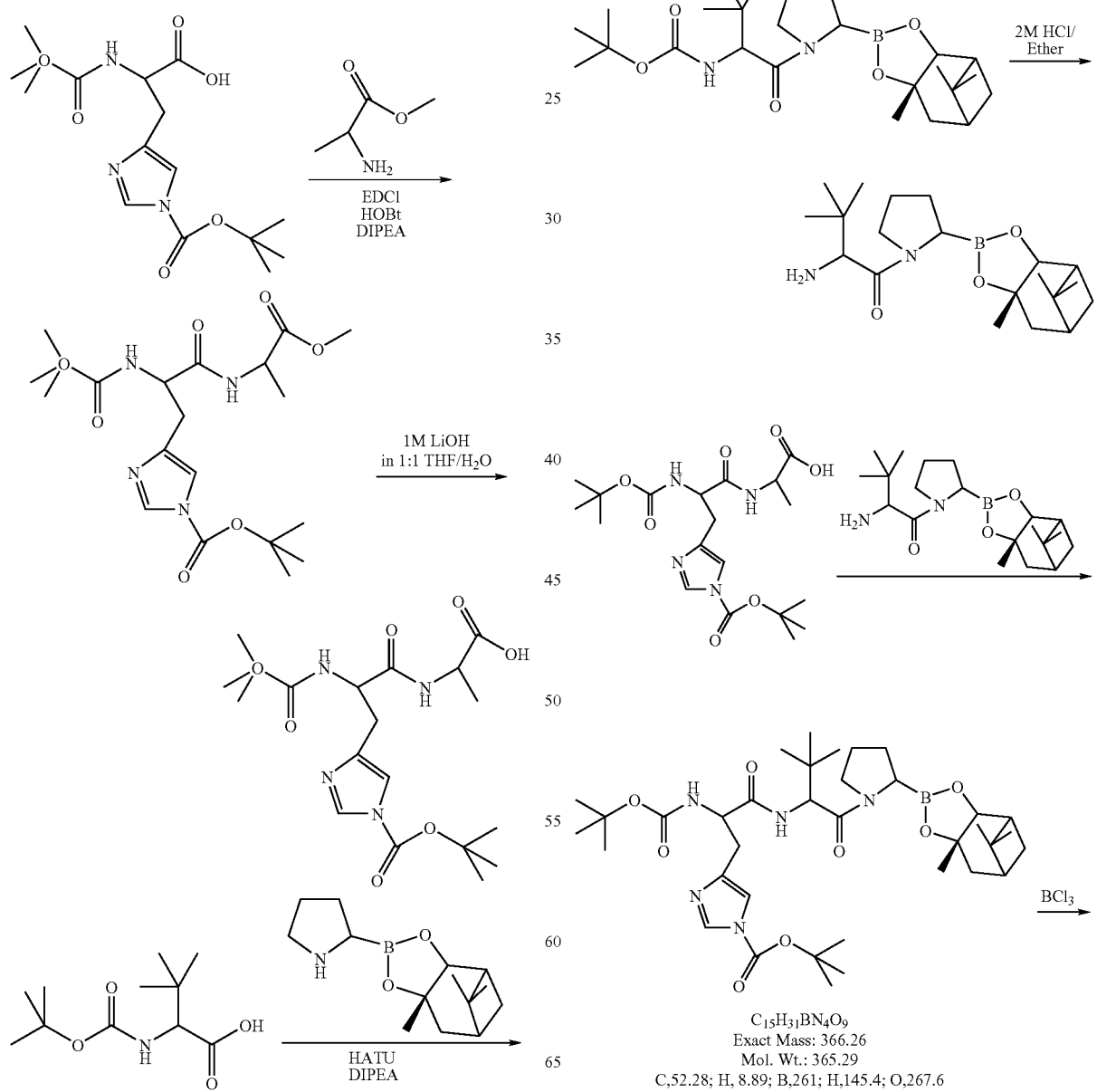

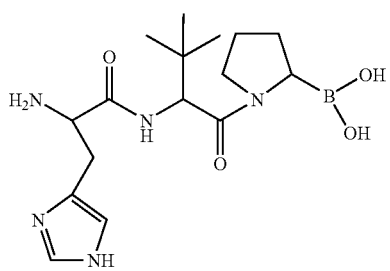

C₁₅H₃₁BN₄O₉
Exact Mass: 366.26
Mol. Wt.: 365.29
C,52.28; H, 8.89; B,261; H,145.4; O,267.6

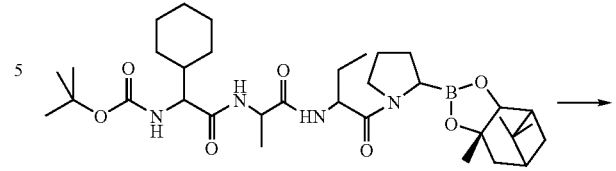

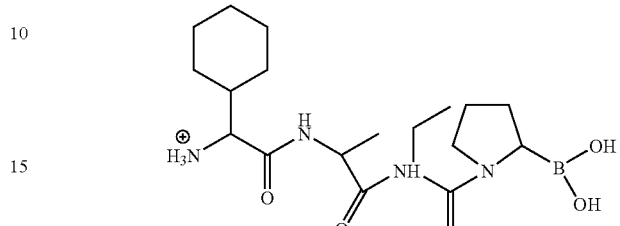

C₁₅H₃₁BN₄O₉
Exact Mass: 366.26
Mol. Wt.: 365.29
C,52.28; H, 8.89; B,261; H,145.4; O,267.6

Scheme 11. Synthetic scheme for Chg-Ala-Etg-boroPro

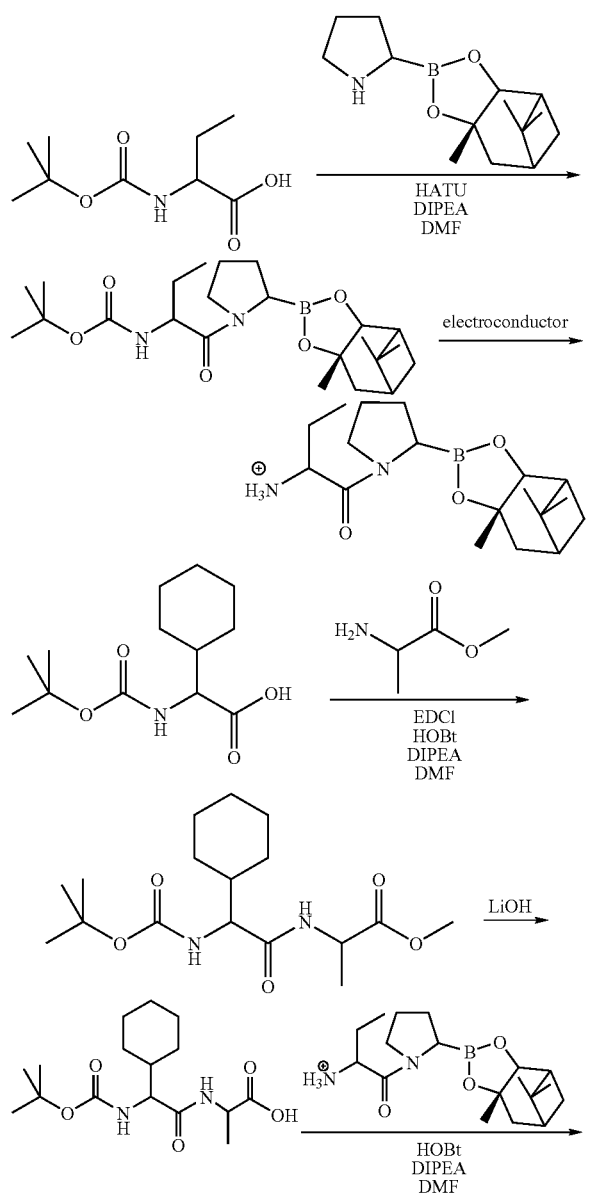

VIII Combinatorial Libraries

The compounds of the present invention, particularly libraries of variants having various representative classes of substituents, are amenable to combinatorial chemistry and other parallel synthesis schemes (see, for example, PCT WO 94/08051). The result is that large libraries of related compounds, e.g., a variegated library of compounds represented above, can be screened rapidly in high throughput assays in order to identify potential protease inhibitor lead compounds, as well as to refine the specificity, toxicity, and/or cytotoxic-kinetic profile of a lead compound.

Simply for illustration, a combinatorial library for the purposes of the present invention is a mixture of chemically related compounds which may be screened together for a desired property. The preparation of many related compounds in a single reaction greatly reduces and simplifies the number of screening processes which need to be carried out. Screening for the appropriate physical properties can be done by conventional methods.

Diversity in the library can be created at a variety of different levels. For instance, the substrate aryl groups used in the combinatorial reactions can be diverse in terms of the core aryl moiety, e.g., a variegation in terms of the ring structure, and/or can be varied with respect to the other substituents.

A variety of techniques are available in the art for generating combinatorial libraries of small organic molecules such as the subject protease inhibitors. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; the ArQule U.S. Pat. Nos. 5,736,412 and 5,712,171; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 100 to 1,000,000 or more diversomers of the subject protease inhibitors can be synthesized and screened for particular activity or property.

In an exemplary embodiment, a library of candidate protease inhibitor diversomers can be synthesized utilizing a scheme adapted to the techniques described in the Still et al. PCT publication WO 94/08051, e.g., being linked to a polymer bead by a hydrolyzable or photolyzable group, optionally located at one of the positions of the candidate agonists or a substituent of a synthetic intermediate. According to the Still et al. technique, the library is synthesized on a set of beads, each bead including a set of tags identifying the particular diversomer on that bead. The bead library can then be "plated" with proteases for which an an inhibitor is sought. The diversomers can be released from the bead, e.g., by hydrolysis. The structures of the compounds useful in the present invention lend themselves readily to efficient synthesis. The nature of the structures of the subject compounds, as generally set forth above, allows the rapid combinatorial assembly of such compounds. For example, as in the scheme set forth below, an activated aryl group, such as an aryl triflate or bromide, attached to a bead or other solid support can be linked to another aryl group by performing a Stille or Suzuki coupling with an aryl stannane or an aryl boronic acid. If the second aryl group is functionalized with an aldehyde, an amine substituent can be added through a reductive amination. Alternatively, the second aryl group could be functionalized with a leaving group, such as a triflate, tosylate, or halide, capable of being displaced by an amine. Or, the second aryl group may be functionalized with an amine group capable of undergoing reductive amination with an amine, e.g., $CyKNH_2$. Other possible coupling techniques include transition metal-mediated amine arylation reactions. The resultant secondary amine can then be further functionalized by an acylation, alkylation, or arylation to generate a tertiary amine or amide which can then be cleaved from the resin or support. These reactions generally are quite mild and have been successfully applied in combinatorial solid-phase synthesis schemes. Furthermore, the wide range of substrates and coupling partners suitable and available for these reactions permits the rapid assembly of large, diverse libraries of compounds for testing in assays as set forth herein. For certain schemes, and for certain substitutions on the various substituents of the subject compounds, one of skill in the art will recognize the need for masking certain functional groups with a suitable protecting group. Such techniques are well known in the art and are easily applied to combinatorial synthesis schemes.

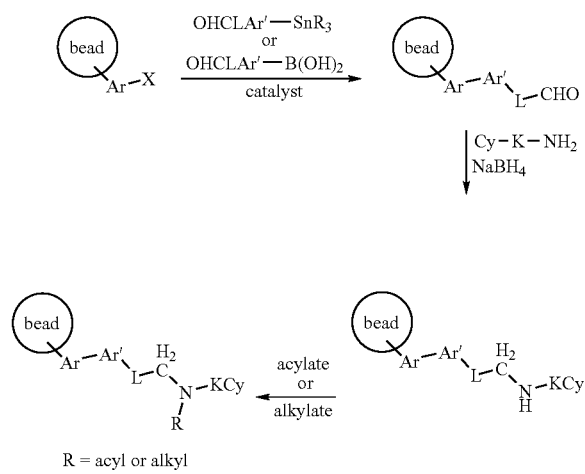

Many variations on the above and related pathways permit the synthesis of widely diverse libraries of compounds which may be tested as protease inhibitors.

IX. Examples

Type 1 or Target-Activated SPIs (TASPIs).

Example 1

DPP IV Activated, DPP IV Inhibitor

Dipeptidyl amino peptidase type IV (DPP IV) is a type II membrane bound protease, distributed widely in the body. It is found, for example, in the intestine, liver and kidney. It is also found on the surface of CD4+ and CD8+ T cells where is it known as CD26. Among other things this enzyme has been demonstrated to hydrolyze and thereby inactivate glucagon like peptide 1 (GLP-1) and gastric inhibitory polypeptide, or glucose-dependent insulinotropic polypeptide (GIP). The activity in degrading these peptides suggests that DPP IV inhibitors could be useful for the treatment of Type 2 diabetes, and DPP IV inhibitors have, in fact, been demonstrated to improve glucose tolerance in animals including in animal models of diabetes. DPP IV inhibitors have also been demonstrated to stimulate the proliferation of hematopoetic stem cells, an activity that also cold prove to have therapeutic application. The mechanism underlying this effect, however is not well understood. In any case, the Xaa-boroPro's (FIG. 1) are the most potent known inhibitors of DPP IV, and molecules of this class have been demonstrated to have hematopoetic stem-cell proliferative, and anti-diabetic effects in vivo in animals.

Type 1 SPI's, activated by DPP IV and targeting DPP IV can be constructed by making the R-A portion of R-A-G a structure recognized and catalytically acted upon by DPP IV so that it is removed to release the DPP IV inhibitory moiety G. A Type 1 SPI (TASPI) for DPP IV would have the general structure shown in 2:

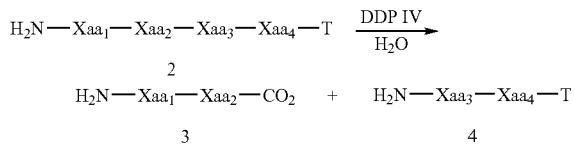

R-A of R-A-G corresponds to $NH_2$-$Xaa_1$-$Xaa_2$ of 2. For DPP IV specificity $Xaa_2$ should preferentially be proline or alanine while $Xaa_1$ can be any natural or non naturally occurring amino acid, but most preferentially with a free amino group. $Xaa_3$-$Xaa_4$-T, for example, can be Xaa-boroPro, Xaa-boroAla, or Xaa-Pro-CN. In general $Xaa_4$ should preferentially be Pro or Ala, $Xaa_3$ can be any natural or non naturally occurring amino acid while T can be boronyl, nitrile, aldehyde, alpha keto amide, trifluoromethy ketone etc.

Working examples of a TASPI's for DPP IV include Cyclohexylglycine-Proline-Valine-boroProline, (CHG-Pro-Val-boroPro)(5), and Cyclohexylglycine-Proline-Ala-boroProline (CHG-Pro-Ala-boroPro). From our prior work on homo- and hetero-conjugates ( ) we know that the P2 side chain of substrates and inhibitors does not make contact with DPP IV but instead must extend away from the enzyme toward the solvent. Thus, DPP IV will cleave dipeptides off the N-terminal of polypeptides regardless of what the N-terminal happens to be, even if it is a non natural amino acid such as CHG. DPP IV will therefore remove the N-terminal CHG-Pro sequence of 5 to release the potent DPP IV inhibitor Val-boroPro, 7. Importantly, the Val-boroPro released will in the open chain form and therefore more potent per unit mass when released in the vicinity of DPP IV than unmodified Val-boroPro can be when prepared in pure form. Placing a CHG (or other similar non naturally occurring amino acids) in the P4 position of the SPI confers several advantages. One is resistance to amino peptidases, as they are less likely to recognize and cleave from the N-terminal non natural amino acids. Another is resistance to degradation by other post prolyl peptidases and dipeptidyl amino peptidases and therefore improved targeting to DPP IV.

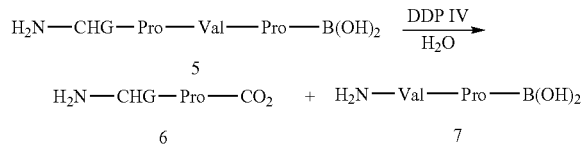

FIG. 3 shows that the SPI versions of Val-boroPro and Ala-boroPro do not exhibit the pH dependence in their inhibition of DPP IV in in vitro enzyme assays characteristic of the corresponding Xaa-boroPro inhibitors and that their apparent affinities are more similar to that of the low pH form of the free Xaa-boroPro derivative, confirming that the Xaa-boroPro moiety is being released in the open chain and more active confomation as expected (FIG. 3). It is important to note that the x-axis in FIG. 3 refers to the concentration of the SPI, not the concentration of the released Xaa-boroPro. It is likely that the amount of the Xaa-boroPro released is substantially lower than the starting concentration of the SPI, and thus FIG. 3 actually underestimates the actual potency of the released Xaa-boroPro.

Table 1 list a number of SPU forms of Xaa-boroPro's showing that essentially all exhibit the pH independence except for those which are "poor" DPP IV substrates, eg., those having Ala in the P3 site where cleavage and activation occur.

FIGS. 6 and 7 shows that CHG-Pro-Val-boroPro is very orally active while FIG. 8 shows it outperforms Val-boroPro in inhibiting serum DPP IV activity. Although the inhibition takes a little longer to develop (compare at 0.5 hour timepoint) the total inhibition achieved and the length of time inhibition is maintained is greater with the SPI form of Val-boroPro than with Val-boroPro (compare inhibition levels at 2, 4 and 8 hours). The SPI form of Val-boroPro also appears to be less toxic than Val-boroPro. For unknown reason Val-boroPro is quite toxic to rats, but apparently not at all to mice (Table 2). Note that a dose of 0.035 mg/kg killed four out of four Zucker rats, but that more than 100-fold larger dose (i.e., 3.5 mg/kg) has no noticeable toxic effect in mice. A corresponding dose of CHG-Pro-Val-boroPro (i.e., equivalent to 0.35 mg/kg of Val-boroPro) killed only one of four rats (FIG. 6). This indicates that inhibiting DPP IV is itself not the cause of toxicity in rats as greater inhibition of serum DPP IV was achieved with CHG-Pro-Val-boroPro than with Val-boroPro itself, with less toxicity.

Table 3 compares the oral activity in mice of Val-boroPro with CHG-Pro-Val-boroPro and CHG-Pro-Ala-boroPro. The results show that like in rats, CHG-Pro-Val-boroPro also outperforms Val-boroPro in mice.

The db/db mice of Table 3 represent an animal model of Type II diabetes. FIG. 9 shows that CHG-Pro-Val-boroPro markedly outperforms Val-boroPro in lowering the glucose excursion following an oral glucose challenge and in aiding the return the excursion to normal.

Thus, the SPI version of Val-boroPro is more effective in inhibiting DPP IV in vivo in rats and in mice, the inhibition is more long lasting, is markedly more effective in lowering the area under the curve following an oral glucose challenge in a diabetic mice model, and appears to be less toxic.

Example 2

FAP Activated, FAP Inhibitor

Fibroblast activating protein is a post proline cleaving serine protease with some homology to DPP IV which seems to be found only on cells immediately surrounding tumors and in some cases healing wounds. There has been speculation that blocking this enzyme's activity could in itself be useful in treating some forms of solid cancers. FAP's specificity resembles that of DPP IV. FAP will for example cleave various dipeptide chromagenic substrates that are also substated for DPP IV such as Xaa-Pro-pNA. However, FAP differs from DPP IV in that it has endopeptidase activity. It will therefore cleave the above Xaa-Pro-pNa substrate even when the N-terminus is blocked by a CBZ or acetyl group. DPP IV will not cleave such blocked dipeptides, nor will Xaa-boroPro inhibitors work well against DPP IV if the N-terminal is blocked. A FAP activated, FAP inhibitor can be constructed by making R-A of structure R-A-G of compounds of the present invention specific for FAP, while the segment G (Xaa-Xaa-T) of R-A-G segment can be most anything that also inhibits DPP IV. One such variation that should work is illustrated in structure 8.

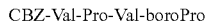
CBZ-Val-Pro-Val-boroPro         8

This molecule would not be activated by DPP IV although the Val-boroPro released by FAP would inhibit DPP IV. However, being liberated in the vicinity of FAP together with the cyclization and inactivation that would occur as it diffuses away from the FAP target site would confer substantion FAP specificity on the released Val-boroPro, or other G moiety (Xaa-Xaa-T) used to inhibit FAP.

Example 3

Thrombin Activated, Thrombin Inhibitor (or Factor X)

The mechanism of blood clotting present special difficulties when designing anti-coagulates targeting thrombin or Factor 10. Both are normally present in active form at very low concentrations. However, when needed, the cascade mechanisms of the intrinsic or extrinsic pathways rapidly produce huge concentrations of activated thrombin or Factor Xa. The problem this present for anti coagulates is that to prevent clotting huge excesses of thrombin or Factor Xa inhibitors have to be given and maintained even when levels of activated thrombin are low. Not having sufficient thrombin or Factor Xa around to bind, the inhibitors are free to block other trypsin like serine proteases causing unwanted side effects. This problem can be overcome by properly designed SPI molecules of the current invention. In this case, R-A should be constructed such that thrombin or Factor Xa removes it to release a thrombin or factor Xa inhibitor. A specific example of such a molecule is illustrated in structure 9.

R-Arg-Leu-boroArg         9

Type 2 or Target Directed SPIs

Millennium Pharmaeuticals has developed a proteosome protease inhibitor, currently in late stage clinical trials for the treatment of various types of cancer. The drug, previously referred to as PS-341, now referred to as LDP-341 is a dipeptide boronic acid inhibitor, R-Phe-boroLeu, as shown in FIG. 11. The R group was added largely to prevent cyclization, thereby increasing potency.

Proteosomes are found in every cell of the body. Their catalytic activity is essentially for cell viability, inhibition of this enzyme is therefore toxic. The potential of LPD-341 as a cancer therapy depends on rapidly proliferating cancer cells being more susceptible to the toxic effects of proteosome inhibition than normal cells. The current invention includes "smart" versions of proteosome inhibitors which should have improved efficacy, reduced side effects, and expand the range of therapeutic uses, to for example infectious diseases. Examples, which belong to the Type 2 or Target Directed class of SPIs are outlined below.

Example 4

FAP Activated, Proteosome Protease Inhibitor

Because FAP is associated only with tumors, an FAP activated proteosome protease inhibitor should provide substantial improvements in efficacy, and safety over the currently existing non-prodrug Milllennium (and other) proteosome protease inhibitors for the treatment of cancer. Structure 10 gives a example of a chemical structure for a FAP activated, proteosome protease inhibitor.

CBZ-Ala-Pro-Phe-boroLeu          10

Example 5

DPP IV Activated, Proteosome Protease Inhibitor

Because DPP IV is upregulated on activated T cells, directing a proteosome protease inhibitor to these cells cold be therapeutic useful in the treatment of various autoimmune and other disorders caused by unwanted but activated population of T cells. One example of a structure for a DPP IV activated, proteosome inhibitor is given in structure 11.

$NH_2$-Ala-Pro-Phe-boroLeu          11

Example 6

Prostate Specific Antigen (PSA) Activated, Proteosome Protease Inhibitor

PSA is a serine protease found in abundance in prostate cells. It has a chymotrypsin like specificity and will cleave polypeptides following Phe, Tyr, Ser, Gln. The most favored cleavage sequence appears to Ser-Tyr-Gln↓. One example of an SPI targeting specifically the proteosome protease within prostate cells and useful therefore for the treatment of prostate cancer is shown is structure 12.

Ac-Ser-Try-Gln-Phe-boroLeu          12

Example 7

Matriptase Activated, Proteosome Protease Inhibitor

Matriptase is a recently discovered serine protease found specifically on the cell surface of certain types of cancer cells. Its specificity has not been entirely elucidated but similar to trypsin it cleaves following Arg. One example of a matriptase activated proteosome inhibitor is illustrated in structure 13.

R-Arg-Phe-boroLeu          13

Example 8

Infected Cell Activated, Proteosome Protease Inhibitor

A number of cellular pathogens encode proteases to perform various functions needed by the pathogen. For example *Plasmodium falciparum*, the microbe that causes malaria invades red blood cells and degrades hemoglobin as it primary energy source. It produces a cysteine proteases with a cathepsin like specificity called falcipain for the purpose of degrading hemoglobin. One example of an falcipain activated proteosome inhibitor useful for the treatment of malaria is illustrates in 14.

ZPhe-Arg-Phe-boroLeu          14

A number of pathogens rely on proteases to process their polypeptide gene product into functional proteins. Pathogens producing such 'maturational' proteases are hepatitis type A, B, and C, and HIV among others. SPIs targeting cells infected by these agents can be constructed by adding the correct R-A, recognized and cleaved by the pathogen's protease to the dipeptide proteosome inhibitor. The resulting SPI should seek out and selectively kill infected cells but not uninfected cells of the same type.

Example 9

Evaluation of dpp iv Inhibition Following Single Oral Administration of New Chemical Entities to Male Sprague Dawley Rats Test Article No. 1: Tyrosine-proline-alanine-proline boronic acid Appearance: White powder with a molecular weight of 446.31 g/mole Test Article No. 2: Phenylalanine-proline-alanine-proline boronic acid Appearance: White powder with a molecular weight of 430.31 g/mole Test Article No. 3: Alanine-proline boronic acid Appearance: White powder with a molecular weight of 186.02 g/mole The test articles were stored at room temperature pending use. The dose formulations were prepared for oral administration in deionized (Type I) water as defined in Study Design (Table 1). Forty-six male Sprague-Dawley rats were received from Charles River Canada (St-Constant, QC, Canada) and acclimated to the animal facilities for at least 96 hr prior to dose administration. Target room conditions were: temperature: 21±3° C.; humidity: 30 to 70%. There were no deviations from these ranges recorded during study conduct. Photoperiod was 12-hr light and 12-hr dark with exceptions, as necessary, for dosing and sample collection.

The day prior to dose administration, animal were randomly assigned to 9 study groups (4 rats/group) according to Study Design (Table 5). On Day 1, and following an overnight fast, animals were weighed (body weight range: 273-301 g) and were administered their respective formulation orally by gavage at a dose volume of 2 mL/kg. Following dose administration, blood samples (0.25 to 0.40 mL) were collected from each animal by jugular venipuncture under isoflurane anesthesia Blood samples were collected (using lithium heparin as the anticoagulant) at pre-dose and again at, 1, 2, 4, 6, 8 and 24 hr post-dose. Blood samples were placed on ice pending centrifugation, (3200 g for 10 min at 4° C. nominal). Following centrifugation, plasma was harvested and stored at −20° C. nominal pending shipment for analysis.

Results

No adverse clinical signs were observed during the conduct of this study, suggesting that single dose of the test articles was essentially innocuous at the dose levels administered.

Example 10

Evaluation of DPP IV Inhibition Following Single Oral Administration of Four Triad Compounds in Male Rats The objectives of this study were to determine the effects of a single oral doses of four Triad Pharmaceuticals on the inhibition of the enzyme dipeptidyl peptidase IV (DPP IV) in male Sprague-Dawley rats and to determine its potential toxicity. Three of the test articles were pro-drugs of alanine proline boronic acid. This document constitutes the report describing the in-life procedures used during the conduct of this study. The assessments of DPP IV activity in plasma samples were performed by the Sponsor. Results of these investigations will be reported separately.

Methods

TEST ARTICLES

Test Article 1: L-2-Chg-PRO-ALA-PRO boronic acid
 Amount Received: ca 0.6 mL at 93.75 mg/mL in water
 Molecular Weight: 422.33 g/mole
 Storage Conditions: −20° C. nominal Test Article 2: N-Me-Phe-PRO-ALA-PRO boronic acid
 Amount Received: ca 0.6 mL at 82.5 mg/mL in water
 Molecular Weight: 444.33 g/mole
 Storage Conditions: −20° C. nominal Test Article 3: N-Me-Gly-3,4 dehydroproline-ALA-PRO boronic acid
 Amount Received: ca 0.6 mL of 66.67 mg/mL in water
 Molecular Weight: 352.19 g/mole
 Storage Conditions: −20° C. nominal A total of 2 vials (each containing ca 0.3 mL) for each of Test Articles 1, 2, and 3 were stored at ca −20° C. nominal upon receipt and pending use. The dose formulations were prepared by the Department of DMPK of MDSPS. All formulations were prepared for oral administration in deionized (Type I) water as described in the Study Design of Table 6. Dose formulations for Test Articles 1, 2, and 3, were prepared such to ensure administration of specifically targeted dose levels of parent drug based on a molecular weight for ALA-PRO Boronic acid of 136.02 g/mole. Thirty-six male Sprague-Dawley rats were received from Charles River Canada (St-Constant, QC, Canada) and acclimated to the animal facilities for at least one week prior to dose administration. Target room conditions were: temperature: 21±3° C.; relative humidity: 30 to 70%. There were no deviations from these ranges during study conduct Photoperiod was 12-hr light and 12-hr dark with exceptions, as necessary, for dosing and sample collection.

On the day prior to dose administration, animal were randomly assigned to 12 study groups (3 rats/group) according to the Study Design described in Table 6. On Day 1 (day of dose administration), and following an overnight fast, animals were weighed (body weight range: 265-292 g) and were administered their respective formulation orally by gavage at a dose volume of 2 mL/kg. Following dose administration, blood samples (0.25 to 0.40 mL) were collected from each animal by jugular venipuncture under isoflurane anesthesia. Blood samples were collected (using lithium heparin as the anticoagulant) at pre-dose and again at 1, 2, 4, 6, 8 and 24 hr post-dose. Blood samples were placed on wet ice pending centrifugation at 3200 g for 10 min at 4° C. nominal. Following centrifugation, plasma was harvested and stored at −20° C. nominal pending shipment, on dry ice, for analysis.

Results

Adverse clinical signs and/or mortality were occasionally observed in some animals of Group Nos.: 3, 5, 6, 8, and 9 Animal Nos.: 3001 (Group 3) and 8001 (Group 8) were humanely sacrificed because of deteriorating conditions at ca 5 and 4 hr post-dose, respectively. Prior to sacrifice, these animals exhibited, in order, redness of the ears and paws, decreased activity and labored respiration. These signs were observed for the first time at ca 2 hr post-dose. Moreover, animal No. 9001 (Group 9) was found dead at ca 7 hr post-dose. No clinical signs were observed on this animal prior to death. Other major clinical signs are summarized in Table 7.

All patents, applications, and published references cited above are hereby incorporated by reference in their entirety.

TABLE 1

Tetrapeptide SPI forms of several Xaa-boroPro inhibitors of DPP IV and their High and low pH Ki values, showing all are essentially pH independend except for those Ala in P3 (corresponding to the DPP IV cleavage and activation site). This is because these Are not such good DPP IV substrates
Tetrapeptide Prodrugs (IC50)

|  | pH 2 | pH 8 |
| --- | --- | --- |
| ChgProValboroPro | 65 nM | 72 nM |
| ChgProAlaboroPro | 19 nM | 15 nM |
| ChgAlaValboroPro | 190 nM | 360 nM |
| ChgProChgboroAla | 180 nM | 170 nM |
| AlaProValboroPro | 20 nM | 21 nM |
| GlyProValboroPro | 17 nM | 46 nM |
| ProProProboroPro | 10 µM | N/A** |
| GlyProProboroPro | 9 µM | 20 nM |
| AlaProProboroPro | 8 nM | N/A |
| AlaAlaProboroPro | 3 nM | 2 nM |
| ChgAlaProboroPro | 2 nM | 30 nM |

TABLE 2

Toxicity of Val-boroPro in rats and mice. Results show that Val-boroPro is quite toxic to rats but not to mice.

| PROJECT # | TEST ARTICLE | GROUP | DOSE LEVEL | ROUTE | SPECIES | NO. OF ANIMAL DOSED | MORTALITY |
| --- | --- | --- | --- | --- | --- | --- | --- |
| 002898 | Val-ProBoronic acid | 1 | 5 mg/kg | Oral | Zucker Obese | 4 | 4 |
|  |  |  |  | Oral | Zucker Lean | 3 | 3 |

TABLE 2-continued

Toxicity of Val-boroPro in rats and mice. Results show that Val-boroPro is quite toxic to rats but not to mice.

| PROJECT # | TEST ARTICLE | GROUP | DOSE LEVEL | ROUTE | SPECIES | NO. OF ANIMAL DOSED | MORTALITY |
|---|---|---|---|---|---|---|---|
| 002969 | Val-ProBoronic acid | 2 | 0.035 mg/kg | Oral | Zucker Obese | 4 | 4 |
| | | | | Oral | Zucker Lean | 4 | 1 |
| | | 3 | 0.35 mg/kg | Oral | Zucker Obese | 4 | 4 |
| | | | | Oral | Zucker Lean | 4 | 4 |
| | | 4 | 1.75 mg/kg | Oral | Zucker Obese | 4 | 2 |
| | | | | Oral | Zucker Lean | 4 | 2 |
| 010757 | Val-ProBoronic acid | 3 | 0.035 mg/kg | | Diabetic Mice | 7 | 0 |
| | | 4 | 0.35 mg/kg | | Diabetic Mice | 7 | 0 |
| | | 5 | 3.5 mg/kg | | Diabetic Mice | 7 | 0 |
| 011050 | Val-ProBoronic acid | 2 (starved) | 0.035 mg/kg | | Diabetic Mice | 8 | 0 |
| | | 3 | 0.035 mg/kg | | Diabetic Mice | 8 | 0 |

TABLE 3

In vivo inhibition of serum DPP IV as a function of time following three different doses levels of CHG-Pro-Ala-boroPro, Val-boroPro, and CHG-Pro-Val-boroPro.

| | Normal-control | Diabetic-control | CHGProAlaboroPro | ValboroPro | CHGProValboroPro |
|---|---|---|---|---|---|
| 0.025 mg/kg | | | | | |
| 1 hr Post Rx-Glucose | 82.65 | 100.00 | 111.42 | 47.49 | 34.70 |
| 4 hrs Post Rx-Glucose | 89.95 | 100.00 | 58.85 | 39.23 | 24.40 |
| 0.01 mg/kg | | | | | |
| 1 hr Post Rx-Glucose | 82.65 | 100.00 | 100.00 | 59.36 | 48.86 |
| 4 hrs Post Rx-Glucose | 89.95 | 100.00 | 77.51 | 58.85 | 40.67 |
| 0.0025 mg/kg | | | | | |
| 1 hr Post Rx-Glucose | 82.65 | 100.00 | 109.59 | 94.52 | 84.47 |
| 4 hrs Post Rx-Glucose | 89.95 | 100.00 | 99.52 | 93.30 | 81.82 |

TABLE 4

$IC_{50}$ Values at Ten Minutes for DPPIV Prodrugs

| | | pH 2 | pH 8 |
|---|---|---|---|
| P3 Proline Analogues | ChgAzeEtgboroPro | 15 nM | 16 nM |
| | ChgDhpEtgboroPro | 15 nM | 17 nM |
| | ChgHypEtgboroPro | 17 nM | 25 nM |
| | ChgPipEtgboroPro | 19 nM | 14 nM |
| | ChgThz4EtgboroPro | 13 nM | 16 nM |
| β-Casomorphin Analogues | TyrProAlaboroPro | 15 nM | 17 nM |
| | PheProAlaboroPro | 6 nM | 8 nM |
| | TyrProPheboroPro | 50 nM | 60 nM |
| P2 Branched Prodrugs | ChgProAlaboroPro | 17 nM | 17 nM |
| | ChgProEtgboroPro | 12 nM | 14 nM |
| | ChgProValboroPro | 70 nM | 70 nM |
| | ChgProBugboroPro | 1.5 μM | 8 μM |
| N-Methyl Prodrugs | N-Me-PheProAlaboroPro | 2 μM | 2.7 μM |
| | SarDhpAlaboroPro | 39 nM | 34 nM |
| ProboroPro Prodrugs | ProProProboroPro | 10 μM | N/A |
| | AlaProProboroPro | 8.3 μM | N/A |

TABLE 4-continued

IC$_{50}$ Values at Ten Minutes for DPPIV Prodrugs

|  |  | pH 2 | pH 8 |
|---|---|---|---|
|  | GlyProProboroPro | 8.6 μM | 20 μM |
|  | AlaAlaProboroPro | 3 μM | N/A |
|  | ChgAlaProboroPro | 2 μM | 30 μM |
| boroAla Prodrugs | ChgProChgboroAla | 180 nM | 170 nM |
|  | ChgAlaEtgboroAla | 1.3 μM | 2.5 μM |
|  | ChgProtBugboroAla | 6.8 μM | 8.4 μM |
| ValboroPro Prodrugs | AlaProValboroPro | 20 nM | 21 nM |
|  | GlyProValboroPro | 17 nM | 46 nM |
|  | ChgAlaValboroPro | 190 nM | 360 nM |
|  | AlaAlaValboroPro | 2 μM | 25 μM |
|  | AibAlaValboroPro | 2 μM | N/A |
| Miscellaneous | ChgAlaEtgboroPro | 600 nM | 802 nM |
|  | ChgProChgboroPro | 14 nM | 14 nM |
|  | tBugProAlaboroPro | 14 nM | 18 nM |

TABLE 5

Study Design for Evaluation of dpp iv inhibition following single oral administration of new chemical entities to male sprague dawley rats

| Group ID | Test Article ID | Route of Administration | Target Dose (mg/kg) | Dose Volume (mL/kg) | No. Rats | Rat ID | Samples Collected |
|---|---|---|---|---|---|---|---|
| 1 |  | Oral | 0.05 | 2 | 4 | 1001-1004 | Blood, Plasma |
| 2 |  |  | 0.5 |  | 4 | 2001-2004 | Blood, Plasma |
| 3 |  |  | 5 |  | 4 | 3001-3004 | Blood, Plasma |
| 4 |  |  | 0.05 |  | 4 | 4001-4004 | Blood, Plasma |
| 5 |  |  | 0.5 |  | 4 | 5001-5004 | Blood, Plasma |
| 6 |  |  | 5 |  | 4 | 6001-6004 | Blood, Plasma |
| 7 |  |  | 0.05 |  | 4 | 7001-7004 | Blood, Plasma |
| 8 |  |  | 0.5 |  | 4 | 8001-8004 | Blood, Plasma |
| 9 |  |  | 5 |  | 4 | 9001-9004 | Blood, Plasma |

TABLE 6

Study Design for evaluation of DPP IV inhibition following single oral administration of four triad compounds in male rats

| Group ID | No. of Rats | Route | Test Article | Dose Level (mg ALA-PRO/kg*) | Rat ID | Samples Collected |
|---|---|---|---|---|---|---|
| 1 | 3 | Oral | 1 | 0.5 | 1001-1003 | Blood, Plasma |
| 2 | 3 | Oral | 1 | 2.5 | 2001-2003 | Blood, Plasma |
| 3 | 3 | Oral | 1 | 10.0 | 3001-3003 | Blood, Plasma |
| 4 | 3 | Oral | 2 | 0.5 | 4001-4003 | Blood Plasma |
| 5 | 3 | Oral | 2 | 2.5 | 5001-5003 | Blood, Plasma |
| 6 | 3 | Oral | 2 | 10.0 | 6001-6003 | Blood, Plasma |
| 7 | 3 | Oral | 3 | 0.5 | 7001-7003 | Blood, Plasma |
| 8 | 3 | Oral | 3 | 2.5 | 8001-8003 | Blood, Plasma |
| 9 | 3 | Oral | 3 | 10.0 | 9001-9003 | Blood, Plasma |

*Expressed as mg equivalent; applies to Test Articles 1, 2 and 3 only
Test Article 1: Chg-PRO-ALA-PRO Boronic acid (administered as ALA-PRO freebase)
Test Article 2: N-ME-PHE-PRO-ALA-PRO Boronic acid (administered as ALA-PRO freebase)
Test Article 3: N-ME-GLY-PRO-ALA-PRO Boronic acid (administered as ALA-PRO freebase)

TABLE 7

Summary of Clinical Signs after DPP IV inhibition following single oral administration of four triad compounds in male rats

| Animal ID | Approximate Onset of Observation (Time post-dose) | Clinical Observation | Approximate Time of Sacrifice or Time Animal was Found Dead (hr post-dose) |
|---|---|---|---|
| | | L-2-Chg-PRO-ALA-PRO boronic acid 0.5 mg/kg* | |
| 1001 | — | None | — |
| 1002 | — | None | — |
| 1003 | — | None | — |
| | | L-2-Chg-PRO-ALA-PRO boronic acid 2.5 mg/kg* | |
| 2001 | — | None | — |
| 2002 | — | None | — |
| 2003 | — | None | — |
| | | L-2-Chg-PRO-ALA-PRO boronic acid 10.0 mg/kg* | |
| 3001 | 2 hr<br>4 to 5 hr<br>5 hr | Redness of ears and paws<br>Decreased activity<br>labored breathing | 5 hr (sacrificed) |
| 3002 | — | None | — |
| 3003 | — | None | — |
| | | N-Me-Phe-PRO-ALA-PRO boronic acid 0.5 mg/kg* | |
| 4001 | — | None | — |
| 4002 | — | None | — |
| 4003 | — | None | — |
| | | N-Me-Phe-PRO-ALA-PRO boronic acid 2.5 mg/kg* | |
| 5001 | 2 hr | Redness of ears and paws | — |
| 5002 | — | None | — |
| 5003 | — | None | — |
| | | N-Me-Phe-PRO-ALA-PRO boronic acid 10.0 mg/kg* | |
| 6001 | — | None | — |
| 6002 | 4 hr | Redness of ears and paws | — |
| 6003 | — | None | — |
| | | N-Me-Gly-3,4 dehydroproline-ALA-PRO boronic acid 0.5 mg/kg* | |
| 7001 | — | None | — |
| 7002 | 8 hr | Redness of ears and paws | — |
| 7003 | — | None | — |
| | | N-Me-Gly-3,4 dehydroproline-ALA-PRO boronic acid 2.5 mg/kg* | |
| 8001 | 2 hr<br>4 hrr | Redness of ears and paws<br>Decreased activity, soft feces, labored breathing, cold to touch | 4 hr (sacrificed) |
| 8002 | 4 hr | Redness of ears and paws | — |
| 8003 | — | None | — |
| | | N-Me-Gly-3,4 dehydroproline-ALA-PRO boronic acid 10.0 mg/kg* | |
| 9001 | — | None | 7 hr (found dead) |
| 9002 | — | None | — |
| 9003 | — | None | — |

*Corresponds to ALA-PRO boronic dose equivalents

I claim:

1. A pro-inhibitor represented by the formula (I) or a pharmaceutically acceptable salt thereof:

A-G     (I)

wherein

A represents Chg-Pro;

A and G are covalently linked by a bond that is cleaved by the activating protease; and G represents Val-boroPro;

wherein, the inhibitor moiety G, when cleaved from A by the activating serine protease, undergoes reversible conformation-dependent inactivation and/or inhibits the target protease with a Ki of 100 nM or less.

2. The pro-inhibitor of claim 1, wherein the target protease is a serine protease.

3. The pro-inhibitor of claim 1, wherein the activating protease is a serine protease.

4. The pro-inhibitor of claim 1, wherein the activating protease is a metalloprotease.

5. The pro-inhibitor of claim 1, wherein the activating protease is a cysteine protease.

6. The pro-inhibitor of claim 1, wherein the $K_i$ for the inactive conformer is at least 5 times greater than the $K_i$ for the active conformer of the inhibitor moiety G.

7. The pro-inhibitor of claim 1, wherein the therapeutic index for the pro-inhibitor is at least 2 times greater than the therapeutic index for the inhibitor moiety G administered alone.

8. The pro-inhibitor of claim 1, provided in a pharmaceutical preparation that is substantially pyrogen-free.

9. The pro-inhibitor of claim 8, wherein a single administration of the pharmaceutical preparation can produce a therapeutically effective amount of the inhibitor moiety G for a period of at least 4 hours.

10. The pro-inhibitor of claim 1, wherein G undergoes reversible pH-dependent inactivation.

11. The pro-inhibitor of claim 1, wherein the amino terminus of A is blocked with an amino-terminal protecting group.

12. The pro-inhibitor of claim 1, wherein the target protease is a post-prolyl cleaving protease.

13. The pro-inhibitor of claim 12, wherein the target protease is selected from the group consisting of DPP IV, DPP II, Prolyl oligopeptidase (PO), Fibroblast Activating Protein (FAP), and prolyl carboxypeptidase.

14. A pharmaceutical composition, comprising a pharmaceutically acceptable carrier; and a pro-inhibitor of claim 1 or a pharmaceutically acceptable salt thereof.

15. A packaged pharmaceutical comprising one or more pro-inhibitors of claim 1, formulated in a pharmaceutically acceptable excipient, in association with instructions (written and/or pictorial) describing the recommended dosage and/or administration of the formulation to a patient.

* * * * *